(12) United States Patent
Shetty et al.

(10) Patent No.: US 8,962,623 B2
(45) Date of Patent: Feb. 24, 2015

(54) AMINOPYRAZINE COMPOUNDS

(75) Inventors: Rupa S. Shetty, Blue Bell, PA (US); Kevin J. Moriarity, East Norriton, PA (US); Dora Do-York Wong, legal representative, East Norriton, PA (US); Martha J. Kelly, Collegeville, PA (US); Bin Liu, Dayton, NJ (US); Jinming Zou, Riverside, CT (US); Kristofer K. Moffett, Middletown, CT (US); Younghee Lee, Blue Bell, PA (US)

(73) Assignee: Locus Pharmaceuticals, Inc., Blue Bell, PA (US)

( * ) Notice: Subject to any disclaimer, the term of this patent is extended or adjusted under 35 U.S.C. 154(b) by 0 days.

(21) Appl. No.: 14/001,936

(22) PCT Filed: Feb. 29, 2012

(86) PCT No.: PCT/US2012/027066
§ 371 (c)(1),
(2), (4) Date: Aug. 28, 2013

(87) PCT Pub. No.: WO2012/121939
PCT Pub. Date: Sep. 13, 2012

(65) Prior Publication Data
US 2014/0187529 A1  Jul. 3, 2014

Related U.S. Application Data

(60) Provisional application No. 61/449,187, filed on Mar. 4, 2011.

(51) Int. Cl.
| A61K 31/5377 | (2006.01) |
| C07D 487/04 | (2006.01) |
| C07D 491/056 | (2006.01) |
| C07D 401/12 | (2006.01) |
| C07D 413/14 | (2006.01) |
| C07D 403/12 | (2006.01) |
| C07D 401/14 | (2006.01) |
| C07D 407/14 | (2006.01) |
| C07D 409/14 | (2006.01) |
| C07D 417/14 | (2006.01) |

(52) U.S. Cl.
CPC ............ *C07D 413/14* (2013.01); *C07D 403/12* (2013.01); *C07D 401/14* (2013.01); *C07D 407/14* (2013.01); *C07D 409/14* (2013.01); *C07D 417/14* (2013.01); *C07D 487/04* (2013.01); *C07D 491/056* (2013.01); *C07D 401/12* (2013.01)
USPC .............. 514/236.5; 514/255.05; 514/255.06; 514/341; 544/120; 544/124; 544/405; 546/276.1

(58) Field of Classification Search
USPC ....................... 544/120, 124, 405; 546/276.1; 514/236.5, 255.05, 255.06, 341
See application file for complete search history.

(56) References Cited

U.S. PATENT DOCUMENTS

| 2008/0234268 A1 | 9/2008 | Booker et al. |
| 2009/0118305 A1 | 5/2009 | Barlaam et al. |
| 2010/0222318 A1 | 9/2010 | Charrier et al. |
| 2010/0239576 A1 | 9/2010 | Xi et al. |
| 2012/0040020 A1 | 2/2012 | Charrier et al. |

FOREIGN PATENT DOCUMENTS

| WO | 2008025820 A1 | 3/2008 |
| WO | 2008086014 A2 | 7/2008 |
| WO | 2010054398 A1 | 5/2010 |
| WO | 2010071837 A1 | 6/2010 |

OTHER PUBLICATIONS

International Search Report (PCT/ISA/210) issued Jun. 8, 2012, in International Application No. PCT/US2012/27066.
Written Opinion (PCT/ISA/237) issued Jun. 8, 2012, in International Application No. PCT/US2012/27066.

*Primary Examiner* — Bruck Kifle
(74) *Attorney, Agent, or Firm* — Sughrue Mion, PLLC

(57) ABSTRACT

A compound of formula (I):

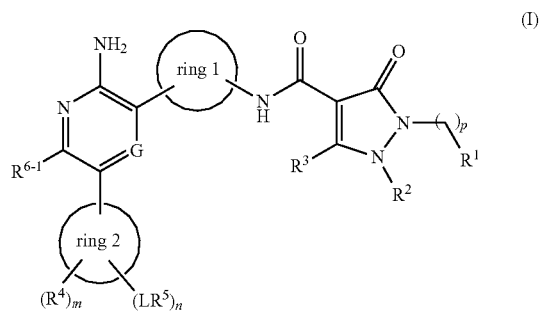

wherein all symbols have the same meanings as defined in the specification; a salt thereof, a solvate thereof, an N-oxide thereof, or a prodrug thereof, has an Itk inhibitory activity, and is useful as a method for preventing and/or treating atopic dermatitis, and the like.

13 Claims, No Drawings

AMINOPYRAZINE COMPOUNDS

FIELD OF THE INVENTION

The present invention relates to pyridine or pyrazine compounds useful as tyrosine kinase inhibitors, particularly Interleukin-2 inducible T-cell kinase (Itk) inhibitors. For more detail, the present invention relates to a novel compound represented by formula (I)

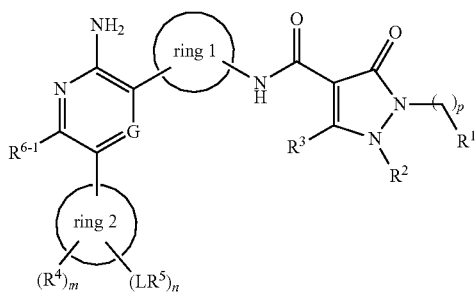

(I)

a salt thereof, a solvate thereof, an N-oxide thereof or a prodrug thereof (herein, which may be abbreviated to "the compounds of present invention", hereinafter).

BACKGROUND OF THE INVENTION

IL-2 inducible T-cell kinase (abbreviated as Itk hereinafter) is a non-receptor tyrosine kinase classified in the Tec kinase family. Itk is known to be expressed in T-cells, natural killer (NK) cells and mast cells. Itk plays an essential role in T-cell differentiation, proliferation and migration, and the production of cytokines such as IL-2, IL-4, IL-5, IL-10 and IL-13 (see, Nature Immunology vol. 2, no. 12, 1183-1188, (2001)). T-cells are activated with antigen presentation to the T-cell receptor (TCR) by the antigen presenting cells. Subsequently, a cascade of T-cell signal transduction initiates to activate Lck, Itk, NFAT etc., and leads to cytokine production (see, Trends in Immunology, vol. 24, no. 5, 249-253, (2003)). It suggests the inhibition of Itk relates to therapy of T-cell mediated diseases.

For example, it was reported that Itk knockout mice showed the reduction of production of cytokines IL-2, IL-4, IL-5, IL-10 and IFN-γ compared to the wild type (see, Nature Immunology vol. 2, no. 12, 1183-1188, (2001)) and the reduction of lung inflammation on allergen challenge with ovalbumin (see, Journal of Immunology vol. 170, 5056-5063, 2003). In addition, Itk gene is highly expressed in peripheral blood T cells from patients with atopic dermatitis (see, International Archives of Allergy and Immunology, vol. 129, No. 4, 327-340, 2002). Recently, it was suggested that inhibition of Itk blocks HIV infection by affecting multiple steps of HIV replication (see, Proceedings of the National Academy of Sciences U.S.A., vol. 105, 6684-6689, 2008). Therefore, the compounds having Itk inhibitory activity are possible remedies for allergic asthma, atopic dermatitis, HIV infection, other T-cell mediated diseases and so on.

As prior arts regarding the present invention, the following patent applications are exemplified.

It has been disclosed that a bis-aryl amide derivative represented by formula (A)

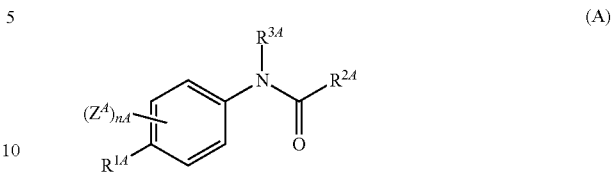

(A)

wherein, $R^{1A}$ is an aryl ring system or a 5-14 membered nitrogen containing heteroaryl or heterocyclic ring system; any of which may be optionally independently substituted with 1 to of 4 $Z^A$ groups; $R^{2A}$ is

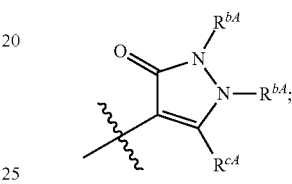

$R^{3A}$ is hydrogen or alkyl substituted with one or more $Z^A$ groups; $R^{bA}$ is independently H, C1-6 alkyl, C6-10 aryl and so on, any of which may be optionally substituted with one or more $Z^A$ groups; $R^{cA}$ is independently H, halo, hydroxyl, C1-6 alkyl and so on; $Z^A$ is an optional substituent independently selected at each occurrence from a*) halo, nitrile, hydroxyl, alkoxy, aryloxy and so on; or b*) alkyl, alkenyl, aryl, heteroaryl, and so on, any of which may be optionally substituted with one or more of the substituents listed in the above section a*; and nA is an integer from 0 to 3 (the definition of each group in the above described formula is excerpted), is useful for c-Met kinase inhibitor (From WO 2008/086014).

Furthermore, it has been described that an aminopyrazine compound represented by formula (B)

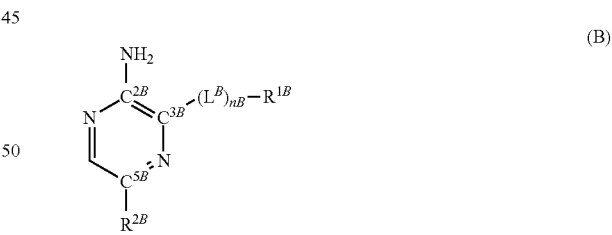

(B)

wherein $R^{1B}$ is a 5-6 membered monocyclic aryl or heteroaryl ring; $R^{1B}$ is optionally substituted with 1-5 $J^{1B}$ groups; $C^{2B}$, $C^{3B}$ and $C^{5B}$ are carbon; $R^{2B}$ is -$Q^B$ or -$Q^B$-$Q^{1B}$; $Q^B$ is a 3-7 membered monocyclic saturated or unsaturated non-aromatic ring; $Q^{1B}$ is a 3-8 membered monocyclic saturated or unsaturated ring; $J^B$ is fluoro, oxo, or a moiety containing a hydrogen bond acceptor; $L^B$ is —C(O)—NH— or —C(O)N(C1-6 alkyl)-; nB is 0 or 1 (the definition of each group in the above described formula is excerpted), is useful for ATR kinase inhibitor (From WO 2010/054398).

In addition, it has been disclosed that an aminopyrazine compound represented by formula (C)

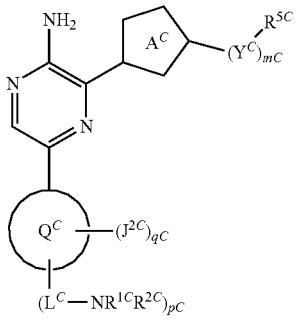

(C)

wherein $Y^C$ is a C 1-10 aliphatic chain wherein up to three methylene units of the aliphatic chain are optionally replaced with O, S, C(O) and so on; ring $A^C$ is a 5 membered heteroaryl ring; $Q^C$ is a 5-6 membered monocyclic aromatic ring or an 8-10 membered bicyclic aromatic ring; $R^{5C}$ is H, 3-7 membered monocyclic fully saturated, partially unsaturated ring, or aromatic ring; an 8-10 membered bicyclic fully saturated, partially unsaturated, or aromatic ring; $L^C$ is a C1-4 alkyl chain wherein up to two methylene units of the alkyl chain are optionally replaced with O, S, —C(O)—, and so on; $R^{1C}$ is H or C1-6 alkyl; $R^{2C}$ is H, C1-6 alkyl, a 4-8 membered cyclic ring and so on; or $R^{1C}$ and $R^{2C}$, taken together with the atom to which they are bound, form a 4-8 membered heterocyclic ring; $J^{2C}$ is halo, CN, a 5-6 membered aromatic or nonaromatic monocyclic ring, and so on; mC is 0 or 1; qC is 0, 1, or 2; pC is 0 or 1 (the definition of each group in the above described formula is excerpted), is useful for ATR kinase inhibitor (From WO2010/071837).

Additionally, it has been disclosed that an aminopyridine compound represented by formula (D)

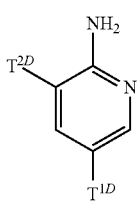

(D)

wherein $T^{1D}$ is aromatic heterocyclic, aromatic heterobicyclic, phenyl, naphthyl, or indenyl, wherein $T^{1D}$ is optionally substituted with one or more $R^{1D}$; $T^{2D}$ is aromatic heterocyclic, aromatic heterobicyclic, phenyl, naphthyl, or indenyl, wherein $T^{2D}$ is optionally substituted with one or more $R^{2D}$; $R^{1D}$, $R^{2D}$ are independently selected from the group consisting of $T^{3D}$, C1-6 alkyl, halogen, CN, and so on; $T^{3D}$ is C3-7 cycloalkyl, heterocyclic, or phenyl (the definition of each group in the above described formula is excerpted), is useful for Itk kinase inhibitor (From WO2008/025820).

Meanwhile, some protein kinases, such as Lck, activate Itk. In addition, it is known that retinal abnormalities are observed in Lck (the Src family of non receptor-type kinases) deficient mice (See oncogene, 16, 2351-2356, (1998)). Therefore, it is important to express selectivity for Itk over Lck in developing Itk inhibitor as pharmaceutical product.

DISCLOSURE OF THE INVENTION

Namely, the present invention relates to
[1] A compound represented by formula (I)

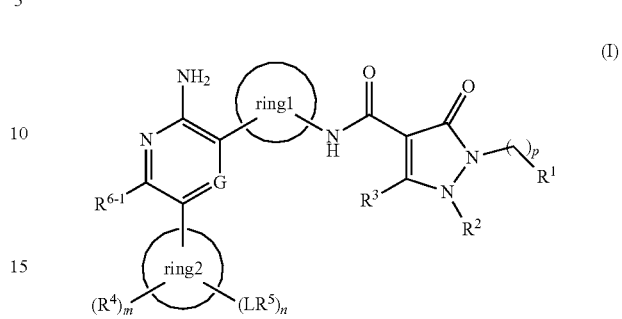

(I)

wherein G represents N, CH or $CR^{6-2}$;

ring1 represents (1) C6 carbocyclic ring, or (2) 6 membered heterocyclic ring, any of which is optionally substituted with 1-4 substituent(s) selected from among (1) C1-4 alkyl, (2) C1-4 alkoxy, (3) halogen, and (4) oxo;

ring2 represents a 5-6 membered aromatic or 5-10 membered heteroaromatic ring;

$R^1$ represents (1) C1-4 alkyl optionally substituted with halogen, (2) C3-6 carbocyclic ring, or (3) 3-6 membered heterocyclic ring, any ring of which is optionally substituted with 1-5 substituent(s) selected from among (1) C1-4 alkyl, (2) C1-4 alkoxy, (3) halogen, (4) $CF_3$, and (5) CN;

$R^2$ and $R^3$ each independently represent (1) $CF_3$, or (2) C1-4 alkyl optionally substituted with 1-3 substituent(s) selected from among (1) $OR^{2-1}$, (2) $NR^{2-2}R^{2-3}$ and (3) halogen;

$R^4$ represents (1) halogen, (2) C1-4 alkyl, (3) C1-4 alkoxy, (4) $CF_3$, (5) OH, (6) CN, (7) ring3, (8) $NR^{4-1}R^{4-2}$, or (9) $NO_2$;

$R^5$ represents (1) ring3, (2) C1-4 alkyl optionally substituted with halogen, OH, C1-4 alkoxy, CN, $COOR^{5-8}$, or $NR^{5-1}R^{5-2}$, (3) C2-4 alkenyl, (4) C1-4 alkoxy, (5) $NR^{5-3}R^{5-4}$, (6) OH, (7) $SO_2R^{5-5}$, (8) $SO_2NR^{5-6}R^{5-7}$, (9) $COOR^{5-8}$, (10) $COR^{5-9}$, (11) $CONR^{5-10}R^{5-11}$, (12) halogen, or (13) hydrogen;

$R^{6-1}$ and $R^{6-2}$ each independently represent (1) hydrogen, (2) C1-4 alkyl, or (3) $NH_2$;

L represents (1) —O—, (2) —C1-6 alkylene-, (3) —C(O)—, (4) —O—C1-6 alkylene-, (5) —C1-6 alkylene-O—, (6) —$NR^{7-1}$—, (7) —S—, (8) —SO—, (9) —$SO_2$—, (10) —CNH— (11) —$NR^{7-2}$C(O)—, (12) —$NR^{7-3}$C(O) $NR^{7-4}$—, (13) —C(O)$NR^{7-5}$—, (14) —$SO_2NR^{7-6}$—, (15) —$NR^{7-7}SO_2$—, (16) C2-4 alkenylene, or (17) C2-4 alkynylene, wherein C1-6 alkylene is optionally substituted with OH;

ring3 represents (1) C3-7 carbocyclic ring, or (2) 3-7 membered heterocyclic ring, any of which is optionally substituted with 1-5 substituent(s) selected from among (1) halogen, (2) C1-4 alkyl optionally substituted with OH, C1-4 alkoxy, or $NR^{8-1}R^{8-2}$, (3) oxo, (4) OH, (5) C1-4 alkoxy, (6) $C(O)CH_3$, (7) $NR^{8-3}R^{8-4}$, (8) $SO_2CH_3$, (9) $COOR^{8-5}$, and (10) $C(O)NR^{8-6}R^{8-7}$;

$R^{2-1}$, $R^{2-2}$ and $R^{2-3}$ each independently represent hydrogen, or C1-4 alkyl;

$R^{4-1}$ and $R^{4-2}$ each independently represent hydrogen or C1-4 alkyl;

$R^{5-1}$, $R^{5-2}$, $R^{5-3}$, $R^{5-4}$, $R^{5-5}$, $R^{5-6}$, $R^{5-7}$, $R^{5-8}$, $R^{5-9}$, $R^{5-10}$ and $R^{5-11}$ each independently represent hydrogen or C1-6 alkyl;

$R^{7-1}$, $R^{7-2}$, $R^{7-3}$, $R^{7-4}R^{7-5}$, $R^{7-6}$ and $R^{7-7}$ each independently represent hydrogen or C1-4 alkyl;

$R^{8-1}$, $R^{8-2}$, $R^{8-3}$, $R^{8-4}$, $R^{8-5}$, $R^{8-6}$ and $R^{8-7}$ each independently represent hydrogen or C1-4 alkyl;

m represents 0 or an integer of 1-3, wherein when m is more than 1, each $R^4$ may be same or different;

n represents 0 or an integer of 1-2, wherein n is 2, each $LR^5$ may be same or different;

p represents 0 or 1;

a salt thereof, a solvate thereof, an N-oxide thereof or a prodrug thereof,

[2] The compound as described above [1], wherein G represents N,

[3] The compound as described above [1], wherein G represents CH,

[4] The compound as described above any of [1]-[3], wherein ring1 represents benzene, pyridine, piperidine, cyclohexene, or cyclohexane, any of which is optionally substituted with 1-4 substituent(s) selected from among (1) C1-4 alkyl, (2) C1-4 alkoxy, (3) halogen, and (4) oxo,

[5] The compound as described above any of [1]-[4], wherein $R^4$ represents (1) C1-4 alkyl, (2) $CF_3$, (3) ring3, or (4) halogen,

[6] The compound as described above any of [1]-[5], wherein L represents (1) —C1-6 alkylene-, (2) —O—C1-6 alkylene-, (3) —C1-6 alkylene-O—, (4) C2-4 alkenylene, or (5) C2-4 alkynylene, wherein C1-6 alkylene is optionally substituted with OH,

[7] The compound as described above any of [1]-[6], wherein L represents (1) —C1-6 alkylene-, (2) —O—C1-6 alkylene-, (3) —C1-6 alkylene-O—, (4) C2-4 alkenylene, or (5) C2-4 alkynylene, wherein C1-6 alkylene is optionally substituted with OH and at least one of $R^4$ and $R^5$ is ring3,

[8] The compound as described above any of [1]-[7], wherein ring3 represents 3-7 membered heterocyclic ring which is optionally substituted with 1-5 substituent(s) selected from among (1) halogen, (2) C1-4 alkyl optionally substituted with OH, C1-4 alkoxy, or $NR^{8-1}R^{8-2}$, (3) oxo, (4) OH, (5) C1-4 alkoxy, (6) $C(O)CH_3$, (7) $NR^{8-3}R^{8-4}$, (8) $SO_2CH_3$, (9) $COOR^{8-5}$, and (10) $C(O)NR^{8-6}R^{8-7}$,

[9] The compound as described above [1], which is the compound represented by formula (I-1)

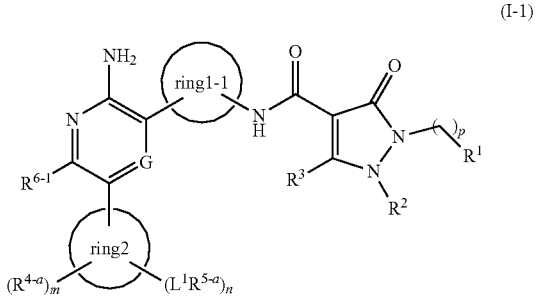

(I-1)

wherein ring 1-1 represents benzene, pyridine, piperidine, cyclohexene, or cyclohexane, any of which is optionally substituted with 1-4 substituent(s) selected from among (1) C1-4 alkyl, (2) C1-4 alkoxy, (3) halogen, and (4) oxo;

$R^{4-a}$ represents (1) C1-4 alkyl, (2) $CF_3$, (3) ring3-1, or (4) halogen;

$R^{5-a}$ represents (1) ring3-1, (2) C1-4 alkyl optionally substituted with halogen, OH, C1-4 alkoxy, CN, $COOR^{5-8}$, or $NR^{5-1}R^{5-2}$, (3) C2-4 alkenyl, (4) C1-4 alkoxy, (5) $NR^{5-3}R^{5-4}$, (6) OH, (7) $SO_2R^{5-5}$, (8) $SO_2NR^{5-6}R^{5-7}$, (9) $COOR^{5-8}$, (10) $COR^{5-9}$, (11) $CONR^{5-10}R^{5-11}$, (12) halogen, or (13) hydrogen; wherein ring3-1 represents 3-7 membered heterocyclic ring which is optionally substituted with 1-5 substituent(s) selected from among (1) halogen, (2) C1-4 alkyl optionally substituted with OH, C1-4 alkoxy, or $NR^{8-1}R^{8-2}$, (3) oxo, (4) OH, (5) C1-4 alkoxy, (6) $C(O)CH_3$, (7) $NR^{8-3}R^{8-4}$, (8) $SO_2CH_3$, (9) $COOR^{8-5}$, and (10) $C(O)NR^{8-6}R^{8-7}$;

$L^1$ represents (1) —C1-6 alkylene-, (2) —O—C1-6 alkylene-, (3) C2-4 alkenylene, or (4) C2-4 alkynylene, wherein C1-6 alkylene is optionally substituted with OH; the other symbols have the same meanings as described above and at least one of $R^{4-a}$ and $R^{5-a}$ is ring3-1,

[10] The compound as described above any of [1] or [9], which is the compound represented by formula (I-2)

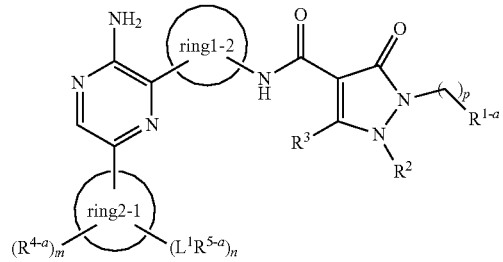

(I-2)

wherein ring1-2 represents benzene, pyridine, or piperidine; ring2-1 represents benzene, pyridine, thiazole, thiophene, pyrazole, pyrazole, pyrazine, triazole, pyrimidine, indole, indazole, benzomidazole, 2,3-dihydro-[1,4]dioxino[2,3-b]pyridine, imidazo[1,5-a]pyridine, 2,3-dihydro-1H-pyrrolo[2,3-b]pyridine, or 3H-imidazo[4,5-b]pyridine;

$R^{1-a}$ represents benzene which is optionally substituted with 1-5 substituent(s) selected from among (1) C1-4 alkyl, (2) C1-4 alkoxy, (3) halogen, (4) $CF_3$, and (5) CN;

the other symbols have the same meanings as the above and at least one of $R^{4-a}$ and $R^{5-a}$ is ring3-1,

[11] The compound as described above [1], which is (1) N-(4-{3-amino-6-[5-(4-morpholinyl)-3-pyridinyl]-2-pyrazinyl}phenyl)-1,5-dimethyl-3-oxo-2-phenyl-2,3-dihydro-1H-pyrazole-4-carboxamide, (2) N-(4-{3-amino-6-[2-(3-methoxy-1-azetidinyl)-4-pyridinyl]-2-pyrazinyl}phenyl)-2-(3-chlorophenyl)-1,5-dimethyl-3-oxo-2,3-dihydro-1H-pyrazole-4-carboxamide, (3) N-(4-{3-amino-6-[6-(3-methoxy-1-azetidinyl)-2-pyridinyl]-2-pyrazinyl}phenyl)-2-(3-chlorophenyl)-1,5-dimethyl-3-oxo-2,3-dihydro-1H-pyrazole-4-carboxamide, (4) N-[4-(3-amino-6-{6-[(2-methoxyethyl)(methyl)amino]-2-pyridinyl}-2-pyrazinyl)phenyl]-2-(3-chlorophenyl)-1,5-dimethyl-3-oxo-2,3-dihydro-1H-pyrazole-4-carboxamide, (5) N-(6-{3-amino-6-[2-(4-morpholinyl)-4-pyridinyl]-2-pyrazinyl}-3-pyridinyl)-1,5-dimethyl-2-(3-methylphenyl)-3-oxo-2,3-dihydro-1H-pyrazole-4-carboxamide, (6) N-(6-{3-amino-6-[2-(4-morpholinyl)-4-pyridinyl]-2-pyrazinyl}-3-pyridinyl)-2-(3-chlorophenyl)-1,5-dimethyl-3-oxo-2,3-dihydro-1H-pyrazole-4-carboxamide, or (7) N-(4-{3-amino-6-[6-(4-methoxy-1-piperidinyl)-2-pyridinyl]-2-pyrazinyl}phenyl)-1,5-dimethyl-2-(3-methylphenyl)-3-oxo-2,3-dihydro-1H-pyrazole-4-carboxamide,

[12] The compound as described above [1], which is (1) N-(6-{3-amino-6-[2-(3-methoxy-1-azetidinyl)-4-pyridinyl]-2-pyrazinyl}-3-pyridinyl)-2-(3-methoxyphenyl)-1,5-dimethyl-3-oxo-2,3-dihydro-1H-pyrazole-4-carboxamide, (2) N-{1-[5-amino-6'-(4-methoxy-1-piperidinyl)-2,2'-bipyrazin-6-yl]-4-piperidinyl}-2-(2-chlorophenyl)-1,5-dimethyl-3-oxo-2,3-dihydro-1H-pyrazole-4-carboxamide, (3) N-{1-[5-amino-6'-(3-methoxy-1-pyrrolidinyl)-2,2'-bipyrazin-6-yl]-4-piperidinyl}-2-(2-chlorophenyl)-1,5-dimethyl-3-oxo-2,3-dihydro-1H-pyrazole-4-carboxamide, or (4) N-{4-[5-amino-6'-(3-methoxy-1-pyrrolidinyl)-2,2'-bipyrazin-6-yl]phenyl}-1,5-dimethyl-3-oxo-2-phenyl-2,3-dihydro-1H-pyrazole-4-carboxamide,

[13] (1) N-{4-[6-(1-acryloyl-3-piperidinyl)-3-amino-2-pyrazinyl]phenyl}-1,5-dimethyl-3-oxo-2-phenyl-2,3-dihydro-1H-pyrazole-4-carboxamide, (2) N-{4-[3-amino-6-(1-piperidinyl)-2-pyrazinyl]phenyl}-1,5-dimethyl-3-oxo-2-phenyl-2,3-dihydro-1H-pyrazole-4-carboxamide, or (3) N-[4-(2-amino-5-cyclohexyl-3-pyridinyl)phenyl]-1,5-dimethyl-3-oxo-2-phenyl-2,3-dihydro-1H-pyrazole-4-carboxamide, a salt thereof, a solvate thereof, an N-oxide thereof or a prodrug thereof,

[14] A pharmaceutical composition comprising the compound represented by formula (I) of described above [1], a salt thereof, a solvate thereof, an N-oxide thereof or a prodrug thereof,

[15] A method for preventing and/or treating an Itk related disease, which comprises administering to a mammal an effective amount of the compound of formula (I) of described above [1], a salt thereof, a solvate thereof, an N-oxide thereof or a prodrug thereof,

[16] The method as described above [15], wherein the Itk related disease is respiratory disease, allergic disease, autoimmune disease, inflammatory disease, cancer, transplant rejection, graft versus host disease, HIV infection, aplastic anemia, or pain, and

[17] A compound of formula (I) of described above [1], a salt thereof, a solvate thereof, an N-oxide thereof or a prodrug thereof, for use in preventing and/or treating an Itk related disease.

In the present invention, halogen includes chlorine, fluorine, bromine, and iodine.

In the present invention, C1-4 alkyl includes straight and branched chain C1-4 alkyl group, such as methyl, ethyl, n-propyl, isopropyl, n-butyl, isobutyl, sec-butyl, and tert-butyl.

In the present invention, C1-6 alkyl includes straight and branched chain C1-6 alkyl group, such as methyl, ethyl, n-propyl, isopropyl, n-butyl, isobutyl, sec-butyl, tert-butyl, pentyl, isopentyl, tert-pentyl, neopentyl, hexyl and isomer thereof.

In the present invention, C1-6 alkylene includes straight and branched chain C1-6 alkylene group, such as methylene, ethylene, trimethylene, tetramethylene, pentamethylene, hexamethylene and isomer thereof.

In the present invention, C2-4 alkenyl includes straight and branched chain C2-4 alkenyl group, such as ethenyl, 1-propenyl, 2-propenyl, 1-butenyl, 2-butenyl, and 3-butenyl.

In the present invention, C2-4 alkenylene includes straight and branched chain C2-4 alkenylene such as ethenylene, propenylene, butenylene and isomer thereof.

In the present invention, C2-4 alkynylene includes straight and branched chain C2-4 alkynylene such as ethynylene, propynylene, butynylene and isomer thereof.

In the present invention, C1-4 alkoxy includes, such as methoxy, ethoxy, propoxy, isopropoxy, butoxy, isobutoxy, sec-butoxy, and tert-butoxy.

In the present invention, C3-7 carbocyclic ring includes, such as cyclopropane, cyclobutane, cyclopentane, cyclohexane, cycloheptane, cyclobutene, cyclopentene, cyclohexene, cycloheptene, cyclobutadiene, cyclopentadiene, cyclohexadiene, cycloheptadiene, and benzene.

In the present invention, C3-6 carbocyclic ring includes, such as cyclopropane, cyclobutane, cyclopentane, cyclohexane, cyclobutene, cyclopentene, cyclohexene, cyclobutadiene, cyclopentadiene, cyclohexadiene, and benzene.

In the present invention, C5-6 carbocyclic ring includes, such as cyclopentane, cyclohexane, cyclopentene, cyclohexene, cyclopentadiene, cyclohexadiene, and benzene.

In the present invention, C6 carbocyclic ring includes, such as cyclohexane, cyclohexene, cyclohexadiene, and benzene.

In the present invention, 5-10 membered heteroaromatic ring includes, for example, 5-10 membered aromatic monocyclic or bicyclic aromatic heterocyclic ring containing 1-4 heteroatom(s) selected from a nitrogen atom, an oxygen atom and/or a sulfur atom optionally oxidized, and includes a monocyclic aromatic heterocyclic ring, a bicyclic aromatic heterocyclic ring, a bicyclic fused ring formed of a monocyclic aromatic heterocyclic ring and an unsaturated or saturated monocyclic carbocyclic ring, a bicyclic fused ring formed of a monocyclic aromatic carbocyclic ring and an unsaturated or saturated monocyclic heterocyclic ring, or a bicyclic fused ring formed of a monocyclic aromatic heterocyclic ring and an unsaturated or saturated monocyclic heterocyclic ring are included therein. For example, pyrrole, imidazole, triazole, pyrazole, pyridine, pyrazine, pyrimidine, pyridazine, furan, thiophene, oxazole, isooxazole, thiazole, isothiazole, furazan, oxadiazole, thiadiazole, indole, isoindole, benzofuran, isobenzofuran, benzothiophene, isobenzothiophene, indazole, quinoline, isoquinoline, purine, phthalazine, pteridine, naphthylidine, quinoxaline, quinazoline, cinnoline, benzooxazole, benzothiazole, benzoimidazole, benzofurazan, benzothiadiazole, benzotriazole, indoline, isoindoline, dihydrobenzofuran, dihydroisobenzofuran, dihydrobenzothiophene, dihydroisobenzothiophene, chromene, chromane, isochromane, tetrahydroquinoline, dihydroquinoline, tetrahydroisoquinoline, dihydroisoquinoline, tetrahydroquinoxaline, dihydroquinoxaline, tetrahydroquinazoline, dihydroquinazoline, dioxaindan, 2,3-dihydro-[1,4]dioxino[2,3-b]pyridine, imidazo[1,5-a]pyridine, 2,3-dihydro-1H-pyrrolo[2,3-b]pyridine, and 3H-imidazo[4,5-b]pyridine rings are given. However, in the case of the indole, isoindole, benzofuran, isobenzofuran, benzothiophene, isobenzothiophene, indazole, phthalazine, quinoxaline, quinazoline, cinnoline, benzooxazole, benzothiazole, benzoimidazole, benzofurazan, benzothiadiazole, benzotriazole, indoline, isoindoline, dihydrobenzofuran, dihydroisobenzofuran, dihydrobenzothiophene, dihydroisobenzothiophene, chromene, chromane, isochromane, and dioxaindan rings, a benzene ring among those rings, or in the case of tetrahydroquinoline, dihydroquinoline, tetrahydroisoquinoline, dihydroisoquinoline, tetrahydroquinoxaline, dihydroquinoxaline, tetrahydroquinazoline, dihydroquinazoline, 2,3-dihydro-[1,4]dioxino[2,3-b]pyridine, imidazo[1,5-a]pyridine, and 2,3-dihydro-1H-pyrrolo[2,3-b]pyridine, 3H-imidazo[4,5-b]pyridine rings, a pyridine, pyrimidine, imidazole or pyrazine ring among those rings binds to L in the formula (I).

In the present invention, 3-7 membered heterocyclic ring includes, for example, 3-7 membered monocyclic unsaturated or saturated heterocyclic ring containing 1-4 heteroatom(s) selected from a nitrogen atom, an oxygen atom and/or a sulfur atom optionally oxidized, such as aziridine, oxirane, thiirane, azetidine, oxetane, thietane, pyrrole, imidazole, triazole, pyrazole, pyridine, pyrazine, pyrimidine, pyridazine, azepine, diazepine, furan, pyran, oxepine, thiophene, thiopyran, thiepine, oxazole, isoxazole, thiazole, thiazole, isothiazole, furazan, oxadiazole, oxazine, oxadiazine, oxazepine, oxadiazepine, thiadiazole, thiazine, thiazine, thiadiazine, thiazepine, thiadiazepine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrofuran, tetrahydrofuran, dihydropyran, tetrahydropyran, dihydrooxepine, tetrahydrooxepine, perhydrooxepine, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, and the like.

In the present invention, 3-6 membered heterocyclic ring includes, for example, 3-6 membered monocyclic unsaturated or saturated heterocyclic ring containing 1-4 heteroatom(s) selected from a nitrogen atom, an oxygen atom and/or a sulfur atom optionally oxidized, such as aziridine, oxirane, thiirane, azetidine, oxetane, thietane, pyrrole, imidazole, triazole, pyrazole, pyridine, pyrazine, pyrimidine, pyridazine, furan, pyran, thiophene, thiopyran, oxazole, isoxazole, thiazole, isothiazole, furazan, oxadiazole, oxazine, oxadiazole, thiadiazole, thiazine, thiadiazine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydrofuran, tetrahydrofuran, dihydropyran, tetrahydropyran, dihydrothiophene, tetrahydrothiophene, dihydrothiopyran, tetrahydrothiopyran, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrothiadiazole, tetrahydrothiadiazole (thiadiazolidine), dihydrothiazine, tetrahydrothiazine, dihydrothiadiazine, tetrahydrothiadiazine, morpholine, thiomorpholine, oxathiane, and the like.

In the present invention, 5-6 membered heterocyclic ring includes, for example, 5-6 membered monocyclic unsaturated or saturated heterocyclic ring containing 1-4 heteroatom(s) selected from a nitrogen atom, an oxygen atom and/or a sulfur atom optionally oxidized, such as pyrrole, imidazole, triazole, pyrazole, pyridine, pyrazine, pyrimidine, pyridazine, furan, pyran, thiophene, thiopyran, oxazole, isoxazole, thiazole, isothiazole, furazan, oxadiazole, oxazine, oxadiazine, thiadiazole, thiazine, thiadiazine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydrofuran, tetrahydrofuran, dihydropyran, tetrahydropyran, dihydrothiophene, tetrahydrothiophene, dihydrothiopyran, tetrahydrothiopyran, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrothiadiazole, tetrahydrothiadiazole (thiadiazolidine), dihydrothiazine, tetrahydrothiazine, dihydrothiadiazine, tetrahydrothiadiazine, morpholine, thiomorpholine, oxathiane, and the like.

In the present invention, 6 membered heterocyclic ring includes, for example, 6 membered unsaturated or saturated heterocyclic ring containing 1-3 heteroatom(s) selected from a nitrogen atom, an oxygen atom and/or a sulfur atom optionally oxidized, such as pyridine, pyrazine, pyrimidine, pyridazine, pyran, thiopyran, oxazine, oxadiazine, thiazine, thiadiazine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydropyran, tetrahydropyran, dihydrothiopyran, tetrahydrothiopyran, dihydrooxazine, tetrahydrooxazine, dihydrooxadiazine, tetrahydrooxadiazine, dihydrothiazine, tetrahydrothiazine, dihydrothiadiazine, tetrahydrothiadiazine, morpholine, thiomorpholine, oxathiane, and the like.

In the present invention, 5-6 membered aromatic or heteroaromatic ring includes, for example, benzene, pyrrole, imidazole, triazole, tetrazole, pyrazole, pyridine, pyrazine, pyrimidine, pyridazine, furan, thiophene, oxazole, isoxazole, thiazole, isothiazole, furazan, oxadiazole, thiadiazole, and the like.

In the present invention, ring1 is preferably benzene, pyridine, piperidine, cyclohexene, or cyclohexane, more preferably benzene, pyridine, or piperidine.

In the present invention, ring2 is preferably benzene, pyridine, thiazole, thiophene, pyrazole, pyrazole, pyrazine, triazole, pyrimidine, indole, indazole, benzomidazole, 2,3-dihydro-[1,4]dioxino[2,3-b]pyridine, imidazo[1,5-a]pyridine, 2,3-dihydro-1H-pyrrolo[2,3-b]pyridine, or 3H-imidazo[4,5-b]pyridine.

In the present invention, $R^1$ is preferably C3-6 carbocyclic ring which is optionally substituted with 1-5 substituent(s) selected from among (1) C1-4 alkyl, (2) C1-4 alkoxy, (3) halogen, (4) $CF_3$, and (5) CN, more preferably benzene which is optionally substituted with 1-5 substituent(s) selected from among (1) C1-4 alkyl, (2) C1-4 alkoxy, (3) halogen, (4) $CF_3$, and (5) CN.

In the present invention, $R^2$ is preferably C1-4 alkyl.

In the present invention, $R^3$ is preferably C1-4 alkyl.

In the present invention, $R^4$ is preferably (1) C1-4 alkyl, (2) $CF_3$, (3) 3-7 membered heterocyclic ring, or (4) halogen, more preferably 3-7 membered heterocyclic ring.

In the present invention, $R^5$ is preferably (1) 3-7 membered heterocyclic ring, (2) C1-4 alkyl optionally substituted with halogen, OH, C1-4 alkoxy, CN, $COOR^{5-8}$, or $NR^{5-1}R^{5-2}$, (3) C2-4 alkenyl, (4) C1-4 alkoxy, (5) $NR^{5-3}R^{5-4}$, (6) OH, (7) $SO_2R^{5-5}$, (8) $SO_2NR^{5-6}R^{5-7}$, (9) $COOR^{5-8}$, (10) $COR^{5-9}$, (11)

CONR$^{5-10}$R$^{5-11}$, (12) halogen, or (13) hydrogen, more preferably 3-7 membered heterocyclic ring.

In the present invention, R$^6$ is preferably hydrogen atom.

In the present invention, L is preferably (1) —C1-6 alkylene-, (2) —O—C1-6 alkylene-, (3) —C1-6 alkylene-O—, (4) C2-4 alkenylene, or (5) C2-4 alkynylene.

In the present invention, ring3 is preferably 3-7 membered heterocyclic ring, more preferably morpholine, piperidine, tetrahydropyran, piperazine, pyrazole, pyrrolidine, tetrahydrofuran, imidazole, azetidine, diazepane, cyclopropane, or oxetane.

In the present invention, G is preferably N.

In the present invention, each preferable group above described may be voluntarily combined.

In the present invention, the compound represented by formula (I) is preferably the compound represented by formula (I-1)

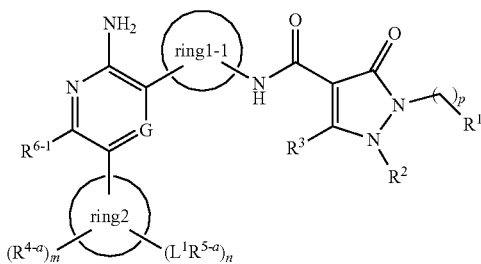

(I-1)

wherein all the symbols have the same meanings as the above.

In the present invention, the compound represented by formula (I) is preferably the compound represented by formula (I-2).

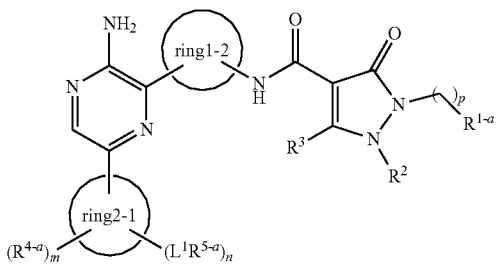

(I-2)

wherein ring1-2 represents benzene, pyridine, or piperidine; ring2-1 represents benzene, pyridine, thiazole, thiophene, pyrazole, pyrazole, pyrazine, triazole, pyrimidine, indole, indazole, benzomidazole, 2,3-dihydro-[1,4]dioxino[2,3-b]pyridine, imidazo[1,5-a]pyridine, 2,3-dihydro-1H-pyrrolo[2,3-b]pyridine, or 3H-imidazo[4,5-b]pyridine; R$^{1-a}$ represents benzene which is optionally substituted with 1-5 substituent(s) selected from among (1) C1-4 alkyl, (2) C1-4 alkoxy, (3) halogen, (4) CF$_3$, and (5) CN; R$^{5-a}$ represents ring3-1 and the other symbols have the same meanings as the above.

In the present invention, the all compounds described in Examples are preferred. More preferred are (1) N-(4-{3-amino-6-[5-(4-morpholinyl)-3-pyridinyl]-2-pyrazinyl}phenyl)-1,5-dimethyl-3-oxo-2-phenyl-2,3-dihydro-1H-pyrazole-4-carboxamide, (2) N-(4-{3-amino-6-[2-(3-methoxy-1-azetidinyl)-4-pyridinyl]-2-pyrazinyl}phenyl)-2-(3-chlorophenyl)-1,5-dimethyl-3-oxo-2,3-dihydro-1H-pyrazole-4-carboxamide, (3) N-(4-{3-amino-6-[6-(3-methoxy-1-azetidinyl)-2-pyridinyl]-2-pyrazinyl}phenyl)-2-(3-chlorophenyl)-1,5-dimethyl-3-oxo-2,3-dihydro-1H-pyrazole-4-carboxamide, (4) N-[4-(3-amino-6-{6-[(2-methoxyethyl)(methyl)amino]-2-pyridinyl}-2-pyrazinyl)phenyl]-2-(3-chlorophenyl)-1,5-dimethyl-3-oxo-2,3-dihydro-1H-pyrazole-4-carboxamide, (5) N-(6-{3-amino-6-[2-(4-morpholinyl)-4-pyridinyl]-2-pyrazinyl}-3-pyridinyl)-1,5-dimethyl-2-(3-methylphenyl)-3-oxo-2,3-dihydro-1H-pyrazole-4-carboxamide, (6) N-(6-{3-amino-6-[2-(4-morpholinyl)-4-pyridinyl]-2-pyrazinyl}-3-pyridinyl)-2-(3-chlorophenyl)-1,5-dimethyl-3-oxo-2,3-dihydro-1H-pyrazole-4-carboxamide, (7) N-(4-{3-amino-6-[6-(4-methoxy-1-piperidinyl)-2-pyridinyl]-2-pyrazinyl}phenyl)-1,5-dimethyl-2-(3-methylphenyl)-3-oxo-2,3-dihydro-1H-pyrazole-4-carboxamide, (8) N-(6-{3-amino-6-[2-(3-methoxy-1-azetidinyl)-4-pyridinyl]-2-pyrazinyl}-3-pyridinyl)-2-(3-methoxyphenyl)-1,5-dimethyl-3-oxo-2,3-dihydro-1H-pyrazole-4-carboxamide, (9) N-{1-[5-amino-6'-(4-methoxy-1-piperidinyl)-2,2'-bipyrazin-6-yl]-4-piperidinyl}-2-(2-chlorophenyl)-1,5-dimethyl-3-oxo-2,3-dihydro-1H-pyrazole-4-carboxamide,

(10) N-{1-[5-amino-6'-(3-methoxy-1-pyrrolidinyl)-2,2'-bipyrazin-6-yl]-4-piperidinyl}-2-(2-chlorophenyl)-1,5-dimethyl-3-oxo-2,3-dihydro-1H-pyrazole-4-carboxamide, or

(11) N-{4-[5-amino-6'-(3-methoxy-1-pyrrolidinyl)-2,2'-bipyrazin-6-yl]phenyl}-1,5-dimethyl-3-oxo-2-phenyl-2,3-dihydro-1H-pyrazole-4-carboxamide.

The prodrug for the compound of the formula (I) means a compound which is converted to the compound represented by the formula (I) by the reaction with an enzyme, a gastric acid, or the like, in the living body. Examples of the prodrug for the compound represented by the formula (I) include a compound wherein the amino group of the compound represented by the formula (I) is acylated, alkylated, phosphorylated, or the like (such as a compound wherein the amino group of the compound represented by the formula (I) is substituted with eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation, acetoxymethylation, tert-butylation, and the like); a compound wherein the hydroxy group of the compound represented by the formula (I) is acylated, alkylated, phosphorylated, borated, or the like (such as a compound wherein the hydroxy group of the compound represented by the formula (I) is modified by acetylation, palmitoylation, propanoylation, pivaloylation, succinylation, fumaration, alanylation, dimethylaminomethylcarbonylation, and the like); a compound wherein the carboxyl of the compound represented by the formula (I) is modified by esterification, amidation, or the like (such as a compound wherein the carboxyl of the compound represented by the formula (I) is esterified or amidated with ethyl ester, phenyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl)methyl ester, cyclohexyloxycarbonylethyl ester, methyl amide, and the like), and the like. These compounds may be prepared by a known method. In addition, the prodrug for the compound represented by the formula (I) may take a hydrate form or a non-hydrate form. In addition, the prodrug for the compound represented by the formula (I) may be a compound which is converted into the compound represented by the formula (I) under the physiological conditions as described in Pharmaceutical Research and Development, Vol. 7 "Molecular Design", pages 163-198 published in 1990 by Hirokawa Publishing Co. In addition, the compound represented by formula (I) may be labeled with an isotope (such as $^2$H, $^3$H, $^{11}$C, $^{13}$C, $^{14}$C, $^{13}$N, $^{15}$N, $^{15}$O, $^{17}$O, $^{18}$O, $^{35}$S, $^{18}$F, $^{36}$Cl, $^{123}$I, $^{125}$I, and the like.) and the like.

Unless otherwise specified, the compound of the present invention includes all isomers thereof. For example, alkyl, alkenyl, alkynyl, alkoxy, alkylthio, alkylene, alkenylene and alkynylene group means straight-chain or branched-chain ones. In addition, isomers on double bond, ring, fused ring (E-, Z-, cis-, trans-isomer), isomers generated from asymmetric carbon atom(s) (R-, S-isomer, α-, β-configuration, enantiomer, diastereomer), optically active isomers (D-, L-, d-, l-isomer), polar compounds generated by chromatographic separation (more polar compound, less polar compound), equilibrium compounds, rotational isomers, mixtures thereof at voluntary ratios and racemic mixtures are also included in the present invention. Further, isomers due to the tautomerism are all included in the present invention.

[Salt]

In the present invention, the compound represented by the formula (I) may form a salt thereof, and may be N-oxide form thereof or quaternary ammonium salt thereof. Furthermore, these compounds may be a solvate thereof. As salts, water-soluble salts with very low toxicity are preferred. Suitable pharmacologically acceptable salts of the compound represented by the formula (I) include, for example, salts of alkali metals (such as potassium, sodium, lithium, and the like); salts of alkaline earth metals (such as calcium, magnesium, and the like); ammonium salts (such as tetramethylammonium salts, tetrabutylammonium salts, and the like); salts of organic amines (such as triethylamine, methylamine, dimethylamine, cyclopentylamine, benzylamine, phenethylamine, piperidine, monoethanolamine, diethanolamine, tris(hydroxymethyl)methylamine, lysine, arginine, N-methyl-D-glucamine, and the like); and acid addition salts such as salts of inorganic acid (such as hydrochloride, hydrobromide, hydroiodide, sulfate, phosphate, nitrate, and the like), and salts of organic acid (such as acetate, trifluoroacetate, lactate, tartrate, oxalate, fumarate, maleate, benzoate, citrate, methansulfonate, ethansulfonate, benzenesulfonate, toluenesulfonate, isethionate, gulcuronate, gluconate, and the like), and the like. The N-oxide form of the compound represented by the formula (I) means the compound of which the nitrogen atom was oxidized. The quaternary ammonium salt of the compound represented by the formula (I) means the compound wherein the nitrogen atom is quaternized by $R^0$ ($R^0$ represents alkyl, alkenyl, or alkynyl (herein, which has the same meaning as described above) which each are optionally substituted, and cyclic ring (which has the same meaning as described above) which may have a substituent(s).) The quaternary ammonium salt of the compound represented by the formula (I) may additionally form the salt described above and the N-oxide form described above. The appropriate solvate of the compound represented by the formula (I), a salt thereof, an N-oxide form thereof, and a quaternary ammonium salt thereof, include water, alcohol solvate (such as ethanol) and the like. The solvates are preferably nontoxic and water-soluble. The compounds represented by the formula (I) can be converted into the salt described above, the N-oxide form described above thereof, or the solvates described above by conventional means.

[Process for Producing the Compounds of the Present Invention]

The compounds of the present invention as represented by the formula (I) can be produced, for example, in accordance with the below-described processes or processes similar thereto, or the processes to be described in examples. In the below-described production processes, the starting compounds may be used as a salt, wherein as such salts, there may be used the pharmaceutically allowable salts of the compound represented by the formula (I) to be described below.

In the Scheme A, Scheme B and Scheme C described below, "Suzuki coupling reaction" may be abbreviated as "Suzuki", X and $X^c$ each independently represents halogen, and $R^{101}$ represents C1-4 alkyl.

The compound represented by the formula (I) can be produced by the below shown Scheme A.

The compound of formula A-1 is subjected to an oxidation reaction to provide the compound of formula A-2. This oxidation reaction is a known method. It can be carried out, for example, in an organic solvent (such as, methanol, ethanol, tetrahydrofuran, dichloromethane, acetic acid and the like) using an oxidizing agent (such as, sodium chlorite, and the like) and an agent (such as monosodium phosphate) at the temperature of −78° C. to reflux temperature.

The compound of formula A-2 is subjected to an amidation with compounds of A-3 to provide the compound of formula A-4.

The method of amidation is known. It includes the method
(1) via an acyl halide,
(2) via a mixed acid anhydride,
(3) using a condensing agent.

These methods are explained as follows.

(1) The method via an acyl halide may be carried out, for example, by reacting carboxylic acid with an acyl halide (such as, oxalyl chloride, thionyl chloride and the like) in an organic solvent (such as, chloroform, methylene chloride, diethyl ether, tetrahydrofuran and the like) or without a solvent at −20° C. to reflux temperature. And then the obtained acyl halide derivative may be reacted with amine in an organic solvent (such as, chloroform, methylene chloride, diethyl ether, tetrahydrofuran and the like), in the presence of a base (such as, pyridine, triethyl amine, dimethyl aniline, dimethylaminopyridine, diisopropylethylamine and the like) at −20 to 40° C. As an alternative, the obtained acyl halide derivative may be reacted with amine in an organic solvent (such as, dioxane, tetrahydrofuran and the like) using an alkaline aqueous solution (such as, sodium bicarbonate, sodium hydroxide and the like) at 0 to 40° C.

(2) The method via a mixed acid anhydride may be carried out, for example, by reacting carboxylic acid with an acyl halide (such as, pivaloyl chloride, tosyl chloride, mesyl chloride and the like), or an acid derivative (such as, ethyl chloroformate, isobutyl chloroformate and the like) in an organic solvent (such as, chloroform, methylene chloride, diethyl ether, tetrahydrofuran and the like) or without a solvent, in the presence of a base (such as, pyridine, triethylamine, dimethylaniline, dimethylaminopyridine, diisopropylethylamine and the like), at 0 to 40° C. And then the obtained mixed acid anhydride derivative may be reacted with amine in an organic solvent (such as, chloroform, methylene chloride, diethyl ether, tetrahydrofuran and the like), at 0 to 40° C.

(3) The method using a condensing agent may be carried out, for example, by reacting carboxylic acid with amine in an organic solvent (such as, chloroform, methylene chloride, dimethylformamide, diethyl ether, tetrahydrofuran and the like) or without a solvent, in the presence or absence of a base (such as, pyridine, triethylamine, dimethylaniline, dimethylaminopyridine and the like), using a condensing agent (such as, 1,3-dicyclohexyl carbodiimide (DCC), 1-ethyl-3-[3-(dimethylamino)propyl]carbodiimide (EDC), 1,1'-carbodiimidazole (CDI), 2-chloro-1-methylpyridinium iodide, O-(7-azabenzotriazol-1-yl)-N,N,N',N'-tetramethyluronium hexafluorophosphate (HATU), 1-propanephosphonic acid cyclic anhydride and the like), in the presence or absence of 1-hydroxybenzothiazole (HOBt), at 0 to 40° C.

The reaction described in (1), (2) and (3) may be carried out under an inert gas (such as, argon, nitrogen) to avoid water in order to obtain a preferable result.

The compound of formula A-4 is subjected to a Suzuki coupling reaction with the compound of A-5 to provide the compound of formula A-6. This reaction is known method. It can be carried out, for example, in an organic solvent (such as, toluene, benzene, N,N-dimethylformamide (DMF), tetrahydrofuran, methanol, acetonitrile, dimethoxyethane, acetone and the like) and in the presence of a base (such as, sodium ethylate, sodium hydroxide, potassium hydroxide, triethylamine, sodium carbonate, sodium hydrogen carbonate, potassium carbonate, cesium carbonate, thallium carnonate, tripotassium phosphate, cesium fluoride, barium hydroxide, tetrabutylammonium fluoride and the like) under the presence of palladium catalyst (such as, tetrakis(triphenylphosphine)palladium (Pd(PPh$_3$)$_4$), (dichlorobis(triphenylphosphine)palladium (Cl$_2$Pd(PPh$_3$)$_2$), palladium acetate (Pd(OAc)$_2$) and the like) at the room temperature to 120° C.

The compound of formula A-6 is subjected to a Suzuki coupling reaction with the compound of A-7 to provide the compound of formula (I) as described above.

If the variable groups of the compounds described in the below scheme contain the protective groups, the deprotection reaction for the protective group can be performed as necessary. The deprotection reactions for the protective groups for carboxyl, hydroxyl, amino or thiol group are well known, and are exemplified by:

(1) Alkali hydrolysis,
(2) Deprotection reaction under acidic conditions,
(3) Deprotection reaction through hydrogenolysis,
(4) Deprotection reaction for a silyl group,
(5) Deprotection reaction with a metal, and
(6) Deprotection reaction with a metal complex.

Specific description of these reactions is to be made below.

(1) The deprotection reaction through alkali hydrolysis is carried out, for example, in an organic solvent (e.g., methanol, tetrahydrofuran, dioxane, etc.) with use of a hydroxide of an alkali metal (sodium hydroxide, potassium hydroxide, lithium hydroxide, etc.), a hydroxide of an alkaline earth metal (barium hydroxide, calcium hydroxide, etc.) or a carbonate (sodium carbonate, potassium carbonate, etc.), an aqueous solution thereof, or their mixtures at a temperature of about 0 to 40° C.

(2) The deprotection reaction under acidic conditions is conducted into practice, for example, in an organic solvent (e.g., dichloromethane, chloroform, dioxane, ethyl acetate, anisole, etc.) and in an organic acid (e.g., acetic acid, trifluoroacetic acid, methanesulfonic acid, p-tosyl acid, etc.), inorganic acid (e.g., hydrochloric acid, sulfuric acid, etc.) or their mixtures (hydrobromic acid/acetic acid, etc.) in the presence or absence of 2,2,2-trifluoroethanol at a temperature of about 0 to 100° C.

(3) The deprotection reaction through hydrogenolysis is carried out, for example, in a solvent (e.g., ether-based ones (e.g., tetrahydrofuran, dioxane, dimethoxyethane, diethyl ether, etc.), alcohol-based ones (e.g., methanol, ethanol, etc.), benzene-based ones (e.g., benzene, toluene, etc.), ketone-based ones (acetone, methyl ethyl ketone, etc.), nitrile-based ones (e.g., acetonitrile, etc.), amide-based ones (e.g., dimethylformamide, etc.), water, ethyl acetate, acetic acid or solvent mixtures of not less than two thereof, etc.) in the presence of a catalyst (e.g., palladium-carbon, palladium black, palladium hydroxide-carbon, platinum oxide, raney-nickel, etc.), under an atmosphere of hydrogen at atmospheric pressure or applied pressure, or in the presence of ammonium formate at a temperature of about 0 to 200° C.

(4) The deprotection reaction for a silyl group is conducted into practice, for example, in a water-miscible organic solvent (e.g., tetrahydrofuran, acetonitrile, etc.) with use of tetrabutylammonium fluoride at a temperature of about 0 to 40° C.

(5) The deprotection reaction with use of a metal is performed, for example, in an acidic solvent (e.g., acetic acid, a buffer of pH about 4.2 to 7.2 or mixed solutions thereof with organic solvents, such as tetrahydrofuran, etc.) in the presence of powdered zinc at a temperature of about 0 to 40° C., under application of ultrasonics, if necessary.

(6) The deprotection reaction with use of a metal complex is carried out, for example, in an organic solvent (e.g., dichloromethane, dimethylformamide, tetrahydrofuran, ethyl acetate, acetonitrile, dioxane, ethanol, etc.), water or solvent mixtures thereof in the presence of a trap reagent (tributyltin hydride, triethylsilane, dimedone, morpholine, diethylamine, pyrrolidine, etc.), organic acid (e.g., acetic acid, formic acid, 2-ethylhexanoic acid, etc.) and/or organic acid salt (sodium 2-ethylhexanoate, potassium 2-ethylhexanoate, etc.), in the presence or absence of a phosphine-based reagent (e.g., triphenylphosphine, etc.), at a temperature of about 0 to 40° C., while using a metal complex (e.g., tetrakis-triphenylphosphine palladium (0), palladium (II) bis(triphenylphosphine) dichloride, palladium (II) acetate, rhodium (I) tris(triphenylphosphine) chloride, etc.).

In addition to the above-described procedures, the deprotection reaction can be carried out, for example, by the methods described in T. W. Greene, Protective Groups in Organic synthesis, Wiley, New York, 1999.

The protective groups for carboxyl group may be exemplified by a methyl, ethyl, allyl, t-butyl, trichloroethyl, benzyl (Bn), phenacyl, methoxybenzyl, trityl or 2-chlorotrityl group, or solid-phase carriers having these chemical structures bonded thereto.

The protecting groups for hydroxyl group include, for example, a methyl, trityl, methoxymethyl (MOM), 1-ethoxyethyl (EE), methoxyethoxymethyl (MEM), 2-tetrahydropyranyl (THP), trimethylsilyl (TMS), triethylsilyl (TES), t-butyldimethylsilyl (TBDPS), t-butyldiphenylsilyl (TBDPS), acetyl (Ac), pivaloyl, benzoyl, benzyl (Bn), methoxybenzyl, allyloxycarbonyl (Alloc) or 2,2,2-trichloroethoxycarbonyl (Troc) group, and the like.

As the protective groups for amino group, there may be mentioned, for example, a benzyloxycarbonyl, t-butoxycarbonyl (Boc), allyloxycarbonyl (Alloc), 1-methyl-1-(4-biphenyl)-ethoxycarbonyl (Bpoc), trifluoroacetyl, 9-fluorenylmethoxy-carbonyl, benzyl (Bn), methoxybenzyl, benzyloxymethyl (BOM) or 2-(trimethylsilyl)ethoxymethyl (SEM) group, etc.

The protective groups for thiol group may be exemplified by a benzyl (bn), methoxybenzyl, methoxymethyl (MOM), 2-tetrahydropyranyl (THP), diphenylmethyl or acetyl group, etc.

The protective groups for carboxyl, hydroxyl, amino or thiol group are not limited particularly to the above-mentioned ones, only if they are easily and selectively removable. For example, use may be made of those described in T. W. Greene, Protective Groups in Organic Synthesis, Wiley, New York, 1999.

As may be easily understandable by an ordinarily skilled person, proper use of these deprotection reactions can facilitate the objective compounds of the present invention to be produced.

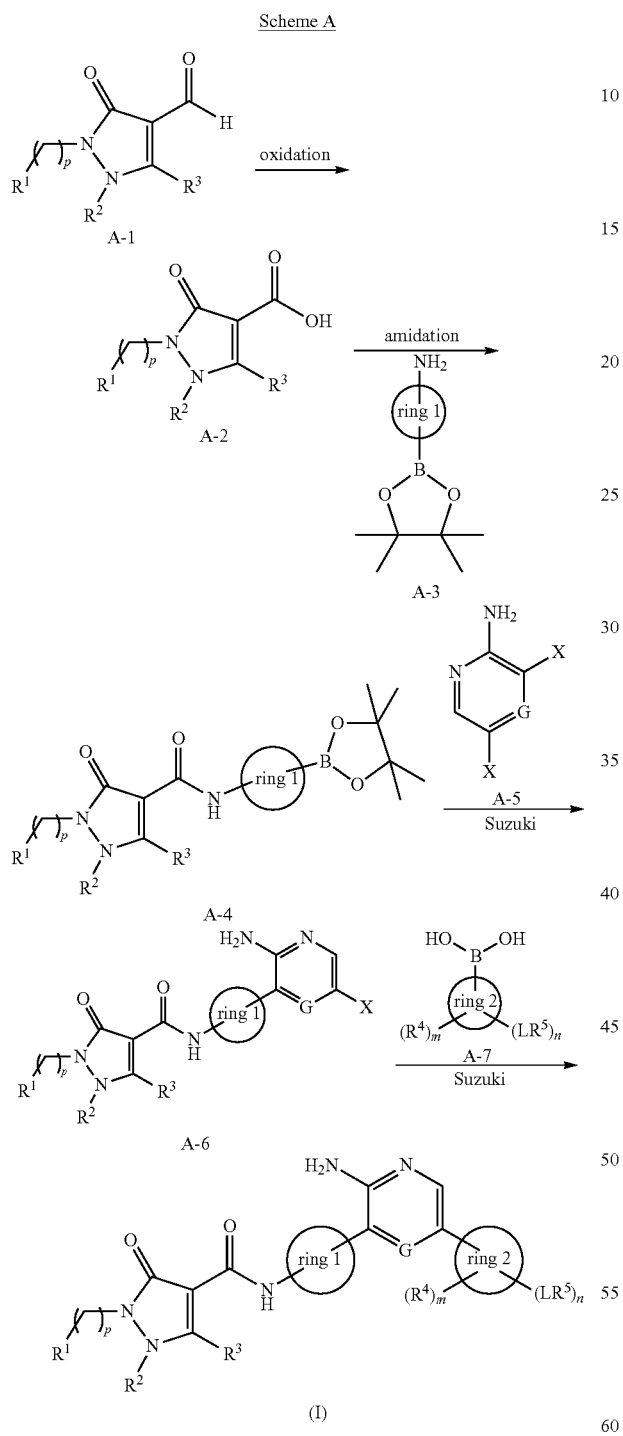

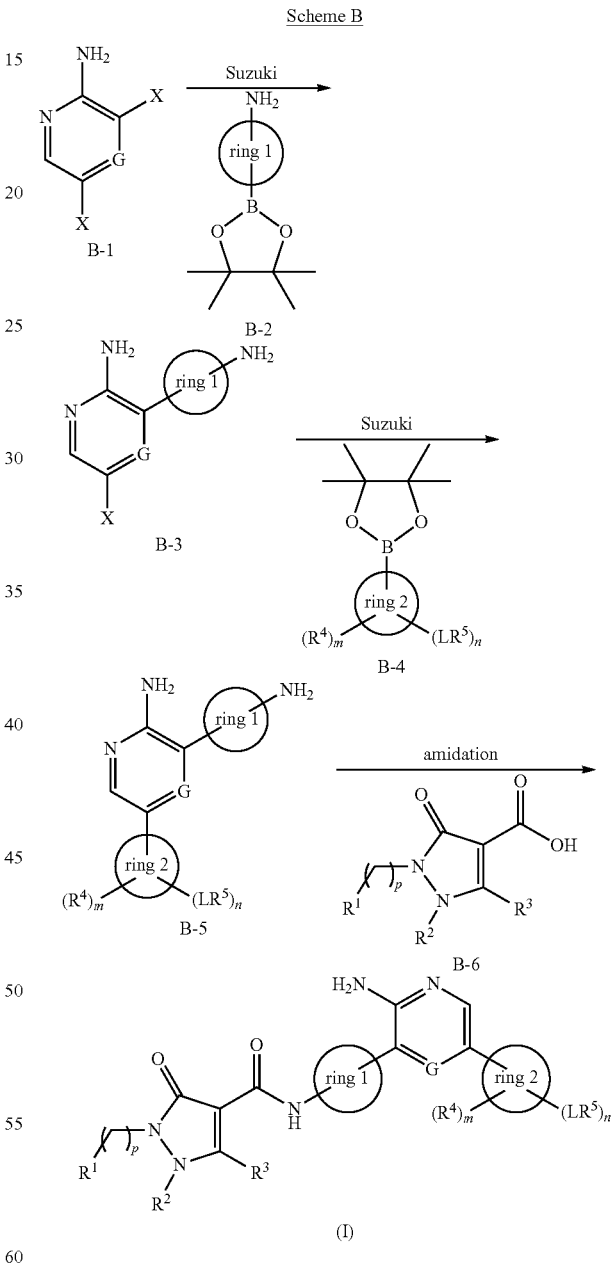

The compounds represented by the formula (I) can be also produced by the below shown Scheme B.

The compound of formula B-1 is subjected to a Suzuki coupling reaction with compounds of formula B-2 to provide the compound of formula B-3 as described above.

The compound of formula B-3 is subjected to a Suzuki coupling reaction with compounds of formula B-4 to provide the compound of formula B-5 as described above.

The compound of formula B-5 is subjected to an amidation with compounds of B-6 to provide the compound of formula (I) as described above.

If the variable groups of the compounds described in the below scheme contain the protective groups, the deprotection reaction for the protective group can be performed as necessary.

The compound represented by the formula A-1 in Scheme A can be produced by the below shown Scheme C.

The compound of formula C-1 is subjected to a condensation reaction with compounds of C-2 to provide the compound of formula C-3. This condensation reaction is a known method. It can be carried out, for example, in an organic solvent (such as, methanol, ethanol, acetic acid and the like) at the temperature of −78° C. to reflux temperature.

The compound of formula C-3 is subjected to an addition reaction with compounds of C-4 to provide the compound of formula C-5. This addition reaction is a known method. It can be carried out, for example, in an organic solvent (such as, acetonitrile and the like) at the temperature of −78° C. to reflux temperature.

The compound of formula C-5 is subjected to a formylation reaction to provide the compound of formula A-1. This formylation reaction is a known method. It can be carried out, for example, in an organic solvent (such as, DMF and the like) using formylation agent (such as, phosphorous oxychloride and the like) at the temperature of −78° C. to reflux temperature.

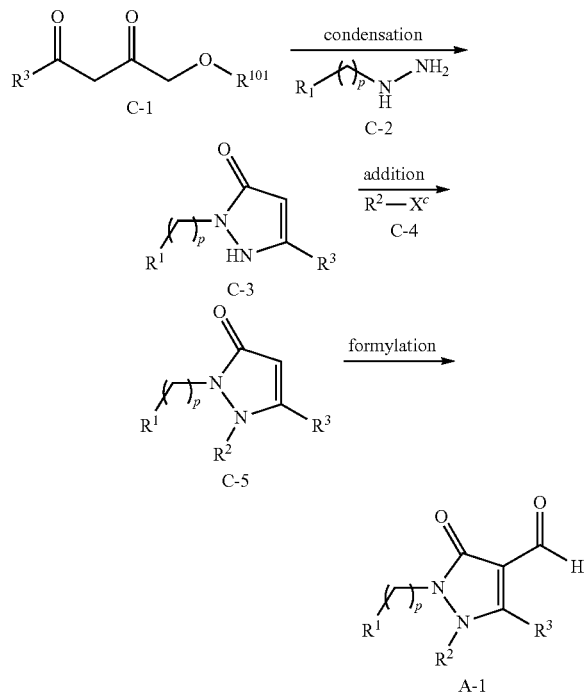

The above-mentioned compounds represented by the formulae A-3, A-5, A-7, B-1, B-2, B-4, B-6, C-1 and C-2 which are usable as a starting compound in the above all the scheme are conventionally known or can be easily produced by utilizing the conventionally known methods, such as the procedures as described in "Comprehensive Organic Transformations: A Guide to Functional Group Preparations, $2^{nd}$ Edition (Richard C. Larock, John Wiley & Sons Inc., 1999)".

Among the compounds of the present invention as represented by the formula (I), any compounds other than the above-indicated compounds can be produced by utilizing in combination the procedures or methods as described in Examples to be given in the present specification or the conventionally known methods, such as those described in "Comprehensive Organic Transformations: A Guide to Functional Group Preparations, $2^{nd}$ Edition (Richard C. Larock, John Wiley & Sons inc., 1999).

In the respective reactions described in the present specification, any reactions being accompanied by heating can be carried out with use of a water bath, oil bath, sand bath or microwave, as may be self-evident to an ordinarily skilled person.

In the respective reactions described in the present specification, appropriate use may be made of solid-phase supported reagents having chemicals supported on high molecular polymers (e.g., polystyrene, polyacrylamide, polypropylene, polyethylene glycol, etc.).

In the respective reactions described in the present specification, the reaction products can be purified by ordinarily employed purification means, such as distillation under atmospheric pressure or reduced pressure, high-performance liquid chromatography using silica gel or magnesium silicate, thin-layer chromatography, ion exchange resins, scavenger resins or column chromatography, or such techniques as washing, recrystallization, etc. Purification may be performed in the reaction-by-reaction manner or after completion of several reactions.

[Toxicity]

The toxicity of the compounds of present invention is very low, and thus it is considered that the compounds are sufficiently safe to be used as a pharmaceutical agent.

[Application to Pharmaceutical Agent]

The compounds of the present invention can be used for a preventive and/or therapeutic agent of Itk related diseases, for example, respiratory disease, allergic disease, autoimmune disease, inflammatory disease, cancer, transplant rejection, graft versus host disease, HIV infection, aplastic anemia, pain and so on.

In the present invention, respiratory disease includes, for example, asthma, chronic obstructive pulmonary disease (COPD), and bronchitis, In the present invention, allergic disease includes, for example, allergies, anaphylaxis, allergic conjunctivitis, allergic rhinitis, and atopic dermatitis.

In the present invention, autoimmune disease includes, for example, inflammatory bowel disease, arthritis, lupus, rheumatoid arthritis, psoriatic arthritis, osteoarthritis, Still's disease, juvenile arthritis, type I diabetes, myasthenia gravis, Hashimoto's thyroiditis, Ord's thyroiditis, Grave's disease, Sjögren's syndrome, multiple sclerosis, Guillain-Barré syndrome, acute disseminated encephalomyelitis, Addison's disease, opsoclonus-myoclonus syndrome, ankylosing spondylitis, antiphospholipid antibody syndrome, aplastic anemia, autoimmune hepatitis, celiac disease, Goodpasture's syndrome, idiopathic thrombocytopenic purpura, optic neuritis, scleroderma, primary biliary cirrhosis, Reiter's disease, Takayasu's arteritis, temporal arteritis, warm autoimmune hemolytic anemia, Wegener's granulomatosis, psoriasis, alopecia universalis, Behçet's disease, chronic fatigue, dysautonomia, endometriosis, interstitial cystitis, neuromyotonia, vulvodynia, systemic lupus erythematosus, and T cell mediated hypersensitivities.

In the present invention, inflammatory disease includes, for example, appendicitis, blepharitis, bronchitis, bursitis, cervicitis, cholangitis, cholecystitis, colitis, conjunctivitis, contact dermatitis, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, hepatitis, hidradenitis suppurativa, laryngitis, mastitis, meningitis, myelitis, myocarditis, myositis, nephritis, oophoritis, orchitis, osteitis, pancreatitis, parotitis, pericarditis, peritonitis, pharyngitis, pleuritis, phlebitis, pneumonitis, pneumonia, proctitis, prostatitis, pyelonephritis, rhinitis, salpingitis, sinusitis, stomatitis, synovitis, tendonitis, tonsillitis, uveitis, vaginitis, vasculitis, and vulvitis.

In the present invention, inflammatory bowel disease includes ulcerative colitis, and Crohn's disease.

In the present invention, cancer includes T-cell and natural killer (NK)-cell neoplasm, for example, T-cell prolymphocytic leukemia, T-cell large granular lymphocytic leukemia, chronic lymphoproliferative disorder of NK-cells, aggressive NK-cell leukemia, systemic EBV$^+$ T-cell lymphoproliferative disease of childhood, hydroa vacciniforme-like lymphoma, adult T-cell leukemia/lymphoma, extranodal NK/T-cell lymphoma (nasal type), enteropathy-associated T-cell lymphoma, hepatosplenic T-cell lymphoma, subcutaneous panniculitis-like T-cell lymphoma, mycosis fungoides, Sézary syndrome, primary cutaneous CD30$^+$ T-cell lymphoproliferative disorder, primary cutaneous aggressive epidermotropic CD8$^+$ cytotoxic T-cell lymphoma, primary cutaneous gamma-delta T-cell lymphoma, primary cutaneous small/medium CD4$^+$ T-cell lymphoma, peripheral T-cell lymphoma (not otherwise specified), angioimmunoblastic T-cell lymphoma, anaplastic large cell lymphoma (ALK$^+$), anaplastic large cell lymphoma (ALK$^-$).

The compounds of the present invention may be administered as a combination preparation by combining with other pharmaceuticals for the purpose of;

1) supplementing and/or enhancing the preventive and/or treatment effect of the compounds of the present invention, 2) improving pharmacokinetics and absorption of the compound, and reducing the dose of the compounds of the present invention, and/or 3) reducing side effect of the compounds of the present invention.

The combination preparations of the compounds of the present invention and a concomitant drug(s) may be administered as one combination preparation comprising these components, or may be administered separately. When they are administered separately as independent preparations, they may be administered simultaneously or with time lag. Administration with time lag includes the method of administering the compounds of the present invention before other drugs and vice versa, and each administration route may be the same or different. There is no limitation on a disease on which the combination preparations of the compounds of the present invention and a concomitant drug(s) have preventive and/or treatment effects, so long as the preventive and/or treatment effect of the combination preparation is supplemented and/or enhanced in the disease. There is no limitation on the weight ratio between the compounds of the present invention and the concomitant drug(s) in a combined preparation by combining the compounds of the present invention with the concomitant drug(s).

Furthermore, the concomitant drug(s) is not limited to a low molecular weight compound, and may be a macromolecule protein, polypeptide, polynucleotide (such as DNA, RNA, gene, and the like), antisense, decoy, antibody, vaccine, and the like. The dosage of the concomitant drug(s) can be properly selected according to the clinical dosage. The compounding ratio of the compounds of the present invention and the concomitant drug(s) can be properly selected by the age and body weight of the object, administration route, administration term, target disease, symptom, combination, and the like. For example, the amount of the concomitant drug(s) may be used 0.01 parts by weight to 100 parts by weight relative to 1 part by weight of the compounds of the present invention.

The concomitant drug(s) may be administrated in the proper combination of arbitrary one or two or more member(s) selected from the same or different groups in arbitrary proportion.

The concomitant drug(s) for supplementation and/or enhancement of the preventive and/or therapeutic effect of the compounds of the present invention includes not only those which have so far been found but also those which will be found on the basis of the aforementioned mechanism. The concomitant drug(s) which can be used in combination with the compounds of the present invention include, for example, those given below.

Examples of the concomitant drug(s) for supplementing and/or enhancing the preventive and/or therapeutic effect for allergic disease of the compounds of the present invention include, for example, an anti-histaminic drug, an anti-leukotriene drug, an anti-allergic drug, a thromboxane A2 receptor antagonist, a thromboxane synthetase inhibitor, a steroid, and the like.

Examples of the concomitant drug(s) for supplementing and/or enhancing the preventive and/or therapeutic effect for autoimmune disease of the compounds of the present invention include, for example, an immunosuppressant, a steroid, a disease modifying anti-rheumatic drug, an elastase inhibitor, a cannabinoid-2 receptor stimulator, a prostaglandin, a prostaglandin synthase inhibitor, a phosphodiesterase inhibitor, a metalloproteinase inhibitor, an adhesion molecule inhibitor, an anti-cytokine protein preparation such as an anti-TNF-α preparation, an anti-IL-1 preparation, an anti-IL-6 preparation, a cytokine inhibitor, a non-steroidal antiinflammatory drug, and the like.

Examples of concomitant drug(s) for supplementing and/or enhancing the preventive and/or therapeutic effect for inflammatory disease of the compounds of the present invention include, for example, a steroid, an elastase inhibitor, a cannabinoid-2 receptor stimulator, a prostaglandin, a prostaglandin synthase inhibitor, a phosphodiesterase inhibitor, a metalloproteinase inhibitor, an adhesion molecule inhibitor, anti-leukotriene drug, an anticholinergic drug, a thromboxane A2 receptor antagonist, a thromboxane synthetase inhibitor, β2-adrenaline receptor stimulator, a xanthine derivative, an expectorant, an antibacterial drug, an anti-histaminic drug, an anti-cytokine protein preparation, a cytokine inhibitor, a forskolin preparation, a mediator release inhibitor, a non-steroidal antiinflammatory drug, and the like.

Examples of concomitant drug(s) for supplementing and/or enhancing the preventive and/or therapeutic effect for T-cell and NK-cell neoplasms of the compounds of the present invention include, for example, an alkylating drug, an anti-metabolite, an antibiotics, a vegetable alkaloid drug, hormonal drug, a platinum-containing drug, HDAC inhibitor, other anti-cancer drugs, and the like.

Examples of the anti-histaminic drug(s) include, for example, azelastine hydrochloride, ebastine, epinastine hydrochloride, emedastine difumarate, auranofin, oxatomide, olopatadine hydrochloride, d-chlorpheniramine maleate, clemastine fumarate, ketotifen fumarate, cimetidine, dimenhydrinate, diphenhydramine hydrochloride, cyproheptadine hydrochloride, cetirizine hydrochloride, desloratadine, terfenadine, famotidine, fexofenadine, fexofenadine hydrochloride, bepotastine, bepotastine besilate, mizolastine, mequitazine, mometasone furoate, ranitidine, ranitidine hydrochloride, loratadine, promethazine hydrochloride, homochlorcyclizine hydrochloride, and the like.

Examples of the anti-leukotriene drug(s) include, for example, pranlukast hydrate, montelukast sodium, zafirlukast, ablukast, pobilukast, sulukast, iralukast sodium, verlukast, ritolukast, cinalukast, pirodomast, tomelukast, doqualast, and the like.

Examples of the anti-allergic drug(s) include, for example, amlexanox, azelastine hydrochloride, israpafant, ibudilast, imitrodast sodium, ebastine, epinastine hydrochloride, emedastine difumarate, oxatomide, ozagrel hydrochloride, olopatadine hydrochloride, cromoglicate, sodium cromoglicate, ketotifen fumarate, seratrodast, cetirizine hydrochloride, suplatast tosilate, tazanolast, terfenadine, domitroban calcium hydrate, tranilast, nedocromil, fexofenadine, fexofenadine hydrochloride, pemirolast potassium, mequitazine, ramatroban, repirinast, loratadine, and the like.

Examples of the thromboxane A2 receptor antagonist include, for example, seratrodast, domitroban calcium hydrate, ramatroban, and the like.

Examples of the thromboxane synthetase inhibitor include, for example, imitrodast sodium, ozagrel hydrochloride, and the like.

Examples of the steroid include, for example, amcinonide, hydrocortisone sodium succinate, prednisolone sodium succinate, methylprednisolone sodium succinate, ciclesonide, difluprednate, betamethasone dipropionate, dexamethasone, deflazacort, triamcinolone, triamcinolone acetonide, halcinonide, dexamethasone palmitate, hydrocortisone, flumetasone pivalate, prednisolone butylacetate, budesonide, prasterone sulfonate, mometasone furoate, fluocinonide, fluocinolone acetonide, fludroxycortide, flunisolide, prednisolone, alclometasonedi propionate, clobetasol propionate, dexamethasone propionate, deprodone propionate, fluticasone propionate, beclometasone dipropionate, betamethasone, methylprednisolone, methylprednisolone suleptanate, methylprednisolone sodium succinate, mometasone furoate, dexamethasone sodium phosphate, hydrocortisone sodium phosphate, prednisolone sodium phosphate, diflucortolone valerate, dexamethasone valerate, betamethasone valerate, prednisolone valerate-acetate, cortisone acetate, diflorasone diacetate, dexamethasone acetate, triamcinolone acetate, paramethason acetate, halopredone acetate, fludrocortisone acetate, prednisolone acetate, methylprednisolone acetate, hydrocortisone butyrate, hydrocortisone butyrate propionate, betamethasone butyrate propionate, and the like.

Examples of the immunosuppressant include, for example, azathioprine, ascomycin, everolimus, salazosulfapyridine, cyclosporine, cyclophosphamide, sirolimus, tacrolimus, bucillamine, methotrexate, leflunomide, and the like.

Examples of the disease modifying anti-rheumatic drug include, for example, D-penicillamine, actarit, auranofin, salazosulfapyridine, hydroxychloroquine, bucillamine, methotrexate, leflunomide, lobenzarit disodium, aurothioglucose, sodium aurothio malate, and the like.

Examples of the elastase inhibitor include, for example, ONO-5046, ONO-6818, MR-889, PBI-1101, EPI-HNE-4, R-665, ZD-0892, ZD-8321, GW-311616, DMP-777, L-659286, L-658758, L-680833, L-683845, AE-3763, and the like.

Examples of the prostaglandin (hereinafter, abbreviated as PG) include, for example, PG receptor agonists, PG receptor antagonists, and the like.

Examples of the PG receptor include PGE receptors ($EP_1$, $EP_2$, $EP_3$ and $EP_4$), PGD receptors (DP, CRTH2), PGF receptors (FP), PGI receptors (IP), TX receptors (TP), and the like.

Examples of the prostaglandin synthase inhibitor include, for example, alazosulfapyridine, mesalazine, olsalazine, 4-aminosalicylic acid, JTE-522, auranofin, carprofen, diphenpyramide, flunoxaprofen, flurbiprofen, indometacin, ketoprofen, lornoxicam, loxoprofen, meloxicam, oxaprozin, parsalmide, piproxen, piroxicam, piroxicam betadex, piroxicam cinnamate, tropineindometacinate, zaltoprofen, pranoprofen, and the like.

Examples of the phosphodiesterase include, for example, PDE4 inhibitors such as rolipram, cilomilast (trade name: Ariflo), Bay19-8004, NIK-616, roflumilast (BY-217), cipamfylline (BRL-61063), atizoram (CP-80633), SCH-351591, YM-976, V-11294A, PD-168787, D-4396, IC-485, PDE5 inhibitors such as sildenafil, and the like.

Examples of the adhesion molecule inhibitor include, for example, α4 integrin antagonist, and the like.

Examples of the anti-TNF-α preparation include antibody against TNF-α, soluble TNF-α receptor, antibody against TNF-α receptor, soluble TNF-α receptor binding protein, and specifically, infliximab, etanercept, and the like.

Examples of the anti-IL-1 preparation include antibody against IL-1, soluble IL-1 receptor, antibody against IL-1Ra and/or IL-1 receptors, and specifically, for example, anakinra, and the like.

Examples of the anti-IL-6 preparation include antibody against IL-6, soluble IL-6 receptor, antibody against IL-6 receptor, and for example, tocilizumab, and the like.

Examples of the cytokine inhibitor include suplatast tosylate (trade name: IPD), T-614, SR-31747, sonatimod, and the like.

Examples of the steroidal agent include clobetasol propionate, diflorasone diacetate, fluocinonide, mometasone furoate, betamethasone dipropionate, betamethasone butyrate propionate, betamethasone valerate, difluprednate, diflucortolone valerate, amcinonide, halcinonide, dexamethasone, dexamethasone propionate, dexamethasone valerate, dexamethasone acetate, hydrocortisone acetate, hydrocortisone butyrate, hydrocortisone butyrate propionate, deprodone propionate, prednisolone valerate-acetate, fluocinolone acetonide, beclometasone dipropionate, triamcinolone acetonide, flumetasone pivalate, alclometasone dipropionate, clobetasone butyrate, prednisolone, fludroxycortide, cortisone acetate, hydrocortisone, hydrocortisone sodium phosphate, hydrocortisone sodium succinate, fludrocortisone acetate, prednisolone acetate, prednisolone sodium succinate, prednisolone butylacetate, prednisolone sodium phosphate, halopredone acetate, methylprednisolone, methylprednisolone acetate, methylprednisolone sodium succinate, triamcinolone, triamcinolone acetate, dexamethasone sodium phosphate, dexamethasone palmitate, paramethasone acetate, betamethasone, fluticasone propionate, budesonide, flunisolide, ST-126P, ciclesonide, dexamethasone palomithionate, mometasone furoate, prasterone sulfonate, deflazacort, methylprednisolone suleptanate, methylprednisolone sodium succinate, and the like.

Examples of the anticholinergic drug include, for example, trihexyphenidyl, trihexyphenidyl hydrochloride, biperiden, biperiden hydrochloride, and the like.

Examples of the β2 adrenaline receptor stimulator include, for example, fenoterol hydrobromide, salbutamol sulfate, terbutaline sulfate, formoterol fumarate, salmeterol xinafoate, isoproterenol sulfate, orciprenaline sulfate, clorprenaline sulfate, epinephrine, trimetoquinol hydrochloride, hexoprenalinemesyl sulfate, procaterol hydrochloride, tulobuterol hydrochloride, tulobuterol, pirbuterol hydrochloride, clenbuterol hydrochloride, mabuterol hydrochloride, ritodrine hydrochloride, bambuterol, dopexamine hydrochloride, meluadrine tartrate, AR-C68397, levosalbutamol, formoterol, KUR-1246, KUL-7211, AR-C89855, S-1319, and the like.

Examples of the xanthine derivative include, for example, aminophylline, theophylline, doxofylline, sipamphylline, diprophylline, and the like.

Examples of the expectorant agent include foeniculated ammonia spirit, sodium hydrogen carbonate, bromhexine hydrochloride, carbocysteine, ambroxol hydrochloride, ambroxol hydrochloride sustained preparation, methylcysteine hydrochloride, acetylcysteine, ethyl L-cysteine hydrochloride, tyloxapol, and the like.

Examples of the antibacterial drug include sodium cefuroxime, meropenem trihydrate, netilmicin sulfate, sisomicin sulfate, ceftibuten, PA-1806, IB-367, tobramycin, PA-1420, doxorubicin, astromicin sulfate, cefetamet pivoxil hydrochloride, and the like.

Examples of the mediator release inhibitor include tranilast, sodium cromoglicate, amlexanox, repirinast, ibudilast, dazanolast, pemirolast potassium, and the like.

Examples of the alkylating drug include, for example, nitrogen mustard N-oxide hydrochloride, cyclophosphamide, ifosfamide, melphalan, thiotepa, carboquone, busulfan, nimustine hydroxychloride, dacarbazine, ranimustine, and the like.

Examples of the anti-metabolite include, for example, methotrexate, pralatrexate, mercaptopurine, 6-mercaptopurine riboside, fluorouracil, tegafur, tegafur/uracil, carmofur, doxifluridine, cytarabine, enocitabine, tegafur/gimestat/otastat, gemcitabine hydrochloride, cytarabine ocfosfate, procarbazine hydrochloride, hydroxycarbamide, and the like.

Examples of the antibiotics include, for example, actinomycin D, mitomycin C, daunorubicin hydrochloride, doxorubicin hydrochloride, aclarubicin hydrochloride, neocarzinostatin, pirarubicin hydrochloride, epirubicin hydrochloride, idarubicin hydrochloride, chromomycin A3, bleomycin hydrochloride, peplomycin sulfate, therarubicin, zinostatin stimalamer, and the like.

Examples of the vegetable alkaloid drug include, for example, vinblastine sulfate, vincristine sulfate, vindesine sulfate, irinotecan hydrochloride, etoposide, flutamide, vinorelbine ditartrate, docetaxel hydrate, paclitaxel, and the like.

Examples of the hormonal drug include, for example, estramustine phosphate sodium, mepitiostane, epitiostanol, goserelin acetate, fosfestrol (diethylstilbestrol phosphate), tamoxifen citrate, toremifene citrate, fadrozole hydrochloride hydrate, medroxyprogesterone acetate, bicalutamide, leuprorelin acetate, anastrozole, exemestane, and the like.

Examples of the platinum-containing drug include, for example, carboplatin, cisplatin, nedaplatin, and the like.

Examples of the HDAC inhibitor include, for example, vorinostat, belinostat, and the like.

Examples of the other anti-cancer drugs include, for example, L-asparaginase, octreotide acetate, porfimer sodium, mitoxantrone hydrochloride, mogamulizumab, denileukin diftitox, bexarotene, and the like.

In order to use the compounds of the present invention, or the compounds of the present invention in combination with the other pharmaceutical preparations by the above described purpose, these compounds are normally administered systemically or topically, and orally or parenterally.

The dose of the compounds of the present invention depends on age, body weight, symptom, therapeutic effect, administration method, treatment period and so on. In practice, however, these compounds are administered orally once or several times per day each in an amount of from 100 μg to 1000 mg per adult, parentally once or several times per day each in an amount of from 50 μg to 500 mg per adult or continuously administered into vein for 1 hour to 24 hours per day.

The dose of these compounds may be less than the above described dose or may need to exceed the above described range because the dose varies under various conditions as above described.

When the compounds of the present invention, or the compounds of the present invention are administered in combination with the other pharmaceutical preparations, they are used in the form of solid or liquid agent for oral administration, injection, agent for external application, suppository, eye drops or inhalant for parenteral administration, and the like.

Examples of the solid agent for oral administration include tablet, pill, capsule, powder, and pellet. Examples of the capsule include hard capsule, and soft capsule.

In such a solid agent for internal application, one or more active materials are used in the form of preparation produced by an ordinary method singly or in admixture with a vehicle (such as lactose, mannitol, glucose, microcrystalline cellulose, starch, and the like), binder (such as hydroxypropyl cellulose, polyvinyl pyrrolidone, magnesium metasilicoaluminate, and the like), disintegrant (such as calcium fibrinoglycolate and the like), glidant (such as magnesium stearate and the like), stabilizer, dissolution aid (such as glutamic acid, aspartic acid and the like) or the like. The solid agent may be coated with a coating agent (such as white sugar, gelatin, hydroxypropyl cellulose, hydroxypropyl methyl cellulose phthalate, and the like) or two or more layers. Alternatively, the solid agent may be capsulized by an absorbable material such as gelatin.

Examples of the liquid agent for oral administration include pharmaceutically acceptable aqueous solution, suspension, emulsion, syrup, and elixir. In such a liquid agent, one or more active agents are dissolved, suspended or emulsified in a commonly used diluent (such as purified water, ethanol, mixture thereof and the like). Furthermore, such a liquid agent may comprise a wetting agent, a suspending agent, an emulsifier, a sweetening agent, a flavor, a fragrance, a preservative, a buffer, and the like.

The agent for parenteral administration may be in the form of, such as ointment, gel, cream, wet compress, paste, liniment, nebula, inhalant, spray, aerosol, eye drops, collunarium, and the like. These agents each contain one or more active materials and are prepared by any known method or commonly used formulation.

The ointment is prepared by any known or commonly used formulation. For example, one or more active materials are triturated or dissolved in a base to prepare such an ointment. The ointment base is selected from known or commonly used materials. In some detail, higher aliphatic acid or higher aliphatic acid ester (such as adipic acid, myristic acid, palmitic acid, stearic acid, oleic acid, adipic acid ester, myristic acid ester, palmitic acid ester, stearic acid ester, oleic acid ester, and the like), wax (such as beeswax, whale wax, ceresin, and the like), surface active agent (such as polyoxyethylenealkylether phosphoric acid ester, and the like), higher alcohol (such as cetanol, stearyl alcohol, setostearyl alcohol, and the like), silicon oil (such as dimethyl polysiloxane and the like), hydrocarbon (such as hydrophilic petrolatum, white petrolatum, purified lanolin, liquid paraffin, and the like), glycol (such as ethylene glycol, diethylene glycol, propylene glycol, polyethylene glycol, macrogol, and the like), vegetable oil (such as castor oil, olive oil, sesame oil, turpentine oil, and the like), animal oil (such as mink oil, vitelline oil, squalane, squalene, and the like), water, absorption accelerator and rash preventive may be used singly or in admixture of two or more thereof. The base may further comprise a humectant, a preservative, a stabilizer, an antioxidant, a perfume, and the like.

The gel is prepared by any known or commonly used formulation. For example, one or more active materials are dissolved in a base to prepare such a gel. The gel base is selected from known or commonly used materials. For example, lower alcohol (such as ethanol, isopropyl alcohol and the like), gelling agent (such as carboxymethyl cellulose, hydroxyethyl cellulose, hydroxypropyl cellulose, ethyl cellulose, and the like), neutralizing agent (such as triethanolamine, diisopropanolamine and the like), surface active agent (such as polyethylene glycol monostearate and the like), gums, water, absorption accelerator, and rash preventive are used singly or in admixture of two or more thereof. The gel base may further comprise a preservative, an antioxidant, a perfume, and the like.

The cream is prepared by any known or commonly used formulation. For example, one or more active materials are dissolved in a base to prepare such a cream. The cream base is selected from known or commonly used materials. For example, higher aliphatic acid ester, lower alcohol, hydrocarbon, polyvalent alcohol (such as propylene glycol, 1,3-butylene glycol and the like), higher alcohol (such as 2-hexyl decanol, cetanol and the like), emulsifier (such as polyoxyethylene alkyl ethers, aliphatic acid esters and the like), water, absorption accelerator, and rash preventive are used singly or in admixture of two or more thereof. The cream base may further comprise a preservative, an antioxidant, a perfume, and the like.

The wet compress is prepared by any known or commonly used formulation. For example, one or more active materials are dissolved in a base to prepare a kneaded mixture which is then spread over a support to prepare such a wet compress. The wet compress base is selected from known or commonly used materials. For example, thickening agent (such as polyacrylic acid, polyvinyl pyrrolidone, gum arabic, starch, gelatin, methyl cellulose, and the like), wetting agent (such as urea, glycerin, propylene glycol and the like), filler (such as kaolin, zinc oxide, talc, calcium, magnesium, and the like), water, dissolution aid, tackifier, and rash preventive may be used singly or in admixture of two or more thereof. The wet compress base may further comprise a preservative, an antioxidant, a perfume, and the like.

The pasting agent is prepared by any known or commonly used formulation. For example, one or more active materials are dissolved in a base to prepare a kneaded mixture which is then spread over a support to prepare such a pasting agent. The pasting agent base is selected from known or commonly used materials. For example, polymer base, fat and oil, higher aliphatic acid, tackifier and rash preventive may be used singly or in admixture of two or more thereof. The pasting agent base may further comprise a preservative, an antioxidant, a perfume, and the like.

The liniment is prepared by any known or commonly used formulation. For example, one or more active materials are dissolved, suspended or emulsified in water, alcohol (such as ethanol, polyethylene glycol and the like), higher aliphatic acid, glycerin, soap, emulsifier, suspending agent, and the like, singly or in combination of two or more thereof, to prepare such a liniment. The liniment may further comprise a preservative, an antioxidant, a perfume, and the like The nebulizer, inhalant, spray and aerosol each may comprise a commonly used diluent, additionally, a stabilizer such as sodium hydrogen sulfite and a buffer capable of providing isotonicity such as isotonic agent (such as sodium chloride, sodium citrate, citric acid, and the like).

The injection for parenteral administration consists of solid injection which is dissolved or suspended in the form of solution, suspension, emulsion and a solvent to be dissolved before use. The injection is prepared by dissolving, suspending or emulsifying one or more active materials in a solvent. As such a solvent, distilled water for injection, physiological saline, vegetable oil, alcohol such as propylene glycol, polyethylene glycol and ethanol, and the like, singly or in combination thereof is used. The injection may further comprise a stabilizer, a dissolution aid (such as glutamic acid, aspartic acid, Polysolvate 80 (trade name), and the like), a suspending agent, an emulsifier, a soothing agent, a buffer, a preservative, and the like. The injection is sterilized at the final step or prepared by an aseptic process. Alternatively, an aseptic solid agent such as freeze-dried product which has previously been prepared may be rendered aseptic or dissolved in aseptic distilled water for injection or other solvents before use.

The eye drops for parenteral administration consist of eye drop, suspension eye drop, emulsion eye drop, eye drop to be dissolved before use and ointment and the like.

These eye drops are prepared by a known method. For example, it is prepared by dissolving, suspending or emulsifying one or more active materials in a solvent. As such a solvent for eye drops, physiological saline, the other aqueous solvent or nonaqueous solvent for injection (such as vegetable oil and the like), and the like, singly or in combination thereof is used. The eye drops may comprise, if necessary, of materials properly selected from tonicity agent (such as sodium chloride, concentrated glycerin and the like), buffer agents (such as sodium phosphate, sodium acetate and the like), surfactants (such as polysorbate 80 (trade name), polyoxyl 40 stearate, polyoxyethylene hydrogenated castor oil, and the like), stabilizer (such as sodium citrate, sodium edentate and the like), antiseptic agent (such as benzalkonium chloride, paraben and the like). These are sterilized at the final step or prepared by an aseptic process. Alternatively, an aseptic solid agent such as freeze-dried product which has previously been prepared may be rendered aseptic or dissolved in aseptic distilled water for injection or other solvents before use.

The inhalant for parenteral administration may be in the form of aerosol, powder for inhalation or liquid for inhalation. The liquid for inhalation may be dissolved or suspended in water or other proper medium in use.

These inhalants are prepared by a known method.

For example, the liquid for inhalation is prepared from materials properly selected from preservatives (such as benzalconium chloride, Paraben and the like), colorants, buffering agents (such as sodium phosphate, sodium acetate and the like), isotonic agents (such as sodium chloride, concentrated glycerin and the like), thickening agents (such as carboxyvinyl polymer and the like), absorption accelerators, and the like as necessary.

The powder for inhalation is prepared from materials properly selected from glidants (such as stearic acid and salt thereof and the like), binders (such as starch, dextrin and the like), vehicles (such as lactose, cellulose and the like), colorants, preservatives (such as benzalconium chloride, Paraben and the like), absorption accelerators, and the like, if necessary.

In order to administer the liquid for inhalation, a sprayer (such as atomizer, nebulizer and the like) is normally used. In order to administer the powder for inhalation, a powder inhaler is normally used.

Other examples of the composition for parenteral administration include suppository for rectal administration and pessary for vaginal administration prepared by an ordinary formulation comprising one or more active materials.

EFFECT OF THE INVENTION

Since the compounds of the present invention have selective Itk inhibitory activity, they are useful as a method for preventing and/or treating Itk related disease.

BEST MODE FOR CARRYING OUT THE INVENTION

The present invention is described below in detail by reference to the following Examples, however, the present invention is not interpreted as being restricted thereto.

The solvents in parentheses at chromatographic separations section and TLC section show the developing or eluting solvents and the ratios of the solvents used are indicated by volume. Unless otherwise indicated, the NMR data are $^1$H-NMR data. The solvents in parentheses indicated in NMR section show solvents used in determination.

The LC/MS data are indicated in the procedures below. Unless otherwise indicated, (LCMS) shows m/z value and RT means retention time. Electron impact mass spectra (EI-MS) were obtained with a Waters Micromass ZQ equipped with a Waters Alliance HT 2795 LC with a Waters Sunfire C-18 column (4×6 mm, 5 microns, Waters Corp, Milford, Mass., USA). The ion source was maintained at 100° C. and spectra were scanned from 105-1200 amu at 0.4 sec per scan.

Electrospray mass spectra (HPLC ES-MS) were obtained using a Waters Alliance HT 2795 HPLC (Waters Corp, Milford, Mass., USA) equipped with dual pumps, a dual wavelength detector set at 254 nm, and a Waters Micromass ZQ (Waters Corp, Milford, Mass., USA). Spectra were scanned from 105-1200 amu using a variable ion time according to the number of ions in the source. The eluents were A: 5% acetonitrile in water with 0.1% trifluoroacetic acid (TFA) and B: acetonitrile with 0.1% TFA. Gradient elution from 1.0% B to 95% over 5.0 minutes at a flowrate of 3.5 ml/min was used with an initial hold of 0.3 minutes and a finial hold at 95% B of 0.3 minutes. Total run time was 5.0 minutes.

Example 1

1,5-dimethyl-3-oxo-2-phenyl-2,3-dihydro-1H-pyrazole-4-carboxylic acid

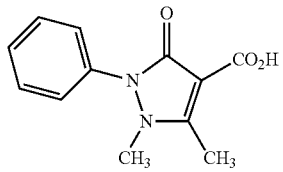 [SMILES: Cc1c(C(=O)O)c(=O)n(-c2ccccc2)n1C]

To a stirred solution of the commercially available 1,5-dimethyl-3-oxo-2-phenyl-2,3-dihydro-1H-pyrazole-4-carbaldehyde (CAS No. 950-81-2) (51.6 g) in tetrahydrofuran (THF) (1 L) at 0° C. was added a solution of sulfamic acid (48.5 g) in water (640 mL). A solution of sodium chlorite (43.7 g) in water (500 mL) was added slowly maintaining the temperature below 8° C. The reaction mixture was allowed to warm to room temperature. After 5 hours, the pH of the reaction was adjusted to 8 with a 6 N aqueous solution of sodium hydroxide (NaOH). The mixture was extracted with ethyl acetate (EtOAc). The aqueous layer was acidified to pH 4 with a 6N solution of hydrochloric acid (HCl) and extracted with dichloromethane (DCM). The combined DCM extracts were washed sequentially with 5% aqueous sodium sulfite and saturated brine, dried over sodium sulfate ($Na_2SO_4$) and concentrated under reduced pressure. The crude solid was triturated with methanol (MeOH) to give the title compound (17 g).

Example 2

1,5-dimethyl-3-oxo-2-phenyl-N-[4-(4,4,5,5-tetramethyl-1,3,2-dioxaborolan-2-yl)phenyl]-2,3-dihydro-1H-pyrazole-4-carboxamide A solution of the compound prepared in Example 1 (5.0 g), O-(7-azabenzotriazol-1-yl)-N,N,N',N'-tetramethyluronium hexafluorophosphate (HATU) (8.6 g), and triethylamine (TEA) (3.3 mL) in dimethylacetamide (DMA) (100 mL) was treated with 4-(4,4,5,5-tetramethyl-1,3,2-dioxaborolan-2-yl) aniline (5.2 g). The reaction was stirred at 70° C. for 3 hours, at which time LC/MS indicated the reaction was complete. The reaction mixture was diluted with water (200 mL) and extracted with EtOAc (3×200 mL). After the first extraction, sodium chloride was added to the aqueous layer to break up the emulsion. The combined organic layers with saturated aqueous sodium bicarbonate (500 mL), water (500 mL) and saturated brine (500 mL), dried over $Na_2SO_4$ and evaporated to dryness under reduced pressure. The product was absorbed onto silica gel (20 g) and purified by flash chromatography (silica gel, 200 g) using a gradient of 40% to 80% EtOAc in heptanes as the eluent. The title compound having the following physical data was obtained as an off white solid (9.5 g).

TLC Rf=0.59 ($CH_2Cl_2$:methanol=19:1).

Example 3

N-[4-(3-amino-6-bromo-2-pyrazinyl)phenyl]-1,5-dimethyl-3-oxo-2-phenyl-2,3-dihydro-1H-pyrazole-4-carboxamide A suspension of the compound prepared in Example 2 (15 g), tetrakis(triphenylphosphine)palladium ($Pd(PPh_3)_4$) (2.0 g), 3,5-dibromopyrazin-2-amine (9.5 g), and sodium carbonate ($Na_2CO_3$) (7.3 g) in 3:1 mixture of dioxane/water (350 mL) was degassed with a stream of nitrogen for 10 minutes. The reaction was heated at 90° C. for 5 hours, at which time LC/MS indicated the reaction was complete. The mixture was concentrated under reduced pressure, diluted with water (200 mL) and extracted with EtOAc (3×300 mL). The organic layers were combined, dried over $Na_2SO_4$, and evaporated under reduced pressure. The product was absorbed onto silica gel (40 g) and purified by flash chromatography (silica gel, 400 g) using a gradient of 1 to 3% MeOH in DCM as the eluent. After purification, $^1$H NMR showed that pinicol was present as an impurity. The product was suspended in 10% aqueous potassium carbonate (300 mL), stirred for 30 minutes, filtered and washed with water (3×100 mL). The resulting solid was then evaporated from absolute ethanol (6×50 mL) to give the title compound (6.6 g) having the following physical data as a yellow solid.

TLC Rf=0.57 (ethyl acetate:methanol=9:1).

Example 4(1)

N-(4-{3-amino-6-[2-(3,3-difluoro-1-azetidinyl)-4-pyridinyl]-2-pyrazinyl}phenyl)-1,5-dimethyl-3-oxo-2-phenyl-2,3-dihydro-1H-pyrazole-4-carboxamide

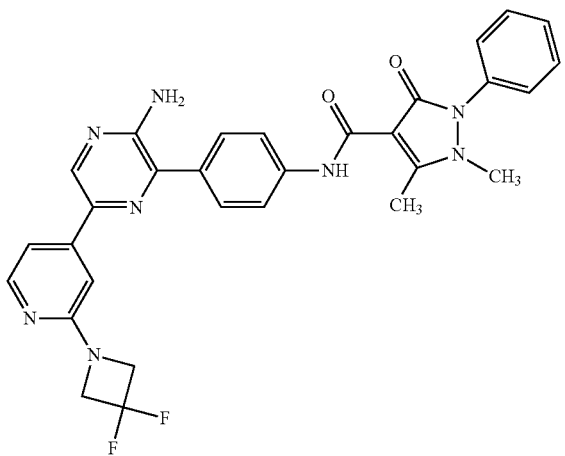 [SMILES: Cc1c(C(=O)Nc2ccc(-c3nc(-c4ccnc(N5CC(F)(F)C5)c4)cnc3N)cc2)c(=O)n(-c2ccccc2)n1C]

2-fluoro-4-iodopyridine (100 mg), 3,3-difluoroazetidine-HCl (1.1 mmol) and K$_2$CO$_3$ (248 mg, 1.8 mmol) were dissolved in dimethyl sulfoxide (DMSO) (500 μL) and stirred at 110° C. for 3 hours. The reaction mixture was then diluted with H$_2$O and washed with diethylether (Et$_2$O) five times. The organic extracts were concentrated and purified by column chromatography giving about 100 mg of product. This product (0.35 mmol) was combined with hexabutylditin (Bu$_3$SnSnBu$_3$) (245 μL) and Pd(PPh$_3$)$_2$Cl$_2$ (5 mol %) and heated to 110° C. in toluene (1 mL) for 4 hours. The reaction mixture was then concentrated, and the residue was purified by column chromatography to give 2-(3,3-difluoro-1-azetidinyl)-4-(tributylstannyl)pyridine. The compound prepared in Example 3 (53 mg), 2-(3,3-difluoro-1-azetidinyl)-4-(tributylstannyl)pyridine (0.22 mmol) and Pd(Ph$_3$)$_2$Cl$_2$ (5 mol %) were suspended in dioxanes (1 mL) and heated to 110° C. for 12 hours. The reaction mixture was then concentrated and purified by prep TLC to give the title compound having the following physical data.

$^1$H NMR (250 MHz, CDCl$_3$) δ 10.90 (s, 1H), 8.43 (s, 1H), 8.24 (d, J=5.4 Hz, 1H), 7.85 (d, J=8.7 Hz, 2H), 7.76 (d, J=8.6 Hz, 2H), 7.62-7.45 (m, 3H), 7.38 (d, J=7.1 Hz, 2H), 7.29-7.26 (m, 1H), 7.01 (s, 1H), 5.03 (s, 2H), 4.43 (t, J=12.1 Hz, 4H), 3.39 (s, 3H), 2.82 (s, 3H).

Example 4(2)-4(4)

The compound having the following physical data was prepared by using the compound prepared in Example 3, and using the corresponding organotin compound instead of 2-(3,3-difluoroazetidin-1-yl)-4-(tributylstannyl)pyridine in the process of Example 4(1).

Example 4(2)

N-(4-{3-amino-6-[2-(3-methoxy-1-azetidinyl)-4-pyridinyl]-2-pyrazinyl}phenyl)-1,5-dimethyl-3-oxo-2-phenyl-2,3-dihydro-1H-pyrazole-4-carboxamide $^1$H NMR (400 MHz, CDCl$_3$) δ 10.86 (s, 1H), 8.40 (s, 1H), 8.19 (d, J=5.4 Hz, 1H), 7.84-7.73 (m, 4H), 7.55 (t, J=7.6 Hz, 2H), 7.46 (t, J=7.4 Hz, 1H), 7.36 (d, J=7.4 Hz, 2H), 7.14 (dd, J=5.4, 1.2 Hz, 1H), 6.89 (s, 1H), 4.92 (s, 2H), 4.41-4.31 (m, 1H), 4.29-4.24 (m, 2H), 3.95 (dd, J=8.8, 4.2 Hz, 2H), 3.36 (s, 3H), 3.33 (s, 3H), 2.80 (s, 3H).

Example 4(3)

N-(4-{3-amino-6-[2-(3-hydroxy-3-methyl-1-azetidinyl)-4-pyridinyl]-2-pyrazinyl}phenyl)-1,5-dimethyl-3-oxo-2-phenyl-2,3-dihydro-1H-pyrazole-4-carboxamide $^1$H NMR (250 MHz, CDCl$_3$) δ 10.86 (s, 1H), 8.36 (s, 1H), 8.15 (d, J=5.4 Hz, 1H), 7.85-7.69 (m, 4H), 7.60-7.42 (m, 3H), 7.36 (d, J=7.2 Hz, 2H), 7.11 (d, J=5.2 Hz, 1H), 6.86 (s, 1H), 5.07 (s, 2H), 4.07-3.92 (m, 4H), 3.35 (s, 3H), 2.78 (s, 3H), 1.59 (s, 3H).

Example 4(4)

N-(4-{3-amino-6-[2-(3-fluoro-1-azetidinyl)-4-pyridinyl]-2-pyrazinyl}phenyl)-1,5-dimethyl-3-oxo-2-phenyl-2,3-dihydro-1H-pyrazole-4-carboxamide $^1$H NMR (250 MHz, CDCl$_3$/CD$_3$OD) δ 10.79 (s, 1H), 8.31 (s, 1H), 8.06 (d, J=5.5 Hz, 1H), 7.77-7.65 (m, 4H), 7.57-7.41 (m, 3H), 7.30 (d, J=6.9 Hz, 2H), 7.13 (d, J=5.5 Hz, 1H), 6.86 (s, 1H), 5.55-5.26 (m, 1H), 4.40-4.23 (m, 2H), 4.11 (ddd, J=24.7, 10.0, 3.1 Hz, 2H), 3.33 (s, 3H), 2.73 (s, 3H).

Example 5(1)

N-{4-[3-amino-6-(3-fluorophenyl)-2-pyrazinyl]phenyl}-1,5-dimethyl-3-oxo-2-phenyl-2,3-dihydro-1H-pyrazole-4-carboxamide

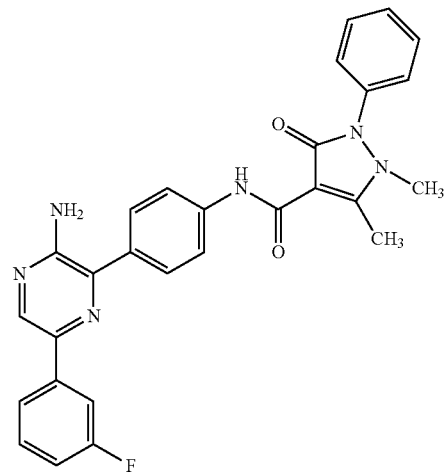 [SMILES: Cc1c(C(=O)Nc2ccc(-c3nc(-c4cccc(F)c4)cnc3N)cc2)c(=O)n(-c2ccccc2)n1C]

To the compound prepared in Example 3 (66 mg), 3-fluorophenylboronic acid (20 mg), Pd(PPh$_3$)$_4$ (16 mg), and Na$_2$CO$_3$ (15 mg) in a pressure vessel were added dimethylformamide (DMF)/H$_2$O (2:1). The vessel was flushed with argon for 5 minutes and sealed. The vessel was microwaved for 10 minutes at 150° C. The reaction was cooled, and the LC/MS indicated desired product was obtained. The reaction mixture was extracted with DCM for three times, dried over Na$_2$SO$_4$, filtered, and concentrated. The crude product was purified by prep-TLC (5% MeOH/CH$_2$Cl$_2$) to afford the title compound (50 mg) having the following physical data.

MS (M+H): 495.0;

$^1$H NMR (400 MHz, CD$_3$OD) δ 10.79 (s, 1H), 8.28 (s, 1H), 7.78-7.71 (m, 4H), 7.69-7.59 (m, 2H), 7.57-7.44 (m, 3H), 7.38-7.31 (m, 3H), 6.99 (td, J=8.4, 2.6, 1H), 3.35 (s, 3H), 2.74 (s, 3H).

Example 5(2)-5(97)

The compound having the following physical data was prepared by using the compound prepared in Example 1 or the corresponding carboxylic acid instead thereof, and using 4-(3-(4,4,5,5-tetramethyl-1,3,2-dioxaborolan-2-yl)benzyl)morpholine or the corresponding dioxaborolane compound instead thereof in the process of Example 1→Example 2→Example 3→Example 5(1).

Example 5(2)

N-(4-{3-amino-6-[3-(4-morpholinylmethyl)phenyl]-2-pyrazinyl}phenyl)-1,5-dimethyl-3-oxo-2-phenyl-2,3-dihydro-1H-pyrazole-4-carboxamide

MS (M+H): 576.2;

$^1$H NMR (400 MHz, DMSO-d$_6$) δ 10.89 (s, 1H), 8.47 (s, 1H), 7.87 (s, 1H), 7.83 (d, J=7.9 Hz, 1H), 7.76-7.70 (m, 4H), 7.56 (d, J=7.8 Hz, 2H), 7.49 (t, J=7.4 Hz, 1H), 7.42 (d, J=7.3 Hz, 2H), 7.35 (d, J=7.6 Hz, 1H), 7.25 (d, J=7.5 Hz, 1H), 6.25 (s, 2H), 3.54 (d, J=4.4 Hz, 4H), 3.49 (s, 2H), 3.34 (s, 3H), 2.70 (s, 3H), 2.35 (bs, 4H).

Example 5(3)

N-(4-{3-amino-6-[4-(4-morpholinylcarbonyl)phenyl]-2-pyrazinyl}phenyl)-1,5-dimethyl-3-oxo-2-phenyl-2,3-dihydro-1H-pyrazole-4-carboxamide MS (M+H): 590.2;
$^1$H NMR (400 MHz, DMSO-$d_6$) δ 10.89 (s, 1H), 8.54 (s, 1H), 8.03 (d, J=8.2 Hz, 2H), 7.77-7.70 (m, 4H), 7.57 (t, J=7.5 Hz, 2H), 7.50 (d, J=7.3 Hz, 1H), 7.46-7.40 (m, 4H), 6.37 (s, 2H), 3.56 (br m, 8H), 3.34 (s, 3H), 2.70 (s, 3H).

Example 5(4)

N-[4-(3-amino-6-{3-[(methylsulfonyl)amino]phenyl}-2-pyrazinyl)phenyl]-1,5-dimethyl-3-oxo-2-phenyl-2,3-dihydro-1H-pyrazole-4-carboxamide MS (M+H): 570.3;
1H NMR (400 MHz, CDCl$_3$) δ 10.84 (s, 1H), 8.40 (s, 1H), 7.77-7.69 (m, 6H), 7.55 (t, J=7.6 Hz, 2H), 7.49-7.39 (m, 2H), 7.39-7.33 (m, 3H), 5.03 (s, 2H), 3.35 (s, 3H), 3.00 (s, 3H), 2.79 (s, 3H).

Example 5(5)

N-{4-[3-amino-6-(3-methoxyphenyl)-2-pyrazinyl]phenyl}-1,5-dimethyl-3-oxo-2-phenyl-2,3-dihydro-1H-pyrazole-4-carboxamide MS (M+H): 507.3;
$^1$H NMR (400 MHz, CDCl$_3$) δ 10.83-10.75 (m, 1H), 8.33 (s, 1H), 7.79-7.69 (m, 5H), 7.52-7.45 (m, 4H), 7.43-7.38 (m, 1H), 7.34-7.24 (m, 4H), 6.87-6.79 (m, 1H), 4.81-4.70 (m, 2H), 3.80 (s, 3H), 3.30 (s, 3H), 2.74 (s, 3H).

Example 5(6)

N-(4-{3-amino-6-[3-(4-morpholinyl)phenyl]-2-pyrazinyl}phenyl)-1,5-dimethyl-3-oxo-2-phenyl-2,3-dihydro-1H-pyrazole-4-carboxamide MS (M+H): 562.4;
$^1$H NMR (400 MHz, CDCl$_3$) δ 10.84 (s, 1H), 8.37 (s, 1H), 7.82-7.76 (m, 4H), 7.57-7.52 (m, 3H), 7.46 (t, J=7.4 Hz, 1H), 7.41 (d, J=7.7 Hz, 1H), 7.37-7.30 (m, 3H), 6.89 (dd, J=8.1, 2.0 Hz, 1H), 4.82 (s, 2H), 3.88-3.85 (m, 4H), 3.35 (s, 3H), 3.23-3.20 (m, 4H), 2.79 (s, 3H).

Example 5(7)

N-{4-[3-amino-6-(6-fluoro-3-pyridinyl)-2-pyrazinyl]phenyl}-1,5-dimethyl-3-oxo-2-phenyl-2,3-dihydro-1H-pyrazole-4-carboxamide MS (M+H): 496.3;
$^1$H NMR (400 MHz, DMSO-$d_6$) δ 10.89 (s, 1H), 8.79 (d, J=2.1 Hz, 1H), 8.56 (s, 1H), 8.50 (td, J=8.3, 2.5 Hz, 1H), 7.76 (d, J=8.7 Hz, 2H), 7.71 (d, J=8.7 Hz, 2H), 7.57 (t, J=7.5 Hz, 2H), 7.49 (t, J=7.4 Hz, 2H), 7.41 (d, J=7.3 Hz, 2H), 7.22 (dd, J=8.6, 2.7 Hz, 1H), 6.41 (s, 2H), 3.34 (s, 3H), 2.69 (s, 3H).

Example 5(8)

N-[4-(3-amino-6-{4-[(methylsulfonyl)amino]phenyl}-2-pyrazinyl)phenyl]-1,5-dimethyl-3-oxo-2-phenyl-2,3-dihydro-1H-pyrazole-4-carboxamide MS (M+H): 570.2;
$^1$H NMR (400 MHz, CD$_3$OD) δ 8.26 (s, 1H), 7.88-7.82 (m, 2H), 7.73 (s, 4H), 7.53 (dt, J=17.5, 7.1 Hz, 3H), 7.36-7.32 (m, 2H), 7.29-7.25 (m, 2H), 3.36 (s, 3H), 2.94 (s, 3H), 2.74 (s, 3H).

Example 5(9)

N-(4-{3-amino-6-[3-(4-morpholinylcarbonyl)phenyl]-2-pyrazinyl}phenyl)-1,5-dimethyl-3-oxo-2-phenyl-2,3-dihydro-1H-pyrazole-4-carboxamide MS (M+H): 590.3;
$^1$H NMR (400 MHz, CDCl$_3$) δ 10.85 (s, 1H), 8.39 (s, 1H), 8.01 (d, J=7.2 Hz, 2H), 7.82 (d, J=8.7 Hz, 2H), 7.76 (d, J=8.7 Hz, 2H), 7.55 (t, J=7.6 Hz, 2H), 7.49-7.44 (m, 2H), 7.37-7.34 (m, 3H), 4.92 (s, 2H), 3.77-3.45 (br m, 8H), 3.35 (s, 3H), 2.80 (s, 3H).

Example 5(10)

N-[4-(3-amino-6-{4-[3-(4-morpholinyl)propoxy]phenyl}-2-pyrazinyl)phenyl]-1,5-dimethyl-3-oxo-2-phenyl-2,3-dihydro-1H-pyrazole-4-carboxamide MS (M+H): 620.5;
$^1$H NMR (400 MHz, CDCl$_3$) δ 10.78 (s, 1H), 8.28 (s, 1H), 7.85-7.78 (m, 2H), 7.78-7.68 (m, 4H), 7.49 (t, J=7.6 Hz, 2H), 7.40 (t, J=7.5 Hz, 1H), 7.32-7.26 (m, 2H), 6.92-6.86 (m, 2H), 4.68 (s, 2H), 4.00 (t, J=6.3 Hz, 2H), 3.70-3.60 (m, 4H), 3.29 (s, 3H), 2.74 (s, 3H), 2.52-2.31 (m, 6H), 1.92 (dd, J=14.1, 6.7 Hz, 2H).

Example 5(11)

N-[4-(3-amino-6-{3-[2-(4-morpholinyl)ethoxy]phenyl}-2-pyrazinyl)phenyl]-1,5-dimethyl-3-oxo-2-phenyl-2,3-dihydro-1H-pyrazole-4-carboxamide MS (M+H): 606.6;
$^1$H NMR (400 MHz, CDCl$_3$) δ 10.84 (s, 1H), 8.40-8.35 (m, 1H), 7.85-7.73 (m, 4H), 7.57-7.49 (m, 4H), 7.48-7.43 (m, 1H), 7.35 (ddd, J=18.1, 9.1, 3.9 Hz, 4H), 6.88 (dd, J=7.7, 2.1 Hz, 1H), 4.81 (s, 2H), 4.17 (t, J=5.6 Hz, 2H), 3.76-3.69 (m, 4H), 3.35 (s, J=6.2 Hz, 3H), 2.82 (t, J=5.7 Hz, 2H), 2.80 (s, 3H), 2.59 (m, 4H).

Example 5(12)

N-{4-[3-amino-6-(3,5-dimethoxyphenyl)-2-pyrazinyl]phenyl}-1,5-dimethyl-3-oxo-2-phenyl-2,3-dihydro-1H-pyrazole-4-carboxamide MS (M+H): 537.4;
$^1$H NMR (400 MHz, CDCl$_3$) δ 10.84 (s, 1H), 8.35 (s, 1H), 7.82-7.75 (m, 4H), 7.54 (t, J=7.6 Hz, 2H), 7.45 (t, J=7.4 Hz, 1H), 7.35 (d, J=7.4 Hz, 2H), 7.11 (d, J=2.2 Hz, 2H), 6.45 (t, J=2.2 Hz, 1H), 4.84 (s, 2H), 3.84 (s, 6H), 3.34 (s, 3H), 2.79 (s, 3H).

Example 5(13)

N-[4-(3-amino-6-{4-[2-(4-morpholinyl)ethoxy]phenyl}-2-pyrazinyl)phenyl]-1,5-dimethyl-3-oxo-2-phenyl-2,3-dihydro-1H-pyrazole-4-carboxamide MS (M+H): 606.5;
$^1$H NMR (400 MHz, CDCl$_3$) δ 10.78 (s, 1H), 8.28 (s, 1H), 7.85-7.80 (m, 2H), 7.76-7.70 (m, 4H), 7.51-7.46 (m, 2H), 7.42-7.38 (m, 1H), 7.34-7.26 (m, 2H), 6.97-6.86 (m, 2H), 4.69 (s, 2H), 4.09 (t, J=5.7 Hz, 2H), 3.67 (m, 4H), 3.29 (s, 3H), 2.77-2.73 (5H), 2.52 (m, 4H).

Example 5(14)

N-(4-{3-amino-6-[5-(4-morpholinylmethyl)-3-thienyl]-2-pyrazinyl}phenyl)-1,5-dimethyl-3-oxo-2-phenyl-2,3-dihydro-1H-pyrazole-4-carboxamide MS (M+H): 582.4;
$^1$H NMR (400 MHz, CDCl$_3$) δ 10.78 (s, 1H), 8.19 (s, 1H), 7.72 (dd, J=22.3, 8.8 Hz, 4H), 7.60 (d, J=1.4 Hz, 1H), 7.52-7.46 (m, 2H), 7.43-7.37 (m, 2H), 7.32-7.28 (m, 2H), 4.77 (s, 2H), 3.70-3.59 (m, 6H), 3.30 (s, 3H), 2.74 (s, 3H), 2.54-2.30 (m, 4H).

Example 5(15)

N-(4-{3-amino-6-[3-(methoxymethyl)phenyl]-2-pyrazinyl}phenyl)-1,5-dimethyl-3-oxo-2-phenyl-2,3-dihydro-1H-pyrazole-4-carboxamide $^1$H NMR (250 MHz, CDCl$_3$) δ 10.88 (s, 1H), 8.40 (s, 1H), 7.97-7.86 (m, 2H), 7.86-7.74 (m, 4H), 7.62-7.31 (7H), 5.07 (s, 2H), 4.53 (s, 2H), 3.42 (s, 3H), 3.37 (s, 3H), 2.81 (s, 3H).

Example 5(16)

N-{4-[3-amino-6-(2-fluoro-3-methoxyphenyl)-2-pyrazinyl]phenyl}-1,5-dimethyl-3-oxo-2-phenyl-2,3-dihydro-1H-pyrazole-4-carboxamide $^1$H NMR (250 MHz, CDCl$_3$) δ 10.89 (s, 1H), 8.46 (d, J=2.0 Hz, 1H), 7.88-7.73 (m, 4H), 7.64-7.44 (m, 4H), 7.37 (d, J=7.4 Hz, 2H), 7.16 (t, J=7.6 Hz, 1H), 6.96 (t, J=8.4 Hz, 1H), 5.31 (s, 2H), 3.93 (s, 3H), 3.38 (s, 3H), 2.81 (s, 3H).

Example 5(17)

N-[4-(3-amino-6-{6-[3-(dimethylamino)propoxy]-3-pyridinyl}-2-pyrazinyl)phenyl]-1,5-dimethyl-3-oxo-2-phenyl-2,3-dihydro-1H-pyrazole-4-carboxamide $^1$H NMR (250 MHz, CDCl$_3$) δ 10.97 (s, 1H), 8.62 (d, J=2.2 Hz, 1H), 8.13 (dd, J=8.7, 2.3 Hz, 1H), 7.99 (s, 1H), 7.87 (d, J=8.6 Hz, 2H), 7.73 (d, J=8.6 Hz, 2H), 7.63-7.49 (m, 3H), 7.37 (d, J=7.0 Hz, 2H), 6.83 (d, J=8.7 Hz, 1H), 4.53-4.35 (m, 4H), 3.39 (s, 3H), 3.35-3.19 (m, 2H), 2.89 (s, 6H), 2.81 (s, 3H), 2.38-2.21 (m, 2H).

Example 5(18)

N-{4-[3-amino-6-(5-methoxy-3-pyridinyl)-2-pyrazinyl]phenyl}-1,5-dimethyl-3-oxo-2-phenyl-2,3-dihydro-1H-pyrazole-4-carboxamide $^1$H NMR (250 MHz, CDCl$_3$) δ 10.92 (s, 1H), 8.83 (s, 1H), 8.43 (s, 1H), 8.37 (d, J=2.5 Hz, 1H), 8.08 (s, 1H), 7.85 (d, J=8.7 Hz, 2H), 7.75 (d, J=8.6 Hz, 2H), 7.62-7.45 (m, 3H), 7.37 (d, J=7.1 Hz, 2H), 5.28 (s, 2H), 3.98 (s, 3H), 3.39 (s, 3H), 2.82 (s, 3H).

Example 5(19)

N-{4-[3-amino-6-(3-fluoro-5-methoxyphenyl)-2-pyrazinyl]phenyl}-1,5-dimethyl-3-oxo-2-phenyl-2,3-dihydro-1H-pyrazole-4-carboxamide $^1$H NMR (250 MHz, CDCl$_3$) δ 10.90 (s, 1H), 8.31 (s, 1H), 7.89-7.73 (m, 4H), 7.62-7.44 (m, 3H), 7.37 (d, J=7.1 Hz, 2H), 7.32-7.25 (m, 2H), 6.62 (d, J=10.6 Hz, 1H), 5.38 (s, 2H), 3.86 (s, 3H), 3.38 (s, 3H), 2.82 (s, 3H).

Example 5(20)

N-{4-[3-amino-6-(5-fluoro-2-methoxy-4-pyridinyl)-2-pyrazinyl]phenyl}-1,5-dimethyl-3-oxo-2-phenyl-2,3-dihydro-1H-pyrazole-4-carboxamide $^1$H NMR (250 MHz, CDCl$_3$) δ 10.92 (s, 1H), 8.53 (s, 1H), 8.08 (d, J=3.0 Hz, 1H), 7.84 (d, J=8.7 Hz, 2H), 7.75 (d, J=8.5 Hz, 2H), 7.62-7.44 (m, 4H), 7.37 (d, J=7.2 Hz, 2H), 5.70 (s, 2H), 3.93 (s, 3H), 3.38 (s, 3H), 2.82 (s, 3H).

Example 5(21)

N-(4-{3-amino-6-[3-(4-morpholinylmethyl)phenyl]-2-pyrazinyl}phenyl)-2-cyclohexyl-1,5-dimethyl-3-oxo-2,3-dihydro-1H-pyrazole-4-carboxamide MS (M+H): 582.5;
$^1$H NMR (400 MHz, CDCl$_3$) δ 10.97 (s, 1H), 8.39 (s, 1H), 7.88 (t, J=1.4 Hz, 1H), 7.86-7.80 (m, 3H), 7.80-7.75 (m, 2H), 7.38 (t, J=7.6 Hz, 1H), 7.34-7.29 (m, 1H), 4.81 (s, 2H), 4.16-4.07 (m, 1H), 3.74-3.66 (m, 4H), 3.55 (s, 2H), 3.49 (s, 3H), 2.68 (s, 3H), 2.53-2.39 (m, 4H), 2.13 (qd, J=13.1, 3.6 Hz, 2H), 1.99-1.78 (m, 4H), 1.78-1.60 (m, 1H), 1.44-1.19 (m, 3H).

Example 5(22)

N-(4-{3-amino-6-[3-(cyclopropylsulfamoyl)phenyl]-2-pyrazinyl}phenyl)-1,5-dimethyl-3-oxo-2-phenyl-2,3-dihydro-1H-pyrazole-4-carboxamide $^1$H NMR (400 MHz, CDCl$_3$) δ 10.90 (s, 1H), 8.44 (s, 1H), 8.36 (s, 1H), 8.18 (d, J=7.7 Hz, 1H), 7.88 (d, J=7.9 Hz, 1H), 7.84 (d, J=8.5 Hz, 2H), 7.76 (d, J=8.5 Hz, 2H), 7.62-7.53 (m, 3H), 7.47 (t, J=7.3 Hz, 1H), 7.36 (d, J=7.5 Hz, 2H), 5.57 (s, 2H), 3.36 (s, 3H), 2.80 (s, 3H), 2.34-2.21 (m, 1H), 0.66-0.58 (m, 4H).

Example 5(23)

N-(4-{3-amino-6-[2-(4-morpholinyl)phenyl]-2-pyrazinyl}phenyl)-1,5-dimethyl-3-oxo-2-phenyl-2,3-dihydro-1H-pyrazole-4-carboxamide $^1$H NMR (400 MHz, CDCl$_3$) δ 10.78 (s, 1H), 8.74 (s, 1H), 7.77-7.70 (m, 4H), 7.60 (d, J=7.5 Hz, 1H), 7.49 (t, J=7.6 Hz, 2H), 7.40 (t, J=7.3 Hz, 1H), 7.30 (d, J=7.6 Hz, 2H), 7.24 (t, J=7.6 Hz, 1H), 7.08 (t, J=7.5 Hz, 1H), 7.01 (d, J=8.0 Hz, 1H), 4.71 (s, 2H), 3.69-3.64 (m, 4H), 3.29 (s, 3H), 2.88-2.83 (m, 4H), 2.74 (s, 3H).

Example 5(24)

N-{4-[3-amino-6-(3-ethoxy-5-fluorophenyl)-2-pyrazinyl]phenyl}-1,5-dimethyl-3-oxo-2-phenyl-2,3-dihydro-1H-pyrazole-4-carboxamide $^1$H NMR (400 MHz, CDCl$_3$) δ 10.85 (s, 1H), 8.35 (s, 1H), 7.84-7.74 (m, 4H), 7.55 (t, J=7.6 Hz, 2H), 7.46 (t, J=7.4 Hz, 1H), 7.36 (d, J=7.4 Hz, 2H), 7.30 (s, 1H), 7.25 (d, J=7.2 Hz, 1H), 6.57 (dt, J=10.5, 2.2 Hz, 1H), 4.85 (s, 2H), 4.07 (q, J=7.0 Hz, 2H), 3.35 (s, 3H), 2.80 (s, 3H), 1.42 (t, J=7.0 Hz, 3H).

Example 5(25)

N-{4-[3-amino-6-(2-methoxyphenyl)-2-pyrazinyl]phenyl}-1,5-dimethyl-3-oxo-2-phenyl-2,3-dihydro-1H-pyrazole-4-carboxamide $^1$H NMR (250 MHz, CDCl$_3$) δ 10.88 (s, 1H), 8.55 (s, 1H), 7.94 (d, J=7.5 Hz, 1H), 7.88-7.72 (m, 4H), 7.61-7.44 (m, 3H), 7.41-7.29 (m, 3H), 7.07 (t, J=7.4 Hz, 1H), 7.00 (d, J=8.2 Hz, 1H), 5.54 (s, 2H), 3.90 (s, 3H), 3.37 (s, 3H), 2.81 (s, 3H).

Example 5(26)

N-(4-{3-amino-6-[3-(methylsulfinyl)phenyl]-2-pyrazinyl}phenyl)-1,5-dimethyl-3-oxo-2-phenyl-2,3-dihydro-1H-pyrazole-4-carboxamide $^1$H NMR (250 MHz, CDCl$_3$) δ 10.89 (s, 1H), 8.46 (s, 1H), 8.19 (s, 1H), 8.10 (d, J=7.2 Hz, 1H), 7.86-7.74 (m, 4H), 7.66-7.44 (m, 5H), 7.37 (d, J=7.1 Hz, 2H), 4.97 (s, 2H), 3.37 (s, 3H), 2.81 (s, 3H), 2.77 (s, 3H).

Example 5(27)

N-[4-(3-amino-6-{4-[2-hydroxy-3-(1-piperidinyl)propoxy]phenyl}-2-pyrazinyl)phenyl]-1,5-dimethyl-3-oxo-2-phenyl-2,3-dihydro-1H-pyrazole-4-carboxamide $^1$H NMR (250 MHz, CDCl$_3$) δ 10.87 (s, 1H), 8.35 (s, 1H), 7.90 (d, J=8.7 Hz, 2H), 7.84-7.76 (m, 4H), 7.57 (t, J=7.3 Hz, 2H), 7.47 (t, J=7.1 Hz, 1H), 7.37 (d, J=7.1 Hz, 2H), 6.99 (d, J=8.8 Hz, 2H), 4.77 (s, 2H), 4.18-4.05 (m, 1H), 4.05-3.96 (m, 2H), 3.37 (s, 3H), 2.81 (s, 3H), 2.70-2.55 (m, 2H), 2.55-2.44 (m, 2H), 2.44-2.29 (m, 2H), 1.59 (s, 4H), 1.53-1.39 (m, 2H).

Example 5(28)

N-{4-[3-amino-6-(5,6-dimethoxy-3-pyridinyl)-2-pyrazinyl]phenyl}-1,5-dimethyl-3-oxo-2-phenyl-2,3-dihydro-1H-pyrazole-4-carboxamide $^1$H NMR (250 MHz, CDCl$_3$) δ 10.89 (s, 1H), 8.37 (s, 1H), 8.24 (d, J=1.8 Hz, 1H), 7.88-7.75 (m, 4H), 7.73 (d, J=1.8 Hz, 1H), 7.57 (t, J=7.3 Hz, 2H), 7.52-7.44 (m, 1H), 7.37 (d, J=7.1 Hz, 2H), 4.86 (s, 2H), 4.07 (s, 3H), 3.96 (s, 3H), 3.38 (s, 3H), 2.82 (s, 3H).

Example 5(29)

4-[5-amino-6-(4-{[(1,5-dimethyl-3-oxo-2-phenyl-2,3-dihydro-1H-pyrazol-4-yl)carbonyl]amino}phenyl)-2-pyrazinyl]-2-methoxyphenyl acetate $^1$H NMR (250 MHz, CDCl$_3$/DMSO-d$_6$) δ 10.91 (s, 1H), 8.39 (s, 1H), 7.80 (s, 4H), 7.64-7.45 (m, 5H), 7.40 (d, J=7.2 Hz, 2H), 7.08 (d, J=8.2 Hz, 1H), 5.54 (s, 2H), 3.91 (s, 3H), 3.42 (s, 3H), 2.81 (s, 3H), 2.32 (s, 3H).

Example 5(30)

N-{4-[3-amino-6-(3,4-dimethoxyphenyl)-2-pyrazinyl]phenyl}-1,5-dimethyl-3-oxo-2-phenyl-2,3-dihydro-1H-pyrazole-4-carboxamide $^1$H NMR (250 MHz, CDCl$_3$) δ 10.87 (s, 1H), 8.36 (s, 1H), 7.86-7.77 (m, 4H), 7.62-7.52 (m, 3H), 7.49 (d, J=7.7 Hz, 2H), 7.37 (d, J=7.2 Hz, 2H), 6.94 (d, J=8.4 Hz, 1H), 4.79 (s, 2H), 3.97 (s, 3H), 3.93 (s, 3H), 3.37 (s, 3H), 2.81 (s, 3H).

Example 5(31)

N-{4-[3-amino-6-(2-fluoro-4-methylphenyl)-2-pyrazinyl]phenyl}-1,5-dimethyl-3-oxo-2-phenyl-2,3-dihydro-1H-pyrazole-4-carboxamide $^1$H NMR (250 MHz, CDCl$_3$) δ 10.87 (s, 1H), 8.47 (d, J=2.3 Hz, 1H), 7.92 (t, J=8.2 Hz, 1H), 7.85-7.75 (m, 4H), 7.62-7.44 (m, 3H), 7.37 (d, J=7.1 Hz, 2H), 7.04 (d, J=9.0 Hz, 1H), 6.96 (d, J=11.6 Hz, 1H), 4.86 (s, 2H), 3.38 (s, 3H), 2.82 (s, 3H), 2.38 (s, 3H).

Example 5(32)

{3-[5-amino-6-(4-{[(1,5-dimethyl-3-oxo-2-phenyl-2,3-dihydro-1H-pyrazol-4-yl)carbonyl]amino}phenyl)-2-pyrazinyl]phenoxy}acetic acid $^1$H NMR (400 MHz, DMSO-d$_6$) δ 12.96 (s, 1H), 10.89 (s, 1H), 8.49 (s, 1H), 7.70-7.78 (m, 4H), 7.54-7.59 (m, 3H), 7.47-7.51 (m, 2H), 7.41-7.43 (m, 2H), 7.32 (t, J=8.0 Hz, 1H), 6.85 (dd, J=8.0, 2.3 Hz, 1H), 6.30 (s, 2H), 4.70 (s, 2H), 3.34 (s, 3H), 2.70 (s, 3H).

Example 5(33)

N-(4-{3-amino-6-[3-(tetrahydro-2H-pyran-4-yloxy)phenyl]-2-pyrazinyl}phenyl)-1,5-dimethyl-3-oxo-2-phenyl-2,3-dihydro-1H-pyrazole-4-carboxamide MS (M+H): 577.3;
$^1$H NMR (400 MHz, CDCl$_3$) δ 10.80 (s, 1H), 8.32 (s, 1H), 7.78-7.70 (m, 4H), 7.52-7.38 (m, 5H), 7.33-7.24 (m, 3H), 6.84 (d, J=7.7 Hz, 1H), 4.75 (s, 2H), 4.50 (s, 1H), 4.03-3.78 (m, 1H), 3.52 (t, J=8.1 Hz, 2H), 3.30 (s, 3H), 2.75 (s, 3H), 2.04-1.92 (m, 2H), 1.81-1.68 (m, 2H).

Example 5(34)

N-[4-(3-amino-6-{3-[(4-hydroxy-1-piperidinyl)methyl]phenyl}-2-pyrazinyl)phenyl]-1,5-dimethyl-3-oxo-2-phenyl-2,3-dihydro-1H-pyrazole-4-carboxamide MS (M+H): 590.3;
$^1$H NMR (400 MHz, CDCl$_3$) δ 10.84 (s, 1H), 8.39 (s, 1H), 7.86 (s, 1H), 7.85-7.76 (5H), 7.56-7.52 (2H), 7.48-7.43 (1H), 7.39-7.29 (4H), 4.79 (s, 2H), 4.79 (s, 2H), 3.68 (m, 1H), 3.55 (s, 2H), 3.35 (s, 3H), 2.79 (s, 2H), 2.75 (m, 2H), 2.16 (m, 2H), 1.87 (m, 2H), 1.59 (m, 2H).

Example 5(35)

N-[4-(6-{3-[(4-acetyl-1-piperazinyl)methyl]phenyl}-3-amino-2-pyrazinyl)phenyl]-1,5-dimethyl-3-oxo-2-phenyl-2,3-dihydro-1H-pyrazole-4-carboxamide MS (M+H): 617.3;
$^1$H NMR (400 MHz, CDCl$_3$) δ 10.84 (s, 1H), 8.38 (s, 1H), 7.87 (s, 1H), 7.85-7.75 (5H), 7.56-7.51 (2H), 7.47-7.42 (1H), 7.39-7.24 (4H), 4.83 (s, 2H), 3.61 (m, 2H), 3.56 (s, 2H), 3.43 (m, 2H), 3.34 (s, 3H), 2.78 (s, 3H), 2.43 (m, 4H), 2.05 (s, 3H).

Example 5(36)

N-{4-[3-amino-6-(3-cyclopropylphenyl)-2-pyrazinyl]phenyl}-1,5-dimethyl-3-oxo-2-phenyl-2,3-dihydro-1H-pyrazole-4-carboxamide $^1$H NMR (250 MHz, CDCl$_3$) δ 10.87 (s, 1H), 8.39 (s, 1H), 7.86-7.77 (m, 4H), 7.75-7.69 (m, 2H), 7.62-7.44 (m, 3H), 7.41-7.29 (m, 3H), 7.03 (d, J=7.7 Hz, 1H), 4.83 (s, 2H), 3.37 (s, 3H), 2.81 (s, 3H), 2.04-1.92 (m, 1H), 1.04-0.94 (m, 2H), 0.80-0.72 (m, 2H).

Example 5(37)

N-(4-{3-amino-6-[3-(dimethylcarbamoyl)phenyl]-2-pyrazinyl}phenyl)-1,5-dimethyl-3-oxo-2-phenyl-2,3-dihydro-1H-pyrazole-4-carboxamide MS (M+H): 548.3;
$^1$H NMR (400 MHz, CDCl$_3$) δ 10.85 (s, 1H), 8.40 (s, 1H), 8.01-7.98 (m, 2H), 7.83-7.76 (m, 4H), 7.55 (t, J=7.6 Hz, 2H), 7.46 (t, J=8.0 Hz, 2H), 7.38-7.34 (m, 3H), 4.84 (s, 2H), 3.35 (s, 3H), 3.12 (s, 3H), 2.99 (s, 3H), 2.80 (s, 3H).

Example 5(38)

N-(4-{3-amino-6-[3-(1-piperazinylsulfonyl)phenyl]-2-pyrazinyl}phenyl)-1,5-dimethyl-3-oxo-2-phenyl-2,3-dihydro-1H-pyrazole-4-carboxamide MS (M+H): 625.3;
$^1$H NMR (400 MHz, CDCl$_3$) δ 10.87 (s, 1H), 8.42 (s, 1H), 8.27 (s, 1H), 8.21 (d, J=7.8 Hz, 1H), 7.82 (d, J=8.7 Hz, 2H), 7.77 (d, J=8.6 Hz, 2H), 7.70 (d, J=7.8 Hz, 1H), 7.61-7.58 (m, J=7.8 Hz, 1H), 7.47 (t, J=7.4 Hz, 1H), 7.36 (d, J=7.5 Hz, 2H), 4.92 (s, 2H), 3.36 (s, 3H), 3.05-2.97 (m, J=3.8 Hz, 4H), 2.95-2.88 (m, 4H), 2.80 (s, 3H).

Example 5(39)

N-[4-(3-amino-6-{3-[(3-oxo-1-piperazinyl)methyl]phenyl}-2-pyrazinyl)phenyl]-1,5-dimethyl-3-oxo-2-phenyl-2,3-dihydro-1H-pyrazole-4-carboxamide MS (M+H): 589.3;
$^1$H NMR (400 MHz, CDCl$_3$) δ 10.84 (s, 1H), 8.38 (s, 1H), 7.89 (s, 1H), 7.85-7.76 (5H), 7.56-7.52 (2H), 7.46-7.43 (1H), 7.40-7.29 (4H), 5.59 (s, 1H), 4.84 (s, 2H), 3.62 (s, 3H), 3.34 (m, 2H), 3.33 (m, 2H), 3.19 (s, 2H), 2.79 (s, 3H), 2.64 (m, 2H).

Example 5(40)

N-(4-{3-amino-6-[2-fluoro-3-(tetrahydro-2H-pyran-4-yloxy)phenyl]-2-pyrazinyl}phenyl)-1,5-dimethyl-3-oxo-2-phenyl-2,3-dihydro-1H-pyrazole-4-carboxamide MS (M+H): 595.2;
$^1$H NMR (400 MHz, CDCl$_3$) δ 10.79 (s, 1H), 8.41 (d, J=2.4 Hz, 1H), 7.75 (d, J=8.7 Hz, 2H), 7.70 (d, J=8.6 Hz, 2H), 7.55 (t, J=7.3 Hz, 1H), 7.52-7.47 (2H), 7.40 (t, J=7.4 Hz, 1H), 7.30 (d, J=7.4 Hz, 2H), 7.05 (t, J=8.0 Hz, 1H), 6.92 (t, J=7.7 Hz, 1H), 4.80 (s, 2H), 4.45-4.38 (m, 1H), 3.99-3.91 (m, 2H), 3.53-3.46 (m, 2H), 3.30 (s, 3H), 2.74 (s, 3H), 2.01-1.92 (m, 2H), 1.85-1.74 (m, 2H).

Example 5(41)

N-(4-{3-amino-6-[3-(3-methoxypropoxy)phenyl]2-pyrazinyl}phenyl)-1,5-dimethyl-3-oxo-2-phenyl-2,3-dihydro-1H-pyrazole-4-carboxamide MS (M+H): 565.3;
$^1$H NMR (400 MHz, CDCl$_3$) δ 10.84 (s, 1H), 8.38 (s, 1H), 7.83-7.76 (m, 4H), 7.57-7.49 (m, 4H), 7.46 (t, J=7.4 Hz, 1H), 7.36 (d, J=7.5 Hz, 2H), 7.32 (t, J=8.0 Hz, 1H), 6.88 (dd, J=8.1, 2.0 Hz, 1H), 4.80 (s, 2H), 4.11 (t, J=6.2 Hz, 2H), 3.56 (t, J=6.2 Hz, 2H), 3.35 (s, 3H), 3.34 (s, 3H), 2.80 (s, 3H), 2.06 (p, J=6.2 Hz, 2H).

Example 5(42)

N-{4-[3-amino-6-(4-pyridinyl)-2-pyrazinyl]phenyl}-1,5-dimethyl-3-oxo-2-phenyl-2,3-dihydro-1H-pyrazole-4-carboxamide MS (M+H): 478.1;
$^1$H NMR (400 MHz, CDCl$_3$) δ 10.88 (s, 1H), 8.65 (d, J=6.1 Hz, 2H), 8.48 (s, 1H), 7.86 (d, J=6.1 Hz, 2H), 7.83 (d, J=8.7 Hz, 2H), 7.76 (d, J=8.6 Hz, 2H), 7.55 (t, J=7.6 Hz, 2H), 7.46 (t, J=7.4 Hz, 1H), 7.36 (d, J=7.4 Hz, 2H), 4.98 (s, 2H), 3.36 (s, 3H), 2.80 (s, 3H).

Example 5(43)

N-(4-{3-amino-6-[3-(3-hydroxy-3-methylbutoxy)phenyl]-2-pyrazinyl}phenyl)-1,5-dimethyl-3-oxo-2-phenyl-2,3-dihydro-1H-pyrazole-4-carboxamide MS (M+H): 579.1;
$^1$H NMR (400 MHz, CDCl$_3$) δ 10.84 (s, 1H), 8.38 (s, 1H), 7.83-7.75 (4H), 7.58-7.50 (4H), 7.46 (t, J=7.5 Hz, 1H), 7.38-7.30 (3H), 6.89 (d, J=8.1, 2.0 Hz, 1H), 4.80 (s, 2H), 4.25 (t, J=6.2 Hz, 2H), 3.35 (s, 3H), 2.80 (s, 3H), 2.27 (s, 1H), 2.01 (t, J=6.2 Hz, 2H), 1.31 (s, 6H).

Example 5(44)

N-(4-{3-amino-6-[3-(1H-pyrazol-1-yl)phenyl]-2-pyrazinyl}phenyl)-1,5-dimethyl-3-oxo-2-phenyl-2,3-dihydro-1H-pyrazole-4-carboxamide MS (M+H): 543.0;
$^1$H NMR (400 MHz, DMSO-d$_6$) δ 10.89 (s, 1H), 8.61 (s, 1H), 8.57 (d, J=2.4 Hz, 1H), 8.37 (s, 1H), 7.91 (d, J=7.9 Hz, 1H), 7.79-7.71 (m, 5H), 7.59-7.46 (m, 4H), 7.42 (d, J=7.3 Hz, 2H), 6.53 (t, 1H), 6.36 (s, 2H), 5.72 (s, 1H), 3.34 (s, 3H), 2.70 (s, 3H).

Example 5(45)

N-(4-{3-amino-6-[3-(tetrahydro-2H-pyran-4-yloxy)phenyl]-2-pyrazinyl}-3-fluorophenyl)-1,5-dimethyl-3-oxo-2-phenyl-2,3-dihydro-1H-pyrazole-4-carboxamide MS (M+H): 595.1;
$^1$H NMR (400 MHz, CDCl$_3$) δ 10.95 (s, 1H), 8.44 (s, 1H), 7.89 (dd, J=12.7, 1.7 Hz, 1H), 7.59-7.42 (6H), 7.38-7.29 (m, 4H), 6.89 (dd, J=8.0, 2.0 Hz, 1H), 4.70 (s, 2H), 4.55 (tt, J=8.0, 3.9 Hz, 1H), 4.03-3.93 (m, 2H), 3.57 (ddd, J=11.5, 8.3, 3.1 Hz, 2H), 3.37 (s, 3H), 2.80 (s, 3H), 2.07-1.97 (m, 2H), 1.80 (dtd, J=12.4, 8.1, 3.9 Hz, 2H).

Example 5(46)

N-(4-{3-amino-6-[3-(1H-pyrazol-3-yl)phenyl]-2-pyrazinyl}phenyl)-1,5-dimethyl-3-oxo-2-phenyl-2,3-dihydro-1H-pyrazole-4-carboxamide MS (M+H) 543.1;
$^1$H NMR (400 MHz, DMSO-d$_6$) δ 10.89 (s, 1H), 8.56 (s, 1H), 8.35 (s, 1H), 7.89 (d, J=7.3 Hz, 1H), 7.80-7.70 (m, 6H), 7.57 (t, J=7.5 Hz, 3H), 7.51-7.40 (m, 5H), 6.77 (d, J=1.9 Hz, 1H), 6.29 (s, 2H), 3.34 (s, 3H), 2.70 (s, 3H).

Example 5(47)

N-{4-[3-amino-6-(6-methoxy-2-pyridinyl)-2-pyrazinyl]phenyl}-1,5-dimethyl-3-oxo-2-phenyl-2,3-dihydro-1H-pyrazole-4-carboxamide MS (M+H): 508.2;
$^1$H NMR (400 MHz, CDCl$_3$) δ 10.85 (s, 1H), 9.00 (s, 1H), 7.87-7.75 (m, 5H), 7.62 (t, J=7.8 Hz, 1H), 7.55 (t, J=7.6 Hz, 2H), 7.46 (t, 1H), 7.36 (d, J=7.4 Hz, 2H), 6.68 (d, J=8.1 Hz, 1H), 4.89 (s, 2H), 4.02 (s, 3H), 3.36 (s, 3H), 2.80 (s, 3H).

Example 5(48)

N-(4-{3-amino-6-[3-fluoro-5-(3-hydroxy-3-methylbutoxy)phenyl]-2-pyrazinyl}phenyl)-1,5-dimethyl-3-oxo-2-phenyl-2,3-dihydro-1H-pyrazole-4-carboxamide MS (M+H): 597.1;
$^1$H NMR (400 MHz, CDCl$_3$) δ 10.85 (s, 1H), 8.34 (s, 1H), 7.83-7.74 (m, 4H), 7.55 (t, J=7.6 Hz, 2H), 7.46 (t, J=7.4 Hz, 1H), 7.36 (d, J=7.4 Hz, 2H), 7.31 (s, 1H), 7.27 (d, J=10.3 Hz, 1H), 6.60 (dt, J=10.3, 2.0 Hz, 1H), 4.87 (s, 2H), 4.21 (t, J=6.3 Hz, 2H), 3.35 (s, 3H), 2.80 (s, 3H), 2.05-1.93 (m, 3H), 1.31 (s, 6H).

Example 5(49)

N-(4-{3-amino-6-[3-fluoro-5-(2-hydroxy-2-methylpropoxy)phenyl]-2-pyrazinyl}phenyl)-1,5-dimethyl-3-oxo-2-phenyl-2,3-dihydro-1H-pyrazole-4-carboxamide MS (M+H): 583.1;
$^1$H NMR (400 MHz, CDCl$_3$) δ 10.86 (s, 1H), 8.35 (s, 1H), 7.82 (d, J=8.6 Hz, 2H), 7.76 (d, J=8.6 Hz, 2H), 7.55 (t, J=7.6 Hz, 2H), 7.46 (t, J=7.4 Hz, 1H), 7.36 (d, J=7.6 Hz, 2H), 7.34 (s, 1H), 7.27 (d, J=10.2 Hz, 1H), 6.60 (d, J=10.3 Hz, 1H), 4.87 (s, 2H), 3.83 (s, 2H), 3.35 (s, 3H), 2.80 (s, 3H), 2.20 (s, 1H), 1.34 (s, 6H).

Example 5(50)

N-(4-{3-amino-6-[3-(2-hydroxy-2-methylpropoxy)phenyl]-2-pyrazinyl}phenyl)-2-(3-chlorophenyl)-1,5-dimethyl-3-oxo-2,3-dihydro-1H-pyrazole-4-carboxamide MS (M+H): 599.1;
$^1$H NMR (400 MHz, CDCl$_3$) δ 10.71 (s, 1H), 8.39 (s, 1H), 7.84-7.76 (m, 4H), 7.57-7.26 (7H), 6.90 (d, J=8.1 Hz, 1H), 4.81 (s, 2H), 3.85 (s, 2H), 3.36 (s, 3H), 2.81 (s, 3H).

Example 5(51)

N-{4-[3-amino-6-(1H-pyrazol-5-yl)-2-pyrazinyl]phenyl}-2-(3-chlorophenyl)-1,5-dimethyl-3-oxo-2,3-dihydro-1H-pyrazole-4-carboxamide MS (M+H): 501.0;
$^1$H NMR (400 MHz, CDCl$_3$) δ 10.72 (s, 1H), 8.38 (s, 1H), 7.81 (d, J=8.6 Hz, 2H), 7.73 (d, J=8.5 Hz, 2H), 7.60 (d, J=1.7 Hz, 1H), 7.48 (t, J=7.9 Hz, 1H), 7.42 (d, J=8.3 Hz, 1H), 7.38 (s, 1H), 7.28 (d, J=7.8 Hz, 1H), 6.68 (d, J=1.9 Hz, 1H), 4.91 (s, 2H), 3.36 (s, 3H), 2.80 (s, 3H).

Example 5(52)

N-(4-{3-amino-6-[4-(methylsulfonyl)phenyl]-2-pyrazinyl}phenyl)-1,5-dimethyl-3-oxo-2-phenyl-2,3-dihydro-1H-pyrazole-4-carboxamide MS (M+H): 555.3;
$^1$H NMR (400 MHz, CD$_3$OD) δ 8.38 (s, 1H), 8.16-8.07 (m, 2H), 7.95-7.88 (m, 2H), 7.74 (s, 4H), 7.59-7.43 (m, 3H), 7.36-7.30 (m, 2H), 3.35 (s, 3H), 3.05 (s, 3H), 2.74 (s, 3H).

Example 5(53)

N-(4-{3-amino-6-[3-(1-piperidinylmethyl)phenyl]-2-pyrazinyl}phenyl)-1,5-dimethyl-3-oxo-2-phenyl-2,3-dihydro-1H-pyrazole-4-carboxamide MS (M+H): 574.5;
$^1$H NMR (400 MHz, CDCl$_3$) δ 10.84 (s, 1H), 8.39 (s, 1H), 7.86-7.76 (m, 6H), 7.53 (t, J=7.6 Hz, 2H), 7.44 (t, J=7.4 Hz, 1H), 7.38-7.30 (m, 4H), 4.83 (s, 2H), 3.55 (s, 2H), 3.33 (s, 3H), 2.78 (s, 3H), 2.41 (br s, 4H), 1.63-1.49 (m, 4H), 1.44-1.38 (m, 2H).

Example 5(54)

N-(4-{3-amino-6-[4-(4-morpholinyl)phenyl]-2-pyrazinyl}phenyl)-1,5-dimethyl-3-oxo-2-phenyl-2,3-dihydro-1H-pyrazole-4-carboxamide $^1$H NMR (250 MHz, CDCl$_3$) δ 10.91 (s, 1H), 8.21 (s, 1H), 7.90-7.75 (6H), 7.62-7.44 (m, 3H), 7.37 (d, J=7.3 Hz, 2H), 6.98 (d, J=8.8 Hz, 2H), 5.73 (s, 2H), 3.93-3.83 (m, 4H), 3.38 (s, 3H), 3.27-3.17 (m, 4H), 2.82 (s, 3H).

Example 5(55)

N-(4-{3-amino-6-[5-(methylsulfonyl)-3-pyridinyl]-2-pyrazinyl}phenyl)-1,5-dimethyl-3-oxo-2-phenyl-2,3-dihydro-1H-pyrazole-4-carboxamide $^1$H NMR (250 MHz, CDCl$_3$) δ 10.91 (s, 1H), 9.41 (s, 1H), 9.11 (s, 1H), 8.76 (s, 1H), 8.41 (s, 1H), 7.92-7.69 (m, 4H), 7.62-7.44 (m, 3H), 7.37 (d, J=7.2 Hz, 2H), 5.78 (s, 2H), 3.38 (s, 3H), 3.16 (s, 3H), 2.81 (s, 3H).

Example 5(56)

N-(4-{3-amino-6-[5-(methylsulfonyl)-3-pyridinyl]-2-pyrazinyl}phenyl)-1,5-dimethyl-3-oxo-2-phenyl-2,3-dihydro-1H-pyrazole-4-carboxamide $^1$H NMR (250 MHz, CDCl$_3$) δ 10.91 (s, 1H), 9.41 (s, 1H), 9.11 (s, 1H), 8.76 (s, 1H), 8.41 (s, 1H), 7.92-7.69 (m, 4H), 7.62-7.44 (m, 3H), 7.37 (d, J=7.2 Hz, 2H), 5.78 (s, 2H), 3.38 (s, 3H), 3.16 (s, 3H), 2.81 (s, 3H).

Example 5(57)

N-(4-{3-amino-6-[3-methoxy-5-(trifluoromethyl)phenyl]-2-pyrazinyl}phenyl)-1,5-dimethyl-3-oxo-2-phenyl-2,3-dihydro-1H-pyrazole-4-carboxamide $^1$H NMR (400 MHz, CDCl$_3$) δ 10.89 (s, 1H), 8.30 (s, 1H), 7.85 (d, J=8.4 Hz, 2H), 7.78-7.72 (m, 3H), 7.67 (s, 1H), 7.55 (t, J=7.6 Hz, 2H), 7.47 (t, J=7.2 Hz, 1H), 7.36 (d, J=8.0 Hz, 2H), 7.11 (s, 1H), 5.74 (s, 2H), 3.89 (s, 3H), 3.36 (s, 3H), 2.80 (s, 3H).

Example 5(58)

N-{4-[3-amino-6-(2-chloro-5-methoxyphenyl)-2-pyrazinyl]phenyl}-1,5-dimethyl-3-oxo-2-phenyl-2,3-dihydro-1H-pyrazole-4-carboxamide $^1$H NMR (400 MHz, CDCl$_3$) δ 10.83 (s, 1H), 8.34 (s, 1H), 7.82-7.73 (m, 4H), 7.54 (t, J=7.6 Hz, 2H), 7.45 (t, J=7.4 Hz, 1H), 7.38-7.31 (m, 3H), 7.17 (d, J=3.0 Hz, 1H), 6.83 (dd, J=8.8, 3.1 Hz, 1H), 4.85 (s, 2H), 3.80 (s, 3H), 3.35 (s, 3H), 2.79 (s, 3H).

Example 5(59)

N-(4-{3-amino-6-[5-(trifluoromethyl)-3-pyridinyl]-2-pyrazinyl}phenyl)-1,5-dimethyl-3-oxo-2-phenyl-2,3-dihydro-1H-pyrazole-4-carboxamide $^1$H NMR (250 MHz, CDCl$_3$) δ 10.91 (s, 1H), 9.34 (s, 1H), 8.84 (s, 1H), 8.52 (s, 1H), 8.48 (s, 1H), 7.89-7.74 (m, 4H), 7.62-7.44 (m, 3H), 7.37 (d, J=7.1 Hz, 2H), 5.04 (s, 2H), 3.38 (s, 3H), 2.82 (s, 3H).

Example 5(60)

N-(4-{3-amino-6-[2-(trifluoromethyl)-4-pyridinyl]-2-pyrazinyl}phenyl)-1,5-dimethyl-3-oxo-2-phenyl-2,3-dihydro-1H-pyrazole-4-carboxamide $^1$H NMR (250 MHz, CDCl$_3$) δ 10.92 (s, 1H), 8.76 (d, J=5.2 Hz, 1H), 8.54 (s, 1H), 8.27 (s, 1H), 8.07 (d, J=5.0 Hz, 1H), 7.89-7.73 (m, 4H), 7.62-7.44 (m, 3H), 7.37 (d, J=7.1 Hz, 2H), 5.16 (s, 2H), 3.38 (s, 3H), 2.82 (s, 3H).

Example 5(61)

N-{4-[3-amino-6-(2-pyridinyl)-2-pyrazinyl]phenyl}-1,5-dimethyl-3-oxo-2-phenyl-2,3-dihydro-1H-pyrazole-4-carboxamide $^1$H NMR (250 MHz, CDCl$_3$) δ 10.89 (s, 1H), 9.02 (s, 1H), 8.62 (d, J=4.0 Hz, 1H), 8.29 (d, J=8.0 Hz, 1H), 7.88-7.75 (m, 5H), 7.57 (t, J=7.3 Hz, 2H), 7.47 (t, J=7.3 Hz, 1H), 7.37 (d, J=7.1 Hz, 2H), 7.23 (dd, J=7.0, 5.4 Hz, 1H), 4.98 (s, 2H), 3.37 (s, 3H), 2.82 (s, 3H).

Example 5(62)

N-(4-{3-amino-6-[3-fluoro-4-(4-morpholinylmethyl)phenyl]-2-pyrazinyl}phenyl)-1,5-dimethyl-3-oxo-2-phenyl-2,3-dihydro-1H-pyrazole-4-carboxamide $^1$H NMR (250 MHz, CDCl$_3$) δ 10.89 (s, 1H), 8.39 (s, 1H), 7.87-7.75 (m, 4H), 7.73-7.65 (m, 2H), 7.62-7.42 (m, 4H), 7.37 (d, J=7.1 Hz, 2H), 4.90 (s, 2H), 3.76-3.68 (m, 4H), 3.61 (s, 2H), 3.38 (s, 3H), 2.82 (s, 3H), 2.56-2.45 (m, 4H).

Example 5(63)

N-(4-{3-amino-6-[2-fluoro-3-(2-propanyloxy)phenyl]-2-pyrazinyl}phenyl)-1,5-dimethyl-3-oxo-2-phenyl-2,3-dihydro-1H-pyrazole-4-carboxamide $^1$H NMR (250 MHz, CDCl$_3$) δ 10.87 (s, 1H), 8.49 (d, J=2.4 Hz, 1H), 7.85-7.74 (m, 4H), 7.61-7.43 (m, 4H), 7.36 (d, J=7.4 Hz, 2H), 7.11 (t, J=8.1 Hz, 1H), 6.97 (t, J=7.7 Hz, 1H), 4.89 (s, 2H), 4.63-4.48 (m, 1H), 3.37 (s, 3H), 2.81 (s, 3H), 1.39 (d, J=6.1 Hz, 6H).

Example 5(64)

N-(4-{3-amino-6-[2-fluoro-5-(1-pyrrolidinylcarbonyl)phenyl]-2-pyrazinyl}phenyl)-1,5-dimethyl-3-oxo-2-phenyl-2,3-dihydro-1H-pyrazole-4-carboxamide $^1$H NMR (250 MHz, CDCl$_3$) δ 10.88 (s, 1H), 8.51 (d, J=2.3 Hz, 1H), 8.24 (dd, J=7.4, 2.1 Hz, 1H), 7.86-7.73 (m, 4H), 7.62-7.43 (m, 4H), 7.37 (d, J=7.2 Hz, 2H), 7.17 (dd, J=10.9, 8.5 Hz, 1H), 4.96 (s, 2H), 3.63 (t, J=6.7 Hz, 2H), 3.46 (t, J=6.3 Hz, 2H), 3.37 (s, 3H), 2.81 (s, 3H), 2.07-1.80 (m, 4H).

Example 5(65)

N-{4-[3-amino-6-(2-fluoro-3-methoxyphenyl)-5-methyl-2-pyrazinyl]phenyl}-1,5-dimethyl-3-oxo-2-phenyl-2,3-dihydro-1H-pyrazole-4-carboxamide

MS (M+H): 539.2;

$^1$H NMR (400 MHz, CD$_3$OD/CDCl$_3$) δ 10.71 (s, 1H), 7.67 (d, J=8.7 Hz, 2H), 7.61 (d, J=8.6 Hz, 2H), 7.51 (t, J=7.4 Hz,

3H), 7.44 (t, J=7.4 Hz, 1H), 7.30 (d, J=10.1 Hz, 2H), 7.08 (t, J=8.0 Hz, 1H), 6.97-6.92 (m, 2H), 3.85 (s, 3H), 3.31 (s, 3H), 2.70 (s, 3H), 2.27 (s, 4H).

Example 5(66)

N-{4-[3-amino-6-(3-{[(2-methyl-2-propanyl)oxy]methyl}phenyl)-2-pyrazinyl]phenyl}-1,5-dimethyl-3-oxo-2-phenyl-2,3-dihydro-1H-pyrazole-4-carboxamide MS (M+H): 563.3;
$^1$H NMR (400 MHz, CDCl$_3$) δ 10.84 (s, 1H), 8.40 (s, 1H), 7.91 (s, 1H), 7.85-7.76 (m, 5H), 7.55 (t, J=7.5 Hz, 2H), 7.46 (t, J=7.5 Hz, 1H), 7.36 (q, J=7.4 Hz, 4H), 4.78 (s, 2H), 4.50 (s, 2H), 3.35 (s, 3H), 2.80 (s, 3H), 1.30 (s, 9H).

Example 5(67)

N-{5-[3-amino-6-(3,5-dimethoxyphenyl)-2-pyrazinyl]-2-pyridinyl}-1,5-dimethyl-3-oxo-2-phenyl-2,3-dihydro-1H-pyrazole-4-carboxamide MS (M+H): 538.2;
$^1$H NMR (400 MHz, CDCl$_3$) δ 11.30 (s, 1H), 8.79 (s, 1H), 8.42-8.31 (m, 2H), 8.14 (dd, J=8.4, 1.9 Hz, 1H), 7.56-7.49 (m, 2H), 7.48-7.40 (m, 1H), 7.38-7.31 (m, 2H), 7.11 (d, J=2.3 Hz, 2H), 6.47 (t, J=2.3 Hz, 1H), 4.89 (s, 2H), 3.84 (s, 6H), 3.36 (s, 3H), 2.78 (s, 3H).

Example 5(68)

N-[4-(3-amino-6-{3-[(1,1-dioxido-4-thiomorpholinyl)methyl]phenyl}-2-pyrazinyl)phenyl]-1,5-dimethyl-3-oxo-2-phenyl-2,3-dihydro-1H-pyrazole-4-carboxamide MS (M+H): 624.0;
$^1$H NMR (400 MHz, CDCl$_3$) δ 10.86 (s, 1H), 8.38 (s, 1H), 7.88 (s, 1H), 7.85 (d, J=8.0 Hz, 1H), 7.83-7.75 (4H), 7.55 (t, J=7.6 Hz, 2H), 7.46 (t, J=7.4 Hz, 1H), 7.40 (t, J=7.7 Hz, 1H), 7.36 (d, J=7.5 Hz, 2H), 7.29 (d, J=7.6 Hz, 1H), 4.82 (s, 2H), 3.70 (s, 2H), 3.36 (s, 3H), 3.08-2.97 (8H), 2.80 (s, 3H).

Example 5(69)

N-[4-(3-amino-6-{4-[2-(1H-pyrazol-1-yl)ethoxy]phenyl}-2-pyrazinyl)phenyl]-1,5-dimethyl-3-oxo-2-phenyl-2,3-dihydro-1H-pyrazole-4-carboxamide MS (M+H): 587.2;
$^1$H NMR (400 MHz, CDCl$_3$) δ 10.83 (s, 1H), 8.32 (s, 1H), 7.87 (d, J=8.8 Hz, 2H), 7.82-7.75 (m, 4H), 7.57-7.50 (m, 4H), 7.47 (d, J=7.4 Hz, 1H), 7.36 (d, J=7.5 Hz, 2H), 6.91 (d, J=8.7 Hz, 2H), 6.25 (s, 1H), 4.73 (s, 2H), 4.53 (t, J=5.2 Hz, 2H), 4.36 (t, J=5.2 Hz, 2H), 3.35 (s, 3H), 2.80 (s, 3H).

Example 5(70)

N-[4-(3-amino-6-phenyl-2-pyrazinyl)phenyl]-1,5-dimethyl-3-oxo-2-phenyl-2,3-dihydro-1H-pyrazole-4-carboxamide MS (M+H): 477.1;
$^1$H NMR (400 MHz, CDCl$_3$) δ 10.84 (s, 1H), 8.40 (s, 1H), 7.96 (d, J=7.4 Hz, 2H), 7.83-7.77 (m, 4H), 7.55 (t, J=7.6 Hz, 2H), 7.51-7.40 (m, 3H), 7.38-7.31 (m, 3H), 4.79 (s, 2H), 3.35 (s, 3H), 2.80 (s, 3H).

Example 5(71)

N-(4-{3-amino-6-[3-(cyclopropyloxy)phenyl]-2-pyrazinyl}phenyl)-1,5-dimethyl-3-oxo-2-phenyl-2,3-dihydro-1H-pyrazole-4-carboxamide MS (M+H): 533.1;
$^1$H NMR (400 MHz, CDCl$_3$) δ 10.84 (s, 1H), 8.38 (s, 1H), 7.82-7.77 (m, 4H), 7.67 (s, 1H), 7.58-7.52 (m, 3H), 7.46 (t, J=7.4 Hz, 1H), 7.38-7.31 (m, 3H), 7.03 (dd, J=8.1, 1.9 Hz, 1H), 4.80 (s, 2H), 3.82-3.78 (m, 1H), 3.35 (s, 3H), 2.80 (s, 3H), 0.78 (d, J=4.5 Hz, 4H).

Example 5(72)

N-(4-{3-amino-6-[3-(cyclopropyloxy)-2-fluorophenyl]-2-pyrazinyl}phenyl)-1,5-dimethyl-3-oxo-2-phenyl-2,3-dihydro-1H-pyrazole-4-carboxamide MS (M+H): 551.0;
$^1$H NMR (400 MHz, CDCl$_3$) δ 10.84 (s, 1H), 8.46 (d, J=2.4 Hz, 1H), 7.82-7.74 (m, 4H), 7.60-7.52 (m, 3H), 7.46 (t, J=7.4 Hz, 1H), 7.36 (d, J=7.4 Hz, 2H), 7.28-7.25 (m, 1H), 7.13 (t, J=8.4 Hz, 1H), 4.85 (s, 2H), 3.86-3.82 (m, 1H), 3.35 (s, 3H), 2.80 (s, 3H), 0.89-0.83 (m, 2H), 0.83-0.76 (m, 2H).

Example 5(73)

N-(4-{3-amino-6-[3-fluoro-2-(4-morpholinyl)-4-pyridinyl]-2-pyrazinyl}phenyl)-1,5-dimethyl-3-oxo-2-phenyl-2,3-dihydro-1H-pyrazole-4-carboxamide MS (M+H): 581.1;
$^1$H NMR (400 MHz, CDCl$_3$) δ 10.86 (s, 1H), 8.51 (d, J=2.4 Hz, 1H), 8.04 (d, J=5.2 Hz, 1H), 7.81 (d, J=8.8 Hz, 2H), 7.73 (d, J=8.8 Hz, 2H), 7.56-7.52 (2H), 7.49-7.45 (2H), 7.36-7.34 (2H), 4.99 (s, 2H), 3.86 (m, 4H), 3.47 (m, 4H), 3.52 (s, 3H), 2.79 (s, 3H).

Example 5(74)

N-{4-[3-amino-6-(2-chloro-3-fluoro-4-pyridinyl)-2-pyrazinyl]phenyl}-1,5-dimethyl-3-oxo-2-phenyl-2,3-dihydro-1H-pyrazole-4-carboxamide MS (M+H): 530.0;
$^1$H NMR (400 MHz, CDCl$_3$) δ 10.88 (s, 1H), 8.61 (d, J=2.0 Hz, 1H), 8.21 (d, J=5.2 Hz, 1H), 8.01 (t, J=5.2 Hz, 1H), 7.82 (d, J=8.8 Hz, 2H), 7.72 (d, J=8.8 Hz, 2H), 7.57-7.53 (2H), 7.48-7.46 (1H), 7.36-7.34 (2H), 5.11 (s, 2H), 3.36 (s, 3H), 2.79 (s, 3H).

Example 5(75)

N-{4-[3-amino-6-(3-{[4-(methylsulfonyl)-1-piperazinyl]methyl}phenyl)-2-pyrazinyl]phenyl}-1,5-dimethyl-3-oxo-2-phenyl-2,3-dihydro-1H-pyrazole-4-carboxamide MS (M+H): 653.1;
$^1$H NMR (400 MHz, CDCl$_3$) δ 10.85 (s, 1H), 8.39 (s, 1H), 7.90 (s, 1H), 7.86-7.73 (5H), 7.57-7.50 (m, 2H), 7.48-7.42

(m, 1H), 7.41-7.32 (m, 3H), 7.27 (d, J=7.6 Hz, 1H), 4.83 (s, 2H), 3.59 (s, 2H), 3.35 (s, 3H), 3.29-3.15 (m, 4H), 2.79 (s, 3H), 2.75 (s, 3H), 2.64-2.50 (m, 4H).

Example 5(76)

N-(4-{3-amino-6-[3-(1,1-dioxido-2-isothiazolidinyl)phenyl]-2-pyrazinyl}phenyl)-1,5-dimethyl-3-oxo-2-phenyl-2,3-dihydro-1H-pyrazole-4-carboxamide MS (M+H): 596.7;
$^1$H NMR (400 MHz, DMSO-d$_6$) δ 10.88 (s, 1H), 8.47 (s, 1H), 7.77-7.69 (m, 5H), 7.57 (t, 2H), 7.49 (t, 1H), 7.43-7.38 (m, 4H), 7.18 (d, J=8.0 Hz, 1H), 6.32 (s, 2H), 3.79 (t, J=6.4 Hz, 2H), 3.51-3.47 (m, 2H), 3.34 (s, 3H), 2.69 (s, 3H), 2.43-2.35 (m, 2H).

Example 5(77)

N-(4-{3-amino-6-[2-(4-morpholinyl)-4-pyridinyl]-2-pyrazinyl}-3-fluorophenyl)-1,5-dimethyl-3-oxo-2-phenyl-2,3-dihydro-1H-pyrazole-4-carboxamide MS (M+H): 581.1;
$^1$H NMR (400 MHz, CDCl$_3$) δ 10.96 (s, 1H), 8.48 (s, 1H), 8.23 (d, J=5.3 Hz, 1H), 7.88 (d, J=14.1 Hz, 1H), 7.56 (t, J=7.6 Hz, 2H), 7.51-7.45 (m, 2H), 7.39-7.33 (m, 4H), 7.14 (d, J=4.9 Hz, 1H), 4.81 (s, 2H), 3.84-3.81 (m, 4H), 3.58-3.55 (m, 4H), 3.37 (s, 3H), 2.79 (s, 3H).

Example 5(78)

N-{4-[3-amino-6-(3-methyl-4-pyridinyl)-2-pyrazinyl]phenyl}-1,5-dimethyl-3-oxo-2-phenyl-2,3-dihydro-1H-pyrazole-4-carboxamide MS (M+H): 492.0;
$^1$H NMR (400 MHz, CDCl$_3$) δ 10.85 (s, 1H), 8.50 (s, 1H), 8.48 (d, J=5.1 Hz, 1H), 8.14 (s, 1H), 7.81 (d, J=8.6 Hz, 2H), 7.73 (d, J=8.6 Hz, 2H), 7.55 (t, J=7.6 Hz, 2H), 7.46 (t, J=7.4 Hz, 1H), 7.39 (d, J=5.0 Hz, 1H), 7.35 (d, J=7.4 Hz, 2H), 4.92 (s, 2H), 3.35 (s, 3H), 2.80 (s, 3H), 2.47 (s, 3H).

Example 5(79)

N-{4-[3-amino-6-(3-cyanophenyl)-2-pyrazinyl]phenyl}-1,5-dimethyl-3-oxo-2-phenyl-2,3-dihydro-1H-pyrazole-4-carboxamide MS (M+H): 502.0;
$^1$H NMR (400 MHz, DMSO-d$_6$) δ 10.89 (s, 1H), 8.62 (s, 1H), 8.39 (s, 1H), 8.31 (d, J=8.1 Hz, 1H), 7.78-7.70 (m, 5H), 7.61 (t, J=7.9 Hz, 1H), 7.57 (t, J=7.6 Hz, 2H), 7.49 (t, J=7.4 Hz, 1H), 7.42 (d, J=7.3 Hz, 2H), 6.46 (s, 2H), 3.34 (s, 3H), 2.69 (s, 3H).

Example 5(80)

N-(4-{3-amino-6-[3-(tetrahydro-2H-pyran-4-yloxy)phenyl]-2-pyrazinyl}-2-methylphenyl)-1,5-dimethyl-3-oxo-2-phenyl-2,3-dihydro-1H-pyrazole-4-carboxamide MS (M+H): 591.1;
$^1$H NMR (400 MHz, CDCl$_3$) δ 10.67 (s, 1H), 8.50 (d, J=8.4 Hz, 1H), 8.37 (s, 1H), 7.69-7.61 (m, 2H), 7.59-7.50 (m, 4H), 7.45 (t, J=7.4 Hz, 1H), 7.37 (d, J=7.4 Hz, 2H), 7.33 (t, J=7.9 Hz, 1H), 6.89 (dd, J=8.1, 2.0 Hz, 1H), 4.82 (s, 2H), 4.59-4.53 (m, 1H), 4.02-3.95 (m, 2H), 3.57 (ddd, J=11.5, 8.3, 3.2 Hz, 2H), 3.34 (s, 3H), 2.81 (s, 3H), 2.45 (s, 3H), 2.08-1.99 (m, 2H), 1.87-1.75 (m, 2H).

Example 5(81)

N-{4-[3-amino-6-(2-fluoro-3-methoxyphenyl)-2-pyrazinyl]-3-fluorophenyl}-1,5-dimethyl-3-oxo-2-phenyl-2,3-dihydro-1H-pyrazole-4-carboxamide MS (M+H): 543.0;
$^1$H NMR (400 MHz, CDCl$_3$) δ 10.94 (s, 1H), 8.55 (d, J=2.5 Hz, 1H), 7.90 (dd, J=12.7, 1.8 Hz, 1H), 7.57-7.49 (m, 4H), 7.47 (t, J=7.4 Hz, 1H), 7.37-7.31 (m, 3H), 7.12 (t, J=8.0 Hz, 1H), 6.93 (dd, J=7.9, 6.8 Hz, 1H), 4.74 (s, 2H), 3.91 (s, 3H), 3.36 (s, 3H), 2.79 (s, 3H).

Example 5(82)

N-{4-[3-amino-6-(3-fluoro-4-pyridinyl)-2-pyrazinyl]phenyl}-1,5-dimethyl-3-oxo-2-phenyl-2,3-dihydro-1H-pyrazole-4-carboxamide MS (M+H): 496.0;
$^1$H NMR (400 MHz, CDCl$_3$) δ 10.83 (s, 1H), 8.57 (d, J=1.6 Hz, 1H), 8.46 (d, J=3.2 Hz, 1H), 8.40 (d, J=5.0 Hz, 1H), 8.01 (dd, J=6.8, 5.2 Hz, 1H), 7.78 (d, J=8.6 Hz, 2H), 7.69 (d, J=8.6 Hz, 2H), 7.50 (t, J=7.6 Hz, 3H), 7.41 (t, J=7.4 Hz, 1H), 7.30 (d, J=7.4 Hz, 2H), 4.98 (s, 2H), 3.31 (s, 3H), 2.75 (s, 3H).

Example 5(83)

N-{4-[3-amino-6-(2-fluoro-3-methoxyphenyl)-2-pyrazinyl]-3-methylphenyl}-1,5-dimethyl-3-oxo-2-phenyl-2,3-dihydro-1H-pyrazole-4-carboxamide MS (M+H): 539.1;
$^1$H NMR (400 MHz, CDCl$_3$) δ 10.77 (s, 1H), 8.51 (d, J=2.4 Hz, 1H), 7.69 (s, 1H), 7.59 (dd, J=8.3, 1.9 Hz, 1H), 7.55-7.50 (m, 2H), 7.49-7.42 (m, 2H), 7.36 (d, J=7.4 Hz, 2H), 7.32 (d, J=8.3 Hz, 1H), 7.09 (t, J=7.6 Hz, 1H), 6.92 (t, J=7.4 Hz, 1H), 4.59 (s, 2H), 3.91 (s, 3H), 3.35 (s, 3H), 2.80 (s, 3H), 2.25 (s, 3H).

Example 5(84)

N-(4-{3-amino-6-[2-(4-morpholinyl)-4-pyridinyl]-2-pyrazinyl}-3-methylphenyl)-1,5-dimethyl-3-oxo-2-phenyl-2,3-dihydro-1H-pyrazole-4-carboxamide MS (M+H): 577.1;
$^1$H NMR (400 MHz, CDCl$_3$) δ 10.80 (s, 1H), 8.45 (s, 1H), 8.22 (d, J=5.2 Hz, 1H), 7.70 (d, J=1.3 Hz, 1H), 7.60 (dd, J=8.3, 1.7 Hz, 1H), 7.55 (t, J=7.6 Hz, 2H), 7.46 (t, J=7.4 Hz, 1H), 7.36 (d, J=7.5 Hz, 2H), 7.32 (d, J=8.3 Hz, 1H), 7.24 (s, 1H), 7.13 (d, J=5.1 Hz, 1H), 4.69 (s, 2H), 3.83-3.80 (m, 4H), 3.56-3.53 (m, 4H), 3.36 (s, 3H), 2.80 (s, 3H), 2.23 (s, 3H).

Example 5(85)

N-(4-{3-amino-6-[3-(tetrahydro-2H-pyran-4-yloxy)phenyl]-2-pyrazinyl}-3-methylphenyl)-1,5-dimethyl-3-oxo-2-phenyl-2,3-dihydro-1H-pyrazole-4-carboxamide MS (M+H): 591.1;
$^1$H NMR (400 MHz, CDCl$_3$) δ 10.78 (s, 1H), 8.40 (s, 1H), 7.70 (d, J=1.2 Hz, 1H), 7.60 (dd, J=8.3, 1.7 Hz, 1H), 7.54 (t, J=7.6 Hz, 2H), 7.50 (s, 1H), 7.49-7.43 (m, 2H), 7.36 (d, J=7.4 Hz, 2H), 7.34-7.28 (m, 2H), 6.87 (dd, J=8.0, 2.0 Hz, 1H), 4.57-4.52 (m, 3H), 4.00-3.94 (m, 2H), 3.56 (ddd, J=11.5, 8.3, 3.1 Hz, 2H), 3.35 (s, 3H), 2.80 (s, 3H), 2.25 (s, 3H), 2.05-1.98 (m, 2H), 1.83-1.74 (m, 2H).

Example 5(86)

N-(4-{3-amino-6-[2-(4-morpholinyl)-4-pyridinyl]-2-pyrazinyl}-3-methoxyphenyl)-1,5-dimethyl-3-oxo-2-phenyl-2,3-dihydro-1H-pyrazole-4-carboxamide MS (M+H): 593.3;
$^1$H NMR (400 MHz, CDCl$_3$) δ 10.92 (s, 1H), 8.45 (s, 1H), 8.22 (d, J=5.2 Hz, 1H), 7.62 (s, 1H), 7.55 (t, J=7.6 Hz, 2H), 7.47 (t, J=7.4 Hz, 1H), 7.41 (d, J=8.2 Hz, 1H), 7.36 (d, J=7.4 Hz, 2H), 7.31 (d, J=8.3 Hz, 1H), 7.28 (s, 1H), 7.15 (d, J=5.2 Hz, 1H), 4.86 (s, 2H), 3.86 (s, 3H), 3.83-3.80 (m, 4H), 3.57-3.54 (m, 4H), 3.37 (s, 3H), 2.80 (s, 3H).

Example 5(87)

N-(4-{3-amino-6-[3-fluoro-5-(tetrahydro-2H-pyran-4-yloxy)phenyl]-2-pyrazinyl}-2-methylphenyl)-1,5-dimethyl-3-oxo-2-phenyl-2,3-dihydro-1H-pyrazole-4-carboxamide MS (M+H): 609.1;
$^1$H NMR (400 MHz, CDCl$_3$) δ 10.68 (s, 1H), 8.51 (d, J=8.5 Hz, 1H), 8.34 (s, 1H), 7.64 (d, J=8.5 Hz, 1H), 7.60 (s, 1H), 7.55 (t, J=7.6 Hz, 2H), 7.46 (t, J=7.4 Hz, 1H), 7.37 (d, J=7.6 Hz, 2H), 7.32 (s, 1H), 7.27 (s, 1H), 6.59 (d, J=10.5 Hz, 1H), 4.87 (s, 2H), 4.53 (tt, J=7.3, 3.5 Hz, 1H), 4.00-3.94 (m, 2H), 3.58 (ddd, J=11.6, 8.3, 3.0 Hz, 2H), 3.34 (s, 3H), 2.81 (s, 3H), 2.45 (s, 3H), 2.06-2.00 (m, 2H), 1.81 (ddd, J=17.3, 8.1, 3.9 Hz, 2H).

Example 5(88)

N-(4-{3-amino-6-[3-fluoro-5-(tetrahydro-2H-pyran-4-yloxy)phenyl]-2-pyrazinyl}-3-methylphenyl)-1,5-dimethyl-3-oxo-2-phenyl-2,3-dihydro-1H-pyrazole-4-carboxamide MS (M+H): 609.1;
NMR (400 MHz, CDCl$_3$) δ 10.74 (s, 1H), 8.32 (s, 1H), 7.65 (s, 1H), 7.55 (d, J=8.2 Hz, 1H), 7.49 (t, J=7.6 Hz, 2H), 7.40 (t, J=7.4 Hz, 1H), 7.35-7.29 (m, 2H), 7.26 (d, J=8.3 Hz, 1H), 7.23 (s, 1H), 7.16 (dd, J=9.8, 1.3 Hz, 1H), 6.53 (dd, J=10.4, 2.0 Hz, 1H), 4.55 (s, 2H), 4.50-4.44 (m, 1H), 3.94-3.88 (m, 2H), 3.52 (ddd, J=11.5, 8.1, 3.2 Hz, 2H), 3.30 (s, 3H), 2.74 (s, 3H), 2.19 (s, 3H), 2.00-1.93 (m, 2H), 1.74 (ddd, J=12.7, 8.2, 4.0 Hz, 2H).

Example 5(89)

N-(4-{3-amino-6-[3-fluoro-5-(tetrahydro-2H-pyran-4-yloxy)phenyl]-2-pyrazinyl}phenyl)-1,5-dimethyl-3-oxo-2-phenyl-2,3-dihydro-1H-pyrazole-4-carboxamide MS (M+H): 595.1;
$^1$H NMR (400 MHz, CDCl$_3$) δ 10.86 (s, 1H), 8.34 (s, 1H), 7.84-7.74 (m, 4H), 7.55 (t, J=7.6 Hz, 2H), 7.46 (t, J=7.4 Hz, 1H), 7.36 (d, J=7.4 Hz, 2H), 7.33 (s, 1H), 7.26 (s, 1H), 6.59 (dt, J=10.4, 2.2 Hz, 1H), 4.86 (s, 2H), 4.57-4.48 (m, 1H), 4.02-3.94 (m, 2H), 3.58 (ddd, J=11.5, 8.2, 3.2 Hz, 2H), 3.36 (s, 3H), 2.80 (s, 3H), 2.07-2.00 (m, 2H), 1.85-1.76 (m, 2H).

Example 5(90)

N-(4-{3-amino-6-[3-fluoro-5-(tetrahydro-2H-pyran-4-yloxy)phenyl]-2-pyrazinyl}-3-fluorophenyl)-1,5-dimethyl-3-oxo-2-phenyl-2,3-dihydro-1H-pyrazole-4-carboxamide MS (M+H): 613.1;
$^1$H NMR (400 MHz, CDCl$_3$) δ 10.96 (s, 1H), 8.41 (s, 1H), 7.90 (d, J=12.7 Hz, 1H), 7.59-7.42 (m, 5H), 7.35 (d, J=7.7 Hz, 2H), 7.29 (s, 1H), 7.23 (d, J=14.0 Hz, 1H), 6.59 (d, J=10.4 Hz, 1H), 4.76 (s, 2H), 4.58-4.46 (m, 1H), 3.97 (dt, J=9.2, 6.4 Hz, 2H), 3.58 (ddd, J=11.5, 8.3, 3.1 Hz, 2H), 3.37 (s, 3H), 2.80 (s, 3H), 2.09-1.96 (m, 2H), 1.79 (dtd, J=12.1, 8.0, 3.9 Hz, 2H).

Example 5(91)

N-(4-{3-amino-6-[2-(4-morpholinyl)-4-pyridinyl]-2-pyrazinyl}-3-cyclohexen-1-yl)-1,5-dimethyl-3-oxo-2-phenyl-2,3-dihydro-1H-pyrazole-4-carboxamide MS (M+H): 567.2;
$^1$H NMR (400 MHz, CDCl$_3$) δ 8.87 (d, J=8.0 Hz, 1H), 8.31 (s, 1H), 8.21 (d, J=5.2 Hz, 1H), 7.50 (t, J=7.6 Hz, 2H), 7.41 (t, J=7.4 Hz, 1H), 7.30 (d, J=7.4 Hz, 2H), 7.20 (s, 1H), 7.11 (dd, J=5.3, 1.0 Hz, 1H), 6.16 (s, 1H), 5.05 (s, 2H), 4.44-4.37 (m, 1H), 3.85-3.82 (m, 4H), 3.58-3.55 (m, 4H), 3.28 (s, 3H), 2.75 (s, 3H), 2.68-2.57 (m, 4H), 2.31-2.21 (m, 1H), 2.11-2.03 (m, 1H), 2.00-1.90 (m, 1H).

Example 5(92)

N-(4-{3-amino-6-[3-(4-morpholinylmethyl)phenyl]-2-pyrazinyl}phenyl)-2-(3-chlorophenyl)-1,5-dimethyl-3-oxo-2,3-dihydro-1H-pyrazole-4-carboxamide MS (M+H): 610.1;
$^1$H NMR (400 MHz, CDCl$_3$) δ 10.70 (s, 1H), 8.40 (s, 1H), 7.89 (s, 1H), 7.84 (d, J=8.1 Hz, 1H), 7.80 (s, 4H), 7.48 (t, J=8.1 Hz, 1H), 7.42 (d, J=8.6 Hz, 1H), 7.40-7.36 (m, 2H), 7.32 (d, J=7.4 Hz, 1H), 7.28 (d, J=8.0 Hz, 1H), 4.79 (s, 2H), 3.73-3.68 (m, 4H), 3.55 (s, 2H), 3.36 (s, 3H), 2.81 (s, 3H), 2.46 (s, 4H).

Example 5(93)

N-[4-(3-amino-6-{3-[(3-oxo-1-piperazinyl)methyl]phenyl}-2-pyrazinyl)phenyl]-2-(3-chlorophenyl)-1,5-dimethyl-3-oxo-2,3-dihydro-1H-pyrazole-4-carboxamide MS (M+H): 623.2;
$^1$H NMR (400 MHz, CD$_3$OD) δ 8.33 (s, 1H), 8.15 (s, 1H), 8.05 (d, J=7.6 Hz, 1H), 7.76-7.70 (4H), 7.54-7.49 (5H), 7.36 (m, 1H), 7.48 (s, 2H), 3.82 (s, 2H), 3.54 (s, 3H), 3.39 (s, 2H), 2.72 (s, 3H).

Example 5(94)

N-(4-{3-amino-6-[3-fluoro-5-(2-hydroxy-2-methylpropoxy)phenyl]-2-pyrazinyl}phenyl)-2-(3-chlorophenyl)-1,5-dimethyl-3-oxo-2,3-dihydro-1H-pyrazole-4-carboxamide MS (M+H): 617.1;
$^1$H NMR (400 MHz, CDCl$_3$) δ 10.71 (s, 1H), 8.36 (s, 1H), 7.83-7.75 (m, 4H), 7.48 (t, J=7.9 Hz, 1H), 7.42 (d, J=8.4 Hz, 1H), 7.39-7.37 (m, 1H), 7.34 (br s, 1H), 7.29-7.28 (m, 1H), 7.27-7.25 (m, 1H), 6.61 (dt, J=10.3, 2.1 Hz, 1H), 4.87 (s, 2H), 3.83 (s, 2H), 3.36 (s, 3H), 2.80 (s, 3H), 2.20 (s, 1H), 1.34 (s, 6H).

Example 5(95)

N-[4-(3-amino-6-{3-[(4-methyl-1-piperazinyl)methyl]phenyl}-2-pyrazinyl)phenyl]-2-(3-chlorophenyl)-1,5-dimethyl-3-oxo-2,3-dihydro-1H-pyrazole-4-carboxamide MS (M+H): 623.3;
$^1$H NMR (400 MHz, CDCl$_3$) δ 10.70 (s, 1H), 8.40 (s, 1H), 7.88-7.86 (m, 1H), 7.85-7.81 (m, 1H), 7.81-7.76 (m, 4H), 7.48 (t, J=7.9 Hz, 1H), 7.42 (ddd, J=8.1, 1.9, 1.3 Hz, 1H), 7.40-7.34 (m, 2H), 7.33-7.29 (m, 1H), 7.28 (ddd, J=7.8, 2.0, 1.3 Hz, 1H), 4.80 (s, 2H), 3.56 (s, 2H), 3.35 (s, 3H), 2.80 (s, 3H), 2.70-2.30 (m, 8H), 2.27 (s, 3H).

Example 5(96)

N-{4-[3-amino-6-(1-methyl-1H-pyrazol-4-yl)-2-pyrazinyl]phenyl}-2-(3-chlorophenyl)-1,5-dimethyl-3-oxo-2,3-dihydro-1H-pyrazole-4-carboxamide MS (M+H): 515.1;
$^1$H NMR (400 MHz, CDCl$_3$) δ 10.69 (s, 1H), 8.15 (s, 1H), 7.88 (s, 1H), 7.83 (s, 1H), 7.80-7.72 (m, 4H), 7.48 (t, J=8.0 Hz, 1H), 7.42 (d, J=8.3 Hz, 1H), 7.38 (s, 1H), 7.28 (d, J=7.9 Hz, 1H), 4.67 (s, 2H), 3.92 (s, 3H), 3.36 (s, 3H), 2.80 (s, 3H).

Example 5(97)

N-{4-[3-amino-6-(1-methyl-1H-pyrazol-3-yl)-2-pyrazinyl]phenyl}-2-(3-chlorophenyl)-1,5-dimethyl-3-oxo-2,3-dihydro-1H-pyrazole-4-carboxamide MS (M+H): 515.1;
$^1$H NMR (400 MHz, CDCl$_3$) δ 10.68 (s, 1H), 8.56 (s, 1H), 7.80-7.74 (m, 4H), 7.48 (t, J=7.9 Hz, 1H), 7.42 (d, J=8.4 Hz, 1H), 7.38 (t, J=1.8 Hz, 1H), 7.36 (d, J=2.2 Hz, 1H), 7.27 (d, J=7.8 Hz, 1H), 6.77 (d, J=2.2 Hz, 1H), 4.76 (s, 2H), 3.95 (s, 3H), 3.35 (s, 3H), 2.80 (s, 3H).

Example 6

N-{4-[3-amino-6-(4,4,5,5-tetramethyl-1,3,2-dioxaborolan-2-yl)-2-pyrazinyl]phenyl}-1, dimethyl-3-oxo-2-phenyl-2,3-dihydro-1H-pyrazole-4-carboxamide The compound prepared in Example 3 (3.4 g) was dissolved in dioxane (100 mL). Bis(pinacolato)diboron (3.2 g), potassium acetate (1.65 g), and [1,1'-Bis(diphenylphosphino)ferrocene]palladium dichloride complex with DCM (0.4 g) were added in succession. The mixture was degassed with nitrogen for several minutes then was stirred at reflux overnight. The reaction was filtered through celite and the celite was washed with EtOAc (50 mL). The mother liquor was concentrated and found to contain no product. The celite was washed with DCM (200 mL) to give a black solution. This solution was concentrated to give the title compound (3.2 g) having the following physical data as a brown solid.

$^1$H NMR (300 MHz, CDCl$_3$) δ 10.80 (s, 1H), 8.36 (s, 1H), 7.75 (d, J=9.0 Hz, 2H), 7.63 (d, J=8.7 Hz, 2H), 7.60-7.42 (m, 3H), 7.39-7.34 (m, 2H), 4.92 (s, 2H), 3.36 (s, 3H), 2.80 (s, 3H), 1.37 (s, 12H).

Example 7(1)

N-[4-(3-amino-6-{2-fluoro-3-[2-hydroxy-3-(1-pyrrolidinyl)propoxy]phenyl}-2-pyrazinyl)phenyl]-1,5-dimethyl-3-oxo-2-phenyl-2,3-dihydro-1H-pyrazole-4-carboxamide

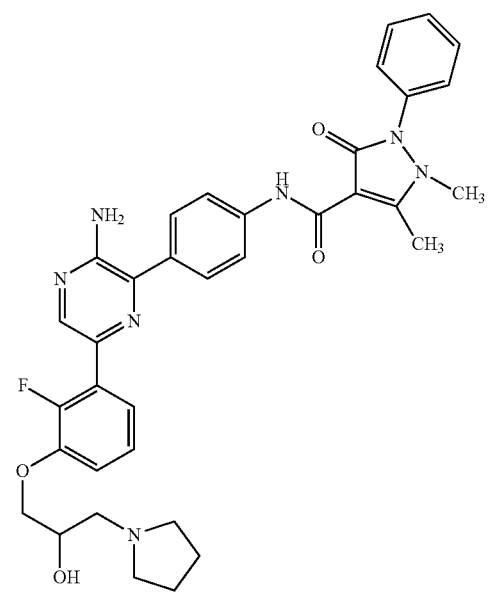 [SMILES: Cc1c(C(=O)Nc2ccc(-c3nc(-c4cccc(OCC(O)CN5CCCC5)c4F)cnc3N)cc2)c(=O)n(-c2ccccc2)n1C]

In a vial was placed the compound prepared in Example 6 (0.199 g) and 1-(3-bromo-2-fluorophenoxy)-3-(pyrrolidin-1-yl)propan-2-ol (0.12 g, 0.377 mmol), tripotassium phosphate (0.754 ml) 2N solution and Pd(PPh$_3$)$_4$ (0.044 g) in 5 mL of dioxane under nitrogen atmosphere. The reaction was left stirring overnight at 85° C. in a heat block. The mixture was cooled down and the dioxane was removed in vacuo. The residue was redissolved in EtOAc and water was added. The product was reextracted with 10% MeOH in DCM three times, dried with Na$_2$SO$_4$, filtered and concentrated to give the crude product. Purification was performed on the Biotage Isolera silica dioxide (SiO$_2$) 50 g cartridge 0-100% DCM (of a 20% MeOH in DCM solution w 2% ammonium hydroxide) to afford product as an orange solid. The solids were triturated in MeOH to give the title compound (0.058 g) having the following physical data as an orange solid.

LCMS: (MH+): 638.3;
$^1$H NMR (400 MHz, CDCl$_3$) δ 10.78 (s, 1H), 8.42 (d, J=2.3 Hz, 1H), 7.75 (d, J=8.7 Hz, 2H), 7.70 (d, J=8.7 Hz, 2H), 7.55-7.45 (3H), 7.40 (t, J=7.5 Hz, 1H), 7.30 (d, J=7.4 Hz, 2H), 7.05 (t, J=8.1 Hz, 1H), 6.92 (t, J=8.0 Hz, 1H), 4.79 (s, 2H), 4.09-3.97 (m, 3H), 3.30 (s, 3H), 2.82-2.76 (m, 1H), 2.74 (s, 3H), 2.69-2.61 (m, 2H), 2.56-2.45 (m, 3H), 1.74 (s, 4H).

Example 7(2)-7(90)

The compound having the following physical data was prepared by using the compound prepared in Example 1 or the corresponding carboxylic acid instead thereof, and using the corresponding bromide instead of 1-(3-bromo-2-fluorophenoxy)-3-(pyrrolidin-1-yl)propan-2-ol in the process of Example 1→Example 2→Example 3→Example 6→Example 7(1).

Example 7(2)

N-[4-(3-amino-6-{2-[3-(hydroxymethyl)-1-piperidinyl]-4-pyridinyl}-2-pyrazinyl)phenyl]-1,5-dimethyl-3-oxo-2-phenyl-2,3-dihydro-1H-pyrazole-4-carboxamide MS (M+H): 591.2;
$^1$H NMR (400 MHz, CDCl$_3$) δ 10.85 (s, 1H), 8.39 (s, 1H), 8.14 (d, J=5.4 Hz, 1H), 7.87-7.71 (m, 4H), 7.57-7.51 (m, 2H), 7.48-7.43 (m, 1H), 7.38-7.33 (m, 2H), 7.30 (s, 1H), 7.04 (dd, J=5.4, 1.3 Hz, 1H), 4.95 (s, 2H), 3.80-3.59 (m, 3H), 3.54-3.37 (m, 3H), 3.35 (s, 3H), 2.79 (s, 3H), 1.99-1.73 (m, 2H), 1.69 (ddt, J=16.2, 8.2, 4.2 Hz, 1H), 1.58-1.47 (m, 1H), 1.41 (ddd, J=12.4, 6.5, 3.8 Hz, 1H).

Example 7(3)

N-{4-[3-amino-6-(4-methoxy-2-pyridinyl)-2-pyrazinyl]phenyl}-1,5-dimethyl-3-oxo-2-phenyl-2,3-dihydro-1H-pyrazole-4-carboxamide MS (M+H): 508.1;
$^1$H NMR (400 MHz, CDCl$_3$) δ 10.85 (s, 1H), 8.99 (s, 1H), 8.42 (d, J=5.7 Hz, 1H), 7.83-7.75 (m, 5H), 7.54 (t, J=7.6 Hz, 2H), 7.45 (t, J=7.4 Hz, 1H), 7.35 (d, J=7.5 Hz, 2H), 6.75 (dd, J=5.6, 2.5 Hz, 1H), 4.95 (s, 2H), 3.89 (s, 3H), 3.35 (s, 3H), 2.79 (s, 3H).

Example 7(4)

N-(4-{3-amino-6-[2-(tetrahydro-2H-pyran-4-yl oxy)-4-pyridinyl]-2-pyrazinyl}phenyl)-1,5-dimethyl-3-oxo-2-phenyl-2,3-dihydro-1H-pyrazole-4-carboxamide MS (M+H): 578.2;
$^1$H NMR (400 MHz, CDCl$_3$) δ 10.86 (s, 1H), 8.42 (s, 1H), 8.15 (dd, J=5.2, 0.8 Hz, 1H), 7.81 (d, J=8.8 Hz, 2H), 7.75 (d, J=8.8 Hz, 2H), 7.57-7.52 (2H), 7.47-7.43 (1H), 7.42 (dd, J=5.2, 1.6 Hz, 1H), 7.36-7.34 (m, 2H), 7.31 (s, 1H), 5.27 (m, 1H), 4.98 (s, 2H), 4.00 (t, J=4.8 Hz, 1H), 3.97 (t, J=4.8 Hz, 1H), 3.62 (dd, J=8.8, 2.8 Hz, 1H), 3.59 (dd, J=8.8, 2.8 Hz, 1H), 3.35 (s, 3H), 2.79 (s, 3H), 2.99 (m, 1H), 2.06 (m, 1H), 1.82 (m, 1H), 1.79 (m, 1H).

Example 7(5)

N-(4-{3-amino-6-[5-(4-morpholinyl)-3-pyridinyl]-2-pyrazinyl}phenyl)-1,5-dimethyl-3-oxo-2-phenyl-2,3-dihydro-1H-pyrazole-4-carboxamide MS (M+H): 563.1;
$^1$H NMR (400 MHz, CDCl$_3$) δ 10.86 (s, 1H), 8.63 (s, 1H), 8.41 (s, 1H), 8.26 (d, J=2.7 Hz, 1H), 7.85-7.73 (m, 5H), 7.55 (t, J=7.6 Hz, 2H), 7.46 (t, J=7.4 Hz, 1H), 7.36 (d, J=7.3 Hz, 2H), 4.87 (s, 2H), 3.92-3.84 (m, 4H), 3.36 (s, 3H), 3.28-3.23 (m, 4H), 2.80 (s, 3H).

Example 7(6)

N-(4-{3-amino-6-[6-(4-morpholinyl)-2-pyridinyl]-2-pyrazinyl}phenyl)-1,5-dimethyl-3-oxo-2-phenyl-2,3-dihydro-1H-pyrazole-4-carboxamide MS (M+H): 563.1;
$^1$H NMR (400 MHz, CDCl$_3$) δ 10.84 (s, 1H), 8.95 (s, 1H), 7.83-7.76 (m, 4H), 7.67 (d, J=7.5 Hz, 1H), 7.60-7.53 (m, 3H), 7.46 (t, J=7.3 Hz, 1H), 7.36 (d, J=7.4 Hz, 2H), 6.59 (d, J=8.3 Hz, 1H), 4.86 (s, 2H), 3.88-3.84 (m, 4H), 3.60-3.57 (m, 4H), 3.36 (s, 3H), 2.80 (s, 3H).

Example 7(7)

N-(4-{3-amino-6-[6-(tetrahydro-2H-pyran-4-yloxy)-2-pyridinyl]-2-pyrazinyl}phenyl)-1,5-dimethyl-3-oxo-2-phenyl-2,3-dihydro-1H-pyrazole-4-carboxamide MS (M+H): 578.1;
$^1$H NMR (400 MHz, CDCl$_3$) δ 10.86 (s, 1H), 8.90 (s, 1H), 7.85-7.75 (m, 5H), 7.62 (t, J=7.8 Hz, 1H), 7.55 (t, J=7.6 Hz, 2H), 7.46 (t, J=7.4 Hz, 1H), 7.36 (d, J=7.4 Hz, 2H), 6.66 (d, J=8.0 Hz, 1H), 5.36 (tt, J=8.8, 4.3 Hz, 1H), 4.89 (s, 2H), 4.04-3.98 (m, 2H), 3.67-3.60 (m, 2H), 3.36 (s, 3H), 2.80 (s, 3H), 2.18-2.11 (m, 2H), 1.89-1.80 (m, 2H).

Example 7(8)

N-(4-{3-amino-6-[3-(tetrahydro-3-furanyloxy)phenyl]-2-pyrazinyl}phenyl)-1,5-dimethyl-3-oxo-2-phenyl-2,3-dihydro-1H-pyrazole-4-carboxamide MS (M+H): 563.1;
$^1$H NMR (400 MHz, CDCl$_3$) δ 10.85 (s, 1H), 8.38 (s, 1H), 7.84-7.75 (m, 4H), 7.57-7.50 (4H), 7.46 (t, J=7.4 Hz, 1H), 7.38-7.30 (3H), 6.86-6.81 (m, 1H), 5.03-4.97 (m, 1H), 4.81 (s, 2H), 4.03-3.95 (3H), 3.89 (td, J=8.0, 4.7 Hz, 1H), 3.36 (s, 3H), 2.80 (s, 3H), 2.23-2.15 (m, 2H).

Example 7(9)

N-[4-(3-amino-6-{2-[3-(methoxymethyl)-1-piperidinyl]-4-pyridinyl}-2-pyrazinyl)phenyl]-1,5-dimethyl-3-oxo-2-phenyl-2,3-dihydro-1H-pyrazole-4-carboxamide MS (M+H): 605.1;
$^1$H NMR (400 MHz, CDCl$_3$) δ 10.85 (s, 1H), 8.40 (s, 1H), 8.20 (d, J=4.9 Hz, 1H), 7.87-7.68 (m, 4H), 7.57-7.51 (m, 2H), 7.49-7.42 (m, 1H), 7.39-7.32 (m, 2H), 7.28 (s, 1H), 7.08 (dd, J=5.3, 1.3 Hz, 1H), 4.93 (s, 2H), 4.26 (dd, J=12.6, 3.8 Hz, 1H), 4.16 (dt, J=7.8, 4.2 Hz, 1H), 3.36-3.27 (8H), 2.99 (ddd, J=12.8, 11.2, 3.0 Hz, 1H), 2.82-2.71 (4H), 2.02-1.69 (3H), 1.68-1.52 (m, 1H), 1.27 (ddd, J=23.8, 11.3, 3.8 Hz, 1H).

Example 7(10)

N-(4-{3-amino-6-[2-(4-methoxy-1-piperidinyl)-4-pyridinyl]-2-pyrazinyl}phenyl)-1,5-dimethyl-3-oxo-2-phenyl-2,3-dihydro-1H-pyrazole-4-carboxamide MS (M+H): 591.1;
$^1$H NMR (400 MHz, CDCl$_3$) δ 10.86 (s, 1H), 8.40 (s, 1H), 8.21 (dd, J=5.6, 1.2 Hz, 1H), 7.81 (d, J=8.8 Hz, 2H), 7.75 (d, J=8.8 Hz, 2H), 7.57-7.52 (2H), 7.47-7.45 (1H), 7.36-7.34 (m, 2H), 7.31 (s, 1H), 7.09 (dd, J=5.2, 1.6 Hz, 1H), 4.93 (s, 2H), 4.07 (m, 1H), 4.04 (m, 1H), 3.41 (m, 1H), 3.37 (s, 3H), 3.35 (s, 3H), 3.24 (dd, J=9.6 and 3.2 Hz, 1H), 3.21 (dd, J=9.6 and 3.2 Hz, 1H), 2.79 (s, 3H), 1.99 (m, 1H), 1.97 (m, 1H), 1.67-1.58 (m, 2H).

Example 7(11)

N-{4-[3-amino-6-(3-pyridinyl)-2-pyrazinyl]phenyl}-2-(3-chlorophenyl)-1,5-dimethyl-3-oxo-2,3-dihydro-1H-pyrazole-4-carboxamide MS (M+H): 512.0;
$^1$H NMR (400 MHz, CDCl$_3$) δ 10.71 (s, 1H), 9.14 (d, J=2.4 Hz, 1H), 8.56 (dd, J=5.2, 1.2 Hz, 1H), 8.41 (s, 1H), 8.26-8.23 (1H), 7.81-7.55 (4H), 7.46 (t, J=8.0 Hz, 1H), 7.42-7.32 (3H), 7.27-7.24 (1H), 4.93 (s, 2H), 3.34 (s, 3H), 2.78 (s, 3H).

Example 7(12)

N-(4-{3-amino-6-[2-(4-morpholinyl)-1,3-thiazol-4-yl]-2-pyrazinyl}phenyl)-1,5-dimethyl-3-oxo-2-phenyl-2,3-dihydro-1H-pyrazole-4-carboxamide MS (M+H): 569.1;
$^1$H NMR (400 MHz, CDCl$_3$) δ 10.84 (s, 1H), 8.59 (s, 1H), 7.79 (d, J=8.8 Hz, 2H), 7.74 (s, J=8.8 Hz, 2H), 7.56-7.52 (2H), 7.47-7.43 (1H), 7.36-7.34 (2H), 7.20 (s, 1H), 4.80 (s, 2H), 3.83 (m, 4H), 3.52 (m, 4H), 2.34 (s, 3H), 2.79 (s, 3H).

Example 7(13)

N-{4-[3-amino-6-(3,5-dimethoxyphenyl)-2-pyrazinyl]phenyl}-2-(3-chlorophenyl)-1,5-dimethyl-3-oxo-2,3-dihydro-1H-pyrazole-4-carboxamide MS (M+H): 571.0;
$^1$H NMR (400 MHz, CDCl$_3$) δ 10.69 (s, 1H), 8.36 (s, 1H), 7.79 (s, 4H), 7.47 (t, J=8.0 Hz, 1H), 7.43-7.40 (1H), 7.38 (m, 1H), 7.28-7.26 (1H), 7.11 (d, J=2.4 Hz, 1H), 6.45 (m, 1H), 4.81 (s, 2H), 3.84 (s, 6H), 3.35 (s, 3H), 2.79 (s, 3H).

Example 7(14)

N-(4-{3-amino-6-[3-(4-methyl-1-piperazinyl)phenyl]-2-pyrazinyl}phenyl)-1,5-dimethyl-3-oxo-2-phenyl-2,3-dihydro-1H-pyrazole-4-carboxamide MS (M+H): 575.2;
$^1$H NMR (400 MHz, CDCl$_3$) δ 10.84 (s, 1H), 8.37 (s, 1H), 7.84-7.74 (m, 4H), 7.58-7.51 (m, 3H), 7.48-7.42 (m, 1H), 7.41-7.28 (4H), 6.91 (dd, J=7.9, 2.1 Hz, 1H), 4.79 (s, 2H), 3.34 (s, 3H), 3.32-3.25 (m, 4H), 2.79 (s, 3H), 2.70-2.53 (m, 4H), 2.37 (s, 3H).

Example 7(15)

N-(4-{3-amino-6-[3-(1H-imidazol-4-yl)phenyl]-2-pyrazinyl}phenyl)-1,5-dimethyl-3-oxo-2-phenyl-2,3-dihydro-1H-pyrazole-4-carboxamide MS (M+H): 543.1;
11 NMR (400 MHz, CDCl$_3$) δ 10.84 (s, 1H), 8.44 (s, 1H), 8.23 (s, 1H), 7.83-7.74 (m, 5H), 7.70-7.64 (m, 2H), 7.57-7.50 (m, 2H), 7.48-7.41 (m, 2H), 7.38-7.33 (m, 2H), 3.35 (s, 3H), 2.78 (s, 3H).

Example 7(16)

N-(4-{3-amino-6-[3-(3-fluoro-2-hydroxypropoxy)phenyl]-2-pyrazinyl}phenyl)-2-(3-chlorophenyl)-1,5-dimethyl-3-oxo-2,3-dihydro-1H-pyrazole-4-carboxamide MS (M+H): 603.1, 605.1;
$^1$H NMR (400 MHz, DMSO-d$_6$) δ 10.76 (s, 1H), 8.50 (s, 1H), 7.78-7.69 (4H), 7.62-7.53 (4H), 7.52 (s, 1H), 7.40 (d, J=7.5 Hz, 1H), 7.32 (t, J=8.0 Hz, 1H), 6.90 (d, J=8.1 Hz, 1H), 6.28 (s, 2H), 5.40 (d, J=4.9 Hz, 1H), 4.58-4.47 (m, 1H), 4.46-4.35 (m, 1H), 4.09-4.02 (m, 1H), 4.01-3.95 (m, 2H), 3.37 (s, 3H), 2.70 (s, 3H).

Example 7(17)

N-(4-{3-amino-6-[3-methoxy-5-(tetrahydro-3-furanyloxy)phenyl]-2-pyrazinyl}phenyl)-2-(3-chlorophenyl)-1,5-dimethyl-3-oxo-2,3-dihydro-1H-pyrazole-4-carboxamide MS (M+H): 627.1;
$^1$H NMR (400 MHz, CDCl$_3$) δ 10.70 (s, 1H), 8.35 (s, 1H), 7.82-7.76 (m, 4H), 7.49-7.41 (m, 2H), 7.39-7.37 (m, 1H), 7.28 (d, J=7.8 Hz, 1H), 7.10 (d, J=12.1 Hz, 2H), 6.42 (t, J=2.1 Hz, 1H), 5.00-4.96 (m, 1H), 4.82 (s, 2H), 4.02-3.96 (3H), 3.89 (td, J=8.1, 4.9 Hz, 1H), 3.84 (s, 3H), 3.36 (s, 3H), 2.80 (s, 3H), 2.25-2.14 (m, 2H).

Example 7(18)

N-(4-{3-amino-6-[3-methoxy-5-(1H-pyrazol-3-yl)phenyl]-2-pyrazinyl}phenyl)-1,5-dimethyl-3-oxo-2-phenyl-2,3-dihydro-1H-pyrazole-4-carboxamide MS (M+H): 573.1;
$^1$H NMR (400 MHz, CDCl$_3$) δ 10.83 (s, 1H), 8.42 (s, 1H), 7.87 (s, 1H), 7.83-7.73 (m, 4H), 7.58 (d, J=2.1 Hz, 1H), 7.54 (t, J=7.6 Hz, 2H), 7.49-7.43 (m, 2H), 7.34 (d, J=7.4 Hz, 2H), 7.28-7.24 (m, 1H), 6.63 (d, J=2.1 Hz, 1H), 3.89 (s, 3H), 3.34 (s, 3H), 2.78 (s, 3H).

Example 7(19)

N-{4-[3-amino-6-(4-methoxy-2-pyridinyl)-2-pyrazinyl]phenyl}-2-(3-chlorophenyl)-1,5-dimethyl-3-oxo-2,3-dihydro-1H-pyrazole-4-carboxamide MS (M+H): 542.0;
$^1$H NMR (400 MHz, CDCl$_3$) δ 10.71 (s, 1H), 9.01 (s, 1H), 8.43 (d, J=5.7 Hz, 1H), 7.83-7.77 (5H), 7.48 (t, J=7.9 Hz, 1H), 7.43 (d, J=8.4 Hz, 1H), 7.39-7.38 (m, 1H), 7.28 (d, J=7.8 Hz, 1H), 6.76 (dd, J=5.7, 2.5 Hz, 1H), 4.92 (s, 2H), 3.90 (s, 3H), 3.36 (s, 3H), 2.81 (s, 3H).

Example 7(20)

N-(4-{3-amino-6-[2-(4-methoxy-1-piperidinyl)-4-pyridinyl]-2-pyrazinyl}phenyl)-2-(3-chlorophenyl)-1,5-dimethyl-3-oxo-2,3-dihydro-1H-pyrazole-4-carboxamide MS (M+H): 625.1;
$^1$H NMR (400 MHz, CDCl$_3$) δ 10.71 (s, 1H), 8.40 (s, 1H), 8.21 (d, J=5.2 Hz, 1H), 7.81 (d, J=8.8 Hz, 1H), 7.75 (d, J=8.8 Hz, 1H), 7.47 (t, J=8.0 Hz, 1H), 7.42-7.40 (1H), 7.37 (m, 1H), 7.30 (s, 1H), 7.28-7.24 (1H), 7.09 (d, J=5.2 Hz, 1H), 4.96 (s, 2H), 4.05 (m, 2H), 3.42 (m, 1H), 3.37 (s, 3H), 3.35 (s, 3H), 3.23 (m, 2H), 2.79 (s, 3H), 1.98 (m, 2H), 1.62 (m, 2H).

Example 7(21)

N-(4-{3-amino-6-[3-(3-pyrrolidinyloxy)phenyl]-2-pyrazinyl}phenyl)-2-(3-chlorophenyl)-1,5-dimethyl-3-oxo-2,3-dihydro-1H-pyrazole-4-carboxamide MS (M+H) 596.1;
$^1$H NMR (400 MHz, CDCl$_3$) δ 10.70 (s, 1H), 8.38 (s, 1H), 7.80 (4H), 7.51-7.28 (7H), 6.87-6.81 (m, 1H), 4.90 (m, 1H), 4.80 (s, 2H), 3.36 (s, 3H), 3.24-3.14 (m, 2H), 3.01 (dd, J=12.6, 4.7 Hz, 1H), 2.89 (ddd, J=11.3, 8.6, 5.6 Hz, 1H), 2.80 (s, 3H), 2.15-2.04 (m, 1H), 1.98 (m, 1H).

Example 7(22)

N-(4-{3-amino-6-[6-(4-methyl-1-piperazinyl)-2-pyridinyl]-2-pyrazinyl}phenyl)-1,5-dimethyl-3-oxo-2-phenyl-2,3-dihydro-1H-pyrazole-4-carboxamide MS (M+H): 576.2;
$^1$H NMR (400 MHz, CDCl$_3$) δ 10.84 (s, 1H), 8.96 (s, 1H), 7.82-7.75 (m, 4H), 7.64 (d, J=7.4 Hz, 1H), 7.58-7.53 (3H), 7.46 (t, J=7.4 Hz, 1H), 7.36 (d, J=7.4 Hz, 2H), 6.61 (d, J=8.3 Hz, 1H), 4.85 (s, 2H), 3.73-3.62 (4H), 3.35 (s, 3H), 2.80 (s, 3H), 2.65-2.53 (4H), 2.45-2.36 (3H).

Example 7(23)

N-(4-{3-amino-6-[3-(2-hydroxy-2-methylpropoxy)-5-methoxyphenyl]-2-pyrazinyl}phenyl)-1,5-dimethyl-3-oxo-2-phenyl-2,3-dihydro-1H-pyrazole-4-carboxamide MS (M+H): 595.2;
$^1$H NMR (400 MHz, CDCl$_3$) δ 10.85 (s, 1H), 8.36 (s, 1H), 7.79 (q, J=8.7 Hz, 4H), 7.55 (t, J=7.6 Hz, 2H), 7.46 (t, J=7.4 Hz, 1H), 7.36 (d, J=7.5 Hz, 2H), 7.14-7.11 (m, 2H), 6.47 (s, 1H), 4.81 (s, 2H), 3.85-3.83 (m, 5H), 3.36 (s, 3H), 2.80 (s, 3H), 2.23 (s, 1H), 1.34 (s, 6H).

Example 7(24)

N-(4-{3-amino-6-[3-(1H-pyrazol-3-ylmethyl)phenyl]-2-pyrazinyl}phenyl)-1,5-dimethyl-3-oxo-2-phenyl-2,3-dihydro-1H-pyrazole-4-carboxamide MS (M+H): 557.1;
$^1$H NMR (400 MHz, CDCl$_3$) δ 10.83 (s, 1H), 8.31 (s, 1H), 7.84 (s, 1H), 7.81-7.73 (m, 5H), 7.54 (t, J=7.6 Hz, 2H), 7.47-7.42 (m, 2H), 7.38-7.33 (m, 3H), 7.19 (d, J=7.6 Hz, 1H), 6.11 (d, J=1.7 Hz, 1H), 4.89 (s, 2H), 4.08 (s, 2H), 3.34 (s, 3H), 2.79 (s, 3H).

Example 7(25)

N-[4-(3-amino-6-{2-fluoro-3-[2-hydroxy-3-(1-pyrrolidinyl)propoxy]phenyl}-2-pyrazinyl)phenyl]-2-(3-chlorophenyl)-1,5-dimethyl-3-oxo-2,3-dihydro-1H-pyrazole-4-carboxamide MS (M+H): 672.2;
$^1$H NMR (400 MHz, CDCl$_3$) δ 10.70 (s, 1H), 8.49 (d, J=2.3 Hz, 1H), 7.84-7.73 (4H), 7.58 (t, J=6.7 Hz, 1H), 7.51-7.41 (2H), 7.38 (s, 1H), 7.28 (d, J=7.9 Hz, 2H), 7.11 (t, J=7.9 Hz, 1H), 6.98 (t, J=7.3 Hz, 1H), 4.85 (s, 2H), 4.15-4.06 (3H), 3.36 (s, 3H), 2.87-2.78 (4H), 2.74-2.66 (m, 2H), 2.61-2.50 (m, 3H), 1.78 (s, 4H).

Example 7(26)

N-{4-[3-amino-6-(6-amino-2-pyridinyl)-2-pyrazinyl]phenyl}-2-(3-chlorophenyl)-1,5-dimethyl-3-oxo-2,3-dihydro-1H-pyrazole-4-carboxamide MS (M+H): 527.1;
$^1$H NMR (400 MHz, CDCl$_3$) δ 10.69 (s, 1H), 8.90 (s, 1H), 7.82-7.76 (m, 4H), 7.64 (d, J=7.3 Hz, 1H), 7.52-7.40 (m, 3H), 7.38 (t, J=1.9 Hz, 1H), 7.28 (d, J=7.8 Hz, 1H), 6.45 (d, J=8.6 Hz, 1H), 4.86 (s, 2H), 4.43 (s, 2H), 3.36 (s, 3H), 2.81 (s, 3H).

Example 7(27)

methyl 1-(4-{5-amino-6-[4-({[2-(3-chlorophenyl)-1,5-dimethyl-3-oxo-2,3-dihydro-1H-pyrazol-4-yl]carbonyl}amino)phenyl]-2-pyrazinyl}-2-pyridinyl)-3-azetidinecarboxylate MS (M+H): 625.2;
$^1$H NMR (400 MHz, CDCl$_3$) δ 10.71 (s, 1H), 8.41 (s, 1H), 8.20 (d, J=5.4 Hz, 1H), 7.81 (d, J=8.6 Hz, 2H), 7.75 (d, J=8.7 Hz, 2H), 7.48 (t, J=7.9 Hz, 1H), 7.43 (d, J=8.8 Hz, 1H), 7.38 (s, 1H), 7.28 (d, J=7.8 Hz, 1H), 7.17 (d, J=5.4 Hz, 1H), 6.89 (s, 1H), 4.93 (s, 2H), 4.26 (4H), 3.74 (s, 3H), 3.62-3.54 (m, 1H), 3.36 (s, 3H), 2.80 (s, 3H).

Example 7(28)

N-(4-{3-amino-6-[2-fluoro-3-(3-fluoro-2-hydroxypropoxy)phenyl]-2-pyrazinyl}phenyl)-2-(3-chlorophenyl)-1,5-dimethyl-3-oxo-2,3-dihydro-1H-pyrazole-4-carboxamide MS (M+H): 621.2;
$^1$H NMR (400 MHz, DMSO-d$_6$) δ 10.76 (s, 1H), 8.30 (d, J=2.0 Hz, 1H), 7.76-7.68 (m, 4H), 7.62-7.53 (3H), 7.47-7.37 (2H), 7.20-7.11 (2H), 6.39 (s, 2H), 5.47 (s, 1H), 4.60-4.50 (m, 1H), 4.48-4.36 (m, 1H), 4.12-3.98 (m, 3H), 3.37 (s, 3H), 2.69 (s, 3H).

Example 7(29)

N-(4-{(3-amino-6-[2-(4-morpholinyl)-1,3-thiazol-4-yl]-2-pyrazinyl}phenyl)-2-(3-chlorophenyl)-1,5-dimethyl-3-oxo-2,3-dihydro-1H-pyrazole-4-carboxamide MS (M+H): 603.1;
$^1$H NMR (400 MHz, CDCl$_3$) δ 10.69 (s, 1H), 8.59 (s, 1H), 7.80-7.73 (4H), 7.47 (t, J=8.0 Hz, 1H), 7.43-7.40 (1H), 7.37 (m, 1H), 7.29-7.25 (1H), 7.20 (s, 1H), 4.80 (s, 2H), 3.83 (m, 4H), 3.52 (m, 4H), 3.35 (s, 3H), 2.79 (s, 3H).

Example 7(30)

N-[4-(3-amino-6-{2-[3-(dimethylcarbamoyl)-1-azetidinyl]-4-pyridinyl}-2-pyrazinyl)phenyl]-2-(3-chlorophenyl)-1,5-dimethyl-3-oxo-2,3-dihydro-1H-pyrazole-4-carboxamide MS (M+H): 638.1;
$^1$H NMR (400 MHz, DMSO-d$_6$) δ 10.77 (s, 1H), 8.57 (s, 1H), 8.06 (d, J=5.4 Hz, 1H), 7.76-7.69 (m, 4H), 7.62-7.54 (m, 3H), 7.42-7.38 (m, 1H), 7.22 (d, J=5.4 Hz, 1H), 6.91 (s, 1H), 6.49 (s, 2H), 4.17-4.11 (m, 2H), 4.04-3.99 (m, 2H), 3.85-3.76 (m, 1H), 3.37 (s, 3H), 2.88 (s, 3H), 2.82 (s, 3H), 2.69 (s, 3H).

Example 7(31)

N-(4-{3-amino-6-[6-(dimethylamino)-2-pyridinyl]-2-pyrazinyl}phenyl)-2-(3-chlorophenyl)-1,5-dimethyl-3-oxo-2,3-dihydro-1H-pyrazole-4-carboxamide MS (M+H): 555.0;
$^1$H NMR (400 MHz, DMSO-$d_6$) δ 10.76 (s, 1H), 8.79 (s, 1H), 7.77-7.69 (m, 4H), 7.63-7.51 (m, 4H), 7.40 (d, J=7.3 Hz, 1H), 7.35 (d, J=7.3 Hz, 1H), 6.57 (d, J=8.5 Hz, 1H), 6.35 (s, 2H), 3.37 (s, 3H), 3.07 (s, 6H), 2.70 (s, 3H).

Example 7(32)

N-[4-(3-amino-6-{6-[4-(2-hydroxyethyl)-1-piperazinyl]-2-pyridinyl}-2-pyrazinyl)phenyl]-2-(3-chlorophenyl)-1,5-dimethyl-3-oxo-2,3-dihydro-1H-pyrazole-4-carboxamide MS (M+H): 640.2, 642.2;
$^1$H NMR (400 MHz, DMSO-$d_6$) δ 10.76 (s, 1H), 8.75 (s, 1H), 7.76-7.69 (m, 4H), 7.60-7.54 (m, 4H), 7.41 (t, J=6.8 Hz, 2H), 6.74 (d, J=8.4 Hz, 1H), 6.38 (s, 2H), 4.40 (t, J=5.3 Hz, 1H), 3.55-3.49 (6H), 3.37 (s, 3H), 2.70 (s, 3H), 2.53-2.50 (m, 2H), 2.44-2.39 (m, 4H).

Example 7(33)

N-{4-[3-amino-6-(2-{3-[(dimethylamino)methyl]-1-azetidinyl}-4-pyridinyl)-2-pyrazinyl]phenyl}-2-(3-chlorophenyl)-1,5-dimethyl-3-oxo-2,3-dihydro-1H-pyrazole-4-carboxamide MS (M+H): 624.3;
$^1$H NMR (400 MHz, DMSO-$d_6$) δ 10.76 (s, 1H), 8.55 (s, 1H), 8.04 (d, J=5.4 Hz, 1H), 7.75-7.69 (m, 4H), 7.62-7.53 (m, 3H), 7.40 (d, J=7.5 Hz, 1H), 7.18 (d, J=4.3 Hz, 1H), 6.85 (s, 1H), 6.48 (s, 2H), 4.06-3.97 (m, J=7.9 Hz, 2H), 3.62-3.53 (m, J=7.8, 5.7 Hz, 2H), 3.37 (s, 3H), 2.88-2.78 (m, 1H), 2.69 (s, 3H), 2.11 (s, 6H).

Example 7(34)

N-(4-{3-amino-6-[2-fluoro-3-(2-hydroxy-2-methylpropoxy)phenyl]-2-pyrazinyl}phenyl)-1,5-dimethyl-3-oxo-2-phenyl-2,3-dihydro-1H-pyrazole-4-carboxamide MS (M+H): 583.1;
$^1$H NMR (400 MHz, CDCl$_3$) δ 10.84 (s, 1H), 8.48 (d, J=2.0 Hz, 1H), 7.81 (d, J=8.6 Hz, 2H), 7.76 (d, J=8.6 Hz, 2H), 7.63-7.52 (3H), 7.49-7.43 (m, 1H), 7.36 (d, J=7.6 Hz, 2H), 7.11 (t, J=8.0 Hz, 1H), 6.94 (t, J=7.7 Hz, 1H), 4.86 (s, 2H), 3.87 (s, 2H), 3.35 (s, 3H), 2.80 (s, 3H), 2.33 (s, 1H), 1.37 (s, 6H).

Example 7(35)

N-(4-{3-amino-6-[2-fluoro-3-(3-hydroxy-3-methylbutoxy)phenyl]-2-pyrazinyl}phenyl)-1,5-dimethyl-3-oxo-2-phenyl-2,3-dihydro-1H-pyrazole-4-carboxamide MS (M+H): 597.1;
$^1$H NMR (400 MHz, CDCl$_3$) δ 10.84 (s, 1H), 8.48 (d, J=2.4 Hz, 1H), 7.80 (d, J=8.7 Hz, 2H), 7.75 (d, J=8.7 Hz, 2H), 7.62-7.57 (m, 1H), 7.57-7.50 (2H), 7.46 (t, J=7.4 Hz, 1H), 7.36 (d, J=7.4 Hz, 2H), 7.12 (t, J=7.6 Hz, 1H), 6.96 (t, J=7.1 Hz, 1H), 4.85 (s, 2H), 4.27 (t, J=6.3 Hz, 2H), 3.65-3.62 (m, 1H), 3.35 (s, 3H), 2.80 (s, 3H), 2.31 (s, 1H), 2.05 (t, J=6.2 Hz, 2H), 1.33 (s, 6H).

Example 7(36)

N-(4-{3-amino-6-[2-fluoro-3-(tetrahydro-3-furanyloxy)phenyl]-2-pyrazinyl}phenyl)-1,5-dimethyl-3-oxo-2-phenyl-2,3-dihydro-1H-pyrazole-4-carboxamide MS (M+H): 581.1;
$^1$H NMR (400 MHz, CDCl$_3$) δ 10.84 (s, 1H), 8.47 (d, J=2.4 Hz, 1H), 7.82-7.73 (m, 4H), 7.60 (t, J=7.3 Hz, 1H), 7.55 (t, J=7.6 Hz, 2H), 7.46 (t, J=7.4 Hz, 1H), 7.36 (d, J=7.4 Hz, 2H), 7.11 (t, J=8.0 Hz, 1H), 6.89 (t, J=7.8 Hz, 1H), 4.98 (br s, 1H), 4.86 (s, 2H), 4.07-3.99 (3H), 3.92 (td, J=8.1, 4.4 Hz, 1H), 3.35 (s, 3H), 2.80 (s, 3H), 2.24-2.16 (m, 2H).

Example 7(37)

N-(4-{3-amino-6-[4-(4-methoxy-1-piperidinyl)-2-pyridinyl]-2-pyrazinyl}phenyl)-1,5-dimethyl-3-oxo-2-phenyl-2,3-dihydro-1H-pyrazole-4-carboxamide MS (M+H): 591.1;
$^1$H NMR (400 MHz, CDCl$_3$) δ 10.84 (s, 1H), 8.97 (s, 1H), 8.28 (s, J=5.6 Hz, 1H), 7.82 (d, J=8.8 Hz, 2H), 7.77 (d, J=8.8 Hz, 2H), 7.56-7.52 (2H), 7.47-7.43 (1H), 7.37-7.34 (2H), 6.61 (dd, J=6.0, 2.8 Hz, 1H), 4.88 (s, 2H), 3.74-3.68 (2H), 3.43 (m, 1H), 3.37 (s, 3H), 3.35 (s, 3H), 3.20-3.13 (2H), 2.79 (s, 3H), 1.99-1.93 (2H), 1.71-1.60 (2H).

Example 7(38)

N-(4-{3-amino-6-[3-fluoro-2-(4-methoxy-1-piperidinyl)-4-pyridinyl]-2-pyrazinyl}phenyl)-1,5-dimethyl-3-oxo-2-phenyl-2,3-dihydro-1H-pyrazole-4-carboxamide MS (M+H): 609.1;
$^1$H NMR (400 MHz, CDCl$_3$) δ 10.85 (s, 1H), 8.52 (d, J=2.4 Hz, 1H), 8.01 (d, J=5.2 Hz, 1H), 7.80 (d, J=8.8 Hz, 2H), 7.73 (d, J=8.8 Hz, 2H), 7.56-7.52 (2H), 7.47-7.41 (2H), 7.36-7.33 (2H), 4.98 (s, 2H), 3.84 (m, 1H), 3.81 (m, 1H), 3.40 (m, 1H), 3.38 (s, 3H), 3.35 (s, 3H), 3.12 (m, 2H), 2.79 (s, 3H), 2.05-2.01 (2H), 1.76-1.66 (2H).

Example 7(39)

N-(4-{3-amino-6-[3-fluoro-4-(4-methoxy-1-piperidinyl)-2-pyridinyl]-2-pyrazinyl}phenyl)-1,5-dimethyl-3-oxo-2-phenyl-2,3-dihydro-1H-pyrazole-4-carboxamide MS (M+H): 609.1;
$^1$H NMR (400 MHz, CDCl$_3$) δ 10.81 (s, 1H), 8.50 (d, J=1.6 Hz, 1H), 8.22 (d, J=5.6 Hz, 1H), 7.78 (d, J=8.8 Hz, 2H), 7.34 (d, J=8.8 Hz, 2H), 7.56-7.52 (2H), 7.47-7.42 (1H), 7.36-7.33 (2H), 6.74 (dd, J=6.8, 5.6 Hz, 1H), 4.91 (s, 2H), 3.58-3.52

(2H), 3.41 (m, 1H), 3.37 (s, 3H), 3.34 (s, 3H), 3.08 (m, 2H), 2.79 (s, 3H), 2.05-1.95 (2H), 1.79-1.70 (2H).

Example 7(40)

N-{4-[3-amino-6-(3-methoxyphenyl)-2-pyrazinyl]phenyl}-2-(3-chlorophenyl)-1,5-dimethyl-3-oxo-2,3-dihydro-1H-pyrazole-4-carboxamide MS (M+H): 541.0;
$^1$H NMR (400 MHz, DMSO-$d_6$) δ 10.78 (s, 1H), 8.49 (s, 1H), 7.77-7.70 (4H), 7.61-7.52 (5H), 7.49 (m, 1H), 7.34 (m, 1H), 7.32 (t, J=8.0 Hz, 1H), 6.88 (m, 1H), 6.27 (s, 2H), 3.78 (s, 3H), 3.37 (s, 3H), 2.69 (s, 3H).

Example 7(41)

N-{4-[6-(3-acetylphenyl)-3-amino-2-pyrazinyl]phenyl}-2-(3-chlorophenyl)-1,5-dimethyl-3-oxo-2,3-dihydro-1H-pyrazole-4-carboxamide MS (M+H): 553.0;
$^1$H NMR (400 MHz, DMSO-$d_6$) δ 10.77 (s, 1H), 8.59 (s, 1H), 8.47 (s, 1H), 8.22 (d, J=8.0 Hz, 1H), 7.88 (d, J=8.0 Hz, 1H), 7.77-7.71 (4H), 7.61-7.54 (4H), 7.41-7.38 (1H), 6.37 (s, 2H), 3.36 (s, 3H), 2.69 (s, 3H), 2.61 (s, 3H).

Example 7(42)

N-(4-{3-amino-6-[4-(tetrahydro-2H-pyran-4-yloxy)-2-pyridinyl]-2-pyrazinyl}phenyl)-1,5-dimethyl-3-oxo-2-phenyl-2,3-dihydro-1H-pyrazole-4-carboxamide MS (M+H): 578.1;
$^1$H NMR (400 MHz, CD$_3$OD/CDCl$_3$) δ 10.78 (s, 1H), 8.77 (s, 1H), 8.31 (d, J=5.7 Hz, 1H), 7.76-7.69 (m, 5H), 7.53 (t, J=6.7 Hz, 2H), 7.49-7.43 (m, 1H), 7.34-7.30 (m, 2H), 6.76-6.72 (m, 1H), 4.67 (br s, 1H), 3.93 (br s, 2H), 3.63-3.52 (m, 2H), 3.34 (s, 3H), 2.73 (s, 3H), 2.04-1.97 (m, 2H), 1.81-1.72 (m, 2H).

Example 7(43)

N-[4-(3-amino-6-{4-[3-(methoxymethyl)-1-piperidinyl]-2-pyridinyl}-2-pyrazinyl)phenyl]-1,5-dimethyl-3-oxo-2-phenyl-2,3-dihydro-1H-pyrazole-4-carboxamide MS (M+H): 605.2;
$^1$H NMR (400 MHz, CDCl$_3$) δ 10.84 (s, 1H), 8.96 (s, 1H), 8.26 (d, J=5.9 Hz, 1H), 7.86-7.73 (m, 4H), 7.70 (d, J=2.6 Hz, 1H), 7.57-7.51 (m, 2H), 7.48-7.42 (m, 1H), 7.35 (dt, J=8.7, 2.0 Hz, 2H), 6.63 (dd, J=6.0, 2.7 Hz, 1H), 4.89 (s, 2H), 3.89 (dd, J=13.1, 3.7 Hz, 1H), 3.80 (dt, J=12.8, 3.9 Hz, 1H), 3.37-3.20 (8H), 3.03-2.91 (m, 1H), 2.84-2.73 (4H), 2.00-1.87 (m, 1H), 1.85-1.69 (m, 2H), 1.67-1.51 (m, 1H), 1.34-1.20 (m, 1H).

Example 7(44)

N-(4-{3-amino-6-[6-(4-methoxy-1-piperidinyl)-2-pyridinyl]-2-pyrazinyl}phenyl)-1,5-dimethyl-3-oxo-2-phenyl-2,3-dihydro-1H-pyrazole-4-carboxamide MS (M+H): 591.1;
$^1$H NMR (400 MHz, CDCl$_3$) δ 10.84 (s, 1H), 8.97 (s, 1H), 7.81 (d, J=8.8 Hz, 2H), 7.77 (s, J=8.8 Hz, 2H), 7.60-7.50 (4H), 7.47-7.44 (1H), 7.37-7.34 (2H), 6.63 (s, J=4.4 Hz, 1H), 6.88 (s, 2H), 4.10 (m, 1H), 4.07 (m, 1H), 3.44 (m, 1H), 3.39 (s, 3H), 3.35 (s, 3H), 3.25 (m, 2H), 2.05-1.97 (2H), 1.69-1.61 (2H).

Example 7(45)

N-(4-{3-amino-6-[4-(4-morpholinyl)-2-pyridinyl]-2-pyrazinyl}phenyl)-1,5-dimethyl-3-oxo-2-phenyl-2,3-dihydro-1H-pyrazole-4-carboxamide MS (M+H): 563.1;
$^1$H NMR (400 MHz, CDCl$_3$) δ 10.85 (s, 1H), 9.00 (s, 1H), 8.33 (d, J=5.9 Hz, 1H), 7.83-7.74 (m, 4H), 7.73 (d, J=2.5 Hz, 1H), 7.55 (t, J=7.6 Hz, 2H), 7.46 (t, J=7.4 Hz, 1H), 7.36 (d, J=7.3 Hz, 2H), 6.61 (dd, J=5.9, 2.6 Hz, 1H), 4.90 (s, 2H), 3.89-3.77 (m, 4H), 3.37-3.34 (m, 7H), 2.80 (s, 3H).

Example 7(46)

N-(4-{3-amino-6-[5-(2-hydroxy-2-methylpropoxy)-3-pyridinyl]-2-pyrazinyl}phenyl)-1,5-dimethyl-3-oxo-2-phenyl-2,3-dihydro-1H-pyrazole-4-carboxamide MS (M+H): 566.1;
$^1$H NMR (400 MHz, CD$_3$OD/CDCl$_3$) δ 10.79 (s, 1H), 8.62 (s, 1H), 8.33 (s, 1H), 8.17 (d, J=2.6 Hz, 1H), 7.82 (s, 1H), 7.76-7.70 (m, 4H), 7.54 (t, J=7.4 Hz, 2H), 7.47 (t, J=7.3 Hz, 1H), 7.33 (d, J=7.2 Hz, 2H), 3.85 (s, 2H), 3.35 (s, 3H), 2.74 (s, 3H), 1.30 (s, 6H).

Example 7(47)

N-(4-{3-amino-6-[4-(3-hydroxy-3-methylbutoxy)phenyl]-2-pyrazinyl}phenyl)-1,5-dimethyl-3-oxo-2-phenyl-2,3-dihydro-1H-pyrazole-4-carboxamide MS (M+H): 579.1;
$^1$H NMR (400 MHz, CDCl$_3$) δ 10.84 (s, 1H), 8.34 (s, 1H), 7.89 (d, J=8.8 Hz, 2H), 7.82-7.76 (m, 4H), 7.55 (t, J=7.6 Hz, 2H), 7.46 (t, J=7.5 Hz, 1H), 7.36 (d, J=7.3 Hz, 2H), 6.97 (d, J=8.8 Hz, 2H), 4.73 (s, 2H), 4.21 (t, J=6.3 Hz, 2H), 3.35 (s, 3H), 2.80 (s, 3H), 2.18 (s, 1H), 2.00 (t, J=6.2 Hz, 2H), 1.31 (s, 6H).

Example 7(48)

N-(4-{3-amino-6-[5-(tetrahydro-2H-pyran-4-yloxy)-3-pyridinyl]-2-pyrazinyl}phenyl)-1,5-dimethyl-3-oxo-2-phenyl-2,3-dihydro-1H-pyrazole-4-carboxamide MS (M+H): 578.1;
$^1$H NMR (400 MHz, CDCl$_3$) δ 10.88 (s, 1H), 8.73 (d, J=1.5 Hz, 1H), 8.41 (s, 1H), 8.27 (d, J=2.7 Hz, 1H), 7.84-7.81 (m, 3H), 7.76 (d, J=8.6 Hz, 2H), 7.55 (t, J=7.6 Hz, 2H), 7.46 (t, J=7.4 Hz, 1H), 7.36 (d, J=7.3 Hz, 2H), 4.92 (s, 2H), 4.64-4.57 (m, 1H), 4.01-3.94 (m, 2H), 3.59 (ddd, J=11.5, 8.2, 3.2 Hz, 2H), 3.36 (s, 3H), 2.80 (s, 3H), 2.08-2.01 (m, 2H), 1.81 (dtd, J=12.2, 8.0, 3.8 Hz, 2H).

Example 7(49)

N-(4-{3-amino-6-[3-(1H-pyrazol-4-yl)phenyl]-2-pyrazinyl}phenyl)-1,5-dimethyl-3-oxo-2-phenyl-2,3-dihydro-1H-pyrazole-4-carboxamide MS (M+H): 543.1;
$^1$H NMR (400 MHz, CDCl$_3$) δ 10.79 (s, 1H), 8.35 (s, 1H), 8.03 (s, 1H), 7.85 (s, 2H), 7.78-7.73 (m, 5H), 7.55-7.49 (m, 2H), 7.47-7.43 (m, 2H), 7.39 (t, J=7.6 Hz, 1H), 7.32 (d, J=7.3 Hz, 2H), 3.33 (s, 3H), 2.74 (s, 3H).

Example 7(50)

N-{4-[3-amino-6-(2-ethoxy-1,3-thiazol-4-yl)-2-pyrazinyl]phenyl}-1,5-dimethyl-3-oxo-2-phenyl-2,3-dihydro-1H-pyrazole-4-carboxamide MS (M+H): 528.0;
$^1$H NMR (400 MHz, CDCl$_3$) δ 10.84 (s, 1H), 8.58 (s, 1H), 7.79 (d, J=8.8 Hz, 2H), 7.73 (d, J=8.8 Hz, 2H), 7.56-7.52 (2H), 7.47-7.43 (1H), 7.36-7.34 (2H), 7.26 (s, 1H), 4.82 (s, 2H), 4.52 (q, J=7.2 Hz, 2H), 3.35 (s, 3H), 2.79 (s, 3H), 1.46 (t, J=7.2 Hz, 3H).

Example 7(51)

N-(4-{3-amino-6-[3-(2-pyrrolidinylmethoxy)phenyl]-2-pyrazinyl}phenyl)-1,5-dimethyl-3-oxo-2-phenyl-2,3-dihydro-1H-pyrazole-4-carboxamide MS (M+H): 576.1;
1H NMR (400 MHz, CDCl$_3$) δ 10.83 (s, 1H), 8.35 (s, 1H), 7.80 (d, J=8.7 Hz, 2H), 7.76 (d, J=8.7 Hz, 2H), 7.57-7.44 (5H), 7.35 (d, J=7.4 Hz, 2H), 7.29 (t, 1H), 6.87 (d, J=8.4 Hz, 1H), 4.82 (s, 2H), 4.16-4.06 (m, 2H), 3.86-3.79 (m, 1H), 3.34 (s, 3H), 3.21 (t, J=6.9 Hz, 2H), 2.79 (s, 3H), 2.14-2.03 (m, 1H), 2.01-1.89 (m, 2H), 1.86-1.77 (m, 1H).

Example 7(52)

N-(4-{3-amino-6-[3-(4-methoxy-1-piperidinyl)phenyl]-2-pyrazinyl}phenyl)-1,5-dimethyl-3-oxo-2-phenyl-2,3-dihydro-1H-pyrazole-4-carboxamide MS (M+H): 590.1;
$^1$H NMR (400 MHz, DMSO-d$_6$) δ 10.88 (s, 1H), 8.46 (s, 1H), 7.76-7.69 (m, 4H), 7.57 (t, J=7.5 Hz, 2H), 7.49 (t, J=7.3 Hz, 2H), 7.42 (d, J=7.3 Hz, 2H), 7.34 (d, J=7.6 Hz, 1H), 7.23 (t, J=7.9 Hz, 1H), 6.89 (d, J=8.2 Hz, 1H), 6.20 (s, 2H), 3.55-3.48 (m, 2H), 3.34 (s, 3H), 3.24 (s, 3H), 2.94-2.85 (m, 2H), 2.70 (s, 3H), 1.93 (dd, J=9.0, 5.6 Hz, 2H), 1.56-1.45 (m, 2H).

Example 7(53)

N-[4-(3-amino-6-{6-[(2-methoxyethyl)(methyl)amino]-2-pyridinyl}-2-pyrazinyl)phenyl]-1,5-dimethyl-3-oxo-2-phenyl-2,3-dihydro-1H-pyrazole-4-carboxamide MS (M+H): 565.1;
$^1$H NMR (400 MHz, CDCl$_3$) δ 10.83 (s, 1H), 8.96 (s, 1H), 7.82-7.76 (4H), 7.57-7.43 (5H), 7.37-7.34 (2H), 7.45 (1H), 6.47 (dd, J=8.0, 1.2 Hz, 1H), 4.83 (s, 2H), 3.83 (t, J=6.0 Hz, 2H), 3.64 (t, J=6.0 Hz, 2H), 3.36 (s, 3H), 3.35 (s, 3H), 3.14 (s, 3H), 2.80 (s, 3H).

Example 7(54)

N-[4-(3-amino-6-{3-[(1-methyl-2-pyrrolidinyl)methoxy]phenyl}-2-pyrazinyl)phenyl]-1,5-dimethyl-3-oxo-2-phenyl-2,3-dihydro-1H-pyrazole-4-carboxamide MS (M+H): 590.2;
$^1$H NMR (400 MHz, CDCl$_3$) δ 10.79 (s, 1H), 8.33 (s, 1H), 7.79-7.69 (m, 4H), 7.53-7.44 (m, 4H), 7.40 (t, J=7.3 Hz, 1H), 7.33-7.24 (m, 3H), 6.84 (d, J=7.9 Hz, 1H), 4.74 (s, 2H), 4.03 (s, 1H), 3.90 (s, 1H), 3.30 (s, 3H), 3.05 (s, 1H), 2.75 (s, 3H), 2.60 (s, 1H), 2.44 (s, 3H), 2.24 (s, 1H), 1.98 (s, 1H), 1.72 (s, 3H).

Example 7(55)

N-[4-(3-amino-6-{3-[2-(dimethylamino)ethoxy]phenyl}-2-pyrazinyl)phenyl]-1,5-dimethyl-3-oxo-2-phenyl-2,3-dihydro-1H-pyrazole-4-carboxamide MS (M+H): 564.1;
$^1$H NMR (400 MHz, CDCl$_3$) δ 10.79 (s, 1H), 8.32 (s, 1H), 7.78-7.70 (m, 4H), 7.52-7.45 (m, 4H), 7.43-7.38 (m, 1H), 7.32-7.25 (m, 3H), 6.84 (d, J=7.7 Hz, 1H), 4.74 (s, 2H), 4.10 (s, 2H), 3.30 (s, 3H), 2.75 (s, 5H), 2.33 (s, 6H).

Example 7(56)

N-[4-(3-amino-6-{3-[2-(aminomethyl)cyclopropyl]phenyl}-2-pyrazinyl)phenyl]-1,5-dimethyl-3-oxo-2-phenyl-2,3-dihydro-1H-pyrazole-4-carboxamide MS (M+H): 546.2;
$^1$H NMR (400 MHz, CDCl$_3$) δ 10.84 (s, 1H), 8.38 (s, 1H), 7.90 (s, 1H), 7.83-7.77 (m, 5H), 7.55 (t, J=7.6 Hz, 2H), 7.46 (t, J=7.4 Hz, 1H), 7.37 (t, J=7.7 Hz, 3H), 7.31 (d, J=7.7 Hz, 1H), 4.80 (s, 2H), 3.35 (s, 3H), 2.81 (s, 2H), 2.80 (s, 3H), 1.26-1.23 (br m, 1H), 1.11-1.01 (br m, 1H), 0.89-0.85 (m, 1H), 0.78-0.73 (m, 2H).

Example 7(57)

N-[4-(3-amino-6-{2-fluoro-3-[(4-methoxy-1-piperidinyl)methyl]phenyl}-2-pyrazinyl)phenyl]-1,5-dimethyl-3-oxo-2-phenyl-2,3-dihydro-1H-pyrazole-4-carboxamide MS (M+H): 622.2;
$^1$H NMR (400 MHz, CDCl$_3$) δ 10.84 (s, 1H), 8.46 (d, J=2.4 Hz, 1H), 7.88 (t, J=7.0 Hz, 1H), 7.82-7.74 (m, 4H), 7.54 (t, J=7.6 Hz, 2H), 7.45 (t, J=7.4 Hz, 1H), 7.37-7.33 (m, 3H), 7.18 (t, J=7.6 Hz, 1H), 4.85 (s, 2H), 3.65 (s, 2H), 3.35 (s, 3H), 3.31 (s, 3H), 3.22-3.15 (m, 1H), 2.82-2.76 (m, 5H), 2.22 (s, 2H), 1.89 (d, J=9.9 Hz, 2H), 1.65-1.55 (m, 2H).

Example 7(58)

N-{4-[3-amino-6-(1H-pyrazol-5-yl)-2-pyrazinyl]phenyl}-1,5-dimethyl-3-oxo-2-phenyl-2,3-dihydro-1H-pyrazole-4-carboxamide MS (M+H): 467.1;
$^1$H NMR (400 MHz, CDCl$_3$) δ 10.87 (s, 1H), 8.37 (s, 1H), 7.82 (d, J=8.6 Hz, 2H), 7.73 (d, J=8.6 Hz, 2H), 7.61 (d, J=1.9 Hz, 1H), 7.55 (t, J=7.6 Hz, 2H), 7.47 (dd, J=15.7, 8.5 Hz, 1H), 7.36 (d, J=7.3 Hz, 2H), 6.68 (d, J=1.9 Hz, 1H), 4.87 (s, 2H), 3.36 (s, 3H), 2.80 (s, 3H).

Example 7(59)

N-(4-{3-amino-6-[3-(3-hydroxy-3-methylbutoxy)-5-methoxyphenyl]-2-pyrazinyl}phenyl)-1,5-dimethyl-3-oxo-2-phenyl-2,3-dihydro-1H-pyrazole-4-carboxamide MS (M+H): 609.2;
$^1$H NMR (400 MHz, CDCl$_3$) δ 10.84 (s, 1H), 8.36 (s, 1H), 7.83-7.75 (m, 4H), 7.55 (t, J=7.7 Hz, 2H), 7.46 (t, J=7.4 Hz, 1H), 7.36 (d, J=7.3 Hz, 2H), 7.12 (d, J=2.2 Hz, 1H), 6.46 (t, J=2.2 Hz, 1H), 4.81 (s, 2H), 4.23 (t, J=6.2 Hz, 2H), 3.84 (s, 3H), 3.36 (s, 3H), 2.80 (s, 3H), 2.00 (t, J=6.2 Hz, 2H), 1.31 (s, 6H).

Example 7(60)

N-{4-[3-amino-6-(2,3-dihydro[1,4]dioxino[2,3-b]pyridin-7-yl)-2-pyrazinyl]phenyl}-1,5-dimethyl-3-oxo-2-phenyl-2,3-dihydro-1H-pyrazole-4-carboxamide MS (M+H): 536.1;
$^1$H NMR (400 MHz, CD$_3$OD/CDCl$_3$) δ 8.23-8.21 (m, 2H), 7.76 (d, J=1.6 Hz, 1H), 7.72 (s, 4H), 7.53 (t, J=7.4 Hz, 2H), 7.46 (t, J=7.0 Hz, 1H), 7.33-7.30 (m, 2H), 4.42-4.40 (m, 2H), 4.25-4.22 (m, 2H), 3.34 (s, 3H), 2.73 (s, 3H).

Example 7(61)

N-(4-{3-amino-6-[3-(3-pyrrolidinyloxy)phenyl]-2-pyrazinyl}phenyl)-1,5-dimethyl-3-oxo-2-phenyl-2,3-dihydro-1H-pyrazole-4-carboxamide MS (M+H): 562.2;
$^1$H NMR (400 MHz, CDCl$_3$) δ 10.85 (s, 1H), 8.38 (s, 1H), 7.83-7.77 (m, 4H), 7.55 (t, J=7.6 Hz, 2H), 7.52-7.49 (m, 2H), 7.46 (t, J=7.4 Hz, 1H), 7.36 (d, J=7.4 Hz, 2H), 7.32 (t, J=8.2 Hz, 1H), 6.84 (d, J=7.2 Hz, 1H), 4.90 (t, J=5.4 Hz, 1H), 4.80 (s, 2H), 3.36 (s, 3H), 3.25-3.13 (m, 2H), 3.05-2.95 (m, 1H), 2.93-2.85 (m, 1H), 2.80 (s, 3H), 2.14-2.05 (m, 1H), 2.02-1.95 (m, 1H).

Example 7(62)

N-[4-(3-amino-6-{3-[(1-methyl-3-pyrrolidinyl)oxy]phenyl}-2-pyrazinyl)phenyl]-1,5-dimethyl-3-oxo-2-phenyl-2,3-dihydro-1H-pyrazole-4-carboxamide MS (M+H): 576.2;
$^1$H NMR (400 MHz, CDCl$_3$) δ 10.84 (s, 1H), 8.37 (s, 1H), 7.82-7.76 (m, 4H), 7.55 (t, J=7.6 Hz, 2H), 7.52-7.48 (m, 2H), 7.45 (t, J=7.4 Hz, 1H), 7.36 (d, J=7.3 Hz, 2H), 7.31 (t, J=8.0 Hz, 1H), 6.85-6.81 (m, 1H), 4.92-4.87 (m, 1H), 4.80 (s, 2H), 3.35 (s, 3H), 2.85-2.77 (m, 6H), 2.46-2.40 (m, 1H), 2.38 (s, 3H), 2.37-2.27 (m, 1H), 2.02 (ddd, J=13.9, 8.1, 2.4 Hz, 1H).

Example 7(63)

N-[4-(3-amino-6-{3-[(4-methoxy-1-piperidinyl)methyl]phenyl}-2-pyrazinyl)phenyl]-1,5-dimethyl-3-oxo-2-phenyl-2,3-dihydro-1H-pyrazole-4-carboxamide MS (M+H): 604.2;
$^1$H NMR (400 MHz, CDCl$_3$) δ 10.84 (s, 1H), 8.39 (s, 1H), 7.85 (s, 2H), 7.83-7.76 (m, 4H), 7.54 (t, J=7.6 Hz, 2H), 7.45 (t, J=7.4 Hz, 1H), 7.40-7.30 (m, 4H), 4.82 (s, 2H), 3.57 (s, 2H), 3.34 (s, 3H), 3.31 (s, 3H), 3.24-3.18 (m, 1H), 2.79 (s, 3H), 2.77-2.73 (m, 2H), 2.19 (br s, 2H), 1.92-1.86 (m, 2H), 1.64-1.55 (m, 2H).

Example 7(64)

N-[4-(3-amino-6-{3-[(1-methyl-2-pyrrolidinyl)methoxy]phenyl}-2-pyrazinyl)phenyl]-2-(3-chlorophenyl)-1,5-dimethyl-3-oxo-2,3-dihydro-1H-pyrazole-4-carboxamide MS (M+H): 624.1;
$^1$H NMR (400 MHz, CDCl$_3$) δ 10.64 (s, 1H), 8.33 (s, 1H), 7.77-7.69 (m, 4H), 7.50-7.44 (m, 2H), 7.41 (d, J=7.9 Hz, 1H), 7.37 (d, J=8.2 Hz, 1H), 7.32 (s, 1H), 7.27 (t, J=7.9 Hz, 1H), 7.22 (d, J=7.9 Hz, 1H), 6.84 (d, J=8.1 Hz, 1H), 4.74 (s, 2H), 4.04 (s, 1H), 3.91 (s, 1H), 3.30 (s, 3H), 3.09 (s, 1H), 2.75 (s, 3H), 2.63 (s, 1H), 2.45 (s, 3H), 2.25 (s, 1H), 1.98 (s, 1H), 1.73 (s, 3H).

Example 7(65)

N-[4-(3-amino-6-{3-[2-(dimethylamino)ethoxy]phenyl}-2-pyrazinyl)phenyl]-2-(3-chlorophenyl)-1,5-dimethyl-3-oxo-2,3-dihydro-1H-pyrazole-4-carboxamide MS (M+H): 598.1;
$^1$H NMR (400 MHz, CDCl$_3$) δ 10.70 (s, 1H), 8.38 (s, 1H), 7.82-7.76 (m, 4H), 7.58-7.26 (m, 7H), 6.91 (d, J=7.6 Hz, 1H), 4.80 (s, 2H), 4.18 (s, 2H), 3.36 (s, 3H), 2.81 (s, 5H), 2.40 (s, 6H).

Example 7(66)

N-(4-{3-amino-6-[2-fluoro-3-(tetrahydro-3-furanyloxy)phenyl]-2-pyrazinyl}phenyl)-2-(3-chlorophenyl)-1,5-dimethyl-3-oxo-2,3-dihydro-1H-pyrazole-4-carboxamide MS (M+H): 615.05;
$^1$H NMR (400 MHz, CDCl$_3$) δ 10.70 (s, 1H), 8.47 (d, J=2.4 Hz, 1H), 7.81-7.75 (m, 4H), 7.60 (t, J=6.7 Hz, 1H), 7.48 (t, J=8.0 Hz, 1H), 7.42 (d, J=8.2 Hz, 1H), 7.38 (s, 1H), 7.28 (d, J=7.9 Hz, 1H), 7.11 (t, J=8.0 Hz, 1H), 6.89 (t, J=7.3 Hz, 1H), 4.98 (s, 1H), 4.86 (s, 2H), 4.04-3.98 (3H), 3.92 (td, J=8.1, 4.4 Hz, 1H), 3.36 (s, 3H), 2.80 (s, 3H), 2.25-2.14 (m, 2H).

Example 7(67)

N-(4-{3-amino-6-[3-(tetrahydro-3-furanyloxy)phenyl]-2-pyrazinyl}phenyl)-2-(3-chlorophenyl)-1,5-dimethyl-3-oxo-2,3-dihydro-1H-pyrazole-4-carboxamide MS (M+H): 597.1;
$^1$H NMR (400 MHz, CDCl$_3$) δ 10.70 (s, 1H), 8.38 (s, 1H), 7.82-7.77 (m, 4H), 7.52 (t, J=5.7 Hz, 2H), 7.47 (d, J=7.9 Hz, 1H), 7.42 (d, J=8.3 Hz, 1H), 7.38 (s, 1H), 7.32 (d, J=8.2 Hz, 1H), 7.28 (d, J=7.8 Hz, 1H), 6.86-6.82 (m, 1H), 5.01 (d, J=2.6

Hz, 1H), 4.81 (s, 2H), 4.03-3.96 (3H), 3.89 (dd, J=8.1, 3.3 Hz, 1H), 3.36 (s, 3H), 2.81 (s, 3H), 2.23-2.15 (2H).

Example 7(68)

N-(4-{3-amino-6-[3-methoxy-5-(tetrahydro-3-furanyloxy)phenyl]-2-pyrazinyl}phenyl)-1,5-dimethyl-3-oxo-2-phenyl-2,3-dihydro-1H-pyrazole-4-carboxamide MS (M+H): 593.1;
$^1$H NMR (400 MHz, CDCl$_3$) δ 10.85 (s, 1H), 8.35 (s, 1H), 7.82-7.76 (m, 4H), 7.55 (t, J=7.6 Hz, 2H), 7.46 (t, J=7.4 Hz, 1H), 7.36 (d, J=7.4 Hz, 2H), 7.09 (s, 2H), 6.41 (t, J=2.1 Hz, 1H), 4.99 (dd, J=5.5, 2.5 Hz, 1H), 4.82 (s, 2H), 4.02-3.95 (3H), 3.91-3.85 (m, 1H), 3.84 (s, 3H), 3.36 (s, 3H), 2.80 (s, 3H), 2.24-2.14 (2H).

Example 7(69)

N-{4-[3-amino-6-(5-methoxy-3-pyridinyl)-2-pyrazinyl]phenyl}-2-(3-chlorophenyl)-1,5-dimethyl-3-oxo-2,3-dihydro-1H-pyrazole-4-carboxamide MS (M+H): 542.0;
$^1$H NMR (400 MHz, CDCl$_3$) δ 10.67 (s, 1H), 8.68 (d, J=1.6 Hz, 1H), 8.37 (s, 1H), 8.22 (d, J=2.8 Hz, 1H), 7.77-7.70 (5H), 7.43 (t, J=8.0 Hz, 1H), 7.37 (d, J=8.4 Hz, 1H), 7.32 (t, J=1.8 Hz, 1H), 7.22 (d, J=7.8 Hz, 1H), 4.84 (s, 2H), 3.85 (s, 3H), 3.31 (s, 3H), 2.75 (s, 3H).

Example 7(70)

N-[4-(3-amino-6-{6-[(2-methoxyethyl)(methyl)amino]-2-pyridinyl}-2-pyrazinyl)phenyl]-2-(3-chlorophenyl)-1,5-dimethyl-3-oxo-2,3-dihydro-1H-pyrazole-4-carboxamide MS (M+H): 599.1;
$^1$H NMR (400 MHz, CDCl$_3$) δ 10.69 (s, 1H), 8.96 (s, 1H), 7.81-7.76 (4H), 7.55-7.43 (3H), 7.42-7.40 (1H), 7.38 (m, 1H), 7.29-7.26 (1H), 6.47 (dd, J=8.0 and 0.8 Hz, 1H), 4.83 (s, 2H), 3.83 (t, J=6.0 Hz, 2H), 3.64 (t, J=6.0 Hz, 2H), 3.36 (s, 3H), 3.35 (s, 3H), 3.13 (s, 3H), 2.80 (s, 3H).

Example 7(71)

N-[4-(3-amino-6-{3-[(1-methyl-3-pyrrolidinyl)oxy]phenyl}-2-pyrazinyl)phenyl]-2-(3-chlorophenyl)-1,5-dimethyl-3-oxo-2,3-dihydro-1H-pyrazole-4-carboxamide MS (M+H): 610.1;
$^1$H NMR (400 MHz, CDCl$_3$) δ 10.70 (s, 1H), 8.37 (s, 1H), 7.79 (s, 4H), 7.53-7.44 (m, 3H), 7.42 (d, J=8.3 Hz, 1H), 7.38 (t, J=1.7 Hz, 1H), 7.30 (dd, J=16.7, 8.7 Hz, 2H), 6.83 (dd, J=7.4, 1.8 Hz, 1H), 4.89 (dt, J=7.6, 3.8 Hz, 1H), 4.78 (s, 2H), 3.35 (s, 3H), 2.85-2.77 (m, 5H), 2.46-2.40 (m, 1H), 2.38 (s, 3H), 2.36-2.27 (m, 1H), 2.07-1.97 (m, 1H).

Example 7(72)

1-(3-amino-2-hydroxypropyl)-N-(4-{3-amino-6-[3-(1H-pyrazol-5-yl)phenyl]-2-pyrazinyl}phenyl)-5-methyl-3-oxo-2-phenyl-2,3-dihydro-1H-pyrazole-4-carboxamide MS (M+H): 602.1;
$^1$H NMR (400 MHz, DMSO-d$_6$) δ 10.89 (s, 1H), 8.57 (s, 1H), 8.36 (s, 1H), 7.87 (s, 1H), 7.81-7.37 (9H), 6.77 (s, 1H), 6.29 (s, 2H), 5.86 (d, J=5.7 Hz, 1H), 4.04-3.92 (m, 1H), 3.82-3.64 (m, 2H), 2.78-2.65 (m, 5H).

Example 7(73)

N-(4-{3-amino-6-[3-(2-pyrrolidinyl)phenyl]-2-pyrazinyl}phenyl)-1,5-dimethyl-3-oxo-2-phenyl-2,3-dihydro-1H-pyrazole-4-carboxamide MS (M+H): 546.2;
$^1$H NMR (400 MHz, DMSO-d$_6$) δ 10.88 (s, 1H), 8.46 (s, 1H), 7.91 (s, 1H), 7.80-7.68 (6H), 7.57 (t, J=7.5 Hz, 2H), 7.49 (t, J=7.4 Hz, 1H), 7.42 (d, J=7.3 Hz, 2H), 7.37-7.27 (m, 2H), 6.22 (s, 2H), 4.03 (t, J=7.6 Hz, 1H), 3.34 (s, 3H), 3.06-2.95 (m, 1H), 2.89-2.80 (m, 1H), 2.70 (s, 3H), 2.17-2.02 (m, 1H), 1.82-1.64 (m, 2H), 1.55-1.41 (m, 1H).

Example 7(74)

N-{4-[3-amino-6-(3-carbamimidoylphenyl)-2-pyrazinyl]phenyl}-1,5-dimethyl-3-oxo-2-phenyl-2,3-dihydro-1H-pyrazole-4-carboxamide MS (M+H): 519.1;
$^1$H NMR (400 MHz, DMSO-d$_6$) δ 10.89 (s, 1H), 8.55 (s, 1H), 8.29 (s, 1H), 8.02 (d, J=7.7 Hz, 1H), 7.78-7.68 (m, 5H), 7.57 (t, J=7.6 Hz, 2H), 7.49 (t, J=7.4 Hz, 1H), 7.46-7.41 (m, 3H), 6.46 (s, 3H), 6.29 (s, 2H), 3.34 (s, 3H), 2.70 (s, 3H).

Example 7(75)

N-{4-[3-amino-6-(3-carbamoylphenyl)-2-pyrazinyl]phenyl}-1,5-dimethyl-3-oxo-2-phenyl-2,3-dihydro-1H-pyrazole-4-carboxamide MS (M+H): 520.1;
$^1$H NMR (400 MHz, DMSO-d$_6$) δ 10.89 (s, 1H), 8.56 (s, 1H), 8.41 (s, 1H), 8.11 (d, J=7.8 Hz, 1H), 8.03 (s, 1H), 7.80-7.70 (m, 5H), 7.57 (t, J=7.6 Hz, 2H), 7.51-7.46 (m, 2H), 7.42 (d, J=7.4 Hz, 2H), 7.37 (s, 1H), 3.34 (s, 3H), 2.70 (s, 3H).

Example 7(76)

N-(4-{3-amino-6-[2-fluoro-3-(2-oxiranylmethoxy)phenyl]-2-pyrazinyl}phenyl)-2-(3-chlorophenyl)-1,5-dimethyl-3-oxo-2,3-dihydro-1H-pyrazole-4-carboxamide MS (M+H): 601.1;
$^1$H NMR (400 MHz, CDCl$_3$) δ 10.70 (s, 1H), 8.48 (d, J=2.3 Hz, 1H), 7.82-7.73 (4H), 7.61 (t, J=7.2 Hz, 1H), 7.48 (t, J=8.0 Hz, 1H), 7.42 (d, J=8.4 Hz, 1H), 7.38 (s, 1H), 7.28 (d, J=7.9 Hz, 1H), 7.11 (t, J=8.0 Hz, 1H), 7.00-6.94 (m, 1H), 4.85 (s, 2H), 4.29 (dd, J=11.2, 3.3 Hz, 1H), 4.09 (dd, J=11.2, 5.5 Hz, 1H), 3.40 (br m, 1H), 3.36 (s, 3H), 2.94-2.86 (m, 1H), 2.84-2.74 (m, 4H).

Example 7(77)

N-(4-{3-amino-6-[5-(3-hydroxy-3-methylbutoxy)-3-pyridinyl]-2-pyrazinyl}phenyl)-1,5-dimethyl-3-oxo-2-phenyl-2,3-dihydro-1H-pyrazole-4-carboxamide MS (M+H): 580.2;
$^1$H NMR (400 MHz, CDCl$_3$) δ 10.86 (s, 1H), 8.74 (d, J=1.5 Hz, 1H), 8.41 (s, 1H), 8.27 (d, J=2.7 Hz, 1H), 7.83-7.74 (m, 5H), 7.55 (t, J=7.6 Hz, 2H), 7.46 (t, J=7.4 Hz, 1H), 7.35 (d, J=7.3 Hz, 2H), 4.91 (s, 2H), 4.28 (t, J=6.4 Hz, 2H), 3.35 (s, 3H), 2.79 (s, 3H), 2.02 (t, J=6.3 Hz, 2H), 1.96 (s, 1H), 1.31 (s, 6H).

Example 7(78)

N-(4-{3-amino-6-[5-(3-hydroxy-3-methylbutoxy)-3-pyridinyl]-2-pyrazinyl}phenyl)-2-(3-chlorophenyl)-1,5-dimethyl-3-oxo-2,3-dihydro-1H-pyrazole-4-carboxamide MS (M+H): 614.1;
$^1$H NMR (400 MHz, CDCl$_3$) δ 10.72 (s, 1H), 8.74 (d, J=1.3 Hz, 1H), 8.41 (s, 1H), 8.27 (d, J=2.7 Hz, 1H), 7.83-7.75 (m, 5H), 7.48 (t, J=7.9 Hz, 1H), 7.42 (d, J=8.4 Hz, 1H), 7.38 (s, 1H), 7.27 (d, J=7.8 Hz, 1H), 4.91 (s, 2H), 4.28 (t, J=6.3 Hz, 2H), 3.36 (s, 3H), 2.80 (s, 3H), 2.02 (t, J=6.3 Hz, 2H), 1.96 (s, 1H), 1.31 (s, 6H).

Example 7(79)

N-(4-{3-amino-6-[3-(4-methyl-1-piperazinyl)phenyl]-2-pyrazinyl}phenyl)-2-(3-chlorophenyl)-1,5-dimethyl-3-oxo-2,3-dihydro-1H-pyrazole-4-carboxamide MS (M+H): 609.2;
$^1$H NMR (400 MHz, CDCl$_3$) δ 10.69 (s, 1H), 8.36 (s, 1H), 7.83-7.74 (m, 4H), 7.58-7.53 (m, 1H), 7.51-7.35 (4H), 7.35-7.25 (m, 2H), 6.91 (dd, J=8.1, 1.9 Hz, 1H), 4.82 (s, 2H), 3.35 (s, 3H), 3.32-3.23 (m, 4H), 2.79 (s, 3H), 2.63-2.56 (m, 4H), 2.35 (s, 3H).

Example 7(80)

N-(4-{3-amino-6-[5-(2-hydroxy-2-methylpropoxy)-3-pyridinyl]-2-pyrazinyl}phenyl)-2-(3-chlorophenyl)-1,5-dimethyl-3-oxo-2,3-dihydro-1H-pyrazole-4-carboxamide MS (M+H): 600.2;
$^1$H NMR (400 MHz, CD$_3$OD/CDCl$_3$) δ 10.67 (s, 1H), 8.61 (d, J=1.5 Hz, 1H), 8.32 (s, 1H), 8.16 (d, J=2.7 Hz, 1H), 7.81-7.80 (m, 1H), 7.75-7.69 (m, 4H), 7.49-7.40 (m, 2H), 7.35 (s, 1H), 7.31 (s, 1H), 7.23 (d, J=7.6 Hz, 1H), 3.84 (s, 2H), 3.35 (s, 3H), 2.73 (s, 3H), 1.29 (s, 6H).

Example 7(81)

N-[4-(3-amino-6-{3-[(1-methyl-3-pyrrolidinyl)oxy]phenyl}-2-pyrazinyl)phenyl]-1,5-dimethyl-2-(3-methylphenyl)-3-oxo-2,3-dihydro-1H-pyrazole-4-carboxamide MS (M+H): 590.2;
$^1$H NMR (400 MHz, CDCl$_3$) δ 10.86 (s, 1H), 8.36 (s, 1H), 7.82-7.76 (m, 4H), 7.51-7.48 (m, 2H), 7.42 (t, J=7.8 Hz, 1H), 7.31 (t, J=8.0 Hz, 1H), 7.28-7.25 (m, 1H), 7.18 (s, 1H), 7.13 (d, J=7.9 Hz, 1H), 6.86-6.78 (m, 1H), 4.90 (dd, J=7.7, 4.7 Hz, 1H), 4.81 (s, 2H), 3.34 (s, 3H), 2.84-2.78 (m, 6H), 2.46-2.40 (m, 4H), 2.38 (s, 3H), 2.36-2.27 (m, 1H), 2.02 (ddd, J=13.9, 8.1, 2.4 Hz, 1H).

Example 7(82)

N-[4-(3-amino-6-{6-[4-(2-hydroxyethyl)-1-piperazinyl]-2-pyridinyl}-2-pyrazinyl)phenyl]-1,5-dimethyl-3-oxo-2-phenyl-2,3-dihydro-1H-pyrazole-4-carboxamide MS (M+H): 606.2;
$^1$H NMR (400 MHz, DMSO-d$_6$) δ 10.89 (s, 1H), 8.75 (s, 1H), 7.76-7.69 (m, 4H), 7.57 (t, J=7.6 Hz, 3H), 7.49 (t, J=7.4 Hz, 1H), 7.42 (d, J=7.3 Hz, 3H), 6.74 (d, J=8.4 Hz, 1H), 6.38 (s, 2H), 4.40 (t, J=4.7 Hz, 1H), 3.56-3.49 (6H), 3.34 (s, 3H), 2.70 (s, 3H), 2.54-2.50 (m, 2H), 2.43-2.39 (m, 4H).

Example 7(83)

N-(4-{3-amino-6-[2-(4-morpholinyl)-1,3-thiazol-5-yl]-2-pyrazinyl}phenyl)-1,5-dimethyl-3-oxo-2-phenyl-2,3-dihydro-1H-pyrazole-4-carboxamide MS (M+H): 569.2;
$^1$H NMR (400 MHz, CDCl$_3$) δ 10.83 (s, 1H), 8.21 (s, 1H), 7.81-7.71 (m, 4H), 7.58-7.52 (m, 3H), 7.46 (t, J=7.1 Hz, 1H), 7.36 (d, J=7.4 Hz, 2H), 4.73 (s, 2H), 3.83-3.78 (m, 4H), 3.53-3.48 (m, 4H), 3.35 (s, 3H), 2.80 (s, 3H).

Example 7(84)

N-(4-{3-amino-6-[6-(methylamino)-2-pyridinyl]-2-pyrazinyl}phenyl)-2-(3-chlorophenyl)-1,5-dimethyl-3-oxo-2,3-dihydro-1H-pyrazole-4-carboxamide MS (M+H): 541.2;
$^1$H NMR (400 MHz, DMSO-d$_6$) δ 10.76 (s, 1H), 8.77 (s, 1H), 7.73 (q, J=8.9 Hz, 4H), 7.58 (dd, J=8.0, 4.5 Hz, 3H), 7.42 (t, J=7.8 Hz, 2H), 7.28 (d, J=7.3 Hz, 1H), 6.45 (d, J=4.9 Hz, 1H), 6.36 (d, J=8.1 Hz, 1H), 6.32 (s, 2H), 3.37 (s, 3H), 2.83 (d, J=4.8 Hz, 3H), 2.70 (s, 3H).

Example 7(85)

N-(4-{3-amino-6-[3-fluoro-5-(4-morpholinyl)phenyl]-2-pyrazinyl}phenyl)-2-(3-chlorophenyl)-1,5-dimethyl-3-oxo-2,3-dihydro-1H-pyrazole-4-carboxamide MS (M+H): 614.2;
$^1$H NMR (400 MHz, CDCl$_3$) δ 10.71 (s, 1H), 8.34 (s, 1H), 7.82-7.75 (m, 4H), 7.48 (t, J=8.1 Hz, 1H), 7.42 (d, J=8.3 Hz, 1H), 7.38 (s, 1H), 7.32 (s, 1H), 7.28 (d, J=7.8 Hz, 1H), 7.12 (d, J=9.6 Hz, 1H), 6.56 (d, J=11.7 Hz, 1H), 4.84 (s, 2H), 3.90-3.80 (m, 4H), 3.36 (s, 3H), 3.26-3.14 (m, 4H), 2.80 (s, 3H).

Example 7(86)

N-(4-{3-amino-6-[6-(3,3-dimethyl-1-piperazinyl)-2-pyridinyl]-2-pyrazinyl}phenyl)-1,5-dimethyl-2-(3-methylphenyl)-3-oxo-2,3-dihydro-1H-pyrazole-4-carboxamide MS (M+H): 604.3;
$^1$H NMR (400 MHz, DMSO-d$_6$) δ 10.90 (s, 1H), 8.75 (s, 1H), 7.77-7.69 (4H), 7.54 (t, J=7.9 Hz, 1H), 7.44 (t, J=7.7 Hz, 1H), 7.37 (d, J=7.4 Hz, 1H), 7.30 (d, J=7.7 Hz, 1H), 7.23 (s, 1H), 7.20 (d, J=7.8 Hz, 1H), 6.72 (d, J=8.5 Hz, 1H), 6.37 (s, 2H), 3.56-3.49 (m, 2H), 3.33 (s, 5H), 2.92-2.84 (m, 2H), 2.69 (s, 3H), 2.37 (s, 3H), 1.15 (s, 6H).

Example 7(87)

N-{4-[3-amino-6-(2-amino-3-pyridinyl)-2-pyrazinyl]phenyl}-2-(3-chlorophenyl)-1,5-dimethyl-3-oxo-2,3-dihydro-1H-pyrazole-4-carboxamide MS (M+H): 527.1;
$^1$H NMR (400 MHz, CD$_3$OD) δ 8.33 (s, 1H), 7.92 (dd, J=5.0, 1.7 Hz, 1H), 7.87 (dt, J=6.7, 3.3 Hz, 1H), 7.79-7.72 (m, 4H), 7.57-7.48 (m, 2H), 7.47-7.42 (m, 1H), 7.33-7.28 (m, 1H), 6.73-6.68 (m, 1H), 3.39 (s, 3H), 2.75 (s, 3H).

Example 7(88)

N-(4-{3-amino-6-[2-(methylamino)-3-pyridinyl]-2-pyrazinyl}phenyl)-2-(3-chlorophenyl)-1,5-dimethyl-3-oxo-2,3-dihydro-1H-pyrazole-4-carboxamide MS (M+H): 541.1;
$^1$H NMR (400 MHz, CD$_3$OD) δ 8.38 (s, 1H), 8.00 (dd, J=5.0, 1.7 Hz, 1H), 7.82 (dt, J=6.7, 3.3 Hz, 1H), 7.79-7.72 (m, 4H), 7.60-7.49 (m, 2H), 7.45-7.41 (m, 1H), 7.35-7.30 (m, 1H), 6.64-6.60 (m, 1H), 3.40 (s, 3H), 2.95 (s, 3H), 2.75 (s, 3H).

Example 7(89)

N-(4-{3-amino-6-[2-(dimethylamino)-1,3-thiazol-4-yl]-2-pyrazinyl}phenyl)-2-(3-chlorophenyl)-1,5-dimethyl-3-oxo-2,3-dihydro-1H-pyrazole-4-carboxamide MS (M+H): 561.1;
$^1$H NMR (400 MHz, CDCl$_3$) δ 10.69 (s, 1H), 8.63 (s, 1H), 7.81-7.73 (m, 4H), 7.51-7.40 (m, 2H), 7.38 (bs, 1H), 7.27 (d, J=8.1 Hz, 1H), 7.12 (s, 1H), 4.77 (s, 2H), 3.36 (s, 3H), 3.14 (s, 6H), 2.80 (s, 3H).

Example 7(90)

N-(4-{3-amino-6-[2-(4-methyl-1-piperazinyl)-1,3-thiazol-4-yl]-2-pyrazinyl}phenyl)-2-(3-chlorophenyl)-1,5-dimethyl-3-oxo-2,3-dihydro-1H-pyrazole-4-carboxamide MS (M+H): 616.2;
$^1$H NMR (400 MHz, CDCl$_3$) δ 10.69 (s, 1H), 8.60 (s, 1H), 7.81-7.72 (m, 4H), 7.47 (d, J=7.9 Hz, 1H), 7.42 (d, J=8.3 Hz, 1H), 7.38 (t, J=1.8 Hz, 1H), 7.28 (d, J=7.9 Hz, 1H), 7.18 (s, 1H), 4.80 (s, 2H), 3.62-3.53 (m, 4H), 3.36 (s, 3H), 2.80 (s, 3H), 2.59-2.51 (m, 4H), 2.36 (s, 3H).

Example 8

2-(3-chlorophenyl)-5-methyl-1,2-dihydro-3H-pyrazol-3-one

To a solution of 3-chlorophenylhydrazine hydrochloride (CAS No. 2312-23-4) (14.2 g) in acetic acid (60 mL) was added methyl acetoacetate (10.70 mL). The reaction was allowed to stir overnight at 60° C. and the volatiles were removed under reduced pressure and partitioned between saturated sodium bicarbonate and EtOAc. The organic layer was separated and concentrated under reduced pressure and purified by silica gel column chromatography using a gradient of 0-75% EtOAc in heptanes. The resulting solid was triturated with heptanes to give the title compound (10.3 g) having the following physical data as a white solid.
TLC Rf=0.46 (ethyl acetate:hexane=1:1).

Example 9

2-(3-chlorophenyl)-1,5-dimethyl-1,2-dihydro-3H-pyrazol-3-one

To a solution of the compound (5 g) prepared in Example 8 in acetonitrile (ACN) (50 mL) was added iodomethane (2.248 mL). The resulting mixture was heated in a sealed tube to 120° C. overnight. The reaction was incomplete by HPLC and additional iodomethane (2.248 mL) was added and heated for another 12 hours at 120° C. Upon completion, the reaction was concentrated under reduced pressure and partitioned between saturated sodium bicarbonate and EtOAc. The organic layer was separated and concentrated under reduced pressure and purified on an AnaLogix (SF25-120 g) column eluting with a gradient of 0-10% MeOH in DCM to give the title compound (3.5 g) having the following physical data as purple oil.
TLC Rf=0.46 (chloroform:methanol=9:1).

Example 10

2-(3-chlorophenyl)-1,5-dimethyl-3-oxo-2,3-dihydro-1H-pyrazole-4-carbaldehyde

DMF (14.97 mL) was cooled to 0° C. and phosphorus oxychloride (4.27 mL) was added dropwise. After addition, the mixture was allowed to stir for 1 hour at 0° C. In another flask, the compound prepared in Example 9 (3.4 g, 15.27 mmol) in DMF (15 mL) was cooled to 0° C. and the solution prepared above was added dropwise via a syringe. After addition, the resulting mixture was stirred at 0° C. for 1 hour and room temperature for 2 hours. Upon completion, the reaction was quenched with an ice cold sodium bicarbonate solution and then concentrated under reduced pressure. The residue was slurried in DCM (250 mL) and the salts were filtered and discarded. The filtrated was concentrated under reduced pressure to give the title compound (3.8 g) having the following physical data. The compound was used without purification in next reaction.
TLC Rf=0.26 (chloroform:ethyl acetate=1:1).

Example 11

2-(3-chlorophenyl)-1,5-dimethyl-3-oxo-2,3-dihydro-1H-pyrazole-4-carboxylic acid

To a mixture of the compound prepared in Example 10 (3.8 g) in THF (72.2 mL) and water (72.2 mL) was added sulfamic acid (3.09 g) and sodium chlorite (2.88 g) at 0° C. The reaction was allowed to stir for several hours at room temperature and then poured into saturated brine and extracted with EtOAc. The organic layer and concentrated under reduced pressure and the residue was triturated with methy tert-butylether (MTBE) to give the title compound (1.0 g) having the following physical data as a white solid.
TLC Rf=0.46 (chloroform:methanol=9:1).

Example 12

3-(4-aminophenyl)-5-bromo-2-pyrazinamine

A suspension of 3,5-dibromopyrazin-2-amine (CAS No. 957230-70-5) (15 g), Pd(PPh$_3$)$_4$ (3.2 g), 5-(4,4,5,5-tetramethyl-1,3,2-dioxaborolan-2-yl)pyridin-2-amine (12 g), and Na₂CO₃ (12 g) in a 3 to 1 mixture of dioxane/water (600 mL) was degassed with a stream of nitrogen for 10 minutes. The reaction was heated at 90° C. overnight, at which time LC/MS indicated the reaction was complete. The mixture was concentrated, diluted with water (200 mL) and extracted with EtOAc (3×300 mL). The organic layers were combined, dried over Na₂SO₄, and evaporated under reduced pressure. The crude solid was triturated with a 1 to 1 mixture of DCM/MTBE (100 mL) to give the title compound (11 g) having the following physical data as a yellow solid.

MS (M+H): 264.9 and 266.9;
¹H NMR (400 MHz, CDCl₃): δ 7.95 (s, 1H), 7.53 (d, J=8.4 Hz, 2H), 6.73 (d, J=8.4 Hz, 2H), 4.77 (bs, NH2, 2H), 3.88 (bs, NH2, 2H).

Example 13

3-(4-aminophenyl)-5-[2-(4-morpholinyl)-4-pyridinyl]-2-pyrazinamine

A suspension of the compound prepared in Example 12 (7.6 g), Pd(PPh₃)₄ (3.3 g), 4-(4-(4,4,5,5-tetramethyl-1,3,2-dioxaborolan-2-yl)pyridin-2-yl)morpholine (8.3 g), and Na₂CO₃ (9.1 g, 85 mmol) in a 3 to 1 mixture of dioxane/water (280 mL) was degassed with a stream of nitrogen for 10 minutes. The reaction was heated at 90° C. overnight, at which time LC/MS indicated the reaction was complete. The mixture was concentrated, diluted with aqueous saturated sodium bicarbonate solution (200 mL) and extracted with EtOAc (3×200 mL). The organic layers were combined, dried over Na₂SO₄, and evaporated under reduced pressure. The crude product was obtained as a brown oil which was precipitated from DCM (50 mL) to give a dark yellow solid. The solid was filtered and triturated with a 1 to 1 solution of DCM/EtOAc (3×50 mL) to give the title compound (8.4 g) having the following physical data as a light yellow solid.

MS (M+H): 349.2;
¹H NMR (300 MHz, DMSO-d₆) δ 8.55 (s, 1H), 8.15 (d, J=5.4 Hz, 1H), 7.51 (d, J=8.4 Hz, 2H), 7.34 (s, 1H), 7.29 (dd, J=5.4, 1.5 Hz, 1H), 7.68 (d, J=8.7 Hz, 2H), 6.34 (s, 2H), 5.45 (s, 2H), 4.74-4.70 (m, 4H), 3.51-3.48 (m, 4H).

Example 14(1)

N-(4-{3-amino-6-[2-(4-morpholinyl)-4-pyridinyl]-2-pyrazinyl}phenyl)-1,5-dimethyl-3-oxo-2-phenyl-2,3-dihydro-1H-pyrazole-4-carboxamide

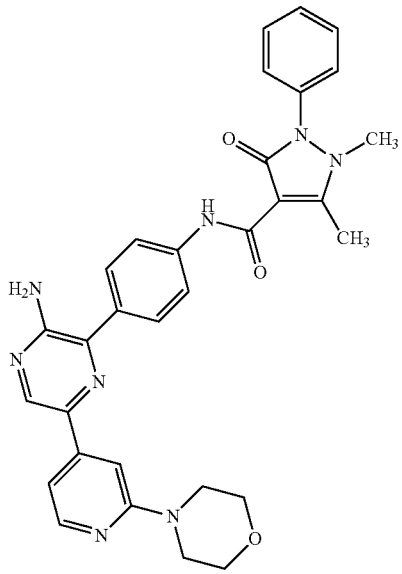 [SMILES: Cc1c(C(=O)Nc2ccc(-c3nc(-c4ccnc(N5CCOCC5)c4)cnc3N)cc2)c(=O)n(-c2ccccc2)n1C]

To the compound prepared in Example 1 (0.100 g) in 5 mL of DCM, 1.0 mL of DMF and N,N-diisopropylethylamine (DIEA) (0.072 g) was added the HATU (0.164 g) and stirred for 30 minutes. To the activated ester was added the compound prepared in Example 13 (0.15 g) and stirred for 1 hour. The reaction mixture was diluted with water, extracted with additional DCM, and the organic layer was washed with water, brine and dried over anhydrous Na₂SO₄. The DCM layer was filtered and concentrated, and the crude was chromatographed on silica gel using 10:1 DCM:MeOH to give the title compound (0.2 g) having the following physical data.

MS (M+H): 563.2;
¹H NMR (400 MHz, CDCl₃) δ 10.86 (s, 1H), 8.41 (s, 1H), 8.24 (d, J=5.3 Hz, 1H), 7.82 (d, J=8.6 Hz, 2H), 7.75 (d, J=8.5 Hz, 2H), 7.55 (t, J=7.6 Hz, 2H), 7.46 (t, J=7.4 Hz, 1H), 7.36 (d, J=7.5 Hz, 2H), 7.30 (s, 1H), 7.17 (d, J=5.3 Hz, 1H), 4.93 (d, J=8.5 Hz, 2H), 3.87-3.79 (m, 4H), 3.60-3.53 (m, 4H), 3.36 (s, 3H), 2.80 (s, 3H).

Example 14(2)-14(39)

The compound having the following physical data was prepared by using the compound prepared in Example 12, 4-(4-(4,4,5,5-tetramethyl-1,3,2-dioxaborolan-2-yl)pyridin-2-yl)morpholine or the corresponding dioxaborolane compound instead thereof, and using the compound prepared in Example 1 or the corresponding carboxylic acid instead thereof in the process of Example 13→Example 14(1).

Example 14(2)

N-(4-{3-amino-6-[4-(4-morpholinylmethyl)phenyl]-2-pyrazinyl}phenyl)-1,5-dimethyl-3-oxo-2-phenyl-2,3-dihydro-1H-pyrazole-4-carboxamide MS (M+H): 576.7;
¹H NMR (400 MHz, CDCl₃) δ 10.84 (s, 1H), 8.38 (s, 1H), 7.94-7.86 (m, 2H), 7.85-7.74 (m, 4H), 7.57-7.52 (m, 2H), 7.48-7.43 (m, 1H), 7.40-7.34 (m, 4H), 4.80 (s, 2H), 3.70 (t, 4H), 3.52 (s, 2H), 3.35 (s, 3H), 2.80 (s, 3H), 2.45 (t, 4H).

Example 14(3)

N-(4-{3-amino-6-[2-(4-morpholinyl)-4-pyridinyl]-2-pyrazinyl}phenyl)-1,5-dimethyl-3-oxo-2-[3-(trifluoromethyl)phenyl]-2,3-dihydro-1H-pyrazole-4-carboxamide MS (M+H): 631.1;
¹H NMR (400 MHz, CDCl₃) δ 10.67 (s, 1H), 8.42 (s, 1H), 8.24 (d, J=5.2 Hz, 1H), 7.83-7.74 (m, 4H), 7.70 (d, J=4.6 Hz, 2H), 7.61 (d, J=5.8 Hz, 2H), 7.29 (s, 1H), 7.17 (d, J=5.2 Hz, 1H), 4.93 (s, 2H), 3.85-3.81 (m, 4H), 3.59-3.54 (m, 4H), 3.37 (s, 3H), 2.83 (s, 3H).

Example 14(4)

N-(4-{3-amino-6-[2-(4-morpholinyl)-4-pyridinyl]-2-pyrazinyl}phenyl)-2-(3-chlorophenyl)-1,5-dimethyl-3-oxo-2,3-dihydro-1H-pyrazole-4-carboxamide MS (M+H): 597.1;
¹H NMR (400 MHz, CDCl₃) δ 10.72 (s, 1H), 8.42 (s, 1H), 8.23 (dd, J=5.2 and 0.8 Hz, 1H), 7.81 (d, J=8.8 Hz, 2H), 7.75 (d, J=8.8 Hz, 2H), 7.50-7.41 (2H), 7.38 (m, 1H), 7.29 (s, 1H), 7.28-7.26 (1H), 7.17 (dd, J=5.2 and 0.8 Hz, 1H), 4.93 (s, 2H), 3.83 (m, 4H), 3.56 (m, 4H), 3.36 (s, 3H), 2.80 (s, 3H).

Example 14(5)

N-{4-[3-amino-6-(2-fluoro-3-methoxyphenyl)-2-pyrazinyl]phenyl}-2-(3-chlorophenyl)-1,5-dimethyl-3-oxo-2,3-dihydro-1H-pyrazole-4-carboxamide MS (M+H): 559.0;
$^1$H NMR (400 MHz, DMSO-d$_6$) δ 10.70 (s, 1H), 8.29 (d, J=2.4 Hz, 1H), 7.75-7.69 (4H), 7.61-7.53 (s, 3H), 7.43-7.38 (2H), 7.17 (t, J=8.4 Hz, 1H), 7.11 (td, J=4.0 and 1.6 Hz, 1H), 6.39 (d, 1H), 3.84 (s, 3H), 3.36 (s, 3H), 2.69 (s, 3H).

Example 14(6)

N-{4-[3-amino-6-(2-fluoro-3-methoxyphenyl)-2-pyrazinyl]phenyl}-2-(2-fluorophenyl)-1,5-dimethyl-3-oxo-2,3-dihydro-1H-pyrazole-4-carboxamide MS (M+H): 543.1;
$^1$H NMR (400 MHz, CDCl$_3$) δ 10.74 (s, 1H), 8.48 (d, J=2.8 Hz, 1H), 7.80-7.74 (4H), 7.58-7.49 (2H), 7.42 (td, J=7.6 and 1.6 Hz, 1H), 7.35-7.28 (2H), 7.12 (td, J=7.6 and 1.6 Hz, 1H), 6.93 (td, J=8.0 and 1.6 Hz, 1H), 4.86 (s, 1H), 3.91 (s, 3H), 3.34 (s, 3H), 3.78 (s, 3H).

Example 14(7)

N-(4-{3-amino-6-[2-(4-morpholinyl)-4-pyridinyl]-2-pyrazinyl}phenyl)-2-(4-chlorophenyl)-1,5-dimethyl-3-oxo-2,3-dihydro-1H-pyrazole-4-carboxamide MS (M+H): 597.5;
$^1$H NMR (400 MHz, DMSO-d$_6$) δ 10.80 (s, 1H), 8.62 (s, 1H), 8.13 (d, J=5.2 Hz, 1H), 7.76-7.69 (4H), 7.63 (d, J=8.8 Hz, 2H), 7.45 (d, J=8.8 Hz, 2H), 7.32 (s, 1H), 7.26 (dd, J=5.2 and 1.2 Hz, 1H), 6.49 (s, 2H), 3.68 (m, 4H), 3.47 (m, 4H), 3.34 (s, 3H), 2.69 (s, 3H).

Example 14(8)

N-(4-{3-amino-6-[2-(4-morpholinyl)-4-pyridinyl]-2-pyrazinyl}phenyl)-2-cyclopentyl-1,5-dimethyl-3-oxo-2,3-dihydro-1H-pyrazole-4-carboxamide MS (M+H): 555.1;
$^1$H NMR (400 MHz, CDCl$_3$) δ 10.98 (s, 1H), 8.41 (s, 1H), 8.24 (d, J=5.2 Hz, 1H), 7.84 (d, J=8.6 Hz, 2H), 7.75 (d, J=8.5 Hz, 2H), 7.31 (s, 1H), 7.17 (d, J=5.2 Hz, 1H), 4.93 (s, 2H), 4.64 (p, J=8.4 Hz, 1H), 3.86-3.81 (m, 4H), 3.60-3.55 (m, 4H), 3.51 (s, 3H), 2.69 (s, 3H), 2.22-2.13 (m, 2H), 2.06-1.92 (4H), 1.72-1.64 (m, 2H).

Example 14(9)

N-{4-[3-amino-6-(2-fluoro-3-methoxyphenyl)-2-pyrazinyl]phenyl}-2-cyclopentyl-1,5-dimethyl-3-oxo-2,3-dihydro-1H-pyrazole-4-carboxamide MS (M+H): 517.1;
$^1$H NMR (400 MHz, CDCl$_3$) δ 10.94 (s, 1H), 8.48 (d, J=2.3 Hz, 1H), 7.84-7.74 (m, 4H), 7.58 (t, J=7.3 Hz, 1H), 7.13 (t, J=8.0 Hz, 1H), 6.94 (t, J=8.0 Hz, 1H), 4.85 (s, 2H), 4.67-4.60 (m, 1H), 3.92 (s, 3H), 3.50 (s, 3H), 2.69 (s, 3H), 2.22-2.13 (m, 2H), 2.05-1.93 (m, 4H), 1.72-1.62 (m, 2H).

Example 14(10)

N-(4-{3-amino-6-[2-(3-methoxy-1-azetidinyl)-4-pyridinyl]-2-pyrazinyl}phenyl)-2-(3-chlorophenyl)-1,5-dimethyl-3-oxo-2,3-dihydro-1H-pyrazole-4-carboxamide MS (M+H): 597.5;
$^1$H NMR (400 MHz, CDCl$_3$) δ 10.70 (s, 1H), 8.38 (s, 1H), 8.16 (d, J=5.4 Hz, 1H), 7.76 (dd, J=21.1, 8.6 Hz, 4H), 7.52-7.33 (m, 3H), 7.26 (s, 1H), 7.17-7.08 (m, 1H), 6.87 (s, 1H), 5.01 (s, 2H), 4.49-4.31 (m, 1H), 4.31-4.19 (m, 2H), 3.93 (dd, J=8.7, 4.1 Hz, 2H), 3.33 (s, 3H), 3.32 (s, 3H), 2.77 (s, 3H).

Example 14(11)

N-(4-{3-amino-6-[6-(3-methoxy-1-azetidinyl)-2-pyridinyl]-2-pyrazinyl}phenyl)-1,5-dimethyl-2-(3-methylphenyl)-3-oxo-2,3-dihydro-1H-pyrazole-4-carboxamide MS (M+H): 577.2;
$^1$H NMR (400 MHz, DMSO-d$_6$) δ 10.89 (s, 1H), 8.75 (s, 1H), 7.76-7.69 (4H), 7.58-7.53 (1H), 7.46-7.42 (2H), 7.31-7.29 (1H), 7.23 (s, 1H), 7.21-7.18 (1H), 6.38 (s, 2H), 6.32 (d, J=7.8 Hz, 1H), 4.32 (m, 1H), 4.18 (dd, J=8.8 and 6.4 Hz, 2H), 3.78 (dd, J=8.8 and 4.4 Hz, 2H), 3.33 (s, 3H), 3.24 (s, 3H) 2.69 (s, 3H), 2.37 (s, 3H).

Example 14(12)

N-(4-{3-amino-6-[6-(3-methoxy-1-azetidinyl)-2-pyridinyl]-2-pyrazinyl}phenyl)-2-(3-chlorophenyl)-1,5-dimethyl-3-oxo-2,3-dihydro-1H-pyrazole-4-carboxamide MS (M+H): 597.0;
$^1$H NMR (400 MHz, CDCl$_3$) δ 10.69 (s, 1H), 8.98 (s, 1H), 7.81-7.75 (4H), 7.60 (dd, J=7.2 and 0.8 Hz, 1H), 7.53-7.45 (2H), 7.43-7.37 (2H), 7.28-7.25 (m, 1H), 6.27 (dd, J=8.0 and 0.8 Hz, 1H), 4.87 (s, 2H), 4.36 (m, 1H), 4.25 (m, 2H), 3.93 (dd, J=9.2 and 4.0 Hz, 2H), 3.35 (s, 6H), 2.79 (s, 3H).

Example 14(13)

N-(4-{3-amino-6-[6-(3-methoxy-1-azetidinyl)-2-pyridinyl]-2-pyrazinyl}phenyl)-2-(2-chlorophenyl)-1,5-dimethyl-3-oxo-2,3-dihydro-1H-pyrazole-4-carboxamide MS (M+H): 597.1;
$^1$H NMR (400 MHz, CDCl$_3$) δ 10.75 (s, 1H), 8.96 (s, 1H), 7.81-7.43 (4H), 7.61-7.58 (2H), 7.52-7.44 (4H), 6.26 (d, J=8.4 Hz, 1H), 4.90 (s, 2H), 4.35 (m, 1H), 4.25 (dd, J=8.0 and 6.4 Hz, 2H), 3.92 (dd, J=8.0 and 6.4 Hz, 2H), 3.33 (s, 3H), 3.28 (s, 3H), 2.77 (s, 3H).

Example 14(14)

N-(4-{3-amino-6-[2-(4-morpholinyl)-4-pyridinyl]-2-pyrazinyl}phenyl)-2-(2,5-difluorophenyl)-1,5-dimethyl-3-oxo-2,3-dihydro-1H-pyrazole-4-carboxamide MS (M+H): 599.2;
$^1$H NMR (400 MHz, CDCl$_3$) δ 10.63 (s, 1H), 8.40 (s, 1H), 8.22 (d, J=5.2 Hz, 1H), 7.79 (d, J=8.8 Hz, 2H), 7.73 (d, J=8.8

Hz, 2H), 7.29-7.15 (5H), 5.00 (s, 2H), 3.81 (m, 4H), 3.55 (m, 4H), 3.35 (s, 3H), 2.77 (s, 3H).

Example 14(15)

N-(4-{3-amino-6-[3-(dimethylcarbamoyl)phenyl]-2-pyrazinyl}phenyl)-2-(3-chlorophenyl)-1,5-dimethyl-3-oxo-2,3-dihydro-1H-pyrazole-4-carboxamide MS (M+H): 582.0;
$^1$H NMR (400 MHz, CDCl$_3$) δ 10.70 (s, 1H), 8.40 (s, 1H), 8.03-7.95 (m, 2H), 7.84-7.73 (m, 4H), 7.50-7.39 (m, 3H), 7.39-7.34 (m, 2H), 7.27 (ddd, J=7.8, 2.0, 1.3 Hz, 1H), 4.86 (s, 2H), 3.35 (s, 3H), 3.11 (s, 3H), 2.99 (s, 3H), 2.79 (s, 3H).

Example 14(16)

N-(4-{3-amino-6-[2-(4-morpholinyl)-4-pyridinyl]-2-pyrazinyl}phenyl)-2-(2,6-dimethylphenyl)-1,5-dimethyl-3-oxo-2,3-dihydro-1H-pyrazole-4-carboxamide MS (M+H): 591.2;
$^1$H NMR (400 MHz, CDCl$_3$) δ 10.97 (s, 1H), 8.41 (s, 1H), 8.23 (d, J=5.2 Hz, 1H), 7.83 (d, J=8.8 Hz, 1H), 7.35-7.30 (2H), 7.21-7.19 (2H), 7.17 (dd, J=5.2, 1.6 Hz, 1H), 4.95 (s, 2H), 3.83 (m, 4H), 3.56 (m, 4H), 3.23 (s, 3H), 2.79 (s, 3H), 2.16 (s, 6H).

Example 14(17)

N-(4-{3-amino-6-[3-(dimethylcarbamoyl)phenyl]-2-pyrazinyl}phenyl)-1,5-dimethyl-2-(3-methylphenyl)-3-oxo-2,3-dihydro-1H-pyrazole-4-carboxamide MS (M+H): 562.1;
$^1$H NMR (400 MHz, CDCl$_3$) δ 10.87 (s, 1H), 8.39 (s, 1H), 8.02-7.95 (m, 2H), 7.84-7.72 (m, 4H), 7.48-7.38 (m, 1H), 7.35 (dt, J=7.6, 1.4 Hz, 1H), 7.27 (s, 1H), 7.17 (s, 1H), 7.12 (d, J=8.5 Hz, 1H), 4.87 (s, 2H), 3.33 (s, 3H), 3.11 (s, 3H), 2.98 (s, 3H), 2.77 (s, 3H), 2.42 (s, 3H).

Example 14(18)

N-(4-{3-amino-6-[4-(4-morpholinylmethyl)phenyl]-2-pyrazinyl}phenyl)-5-methyl-3-oxo-2-phenyl-1-(2-propanyl)-2,3-dihydro-1H-pyrazole-4-carboxamide MS (M+H): 604.3;
$^1$H NMR (400 MHz, CDCl$_3$) δ 10.85 (s, 1H), 8.32 (s, 1H), 7.84 (d, J=8.2 Hz, 2H), 7.78-7.67 (m, 4H), 7.49-7.43 (m, 2H), 7.38 (ddd, J=6.4, 3.9, 1.2 Hz, 1H), 7.31 (dd, J=9.9, 7.9 Hz, 4H), 4.75 (s, 2H), 4.26-4.10 (m, 1H), 3.68-3.59 (m, 4H), 3.46 (s, 2H), 2.82 (s, 3H), 2.45-2.31 (m, 4H), 1.26 (d, J=7.0 Hz, 6H).

Example 14(19)

N-(4-{3-amino-6-[2-(4-morpholinyl)-4-pyridinyl]-2-pyrazinyl}phenyl)-1,5-dimethyl-2-(4-methylphenyl)-3-oxo-2,3-dihydro-1H-pyrazole-4-carboxamide MS (M+H): 577.0;
$^1$H NMR (400 MHz, CDCl$_3$) δ 10.88 (s, 1H), 8.39 (s, 1H), 8.21 (dd, J=5.2 and 0.8 Hz, 1H), 7.79 (d, J=8.8 Hz, 2H), 7.72 (s, J=8.8 Hz, 2H), 7.31 (dd, J=4.8 and 0.8 Hz, 2H), 7.28 (s, 1H), 7.21-7.19 (2H), 7.15 (dd, J=5.2 and 1.2 Hz, 1H), 5.00 (s, 2H), 3.81 (m, 4H), 3.55 (m, 4H), 3.31 (s, 3H), 2.76 (s, 3H), 2.40 (s, 3H).

Example 14(20)

N-(4-{3-amino-6-[2-(4-morpholinyl)-4-pyridinyl]-2-pyrazinyl}phenyl)-2-(3-fluorophenyl)-1,5-dimethyl-3-oxo-2,3-dihydro-1H-pyrazole-4-carboxamide MS (M+H): 581.1;
$^1$H NMR (400 MHz, CDCl$_3$) δ 10.72 (s, 1H), 8.40 (s, 1H), 7.79 (d, J=8.8 Hz, 2H), 7.74 (d, J=8.8 Hz, 2H), 7.50 (m, 1H), 7.28 (s, 1H), 7.16-7.09 (4H), 4.99 (bs, 2H), 3.82 (m, 4H), 3.55 (m, 4H), 3.35 (s, 3H), 2.78 (s, 3H).

Example 14(21)

N-(4-{3-amino-6-[2-(4-morpholinyl)-4-pyridinyl]-2-pyrazinyl}phenyl)-2-(4-methoxyphenyl)-1,5-dimethyl-3-oxo-2,3-dihydro-1H-pyrazole-4-carboxamide MS (M+H): 593.1;
$^1$H NMR (400 MHz, CDCl$_3$) δ 10.92 (s, 1H), 8.41 (s, 1H), 8.24 (d, J=5.2 Hz, 1H), 7.82 (d, J=8.6 Hz, 2H), 7.74 (d, J=8.6 Hz, 2H), 7.29 (d, J=7.8 Hz, 2H), 7.26 (s, 1H), 7.17 (d, J=5.2 Hz, 1H), 7.04 (d, J=8.8 Hz, 2H), 4.93 (s, 2H), 3.86 (s, 3H), 3.85-3.80 (m, 4H), 3.59-3.55 (m, 4H), 3.33 (s, 3H), 2.78 (s, 3H).

Example 14(22)

N-{4-[3-amino-6-(2-fluoro-3-methoxyphenyl)-2-pyrazinyl]phenyl}-1,5-dimethyl-3-oxo-2-[3-(trifluoromethyl)phenyl]-2,3-dihydro-1H-pyrazole-4-carboxamide MS (M+H): 593.1;
$^1$H NMR (400 MHz, CDCl$_3$) δ 10.64 (s, 1H), 8.49 (d, J=2.3 Hz, 1H), 7.82-7.74 (m, 4H), 7.71-7.65 (m, 2H), 7.61 (s, 2H), 7.56 (t, J=7.5 Hz, 1H), 7.13 (t, J=8.0 Hz, 1H), 6.94 (t, J=7.6 Hz, 1H), 4.84 (s, 2H), 3.92 (s, 3H), 3.36 (s, 3H), 2.82 (s, 3H).

Example 14(23)

N-{4-[3-amino-6-(2-fluoro-3-methoxyphenyl)-2-pyrazinyl]phenyl}-2-(4-methoxyphenyl)-1,5-dimethyl-3-oxo-2,3-dihydro-1H-pyrazole-4-carboxamide MS (M+H): 555.1;
$^1$H NMR (400 MHz, CDCl$_3$) δ 10.90 (s, 1H), 8.49 (d, J=2.4 Hz, 1H), 7.82-7.73 (m, 4H), 7.57 (t, J=7.3 Hz, 1H), 7.27 (d, J=8.9 Hz, 2H), 7.13 (t, J=8.0 Hz, 1H), 7.04 (d, J=8.8 Hz, 2H), 6.93 (t, J=7.9 Hz, 1H), 4.85 (s, 2H), 3.92 (s, 3H), 3.86 (s, 3H), 3.32 (s, 3H), 2.78 (s, 3H).

Example 14(24)

N-(4-{3-amino-6-[2-(4-morpholinyl)-4-pyridinyl]-2-pyrazinyl}phenyl)-5-ethyl-1-methyl-3-oxo-2-phenyl-2,3-dihydro-1H-pyrazole-4-carboxamide MS (M+H): 577.1;
$^1$H NMR (400 MHz, CDCl$_3$) δ 10.90 (s, 1H), 8.41 (s, 1H), 8.24 (d, J=5.2 Hz, 1H), 7.82 (d, J=8.6 Hz, 2H), 7.74 (d, J=8.5 Hz, 2H), 7.55 (t, J=7.6 Hz, 2H), 7.46 (t, J=7.4 Hz, 1H), 7.36 (d, J=8.2 Hz, 2H), 7.30 (s, 1H), 7.17 (d, J=5.2 Hz, 1H), 4.93

(s, 2H), 3.85-3.81 (m, 4H), 3.58-3.55 (m, 4H), 3.38 (s, 3H), 3.25 (q, J=7.5 Hz, 2H), 1.38 (t, J=7.5 Hz, 3H).

Example 14(25)

N-(4-{3-amino-6-[2-(4-morpholinyl)-4-pyridinyl]-2-pyrazinyl}phenyl)-2-(2-chlorophenyl)-1,5-dimethyl-3-oxo-2,3-dihydro-1H-pyrazole-4-carboxamide MS (M+H): 597.1;
$^1$H NMR (400 MHz, CDCl$_3$) δ 10.78 (s, 1H), 8.41 (s, 1H), 8.23 (d, J=5.2 Hz, 1H), 7.81 (d, J=8.8 Hz, 2H), 7.75 (d, J=8.8 Hz, 2H), 7.62-7.60 (1H), 7.53-7.44 (3H), 7.30 (s, 1H), 7.16 (dd, J=5.2 and 1.2 Hz, 1H), 4.95 (s, 2H), 3.83 (m, 4H), 3.56 (m, 4H), 3.30 (s, 3H), 2.79 (s, 3H).

Example 14(26)

N-(4-{3-amino-6-[2-(4-morpholinyl)-4-pyridinyl]-2-pyrazinyl}phenyl)-1-ethyl-5-methyl-3-oxo-2-phenyl-2,3-dihydro-1H-pyrazole-4-carboxamide MS (M+H): 577.1;
$^1$H NMR (400 MHz, CDCl$_3$) δ 10.87 (s, 1H), 8.41 (s, 1H), 8.23 (d, J=5.3 Hz, 1H), 7.87-7.70 (m, 4H), 7.57-7.50 (m, 2H), 7.48-7.42 (m, 1H), 7.40-7.34 (m, 2H), 7.29 (s, 1H), 7.16 (dd, J=5.3, 1.3 Hz, 1H), 4.96 (s, 2H), 3.89-3.76 (6H), 3.61-3.52 (m, 4H), 2.80 (s, 3H), 1.05 (t, J=7.1 Hz, 3H).

Example 14(27)

N-{4-[3-amino-6-(2-fluoro-3-methoxyphenyl)-2-pyrazinyl]phenyl}-1-ethyl-5-methyl-3-oxo-2-phenyl-2,3-dihydro-1H-pyrazole-4-carboxamide MS (M+H): 539.1;
$^1$H NMR (400 MHz, CDCl$_3$) δ 10.85 (s, 1H), 8.48 (d, J=2.5 Hz, 1H), 7.85-7.69 (m, 4H), 7.55 (dtt, J=8.9, 3.7, 1.9 Hz, 3H), 7.47-7.41 (m, 1H), 7.40-7.33 (m, 2H), 7.12 (td, J=8.1, 1.4 Hz, 1H), 6.93 (td, J=8.0, 1.5 Hz, 1H), 4.87 (s, 2H), 3.91 (s, 3H), 3.81 (q, J=7.1 Hz, 2H), 2.80 (s, 3H), 1.05 (t, J=7.1 Hz, 3H).

Example 14(28)

N-{4-[3-amino-6-(2-fluoro-3-methoxyphenyl)-2-pyrazinyl]phenyl}-2-(2-chlorophenyl)-1,5-dimethyl-3-oxo-2,3-dihydro-1H-pyrazole-4-carboxamide MS (M+H): 559.0;
$^1$H NMR (400 MHz, CDCl$_3$) δ 10.77 (s, 1H), 8.45 (d, J=2.4 Hz, 1H), 7.80 (d, J=8.8 Hz, 2H), 7.75 (d, J=8.8 Hz, 2H), 7.62-7.43 (5H), 7.13 (td, J=8.0 and 1.6 Hz, 1H), 6.94 (td, J=8.0 and 1.6 Hz, 1H), 5.09 (bs, 2H), 3.91 (s, 3H), 3.30 (s, 3H), 2.79 (s, 3H).

Example 14(29)

N-(4-{3-amino-6-[2-(4-morpholinyl)-4-pyridinyl]-2-pyrazinyl}phenyl)-1,5-dimethyl-2-(3-methylphenyl)-3-oxo-2,3-dihydro-1H-pyrazole-4-carboxamide MS (M+H): 577.1;
$^1$H NMR (400 MHz, CDCl$_3$) δ 10.88 (s, 1H), 8.40 (s, 1H), 8.23 (dd, J=5.2 and 0.4 Hz, 1H), 7.81 (d, J=8.8 Hz, 2H), 7.73 (d, J=8.8 Hz, 2H), 7.41 (t, J=8.0 Hz, 1H), 7.29 (s, 1H), 7.27-7.24 (1H), 7.17-7.15 (2H), 7.13-7.11 (1H), 4.98 (s, 2H), 3.82 (m, 4H), 3.56 (m, 4H), 3.33 (s, 3H), 2.77 (s, 3H), 2.42 (s, 3H).

Example 14(30)

N-(4-{3-amino-6-[6-(3-methoxy-1-azetidinyl)-2-pyridinyl]-2-pyrazinyl}phenyl)-1,5-dimethyl-3-oxo-2-phenyl-2,3-dihydro-1H-pyrazole-4-carboxamide MS (M+H): 563.1;
$^1$H NMR (400 MHz, CDCl$_3$) δ 10.83 (s, 1H), 8.98 (s, 1H), 7.80 (d, J=8.8 Hz, 2H), 7.76 (d, J=8.8 Hz, 2H), 7.61 (d, J=7.6 Hz, 1H), 7.56-7.43 (4H), 7.37-7.34 (2H), 6.27 (d, J=8.0 Hz, 1H), 4.85 (s, 2H), 4.36 (m, 1H), 4.26 (m, 2H), 3.93 (dd, J=8.8 and 4.0 Hz, 2H), 3.35 (s, 6H), 2.79 (s, 3H).

Example 14(31)

N-(4-{3-amino-6-[6-(3-methoxy-1-azetidinyl)-2-pyridinyl]-2-pyrazinyl}phenyl)-2-(3-fluorophenyl)-1,5-dimethyl-3-oxo-2,3-dihydro-1H-pyrazole-4-carboxamide MS (M+H): 581.1;
$^1$H NMR (400 MHz, CDCl$_3$) δ 10.70 (s, 1H), 8.97 (s, 1H), 7.81-7.75 (4H), 7.61 (dd, J=7.6 and 0.8 Hz, 1H), 7.53-7.47 (2H), 7.17-7.10 (3H), 6.26 (dd, J=8.0 and 0.8 Hz, 1H), 4.88 (s, 2H), 4.36 (m, 1H), 4.25 (m, 2H), 3.93 (dd, J=9.2 and 4.0 Hz, 2H), 3.35 (s, 3H), 3.34 (s, 3H), 2.79 (s, 3H).

Example 14(32)

N-(4-{3-amino-6-[2-(3-fluoro-1-azetidinyl)-4-pyridinyl]-2-pyrazinyl}phenyl)-2-(3-chlorophenyl)-1,5-dimethyl-3-oxo-2,3-dihydro-1H-pyrazole-4-carboxamide MS (M+H): 585.1;
$^1$H NMR (400 MHz, CDCl$_3$) δ 10.72 (s, 1H), 8.41 (s, 1H), 8.20 (dd, J=5.4, 0.7 Hz, 1H), 7.85-7.72 (m, 4H), 7.48 (dd, J=12.0, 4.3 Hz, 1H), 7.42 (ddd, J=8.1, 2.0, 1.3 Hz, 1H), 7.39-7.37 (m, 1H), 7.28 (ddd, J=7.8, 2.0, 1.3 Hz, 1H), 7.18 (dd, J=5.4, 1.5 Hz, 1H), 6.92 (dd, J=1.4, 0.8 Hz, 1H), 5.55-5.47 (m, 1H), 5.41-5.33 (m, 1H), 4.95 (d, J=8.5 Hz, 2H), 4.44-4.29 (m, 2H), 4.18 (ddd, J=23.2, 10.5, 3.0 Hz, 2H), 3.36 (d, J=3.5 Hz, 3H), 2.80 (d, J=3.5 Hz, 3H).

Example 14(33)

N-(4-{3-amino-6-[2-(4-morpholinyl)-4-pyridinyl]-2-pyrazinyl}phenyl)-1,5-dimethyl-3-oxo-2-(4-pyridinyl)-2,3-dihydro-1H-pyrazole-4-carboxamide MS (M+H): 564.1;
$^1$H NMR (400 MHz, CDCl$_3$) δ 10.55 (s, 1H), 8.77-8.75 (2H), 8.42 (s, 1H), 8.24-8.23 (m, 1H), 7.82-7.75 (4H), 7.35-7.33 (2H), 7.28 (s, 1H), 7.17 (dd, J=5.6 and 1.6 Hz, 1H), 4.94 (broad s, 2H), 3.82 (m, 4H), 3.56 (m, 4H), 3.39 (s, 3H), 2.83 (s, 3H).

Example 14(34)

N-[4-(3-amino-6-{3-[(dimethylamino)methyl]phenyl}-2-pyrazinyl)phenyl]-1,5-dimethyl-2-(3-methylphenyl)-3-oxo-2,3-dihydro-1H-pyrazole-4-carboxamide MS (M+H): 548.2;
$^1$H NMR (400 MHz, CDCl$_3$) δ 10.86 (s, 1H), 7.87-7.83 (m, 2H), 7.83-7.76 (m, 4H), 7.46-7.34 (m, 2H), 7.32-7.25 (m, 2H), 7.18 (s, 1H), 7.14-7.10 (m, 1H), 4.80 (s, 2H), 3.48 (s, 2H), 3.34 (s, 3H), 2.79 (s, 3H), 2.43 (s, 3H), 2.25 (s, 6H).

Example 14(35)

N-(4-{3-amino-6-[2-(4-morpholinyl)-4-pyridinyl]-2-pyrazinyl}phenyl)-1,5-dimethyl-3-oxo-2-(3-pyridinyl)-2,3-dihydro-1H-pyrazole-4-carboxamide

MS (M+H): 564.2;

$^1$H NMR (400 MHz, CDCl$_3$) δ 10.64 (s, 1H), 8.68 (dd, J=8.0, 1.2, 1H), 8.62 (d, J=2.8, 1H), 8.42 (s, 1H), 8.23 (d, J=5.2, 1H), 7.82-7.74 (5H), 7.50 (ddd, J=6.8, 4.8, 0.8, 1H), 7.29 (s, 1H), 7.16 (dd, J=5.6, 1.2, 1H), 4.95 (s, 2H), 3.83 (m, 4H), 3.56 (m, 4H), 3.37 (s, 3H), 2.82 (s, 3H).

Example 14(36)

N-(4-{3-amino-6-[3-(1H-pyrazol-3-yl)phenyl]-2-pyrazinyl}phenyl)-1,5-dimethyl-2-(3-methylphenyl)-3-oxo-2,3-dihydro-1H-pyrazole-4-carboxamide

MS (M+H): 557.2;

$^1$H NMR (400 MHz, DMSO-d$_6$ with D$_2$O) δ 10.87 (s, 1H), 8.53 (s, 1H), 8.40-8.26 (m, 1H), 7.86 (d, J=7.4 Hz, 1H), 7.80-7.69 (m, 5H), 7.53-7.41 (m, 3H), 7.30 (d, J=7.6 Hz, 1H), 7.20 (dd, J=13.0, 4.1 Hz, 2H), 6.76 (s, 1H), 3.31 (s, 3H), 2.67 (s, 3H), 2.36 (s, 3H).

Example 14(37)

N-[4-(3-amino-6-{3-[(2-methoxyethyl)sulfamoyl]phenyl}-2-pyrazinyl)phenyl]-2-(3-chlorophenyl)-1,5-dimethyl-3-oxo-2,3-dihydro-1H-pyrazole-4-carboxamide

MS (M+H): 648.3;

$^1$H NMR (400 MHz, CD$_3$OD) δ 8.42 (s, 2H), 8.17 (d, J=7.9 Hz, 1H), 7.77 (q, J=8.8 Hz, 4H), 7.70 (s, 2H), 7.55 (ddd, J=29.8, 14.7, 8.3 Hz, 3H), 7.34 (d, J=7.5 Hz, 1H), 3.42 (s, 3H), 3.36 (t, J=5.5 Hz, 2H), 3.21 (s, 3H), 3.06 (t, J=5.5 Hz, 2H), 2.77 (s, 3H).

Example 14(38)

N-(4-{3-amino-6-[6-(3-methoxy-1-azetidinyl)-2-pyridinyl]-2-pyrazinyl}phenyl)-1,5-dimethyl-2-(6-methyl-2-pyridinyl)-3-oxo-2,3-dihydro-1H-pyrazole-4-carboxamide

MS (M+H): 577.64;

$^1$H NMR (400 MHz, CDCl$_3$) δ 10.70 (s, 1H), 8.97 (s, 1H), 7.82-7.75 (5H), 7.62-7.58 (m, 2H), 7.51 (dd, J=8.0 and 7.6 Hz, 1H), 7.13 (d, J=7.2 Hz, 1H), 6.27 (d, J=8.0 Hz, 1H), 4.87 (s, 2H), 4.36 (m, 1H), 4.25 (m, 2H), 3.93 (dd, J=9.2 and 4.0 Hz, 2H), 3.61 (s, 3H), 3.34 (s, 3H), 2.80 (s, 3H), 2.56 (s, 3H).

Example 14(39)

N-{4-[3-amino-6-(1H-pyrazol-4-yl)-2-pyrazinyl]phenyl}-1,5-dimethyl-2-(3-methylphenyl)-3-oxo-2,3-dihydro-1H-pyrazole-4-carboxamide

MS (M+H): 481.1;

$^1$H NMR (400 MHz, DMSO-d$_6$) δ 12.89 (s, 1H), 10.88 (s, 1H), 8.25 (s, 1H), 8.14 (s, 1H), 7.91 (s, 1H), 7.73-7.67 (m, 4H), 7.44 (t, J=7.7 Hz, 1H), 7.30 (d, J=7.6 Hz, 1H), 7.23 (s, 1H), 7.20 (d, J=7.9 Hz, 1H), 5.95 (s, 2H), 3.33 (s, 3H), 2.69 (s, 3H), 2.37 (s, 3H).

Example 15

3-(4-aminophenyl)-5-(4,4,5,5-tetramethyl-1,3,2-dioxaborolan-2-yl)-2-pyrazinamine The compound prepared in Example 12 (5.0 g) was dissolved in dioxane (50 mL). Bis(pinacolato)diboron (6.0 g), potassium acetate (2.4 g), and [1,1'-Bis(diphenylphosphino)ferrocene]palladium dichloride complex with DCM (0.25 mL) were added in succession. The reaction was heated at reflux for 3 hours, at which time LC/MS indicated the reaction was complete. The reaction was filtered through celite and the celite was washed with EtOAc (150 mL). The mother liquor was concentrated and the crude solid was triturated with methyl tert-butylether (10 mL) and EtOAc (10 mL) to give the title compound (4.5 g) having the following physical data as an orange solid.

$^1$H NMR (300 MHz, CDCl$_3$) δ 8.32 (s, 1H), 7.49 (dd, J=6.6, 1.8 Hz, 2H), 6.73 (dd, J=6.6, 1.8 Hz, 2H), 4.92 (s, 2H), 3.80 (s, 2H), 1.36 (s, 12H).

Example 16

3-(4-aminophenyl)-5-[2-fluoro-3-(tetrahydro-2H-pyran-4-yloxy)phenyl]-2-pyrazinamine To a 80 mL microwave vessel containing the compound prepared in Example 15 (263.9 mg) was added Na$_2$CO$_3$ (181.7 mg) and Pd(PPh$_3$)$_4$ (48.8 mg). The 4-(3-bromo-2-fluorophenoxy)tetrahydro-2H-pyran (253.6 mg) was added by dissolving in 3:1 1,4-dioxane:H$_2$O then adding via pipet and using the remainder of the solvent to wash over any remaining material (total volume: 8.5 mL). The mixture was stirred and sparged with argon for 5 minutes. The vial was placed in the microwave then heated to 150° C. After 15 minutes at 150° C., the mixture was allowed to cool. The dark brown mixture was diluted with EtOAc and washed with H$_2$O two times. The aqueous layers were back extracted with EtOAc. The combined organic layers were washed with brine then dried over Na$_2$SO$_4$, filtered and solvent was removed in vacuo. The material was absorbed onto silica and purified on the Isolera (50 g silica column; 0-15% MeOH in EtOAc) followed by purification via reverse phase on the Isolera (60 g C18 column; 5-95% ACN with 0.1% trifluoroacetic acid (TFA) in H$_2$O with 0.1% TFA). Fractions containing product were combined and solvent was removed in vacuo. The material was taken up in MeOH and desalted by passing through a StratoSphere 200 mg PL-HCO$_3$ MP SPE cartridge. Resin was washed with MeOH and 20% MeOH in DCM. Solvent was removed in vacuo to give the title compound (94.9 mg) having the following data as a dark amber solid/film solid.

MS (M+H): 381.0.

Example 17(1)

N-(4-{3-amino-6-[2-fluoro-3-(tetrahydro-2H-pyran-4-yloxy)phenyl]-2-pyrazinyl}phenyl)-2-(3-chlorophenyl)-1,5-dimethyl-3-oxo-2,3-dihydro-1H-pyrazole-4-carboxamide

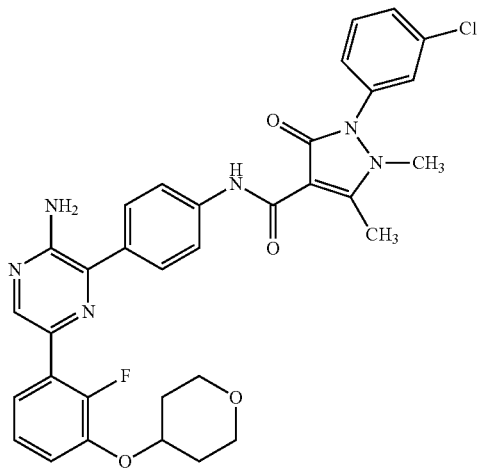 [SMILES: Cc1c(C(=O)Nc2ccc(-c3nc(-c4cccc(OC5CCOCC5)c4F)cnc3N)cc2)c(=O)n(-c2cccc(Cl)c2)n1C]

To vial containing the compound prepared in Example 11 (23.0 mg) was added HATU (40.0 mg), 0.5 mL DMA and TEA (0.015 mL). After stirring for 5 minutes the compound prepared in Example 16 (41.3 mg) was added, via pipet, as a solution in 0.5 mL DMA. The vial was capped and the amber mixture was stirred at room temperature. At 21.5 hours, the solution was diluted with EtOAc and washed with 1M NaOH. The aqueous layers were back extracted with EtOAc. The organic layers were washed with $H_2O$ and brine then dried over $Na_2SO_4$, filtered and solvent was removed in vacuo. The material was purified by prep TLC (95:5 EtOAc:MeOH) followed by a second prep TLC (95:5 DCM:MeOH) to give the title compound (44.4 mg) having the following physical data as a brown amber solid.

MS (M+H): 629.1;
$^1$H NMR (400 MHz, CDCl$_3$) δ 10.64 (s, 1H), 8.42 (d, J=2.4 Hz, 1H), 7.76-7.69 (m, 4H), 7.55 (t, J=7.3 Hz, 1H), 7.42 (t, J=7.9 Hz, 1H), 7.37 (d, J=8.4 Hz, 1H), 7.34-7.30 (m, 1H), 7.22 (d, J=7.8 Hz, 1H), 7.05 (t, J=8.0 Hz, 1H), 6.92 (t, J=7.8 Hz, 1H), 4.81 (s, 2H), 4.41 (tt, J=7.8, 3.8 Hz, 1H), 4.01-3.89 (m, 2H), 3.50 (ddd, J=11.6, 8.4, 3.1 Hz, 2H), 3.30 (s, 3H), 2.75 (s, 3H), 2.00-1.94 (m, 2H), 1.84-1.75 (m, 2H).

Example 17(2)-17(33)

The compound having the following physical data was prepared by using the compound prepared in Example 15, 4-(3-bromo-2-fluorophenoxy)tetrahydro-2H-pyran or the corresponding bromide compound instead thereof, and using the compound prepared in Example 1 or the corresponding carboxylic acid instead thereof in the process of Example 16→Example 17(1).

Example 17(2)

N-(4-{3-amino-6-[2-(3-hydroxy-3-methyl-1-azetidinyl)-4-pyridinyl]-2-pyrazinyl}phenyl)-2-(3-chlorophenyl)-1,5-dimethyl-3-oxo-2,3-dihydro-1H-pyrazole-4-carboxamide MS (M+H): 597.0;
$^1$H NMR (400 MHz, CD$_3$OD) δ 10.72 (s, 1H), 8.42 (s, 1H), 7.97 (d, J=5.7 Hz, 1H), 7.74 (s, 4H), 7.67 (s, 1H), 7.60-7.42 (m, 3H), 7.33 (d, J=7.5 Hz, 1H), 7.22 (d, J=5.4 Hz, 1H), 6.98 (s, 1H), 4.71 (s, 1H), 3.98 (q, J=8.4 Hz, 4H), 3.41 (s, 3H), 3.33 (s, 3H), 2.76 (s, 3H), 1.55 (s, 3H).

Example 17(3)

N-(4-{3-amino-6-[6-(4-methyl-1-piperazinyl)-2-pyridinyl]-2-pyrazinyl}phenyl)-2-(3-chlorophenyl)-1,5-dimethyl-3-oxo-2,3-dihydro-1H-pyrazole-4-carboxamide MS (M+H): 610.1;
$^1$H NMR (400 MHz, CDCl$_3$) δ 10.70 (s, 1H), 8.96 (s, 1H), 7.83-7.75 (m, 4H), 7.64 (d, J=7.4 Hz, 1H), 7.56 (t, J=7.8 Hz, 1H), 7.51-7.45 (m, 1H), 7.42 (d, J=8.1 Hz, 1H), 7.39-7.36 (m, 1H), 7.28 (d, J=8.1 Hz, 1H), 6.61 (d, J=8.3 Hz, 1H), 4.85 (s, 2H), 3.75-3.59 (m, 4H), 3.36 (s, 3H), 3.13-3.00 (m, 1H), 2.81 (s, 3H), 2.68-2.51 (3H), 2.44-2.31 (3H).

Example 17(4)

N-[4-(3-amino-6-{6-[(3-fluoro-1-azetidinyl)methyl]-2-pyridinyl}-2-pyrazinyl)phenyl]-2-(3-chlorophenyl)-1,5-dimethyl-3-oxo-2,3-dihydro-1H-pyrazole-4-carboxamide MS (M+H): 599.1;
$^1$H NMR (400 MHz, CDCl$_3$) δ 10.70 (s, 1H), 9.02 (s, 1H), 8.14 (d, J=7.1 Hz, 1H), 7.83-7.75 (m, 4H), 7.69 (t, J=7.8 Hz, 1H), 7.51-7.44 (m, 1H), 7.43 (dd, J=2.0, 1.3 Hz, 1H), 7.41 (dd, J=2.0, 1.3 Hz, 1H), 7.38 (dt, J=2.0, 1.0 Hz, 1H), 7.28 (dd, J=2.0, 1.3 Hz, 1H), 7.21 (d, J=0.9 Hz, 1H), 5.25-5.10 (m, 1H), 4.93 (s, 2H), 3.87 (s, 2H), 3.85-3.76 (m, 2H), 3.44-3.38 (m, 1H), 3.35 (s, 3H), 2.80 (s, 3H).

Example 17(5)

N-(4-{3-amino-6-[3-(1H-pyrazol-3-yl)phenyl]-2-pyrazinyl}phenyl)-2-(3-chlorophenyl)-1,5-dimethyl-3-oxo-2,3-dihydro-1H-pyrazole-4-carboxamide MS (M+H): 577.1;
$^1$H NMR (400 MHz, DMSO-d$_6$) δ 10.74 (s, 1H), 8.59-8.52 (m, 1H), 8.38-8.32 (m, 1H), 7.91-7.83 (m, 1H), 7.80-7.69 (m, 6H), 7.61-7.53 (m, 3H), 7.45 (t, J=6.4 Hz, 1H), 7.38 (d, J=7.6 Hz, 1H), 6.75 (s, 1H), 3.34 (s, 3H), 2.67 (s, 3H).

Example 17(6)

N-{4-[3-amino-6-(3,4-dimethoxyphenyl)-2-pyrazinyl]phenyl}-2-(3-chlorophenyl)-1,5-dimethyl-3-oxo-2,3-dihydro-1H-pyrazole-4-carboxamide MS (M+H): 571.0;
$^1$H NMR (400 MHz, CDCl$_3$) δ 10.70 (s, 1H), 8.35 (s, 1H), 7.83-7.76 (m, 4H), 7.56 (d, J=1.7 Hz, 1H), 7.51-7.40 (3H), 7.38 (s, 1H), 7.28 (d, J=7.9 Hz, 1H), 6.93 (d, J=8.4 Hz, 1H), 4.74 (s, 2H), 3.95 (s, 3H), 3.91 (s, 3H), 3.36 (s, 3H), 2.81 (s, 3H).

Example 17(7)

N-[4-(3-amino-6-{3-[(dimethylamino)methyl]phenyl}-2-pyrazinyl)phenyl]-2-(3-chlorophenyl)-1,5-dimethyl-3-oxo-2,3-dihydro-1H-pyrazole-4-carboxamide MS (M+H): 568.1;
$^1$H NMR (400 MHz, CDCl$_3$) δ 10.69 (s, 1H), 8.41 (s, 1H), 7.87-7.83 (m, 2H), 7.83-7.76 (m, 4H), 7.50-7.39 (m, 2H), 7.39-7.36 (m, 2H), 7.32-7.25 (m, 2H), 4.80 (s, 2H), 3.48 (s, 2H), 3.35 (s, 3H), 2.80 (s, 3H), 2.25 (s, 6H).

Example 17(8)

N-(4-{3-amino-6-[2-(4-methoxy-1-piperidinyl)-4-pyridinyl]-2-pyrazinyl}phenyl)-2-(2-chlorophenyl)-1,5-dimethyl-3-oxo-2,3-dihydro-1H-pyrazole-4-carboxamide MS (M+H): 625.2;
$^1$H NMR (400 MHz, DMSO-$d_6$) δ 10.79 (s, 1H), 8.60 (s, 1H), 8.09 (d, J=5.2 Hz, 1H), 7.78-7.68 (m, 5H), 7.67-7.61 (m, 2H), 7.61-7.54 (m, 1H), 7.32 (s, 1H), 7.18 (d, J=5.4 Hz, 1H), 6.47 (s, 2H), 4.04-3.94 (m, 2H), 3.43-3.35 (m, 1H), 3.28 (s, 3H), 3.25 (s, 3H), 3.19-3.12 (m, 2H), 2.70 (s, 3H), 1.95-1.80 (m, 2H), 1.48-1.33 (m, 2H).

Example 17(9)

N-(4-{3-amino-6-[2-(4-methoxy-1-piperidinyl)-4-pyridinyl]-2-pyrazinyl}phenyl)-1,5-dimethyl-2-(3-methylphenyl)-3-oxo-2,3-dihydro-1H-pyrazole-4-carboxamide MS (M+H): 605.2;
$^1$H NMR (400 MHz, DMSO-$d_6$) δ 10.90 (s, 1H), 8.60 (s, 1H), 8.09 (d, J=5.2 Hz, 1H), 7.77-7.69 (m, 4H), 7.48-7.42 (m, 1H), 7.35-7.28 (m, 2H), 7.26-7.15 (m, 3H), 6.47 (s, 2H), 4.03-3.95 (m, 2H), 3.43-3.36 (m, 1H), 3.33 (s, 3H), 3.25 (s, 3H), 3.21-3.14 (m, 2H), 2.69 (s, 3H), 2.37 (s, 3H), 1.93-1.82 (m, 2H), 1.46-1.34 (m, J=9.2 Hz, 2H).

Example 17(10)

N-(4-{3-amino-6-[6-(4-methoxy-1-piperidinyl)-2-pyridinyl]-2-pyrazinyl}phenyl)-2-(2-chlorophenyl)-1,5-dimethyl-3-oxo-2,3-dihydro-1H-pyrazole-4-carboxamide MS (M+H): 625.2;
$^1$H NMR (400 MHz, DMSO-$d_6$) δ 10.79 (s, 1H), 8.75 (s, 1H), 7.77-7.68 (5H), 7.66-7.61 (m, 2H), 7.60-7.52 (m, 2H), 7.39 (d, J=7.4 Hz, 1H), 6.76 (d, J=8.5 Hz, 1H), 6.37 (s, 2H), 4.06-3.97 (m, 2H), 3.44-3.36 (m, 1H), 3.28 (s, 3H), 3.26 (s, 3H), 3.22-3.14 (m, 2H), 2.69 (s, 3H), 1.96-1.85 (m, 2H), 1.50-1.37 (m, 2H).

Example 17(11)

N-(4-{3-amino-6-[6-(4-methoxy-1-piperidinyl)-2-pyridinyl]-2-pyrazinyl}phenyl)-1,5-dimethyl-2-(3-methylphenyl)-3-oxo-2,3-dihydro-1H-pyrazole-4-carboxamide MS (M+H): 605.3;
$^1$H NMR (400 MHz, DMSO-$d_6$) δ 10.90 (s, 1H), 8.75 (s, 1H), 7.78-7.67 (m, 4H), 7.55 (t, J=7.9 Hz, 1H), 7.44 (t, J=7.8 Hz, 1H), 7.39 (d, J=7.5 Hz, 1H), 7.30 (d, J=7.6 Hz, 1H), 7.25-7.17 (m, 2H), 6.76 (d, J=8.4 Hz, 1H), 6.37 (s, 2H), 4.06-3.96 (m, 2H), 3.44-3.37 (m, 1H), 3.33 (s, 3H), 3.26 (s, 3H), 3.22-3.15 (m, 2H), 2.69 (s, 3H), 2.37 (s, 3H), 1.95-1.85 (m, 2H), 1.43 (d, J=9.4 Hz, 2H).

Example 17(12)

N-{4-[3-amino-6-(2-fluoro-3-methoxyphenyl)-2-pyrazinyl]phenyl}-2-(4-chlorophenyl)-1,5-dimethyl-3-oxo-2,3-dihydro-1H-pyrazole-4-carboxamide MS (M+H): 559.1;
$^1$H NMR (400 MHz, DMSO-$d_6$) δ 10.80 (s, 1H), 8.29 (d, J=2.8 Hz, 1H), 7.74-7.68 (4H), 7.65-7.61 (2H), 7.47-7.44 (2H), 7.43-7.39 (1H), 7.17 (t, J=8.0 Hz, 1H), 7.11 (td, J=8.0 and 1.6 Hz, 1H), 6.38 (s, 2H), 3.85 (s, 3H), 3.34 (s, 3H), 2.68 (s, 3H).

Example 17(13)

N-(4-{3-amino-6-[2-(4-amino-1-piperidinyl)-4-pyridinyl]-2-pyrazinyl}phenyl)-1,5-dimethyl-2-(3-methylphenyl)-3-oxo-2,3-dihydro-1H-pyrazole-4-carboxamide MS (M+H): 590.3;
$^1$H NMR (400 MHz, CDCl$_3$) δ 10.88 (s, 1H), 8.39 (s, 1H), 8.20 (d, J=5.3 Hz, 1H), 7.83-7.72 (m, 4H), 7.42 (t, J=7.8 Hz, 1H), 7.30 (s, 1H), 7.27 (d, J=8.5 Hz, 1H), 7.18 (s, 1H), 7.12 (d, J=9.4 Hz, 1H), 7.09 (dd, J=5.3, 1.3 Hz, 1H), 4.94 (s, 2H), 4.31 (d, J=13.3 Hz, 2H), 3.34 (s, 3H), 2.98-2.84 (m, 3H), 2.78 (s, 3H), 2.43 (s, 3H), 1.91 (d, J=12.8 Hz, 2H), 1.43-1.32 (m, 2H).

Example 17(14)

N-(4-{3-amino-6-[2-(3-methoxy-1-azetidinyl)-4-pyridinyl]-2-pyrazinyl}phenyl)-2-benzyl-1,5-dimethyl-3-oxo-2,3-dihydro-1H-pyrazole-4-carboxamide MS (M+H): 577.2;
$^1$H NMR (400 MHz, CDCl$_3$) δ 10.92 (s, 1H), 8.38 (s, 1H), 8.17 (d, J=5.4 Hz, 1H), 7.86-7.73 (m, 4H), 7.37-7.27 (m, 3H), 7.17-7.11 (m, 3H), 6.89 (s, 1H), 5.14 (s, 2H), 5.04 (s, 2H), 4.37-4.30 (m, 1H), 4.28-4.23 (m, 2H), 3.97-3.91 (m, 2H), 3.34 (s, 3H), 3.32 (s, 3H), 2.63 (s, 3H).

Example 17(15)

N-(4-{3-amino-6-[2-(3-methoxy-1-azetidinyl)-4-pyridinyl]-2-pyrazinyl}phenyl)-2-(3-chlorophenyl)-1-(2-hydroxy-2-methylpropyl)-5-methyl-3-oxo-2,3-dihydro-1H-pyrazole-4-carboxamide MS (M+H): 655.2;
$^1$H NMR (400 MHz, CDCl$_3$) δ 10.71 (s, 1H), 8.39 (s, 1H), 8.17 (d, J=5.4 Hz, 1H), 7.82-7.72 (m, 4H), 7.45 (t, J=8.0 Hz, 1H), 7.38 (d, J=8.8 Hz, 1H), 7.27 (s, 1H), 7.19 (d, J=7.9 Hz, 1H), 7.14 (dd, J=5.4, 1.4 Hz, 1H), 6.88 (s, 1H), 4.97 (s, 2H), 4.41-4.30 (m, 1H), 4.29-4.21 (m, 2H), 3.97-3.91 (m, 2H), 3.84 (s, 2H), 3.33 (s, 3H), 2.87 (s, 3H), 1.15 (s, 6H).

Example 17(16)

N-(4-{3-amino-6-[2-(3-methoxy-1-azetidinyl)-4-pyridinyl]-2-pyrazinyl}phenyl)-2-(3-chlorophenyl)-1-(2-hydroxypropyl)-5-methyl-3-oxo-2,3-dihydro-1H-pyrazole-4-carboxamide MS (M+H): 641.2;
$^1$H NMR (400 MHz, CDCl$_3$) δ 10.72 (s, 1H), 8.38 (s, 1H), 8.14 (d, J=5.4 Hz, 1H), 7.79-7.70 (m, 4H), 7.42 (t, J=8.0 Hz, 1H), 7.35 (d, J=8.1 Hz, 1H), 7.27 (s, 1H), 7.14 (d, J=5.4 Hz, 1H), 7.10 (d, J=6.5 Hz, 1H), 6.89 (s, 1H), 5.01 (s, 2H), 4.39-4.31 (m, 1H), 4.28-4.21 (m, 2H), 3.95-3.90 (m, 2H), 3.89-3.77 (m, 2H), 3.62 (d, J=14.6 Hz, 1H), 3.32 (s, 3H), 2.82 (s, 3H), 1.09 (d, J=6.0 Hz, 3H).

Example 17(17)

N-(4-{3-amino-6-[6-(3-methoxy-1-azetidinyl)-2-pyridinyl]-2-pyrazinyl}phenyl)-2-(2,5-dichlorophenyl)-1,5-dimethyl-3-oxo-2,3-dihydro-1H-pyrazole-4-carboxamide TLC Rf=0.74 (ethyl acetate:methanol=4:1);
$^1$H NMR (300 MHz, CDCl$_3$) δ 10.70, 8.76, 7.87, 7.70-7.81, 7.58, 7.62, 6.43, 6.37, 4.37, 4.20, 3.80, 3.33, 3.24, 2.70.

Example 17(18)

N-(4-{3-amino-6-[6-(3-methoxy-1-azetidinyl)-2-pyridinyl]-2-pyrazinyl}phenyl)-2-(3-methoxyphenyl)-1,5-dimethyl-3-oxo-2,3-dihydro-1H-pyrazole-4-carboxamide TLC Rf=0.71 (ethyl acetate:methanol=4:1);
$^1$H NMR (300 MHz, CDCl$_3$) δ 10.90, 8.77, 7.77, 7.60, 7.45, 7.18, 7.00, 6.45, 6.38, 4.37, 4.20, 3.80, 3.37, 3.26, 2.70.

Example 17(19)

N-{4-[5-amino-6'-(4-morpholinyl)-2,2'-bipyrazin-6-yl]phenyl}-2-(2-chlorophenyl)-1,5-dimethyl-3-oxo-2,3-dihydro-1H-pyrazole-4-carboxamide TLC Rf=0.29 (ethyl acetate:methanol=9:1);
$^1$H NMR (300 MHz, CDCl$_3$) δ 10.79, 8.84, 8.09, 7.80, 7.62, 7.42-7.58, 5.02, 3.90, 3.66, 3.34, 2.80.

Example 17(20)

N-(4-{3-amino-6-[6-(3-methoxy-1-pyrrolidinyl)-2-pyridinyl]-2-pyrazinyl}phenyl)-2-(2-chlorophenyl)-1,5-dimethyl-3-oxo-2,3-dihydro-1H-pyrazole-4-carboxamide TLC Rf=0.55 (ethyl acetate:methanol=10:1);
$^1$H NMR (300 MHz, CDCl$_3$) δ 2.10-2.21, 2.81, 3.32, 3.40, 3.58-3.70, 4.05-4.18, 5.85, 6.30-6.40, 7.40-7.65, 7.79, 9.00, 10.8.

Example 17(21)

N-[4-(3-amino-6-{6-[3-(hydroxymethyl)-1-piperidinyl]-2-pyridinyl}-2-pyrazinyl)phenyl]-1,5-dimethyl-3-oxo-2-phenyl-2,3-dihydro-1H-pyrazole-4-carboxamide TLC Rf=0.50 (ethyl acetate:methanol=10:1);
$^1$H NMR (300 MHz, CDCl$_3$) δ 1.30-2.00, 2.30-2.38, 2.80, 3.20-3.50, 3.55-3.60, 3.90-4.05, 4.85, 6.59-6.70, 7.35-7.60, 7.76-7.84, 8.90, 10.8.

Example 17(22)

N-(4-{5-amino-6'-[4-(dimethylamino)-1-piperidinyl]-2,2'-bipyrazin-6-yl}phenyl)-1,5-dimethyl-3-oxo-2-phenyl-2,3-dihydro-1H-pyrazole-4-carboxamide TLC Rf=0.30 (ethyl acetate:methanol=10:1, NH-Silica);
$^1$H NMR (300 MHz, CDCl$_3$) δ 1.47-1.65, 1.90-2.04, 2.32, 2.38-3.47, 2.81, 2.84-3.05, 3.38, 4.40-4.51, 4.98, 7.36-7.60, 7.75-7.87, 8.10, 8.75, 8.85, 10.8.

Example 17(23)

N-{4-[5-amino-6'-(4,4-difluoro-1-piperidinyl)-2,2'-bipyrazin-6-yl]phenyl}-1,5-dimethyl-3-oxo-2-phenyl-2,3-dihydro-1H-pyrazole-4-carboxamide TLC Rf=0.63 (ethyl acetate:methanol=9:1);
$^1$H NMR (300 MHz, CDCl$_3$) δ10.90, 8.76, 8.59, 8.36, 7.40-7.80, 6.60, 3.82, 3.38, 2.70, 2.05.

Example 17(24)

N-{4-[5-amino-6'-(3-hydroxy-3-methyl-1-azetidinyl)-2,2'-bipyrazin-6-yl]phenyl}-1,5-dimethyl-3-oxo-2-phenyl-2,3-dihydro-1H-pyrazole-4-carboxamide TLC Rf=0.47 (ethyl acetate:methanol=9:1);
$^1$H NMR (300 MHz, CDCl$_3$) δ10.91, 8.70, 8.55, 7.40-7.81, 6.60, 5.63, 3.95, 3.37, 2.70, 1.47.

Example 17(25)

N-{4-[5-amino-6'-(4-methoxy-1-piperidinyl)-2,2'-bipyrazin-6-yl]phenyl}-1,5-dimethyl-3-oxo-2-phenyl-2,3-dihydro-1H-pyrazole-4-carboxamide TLC Rf=0.20 (ethyl acetate:methanol=10:1);
$^1$H NMR (300 MHz, CDCl$_3$) δ 1.61-1.79, 1.95-2.05, 2.81, 3.25-3.41, 3.42-3.59, 3.99-4.16, 4.96, 7.31-7.62, 7.72-7.85, 8.10, 8.77, 8.90, 10.8.

Example 17(26)

N-(4-{3-amino-6-[6-(1H-imidazol-1-yl)-2-pyridinyl]-2-pyrazinyl}phenyl)-1,5-dimethyl-3-oxo-2-phenyl-2,3-dihydro-1H-pyrazole-4-carboxamide TLC Rf=0.26 (dichloromethane:methanol=9:1);
$^1$H NMR (300 MHz, CDCl$_3$) δ 10.92, 9.01, 8.70, 8.00-8.20, 7.78, 7.40-7.60, 7.16, 6.83, 3.36, 2.70.

Example 17(27)

N-(4-{5-amino-6'-[4-(2-hydroxyethyl)-1-piperazinyl]-2,2'-bipyrazin-6-yl}phenyl)-1,5-dimethyl-3-oxo-2-phenyl-2,3-dihydro-1H-pyrazole-4-carboxamide TLC Rf=0.20 (chloroform:methanol=10:1, NH-Silica);
$^1$H NMR (300 MHz, CDCl$_3$) δ 2.58-2.80, 2.81, 3.37, 3.63-3.71, 4.99, 7.34-7.60, 7.72-7.83, 8.08, 8.78, 8.86, 10.8.

Example 17(28)

N-{4-[5-amino-6'-(3-methoxy-1-pyrrolidinyl)-2,2'-bipyrazin-6-yl]phenyl}-1,5-dimethyl-3-oxo-2-phenyl-2,3-dihydro-1H-pyrazole-4-carboxamide TLC Rf=0.20 (ethyl acetate:methanol=10:1);
$^1$H NMR (300 MHz, CDCl$_3$) δ 2.05-2.32, 2.81, 3.33-3.40, 3.60-3.80, 4.08-4.20, 4.96, 7.36-7.61, 7.75-7.85, 8.73, 8.92, 10.8.

Example 17(29)

N-{4-[5-amino-6'-(4-morpholinyl)-2,2'-bipyrazin-6-yl]phenyl}-1,5-dimethyl-3-oxo-2-phenyl-2,3-dihydro-1H-pyrazole-4-carboxamide TLC Rf=0.15 (ethyl acetate:methanol=10:1);
$^1$H NMR (300 MHz, CDCl$_3$) δ 2.81, 3.37, 3.60-3.68, 3.85-3.91, 5.00, 7.35-7.60, 7.80, 8.07, 8.82, 8.85, 10.8.

Example 17(30)

N-{4-[5-amino-6'-(1-pyrrolidinyl)-2,2'-bipyrazin-6-yl]phenyl}-1,5-dimethyl-3-oxo-2-phenyl-2,3-dihydro-1H-pyrazole-4-carboxamide TLC Rf=0.50 (ethyl acetate:methanol=10:1);
$^1$H NMR (300 MHz, CDCl$_3$) δ 1.98-2.08, 2.82, 3.37, 3.56-3.62, 4.99, 7.35-7.61, 7.78-7.85, 8.71, 8.92, 10.8.

Example 17(31)

N-{4-[5-amino-6'-(3-fluoro-1-pyrrolidinyl)-2,2'-bipyrazin-6-yl]phenyl}-1,5-dimethyl-3-oxo-2-phenyl-2,3-dihydro-1H-pyrazole-4-carboxamide TLC Rf=0.50 (ethyl acetate:methanol=10:1);
$^1$H NMR (300 MHz, CDCl$_3$) δ 2.02-2.50, 2.81, 3.37, 3.61-4.07, 4.97, 6.36-6.59, 7.37-7.58, 7.78-7.89, 8.76, 8.92, 10.8.

Example 17(32)

N-{4-[3-amino-6-(imidazo[1,5-a]pyridin-1-yl)-2-pyrazinyl]phenyl}-1,5-dimethyl-3-oxo-2-phenyl-2,3-dihydro-1H-pyrazole-4-carboxamide TLC Rf=0.48 (ethyl acetate:methanol=10:1);
$^1$H NMR (300 MHz, CDCl$_3$) δ 2.82, 3.37, 4.67, 6.60, 6.80, 7.37-7.60, 7.80-7.86, 7.90, 8.16, 8.42, 8.82, 10.8.

Example 17(33)

N-{4-[5-amino-6'-(3-methoxy-1-azetidinyl)-2,2'-bipyrazin-6-yl]phenyl}-2-(2-chlorophenyl)-1,5-dimethyl-3-oxo-2,3-dihydro-1H-pyrazole-4-carboxamide TLC Rf=0.27 (ethyl acetate:methanol=9:1);
$^1$H NMR (300 MHz, CDCl$_3$) δ 10.77, 8.88, 8.02, 7.80, 7.65, 7.51, 4.87, 4.36, 4.03, 3.37, 2.79.

Example 18(1)

N-[4-(3-amino-6-{3-[3-(dimethylamino)-2-hydroxypropoxy]-2-fluorophenyl}-2-pyrazinyl)phenyl]-2-(3-chlorophenyl)-1,5-dimethyl-3-oxo-2,3-dihydro-1H-pyrazole-4-carboxamide

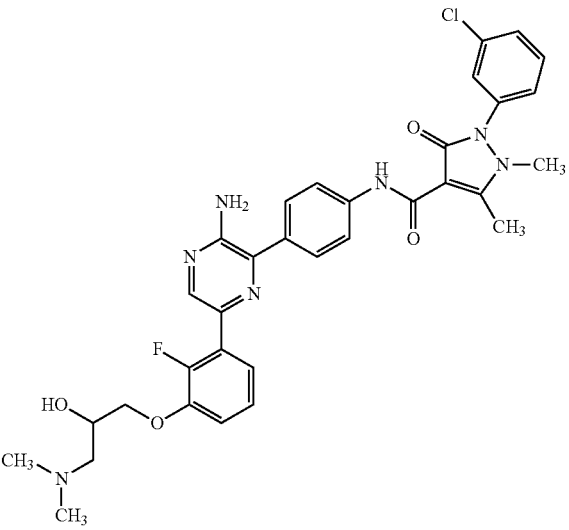 [SMILES: Cc1c(C(=O)Nc2ccc(-c3nc(-c4cccc(OCC(O)CN(C)C)c4F)cnc3N)cc2)c(=O)n(-c2cccc(Cl)c2)n1C]

In a vial was placed the compound prepared in Example 7(76) (0.050 g) in 5 mL of ethanol. To the mixture was added potassium carbonate (0.023 g), sodium iodide (0.035 g) and dimethylamine (0.250 ml) 2M solution in THF. The yellow turbid reaction mixture was left stirring overnight at 80° C. The reaction was concentrated under vacuo, added water, extracted with 10% MeOH in DCM, dried (Na$_2$SO$_4$), filtered and concentrated in vacuo. Purification was performed on the Biotage Isolera SiO$_2$-25 g 0-100% (of a 20% MeOH in DCM w 2% ammonium hydroxide)-DCM solution to give a light yellow solid which were triturated with diethyl ether and dried to give the title compound (0.024 g) having the following physical data.

MS (M+H): 646.1;
$^1$H NMR (400 MHz, CDCl$_3$) δ 10.70 (s, 1H), 8.47 (d, J=2.2 Hz, 1H), 7.82-7.73 (m, 4H), 7.59 (t, J=7.0 Hz, 1H), 7.48 (t, J=8.0 Hz, 1H), 7.42 (d, J=8.3 Hz, 1H), 7.38 (s, 1H), 7.30-7.26 (m, 1H), 7.11 (t, J=8.2 Hz, 1H), 7.01-6.94 (m, 1H), 4.85 (s, 2H), 4.25-4.16 (m, 1H), 4.15-4.09 (m, 1H), 4.07-4.01 (m, 1H), 3.36 (s, 3H), 2.80 (s, 3H), 2.75-2.68 (m, 1H), 2.67-2.59 (m, 1H), 2.45 (s, 6H).

Example 18(2)-18(3)

The compound having the following physical data was prepared by using the corresponding oxirane compound instead of the compound prepared in Example 7(76) or the corresponding bromide compound instead thereof, and using dimethylamine or the corresponding amine compound instead thereof in the process of Example 18(1).

Example 18(2)

N-[4-(3-amino-6-{3-[3-(dimethylamino)-2-hydroxypropoxy]phenyl}-2-pyrazinyl)phenyl]-2-(3-chlorophenyl)-1,5-dimethyl-3-oxo-2,3-dihydro-1H-pyrazole-4-carboxamide MS (M+H): 628.2;
$^1$H NMR (400 MHz, CDCl$_3$) δ 10.70 (s, 1H), 8.38 (s, 1H), 7.83-7.75 (4H), 7.56 (s, 1H), 7.52 (d, J=7.7 Hz, 1H), 7.47 (t, J=7.9 Hz, 1H), 7.41 (d, J=8.2 Hz, 1H), 7.38 (s, 1H), 7.32 (t, J=7.9 Hz, 1H), 7.27 (d, J=7.8 Hz, 1H), 6.91 (d, J=8.1 Hz, 1H), 4.83 (s, 2H), 4.11-4.05 (m, 1H), 4.05-3.99 (m, 2H), 3.35 (s, 3H), 2.79 (s, 3H), 2.59-2.52 (m, 1H), 2.42-2.35 (m, 1H), 2.31 (s, 6H).

Example 18(3)

N-{4-[3-amino-6-(3-{3-[(3,3-dimethyl-2-butanyl)amino]-2-hydroxypropoxy}phenyl)-2-pyrazinyl]phenyl}-2-(3-chlorophenyl)-1,5-dimethyl-3-oxo-2,3-dihydro-1H-pyrazole-4-carboxamide MS (M+H): 684.2;
$^1$H NMR (400 MHz, CDCl$_3$) δ 10.70 (s, 1H), 8.38 (s, 1H), 7.83-7.76 (4H), 7.57-7.49 (2H), 7.47 (d, J=7.9 Hz, 1H), 7.42 (d, J=8.2 Hz, 1H), 7.38 (s, 1H), 7.33 (t, J=7.9 Hz, 1H), 7.28 (d, J=7.9 Hz, 1H), 6.90 (d, J=8.0 Hz, 1H), 4.81 (s, 2H), 4.09-4.01 (m, 2H), 4.01-3.93 (m, 1H), 3.36 (s, 3H), 3.11-3.04 (m, 1H), 2.93-2.85 (m, 1H), 2.80 (s, 3H), 2.79-2.73 (m, 1H), 2.60-2.52 (m, 1H), 2.32-2.22 (m, 1H), 1.01 (dd, J=6.3, 2.7 Hz, 3H), 0.90 (s, 9H).

Example 19

2-methyl-2-propanyl[1-(3-amino-6-bromo-2-pyrazinyl)-4-piperidinyl]carbamate

To a vial was added 3,5-dibromopyrazin-2-amine (512.0 mg) and tert-butyl piperidin-4-ylcarbamate (466 mg). The reaction was flushed with N$_2$ and heated to 130° C. for 2 days. The brown solid was dissolved in MeOH (1 mL) and adsorbed onto a bed of celite then purified on the Reverse Phase Isolera (50 g column, 5-95% H$_2$O in ACN, 0.1% TFA) to give the title compound (296 mg) having the following physical data as a TFA salt.
MS (M+H): 371.9.

Example 20

3-(4-amino-1-piperidinyl)-5-[2-(4-morpholinyl)-4-pyridinyl]-2-pyrazinamine

To a solution of the compound prepared in Example 19 (186.0 mg) dissolved in dioxane (3.00 ml) was added 4-(4-(4,4,5,5-tetramethyl-1,3,2-dioxaborolan-2-yl)pyridin-2-yl)morpholine (159 mg) and a 2M solution of potassium carbonate (0.824 ml). The reaction was flushed with N$_2$ before [1,1'-Bis(diphenylphosphino)ferrocene]palladium dichloride complex with DCM (20.40 mg) was added. The reaction mixture was stirred overnight at 100° C. The reaction mixture was partitioned between DCM and saturated sodium hydrogen carbonate (NaHCO$_3$) and stirred vigorously for 30 minutes. The organic phase was pipetted out and dried over Na$_2$SO$_4$ then filtered and concentrated under reduced pressure. The crude product was dissolved in MeOH (1 mL), and adsorbed onto a bed of celite then purified on the Reverse Phase Isolera (25 g column, 5-95% H$_2$O in ACN, 0.1% TFA). The corresponding fractions were combined then concentrated under reduced pressure to give the title compound (121 mg) having the following physical data as a TFA salt.
MS (M+H): 356.1.

Example 21(1)

N-(1-{3-amino-6-[2-(4-morpholinyl)-4-pyridinyl]-2-pyrazinyl}-4-piperidinyl)-2-(3-chlorophenyl)-1,5-dimethyl-3-oxo-2,3-dihydro-1H-pyrazole-4-carboxamide

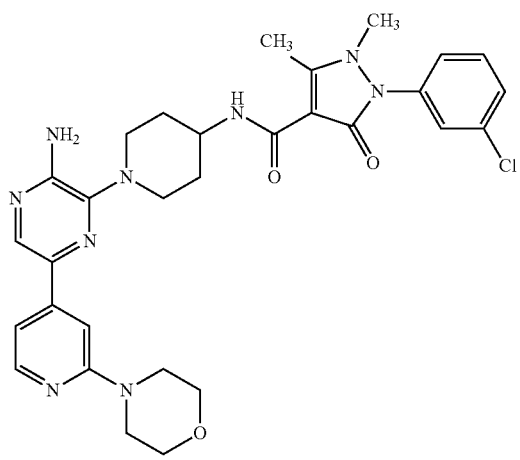 [SMILES: Cc1c(C(=O)NC2CCN(c3nc(-c4ccnc(N5CCOCC5)c4)cnc3N)CC2)c(=O)n(-c2cccc(Cl)c2)n1C]

To a solution of the compound prepared in Example 20 (27.5 mg) dissolved in DCM (3.00 mL) was added 2-(3-chlorophenyl)-1,5-dimethyl-3-oxo-2,3-dihydro-1H-pyrazole-4-carboxylic acid (22.70 mg), DIEA (0.148 ml) and HATU (35.3 mg). The reaction mixture was stirred overnight at room temperature. The reaction mixture was partitioned between DCM and saturated NaHCO$_3$ and stirred vigorously for 30 minutes. The organic phase was pipetted out and dried over Na$_2$SO$_4$ then filtered and concentrated under reduced pressure. The crude product was dissolved in MeOH (1 mL), and adsorbed onto a bed of celite then purified on the Reverse Phase Isolera (25 g column, 5-95% H$_2$O in ACN, 0.1% TFA) to yield the product as a TFA salt. The corresponding fractions were combined then passed through a StratoSpheres PL-HCO$_3$ MP SPE cartridge to remove the TFA. The eluent was concentrated under reduced pressure to afford the title compound (22 mg) having the following physical data.

MS (M+H): 604.1;
$^1$H NMR (400 MHz, DMSO-d$_6$) δ 8.49 (d, J=7.8 Hz, 1H), 8.31 (s, 1H), 8.09 (d, J=5.2 Hz, 1H), 7.57-7.51 (m, 1H), 7.51-7.46 (m, 2H), 7.32 (d, J=7.9 Hz, 1H), 7.26 (s, 1H), 7.20 (d, J=5.3 Hz, 1H), 6.29 (s, 2H), 3.95 (s, 1H), 3.72-3.65 (m, 4H), 3.51-3.44 (m, 4H), 3.41 (s, 2H), 3.28 (s, 3H), 2.91 (t, J=10.7 Hz, 2H), 2.62 (s, 3H), 1.99-1.90 (m, 2H), 1.71-1.59 (m, 2H).

Example 21(2)-21(69)

The compound having the following physical data was prepared by using the compound prepared in Example 19, 4-(4-(4,4,5,5-tetramethyl-1,3,2-dioxaborolan-2-yl)pyridin-2-yl)morpholine or the corresponding borolane compound instead thereof, and using the compound prepared in Example 1 or the corresponding carboxylic acid instead thereof in the process of Example 20→Example 21(1).

Example 21(2)

N-(1-{3-amino-6-[2-(4-morpholinyl)-4-pyridinyl]-2-pyrazinyl}-4-piperidinyl)-2-(2-chlorophenyl)-1,5-dimethyl-3-oxo-2,3-dihydro-1H-pyrazole-4-carboxamide MS (M+H): 604.2;
$^1$H NMR (400 MHz, DMSO-d$_6$) δ 8.50 (d, J=7.6 Hz, 1H), 8.30 (s, 1H), 8.09 (d, J=5.3 Hz, 1H), 7.70 (d, J=7.7 Hz, 1H), 7.61-7.55 (m, 1H), 7.55-7.51 (m, 2H), 7.26 (s, 1H), 7.20 (d, J=5.3 Hz, 1H), 6.28 (s, 2H), 4.00-3.87 (m, 1H), 3.73-3.62 (m, 4H), 3.50-3.36 (6H), 3.19 (s, 3H), 2.89 (t, J=10.6 Hz, 2H), 2.62 (s, 3H), 2.02-1.87 (m, 2H), 1.73-1.52 (m, 2H).

Example 21(3)

N-(1-{3-amino-6-[3-fluoro-5-(2-hydroxy-2-methyl-propoxy)phenyl]-2-pyrazinyl}-4-piperidinyl)-2-(3-chlorophenyl)-1,5-dimethyl-3-oxo-2,3-dihydro-1H-pyrazole-4-carboxamide MS (M+H): 624.2;
$^1$H NMR (400 MHz, CDCl$_3$) δ 8.57 (d, J=7.7 Hz, 1H), 8.08 (s, 1H), 7.43 (t, J=7.9 Hz, 1H), 7.37 (d, J=8.3 Hz, 1H), 7.34-7.33 (m, 1H), 7.27 (br s, 1H), 7.22 (br s, 1H), 7.19 (br s, 1H), 6.57 (dt, J=10.3, 2.1 Hz, 1H), 4.65 (s, 2H), 4.19-4.10 (m, 1H), 3.82 (s, 2H), 3.58 (d, J=13.1 Hz, 2H), 3.29 (s, 3H), 3.04 (t, J=10.9 Hz, 2H), 2.74 (s, 3H), 2.31 (s, 1H), 2.12 (d, J=10.3 Hz, 2H), 1.76-1.66 (m, 2H), 1.34 (s, 6H).

Example 21(4)

N-{1-[3-amino-6-(3-fluorophenyl)-2-pyrazinyl]-4-piperidinyl}-1,5-dimethyl-3-oxo-2-phenyl-2,3-dihydro-1H-pyrazole-4-carboxamide MS (M+H): 502.1;
$^1$H NMR (400 MHz, DMSO-d$_6$) δ 8.59 (d, J=7.7 Hz, 1H), 8.22 (s, 1H), 7.74 (d, J=7.9 Hz, 1H), 7.68 (d, J=10.9 Hz, 1H), 7.52 (t, J=7.6 Hz, 2H), 7.46-7.36 (m, 2H), 7.34 (d, J=7.4 Hz, 2H), 7.09-7.01 (m, 1H), 6.16 (s, 2H), 4.00-3.88 (m, 1H), 3.50-3.38 (m, 2H), 3.25 (s, 3H), 2.91 (t, J=10.3 Hz, 2H), 2.62 (s, 3H), 1.99-1.92 (m, 2H), 1.70-1.58 (m, 2H).

Example 21(5)

N-(1-{3-amino-6-[3-(1H-pyrazol-3-yl)phenyl]-2-pyrazinyl}-4-piperidinyl)-2-(3-chlorophenyl)-1,5-dimethyl-3-oxo-2,3-dihydro-1H-pyrazole-4-carboxamide MS (M+H): 584.2;
$^1$H NMR (400 MHz, DMSO-d$_6$ with D$_2$O) δ 8.51 (d, J=7.7 Hz, 1H), 8.30 (s, 1H), 8.22 (s, 1H), 7.81 (s, 1H), 7.77-7.64 (m, 1H), 7.53 (t, J=8.1 Hz, 1H), 7.50-7.45 (m, 2H), 7.41 (t, J=6.9 Hz, 1H), 7.31 (d, J=7.9 Hz, 1H), 6.73 (s, 1H), 6.02 (bs, 1H), 4.02-3.86 (m, 1H), 3.52-3.41 (m, 2H), 3.27 (s, 3H), 2.93 (t, J=10.7 Hz, 2H), 2.61 (s, 3H), 1.96 (d, J=10.4 Hz, 2H), 1.65 (q, J=9.5 Hz, 2H).

Example 21(6)

N-{1-[3-amino-6-(1-methyl-1H-pyrazol-3-yl)-2-pyrazinyl]-4-piperidinyl}-2-(3-chlorophenyl)-1,5-dimethyl-3-oxo-2,3-dihydro-1H-pyrazole-4-carboxamide TLC Rf=0.50 (ethyl acetate:methanol=5:1);
$^1$H NMR (300 MHz, CDCl$_3$) δ 2.76, 2.98-3.07, 3.30, 3.53-3.60, 3.95, 4.08-4.22, 4.58, 6.67-6.70, 7.20-7.50, 8.28, 8.57.

Example 21(7)

N-(1-{3-amino-6-[2-(4-morpholinyl)-1,3-thiazol-4-yl]-2-pyrazinyl}-4-piperidinyl)-2-(3-chlorophenyl)-1,5-dimethyl-3-oxo-2,3-dihydro-1H-pyrazole-4-carboxamide TLC Rf=0.63 (ethyl acetate:methanol=5:1);
$^1$H NMR (300 MHz, CDCl$_3$) δ 1.60-1.73, 2.03-2.15, 2.76, 2.95-3.06, 3.30, 3.47-3.55, 3.80-3.85, 4.08-4.22, 4.62, 7.10, 7.20-7.48, 8.31, 8.59.

Example 21(8)

N-(1-{3-amino-6-[6-(4-morpholinyl)-2-pyridinyl]-2-pyrazinyl}-4-piperidinyl)-2-(3-chlorophenyl)-1,5-dimethyl-3-oxo-2,3-dihydro-1H-pyrazole-4-carboxamide TLC Rf=0.62 (ethyl acetate:methanol=5:1);
$^1$H NMR (300 MHz, CDCl$_3$) δ 1.70-1.80, 2.06-2.17, 2.76, 2.98-3.09, 3.30, 3.28-3.34, 3.41-3.58, 3.82-3.89, 4.13-4.22, 4.69, 6.52-6.60, 7.20-7.28, 7.32-7.62, 8.68.

Example 21(9)

N-(1-{3-amino-6-[6-(1,4-diazepan-1-yl)-2-pyridinyl]-2-pyrazinyl}-4-piperidinyl)-2-(3-chlorophenyl)-1,5-dimethyl-3-oxo-2,3-dihydro-1H-pyrazole-4-carboxamide TLC Rf=0.50 (ethyl acetate:methanol=5:1);
$^1$H NMR (300 MHz, CDCl$_3$) δ 1.60-1.80, 1.83-2.00, 2.08-2.20, 2.78, 2.80-2.87, 2.95-3.10, 3.30, 3.45-3.60, 3.70-3.82, 4.10-4.27, 4.65, 6.44, 7.18-7.53, 8.68.

Example 21(10)

N-(1-{3-amino-6-[6-(4-methyl-1,4-diazepan-1-yl)-2-pyridinyl]-2-pyrazinyl}-4-piperidinyl)-2-(3-chlorophenyl)-1,5-dimethyl-3-oxo-2,3-dihydro-1H-pyrazole-4-carboxamide TLC Rf=0.20 (ethyl acetate:methanol=10:1);
$^1$H NMR (300 MHz, CDCl$_3$) δ 1.59-1.78, 2.00-2.13, 2.15, 2.56, 2.70-2.75, 2.76, 2.97-3.10, 3.30, 3.53-3.60, 3.70, 3.79-3.93, 4.10-4.18, 4.65, 5.29, 6.42, 7.22-7.30, 7.33-7.55, 8.58, 8.69.

Example 21(11)

N-(1-{3-amino-6-[6-(4-methoxy-1-piperidinyl)-2-pyridinyl]-2-pyrazinyl}-4-piperidinyl)-2-(3-chlorophenyl)-1,5-dimethyl-3-oxo-2,3-dihydro-1H-pyrazole-4-carboxamide TLC Rf=0.40 (toluene:methanol=10:1);
$^1$H NMR (300 MHz, CDCl$_3$) δ 1.56-2.04, 2.08-2.16, 2.76, 2.97-3.10, 3.17-3.32, 3.38-3.60, 4.00-4.15, 4.67, 6.60, 7.23-7.36, 7.37-7.57, 8.58, 8.70.

Example 21(12)

N-(1-{3-amino-6-[3-(1H-pyrazol-3-yl)phenyl]-2-pyrazinyl}-3-methyl-4-piperidinyl)-2-(3-chlorophenyl)-1,5-dimethyl-3-oxo-2,3-dihydro-1H-pyrazole-4-carboxamide TLC Rf=0.38 (chloroform:methanol=9:1);
$^1$H NMR (300 MHz, CDCl$_3$) δ 1.13, 1.97, 2.22-2.33, 2.78, 3.20-3.25, 3.31, 3.32-3.37, 4.31-4.44, 4.73, 6.67, 7.25-7.31, 7.35-7.51, 7.64, 7.69, 7.89, 8.21, 8.30, 8.83.

Example 21(13)

N-(1-{3-amino-6-[3-(1H-pyrazol-3-yl)phenyl]-2-pyrazinyl}-4-methyl-4-piperidinyl)-2-(3-chlorophenyl)-1,5-dimethyl-3-oxo-2,3-dihydro-1H-pyrazole-4-carboxamide TLC Rf=0.39 (chloroform:methanol=9:1);
$^1$H NMR (300 MHz, CDCl$_3$) δ 8.61, 8.27, 8.17, 7.85, 7.67, 7.61, 7.20-7.48, 6.63, 4.80, 3.40, 3.26, 3.20, 2.72, 2.41, 1.80, 1.56.

Example 21(14)

N-(1-{3-amino-6-[2-(3-methoxy-1-azetidinyl)-4-pyridinyl]-2-pyrazinyl}-4-piperidinyl)-2-(2,5-dichlorophenyl)-1,5-dimethyl-3-oxo-2,3-dihydro-1H-pyrazole-4-carboxamide TLC Rf=0.33 (chloroform:ethyl acetate:methanol=20:10:3);
$^1$H NMR (300 MHz, CDCl$_3$) δ 1.50-1.85, 2.10-2.25, 2.75, 2.95-3.15, 3.27, 3.35, 3.50-3.65, 3.97, 4.05-4.20, 4.25-4.33, 4.35-4.45, 4.73, 6.82, 7.12, 7.35-7.60, 8.13-8.20, 8.53.

Example 21(15)

N-(1-{3-amino-6-[2-(3-methoxy-1-azetidinyl)-4-pyridinyl]-2-pyrazinyl}-4-piperidinyl)-2-(2-fluoro-5-methylphenyl)-1,5-dimethyl-3-oxo-2,3-dihydro-1H-pyrazole-4-carboxamide TLC Rf=0.33 (chloroform:ethyl acetate:methanol=20:10:3);
$^1$H NMR (300 MHz, CDCl$_3$) δ 1.52-1.85, 2.05-2.25, 2.39, 2.75, 2.95-3.15, 3.31, 3.37, 3.52-3.65, 3.96, 4.10-4.24, 4.25-4.33, 4.35-4.44, 4.75, 6.84, 7.09-7.15, 7.18, 7.25-7.33, 8.14-8.20, 8.67.

Example 21(16)

N-(1-{3-amino-6-[2-(3-methoxy-1-azetidinyl)-4-pyridinyl]-2-pyrazinyl}-4-piperidinyl)-1,5-dimethyl-2-(3-methylphenyl)-3-oxo-2,3-dihydro-1H-pyrazole-4-carboxamide TLC Rf=0.33 (chloroform:ethyl acetate:methanol=20:10:3);
$^1$H NMR (300 MHz, CDCl$_3$) δ 1.60-1.80, 2.10-2.20, 2.43, 2.76, 3.00-3.13, 3.31, 3.37, 3.53-3.65, 3.96, 4.10-4.24, 4.25-4.34, 4.34-4.45, 4.75, 6.84, 7.05-7.20, 7.20-7.28, 7.40, 8.13-8.20, 8.75.

Example 21(17)

N-(1-{3-amino-6-[2-(3-methoxy-1-azetidinyl)-4-pyridinyl]-2-pyrazinyl}-4-piperidinyl)-1,5-dimethyl-2-(2-methylphenyl)-3-oxo-2,3-dihydro-1H-pyrazole-4-carboxamide TLC Rf=0.29 (chloroform:ethyl acetate:methanol=20:10:3);
$^1$H NMR (300 MHz, CDCl$_3$) δ 1.60-1.85, 2.10-2.25, 2.76, 3.00-3.13, 3.27, 3.07, 3.53-3.65, 3.98, 4.10-4.25, 4.30, 4.35-4.42, 4.75, 6.85, 7.13, 7.19, 7.30-7.45, 8.15-8.19, 8.76.

Example 21(18)

N-(1-{3-amino-6-[2-(3-methoxy-1-azetidinyl)-4-pyridinyl]-2-pyrazinyl}-4-piperidinyl)-2-(2-chlorophenyl)-1,5-dimethyl-3-oxo-2,3-dihydro-1H-pyrazole-4-carboxamide TLC Rf=0.29 (chloroform:ethyl acetate:methanol=20:10:3);
$^1$H NMR (300 MHz, CDCl$_3$) δ 1.45-1.88, 2.08-2.23, 2.76, 3.00-3.12, 3.27, 3.37, 3.52, 3.65, 3.98, 4.08-4.25, 4.29, 4.35-4.44, 4.76, 6.85, 7.13, 7.38-7.53, 7.61, 8.17, 8.65.

Example 21(19)

N-(1-{3-amino-6-[2-(3-methoxy-1-azetidinyl)-4-pyridinyl]-2-pyrazinyl}-4-piperidinyl)-2-(2,6-dichlorophenyl)-1,5-dimethyl-3-oxo-2,3-dihydro-1H-pyrazole-4-carboxamide TLC Rf=0.33 (chloroform:ethyl acetate:methanol=20:10:3);
$^1$H NMR (300 MHz, CDCl$_3$) δ 1.65-1.85, 2.10-2.25, 2.77, 3.05, 3.28, 3.37, 3.54-3.66, 3.98, 4.08-4.24, 4.30, 4.34-4.44, 4.75, 6.85, 7.12, 7.52, 7.55, 8.15-8.19, 8.56.

Example 21(20)

N-(1-{3-amino-6-[2-(3-methoxy-1-azetidinyl)-4-pyridinyl]-2-pyrazinyl}-4-piperidinyl)-1,5-dimethyl-2-(2-methylbenzyl)-3-oxo-2,3-dihydro-1H-pyrazole-4-carboxamide TLC Rf=0.23 (dichloromethane:methanol=20:1);
$^1$H NMR (300 MHz, CDCl$_3$) δ 1.68-1.85, 2.11-2.22, 2.36, 2.66, 2.98-3.12, 3.29, 3.35, 3.55-3.68, 3.96, 4.08-4.23, 4.24-4.31, 4.33-4.40, 4.74, 5.10, 6.77, 6.83, 7.09-7.27, 8.14-8.18, 8.76.

Example 21(21)

N-(1-{3-amino-6-[2-(4-morpholinyl)-1,3-thiazol-4-yl]-2-pyrazinyl}-4-piperidinyl)-1,5-dimethyl-3-oxo-2-phenyl-2,3-dihydro-1H-pyrazole-4-carboxamide TLC Rf=0.28 (chloroform:methanol=20:1);
$^1$H NMR (300 MHz, CDCl$_3$) δ 1.63-1.77, 2.08-2.19, 2.75, 2.95-3.06, 3.30, 3.48-3.60, 3.80-3.86, 4.09-4.22, 4.61, 7.10, 7.30-7.35, 7.38-7.45, 7.48-7.56, 8.31, 8.71.

Example 21(22)

N-(1-{3-amino-6-[2-(4-morpholinyl)-1,3-thiazol-4-yl]-2-pyrazinyl}-4-piperidinyl)-2-(2-chlorophenyl)-1,5-dimethyl-3-oxo-2,3-dihydro-1H-pyrazole-4-carboxamide TLC Rf=0.24 (chloroform:methanol=20:1);
$^1$H NMR (300 MHz, CDCl$_3$) δ 1.62-1.79, 2.08-2.20, 2.75, 2.95-3.07, 3.26, 3.48-3.60, 3.79-3.87, 4.08-4.21, 4.60, 7.10, 7.37-7.52, 7.57-7.62, 8.30, 8.62.

Example 21(23)

N-{1-[6-(6-acetyl-2-pyridinyl)-3-amino-2-pyrazinyl]-4-piperidinyl}-2-(2-chlorophenyl)-1,5-dimethyl-3-oxo-2,3-dihydro-1H-pyrazole-4-carboxamide TLC Rf=0.67 (ethyl acetate:methanol=10:1);
$^1$H NMR (300 MHz, CDCl$_3$) δ 1.55-1.84, 2.10-2.22, 2.75, 2.79, 3.05-3.12, 3.26, 3.55-3.62, 4.16-4.22, 4.77, 7.45-7.51, 7.53-7.61, 7.79-7.94, 8.32, 8.65, 8.83.

Example 21(24)

N-[1-(3-amino-6-phenyl-2-pyrazinyl)-4-piperidinyl]-2-(2-chlorophenyl)-1,5-dimethyl-3-oxo-2,3-dihydro-1H-pyrazole-4-carboxamide TLC Rf=0.55 (ethyl acetate:methanol=10:1);
$^1$H NMR (300 MHz, CDCl$_3$) δ 1.66-1.80, 2.10-2.21, 2.75, 2.99-3.10, 3.26, 3.57-3.65, 4.12-4.21, 4.59, 7.24-7.28, 7.29-7.53, 7.59, 7.98, 8.13, 8.63.

Example 21(25)

N-(1-{3-amino-6-[3-(1H-pyrazol-1-yl)phenyl]-2-pyrazinyl}-4-piperidinyl)-2-(2-chlorophenyl)-1,5-dimethyl-3-oxo-2,3-dihydro-1H-pyrazole-4-carboxamide TLC Rf=0.55 (ethyl acetate:methanol=10:1);
$^1$H NMR (300 MHz, CDCl$_3$) δ 1.58-1.81, 2.12-2.21, 2.75, 3.06, 3.26, 3.57-3.65, 4.10-4.21, 4.66, 6.48, 7.24-7.65, 7.66, 7.74, 7.83, 8.00, 8.21, 8.64.

Example 21(26)

N-(1-{3-amino-6-[2-(3-methoxy-1-azetidinyl)-4-pyridinyl]-2-pyrazinyl}-4-piperidinyl)-2-(2-chloro-6-methylphenyl)-1,5-dimethyl-3-oxo-2,3-dihydro-1H-pyrazole-4-carboxamide TLC Rf=0.27 (ethyl acetate:methanol=9:1);
$^1$H NMR (300 MHz, CDCl$_3$) δ 8.53, 8.32, 8.04, 7.40-7.57, 7.17, 6.85, 6.36, 4.32, 4.16, 3.95, 3.76, 3.47, 3.23, 3.20, 2.91, 2.65, 2.17, 1.97, 1.68.

Example 21(27)

N-[1-(3-amino-6-{3-[(methylsulfonyl)amino]phenyl}-2-pyrazinyl)-4-piperidinyl]-2-(2-chlorophenyl)-1,5-dimethyl-3-oxo-2,3-dihydro-1H-pyrazole-4-carboxamide TLC Rf=0.24 (dichloromethane:methanol=20:1);
$^1$H NMR (300 MHz, CDCl$_3$) δ 1.71-1.84, 2.07-2.18, 2.75, 2.98-3.09, 3.26, 3.52-3.61, 4.13-4.25, 4.89, 7.33-7.52, 7.57-7.61, 7.65-7.71, 8.15, 8.66.

Example 21(28)

N-{1-[3-amino-6-(1-methyl-1H-indol-4-yl)-2-pyrazinyl]-4-piperidinyl}-2-(2-chlorophenyl)-1,5-dimethyl-3-oxo-2,3-dihydro-1H-pyrazole-4-carboxamide TLC Rf=0.52 (ethyl aceate:methanol=20:1, NH Silica);
$^1$H NMR (300 MHz, CDCl$_3$) δ 1.67-1.80, 2.10-2.23, 2.62, 2.75, 3.00-3.11, 3.25, 3.58-3.68, 3.82, 4.07-4.21, 4.62, 7.02, 7.12, 7.27-7.34, 7.37-7.52, 7.57-7.62, 8.24, 8.60.

Example 21(29)

N-{1-[3-amino-6-(1H-indazol-5-yl)-2-pyrazinyl]-4-piperidinyl}-2-(2-chlorophenyl)-1,5-dimethyl-3-oxo-2,3-dihydro-1H-pyrazole-4-carboxamide TLC Rf=0.21 (ethyl acetate:methanol=20:1, NH Silica);
$^1$H NMR (300 MHz, CDCl$_3$) δ 1.58-1.82, 2.10-2.22, 2.76, 2.98-3.13, 3.26, 3.51-3.69, 4.08-4.25, 4.60, 7.37-7.61, 7.98, 8.12, 8.17, 8.28, 8.66.

Example 21(30)

N-{1-[3-amino-6-(1H-indol-7-yl)-2-pyrazinyl]-4-piperidinyl}-2-(2-chlorophenyl)-1,5-dimethyl-3-oxo-2,3-dihydro-1H-pyrazole-4-carboxamide TLC Rf=0.47 (ethyl acetate:methanol=20:1, NH Silica);
$^1$H NMR (300 MHz, CDCl$_3$) δ 1.72-1.86, 2.17-2.26, 2.75, 3.02-3.13, 3.26, 3.57-3.67, 4.15-4.27, 4.68, 6.54, 7.14, 7.30, 7.38-7.53, 7.55, 7.68, 8.44, 8.72, 10.7.

Example 21(31)

N-(1-{3-amino-6-[2-(4-hydroxy-1-piperidinyl)-1,3-thiazol-4-yl]-2-pyrazinyl}-4-piperidinyl)-2-(2-chlorophenyl)-1,5-dimethyl-3-oxo-2,3-dihydro-1H-pyrazole-4-carboxamide TLC Rf=0.21 (ethyl acetate:methanol=20:1, NH Silica);
$^1$H NMR (300 MHz, CDCl$_3$) δ 1.60-1.78, 1.95-2.20, 2.61, 2.93-3.05, 3.18-3.33, 3.51-3.60, 3.85-3.98, 4.06-4.21, 4.60, 7.04, 7.36-7.52, 7.54-7.61, 8.30, 8.61.

Example 21(32)

N-{1-[5-amino-6'-(4-morpholinyl)-2,2'-bipyrazin-6-yl]-4-piperidinyl}-2-(2-chlorophenyl)-1,5-dimethyl-3-oxo-2,3-dihydro-1H-pyrazole-4-carboxamide TLC Rf=0.60 (ethyl acetate:methanol=10:1, NH-Silica);
$^1$H NMR (300 MHz, CDCl$_3$) δ 1.68-1.79, 2.10-2.20, 2.75, 2.99-3.10, 3.26, 3.53-3.65, 3.82-3.89, 4.13-4.21, 4.76, 7.37-7.52, 7.54-7.61, 8.03, 8.57, 8.63, 8.70.

Example 21(33)

N-{1-[3-amino-6-(imidazo[1,5-a]pyridin-1-yl)-2-pyrazinyl]-4-piperidinyl}-2-(2-chlorophenyl)-1,5-dimethyl-3-oxo-2,3-dihydro-1H-pyrazole-4-carboxamide TLC Rf=0.25 (ethyl acetate:methanol=5:1);
$^1$H NMR (300 MHz, CDCl$_3$) δ 1.52-1.88, 2.14-2.31, 2.78, 2.98-3.16, 3.28, 3.56-3.70, 4.06-4.34, 4.63, 6.57-6.63, 6.81, 7.37-7.54, 7.55-7.68, 7.90, 8.09, 8.39, 8.53, 8.65.

Example 21(34)

N-{1-[3-amino-6-(1-methyl-1H-indol-6-yl)-2-pyrazinyl]-4-piperidinyl}-2-(2-chlorophenyl)-1,5-dimethyl-3-oxo-2,3-dihydro-1H-pyrazole-4-carboxamide TLC Rf=0.55 (ethyl acetate:methanol=9:1);
$^1$H NMR (300 MHz, CDCl$_3$) δ 1.67-1.89, 2.08-2.32, 2.77, 2.99-3.18, 3.28, 3.50-3.73, 3.87, 4.06-4.31, 4.56, 6.48, 7.08, 7.37-7.54, 7.60, 7.64-7.67, 7.91, 8.21, 8.65.

Example 21(35)

N-[1-[3-amino-6-[6-[(2R,6S)-2,6-dimethylmorpholin-4-yl]pyrazin-2-yl]pyrazin-2-yl]-4-piperidyl]-1-(2-chlorophenyl)-2,3-dimethyl-5-oxo-pyrazole-4-carboxamide TLC Rf=0.10 (ethyl acetate:methanol=10:1);
$^1$H NMR (300 MHz, CDCl$_3$) δ 1.20-1.38, 1.60-1.80, 2.15-2.20, 2.58-2.70, 2.75, 2.99-3.12, 3.26, 3.56-3.63, 3.69-3.81, 4.10-4.22, 4.76, 7.39-7.46, 7.50-7.59, 8.03, 8.58-8.70.

Example 21(36)

N-{1-[3-amino-6-(1H-benzimidazol-4-yl)-2-pyrazinyl]-4-piperidinyl}-2-(2-chlorophenyl)-1,5-dimethyl-3-oxo-2,3-dihydro-1H-pyrazole-4-carboxamide TLC Rf=0.31 (ethyl acetate:methanol=5:1);
$^1$H NMR (300 MHz, CDCl$_3$) δ 1.76-1.98, 2.12-2.24, 2.78, 3.00-3.22, 3.29, 3.49-3.62, 4.18-4.44, 4.79, 7.33, 7.40-7.59, 7.60-7.65, 7.72, 7.80, 7.95, 8.46, 8.92, 11.23.

Example 21(37)

N-(1-{5-amino-6'-[4-(2-hydroxyethyl)-1-piperazinyl]-2,2'-bipyrazin-6-yl}-4-piperidinyl)-2-(2-chlorophenyl)-1,5-dimethyl-3-oxo-2,3-dihydro-1H-pyrazole-4-carboxamide TLC Rf=0.25 (chloroform:methanol=5:1);
$^1$H NMR (300 MHz, CDCl$_3$) δ 1.70-1.80, 2.10-2.20, 2.58-2.70, 2.75, 3.00-3.10, 3.26, 3.55-3.63, 3.64-3.71, 4.10-4.22, 4.78, 7.38-7.61, 8.05, 8.57-8.65.

Example 21(38)

N-{1-[3-amino-6-(2,3-dihydro-1H-pyrrolo[2,3-b]pyridin-5-yl)-2-pyrazinyl]-4-piperidinyl}-2-(2-chlorophenyl)-1,5-dimethyl-3-oxo-2,3-dihydro-1H-pyrazole-4-carboxamide TLC Rf=0.31 (chloroform:methanol=9:1);
$^1$H NMR (300 MHz, CDCl$_3$) δ 1.60-1.80, 2.10-2.22, 2.75, 2.96-3.17, 3.26, 3.52-3.70, 4.10-4.22, 4.51, 7.41-7.53, 7.55-7.61, 7.81, 7.99, 8.32, 8.59-8.66.

Example 21(39)

N-[1-(5-amino-2,2'-bipyrazin-6-yl)-4-piperidinyl]-2-(2-chlorophenyl)-1,5-dimethyl-3-oxo-2,3-dihydro-1H-pyrazole-4-carboxamide TLC Rf=0.44 (ethyl acetate:methanol=5:1);
$^1$H NMR (300 MHz, CDCl$_3$) δ 1.65-1.87, 2.07-2.33, 2.77, 2.94-3.18, 3.28, 3.49-3.72, 4.06-4.35, 4.83, 7.38-7.54, 7.57-7.63, 8.41-8.54, 8.66-8.68, 8.70, 9.39.

Example 21(40)

2-(2-chlorophenyl)-N-[1-(5,5'-diamino-2,2'-bipyrazin-6-yl)-4-piperidinyl]-1,5-dimethyl-3-oxo-2,3-dihydro-1H-pyrazole-4-carboxamide TLC Rf=0.38 (ethyl acetate:methanol=5:1);
$^1$H NMR (300 MHz, CDCl$_3$) δ 1.69-1.87, 2.02-2.28, 2.77, 2.94-3.12, 3.27, 3.48-3.70, 4.03-4.28, 4.61, 4.67, 7.33-7.54, 7.54-7.66, 7.96, 8.48, 8.64, 8.81.

Example 21(41)

N-(1-{3-amino-6-[6-(1H-imidazol-1-yl)-2-pyridinyl]-2-pyrazinyl}-4-piperidinyl)-2-(2-chlorophenyl)-1,5-dimethyl-3-oxo-2,3-dihydro-1H-pyrazole-4-carboxamide TLC Rf=0.25 (ethyl acetate:methanol=5:1);
$^1$H NMR (300 MHz, CDCl$_3$) δ 1.68-1.89, 2.01-2.34, 2.77, 2.95-3.16, 3.27, 3.44-3.72, 4.05-4.36, 4.83, 7.19-7.26, 7.35-7.54, 7.55-7.64, 7.74, 7.86, 8.11, 8.43, 8.67, 8.79.

Example 21(42)

N-(1-{3-amino-6-[6-(4-morpholinyl)-2-pyridinyl]-2-pyrazinyl}-4-piperidinyl)-2-(2-chlorophenyl)-1,5-dimethyl-3-oxo-2,3-dihydro-1H-pyrazole-4-carboxamide TLC Rf=0.68 (ethyl acetate:methanol=5:1);
$^1$H NMR (300 MHz, CDCl$_3$) δ 1.64-1.87, 2.09-2.29, 2.76, 2.97-3.15, 3.27, 3.49-3.66, 3.78-3.92, 4.06-4.28, 4.69, 6.52-6.62, 7.38-7.53, 7.54-7.64, 8.64, 8.68.

Example 21(43)

N-{1-[5-amino-6'-(4-methoxy-1-piperidinyl)-2,2'-bipyrazin-6-yl]-4-piperidinyl}-2-(2-chlorophenyl)-1,5-dimethyl-3-oxo-2,3-dihydro-1H-pyrazole-4-carboxamide TLC Rf=0.50 (ethyl acetate:methanol=2:1);
$^1$H NMR (300 MHz, CDCl$_3$) δ 1.58-1.80, 1.95-2.05, 2.10-2.22, 2.75, 2.97-3.10, 3.23-3.27, 3.40, 3.50-3.62, 3.99-4.10, 4.11-4.22, 4.75, 7.48-7.56, 7.58-7.61, 8.08, 8.59-8.66.

Example 21(44)

N-{1-[5-amino-6'-(3-methoxy-1-azetidinyl)-2,2'-bipyrazin-6-yl]-4-piperidinyl}-2-(2-chlorophenyl)-1,5-dimethyl-3-oxo-2,3-dihydro-1H-pyrazole-4-carboxamide TLC Rf=0.60 (ethyl acetate:methanol=5:1);
$^1$H NMR (300 MHz, CDCl$_3$) δ 1.57-1.79, 2.01-2.20, 2.75, 2.96-3.10, 3.26, 3.36, 3.42-3.62, 3.96-4.05, 4.08-4.42, 4.77, 7.36-7.62, 7.73, 8.58-8.70.

Example 21(45)

N-(1-{5-amino-6'-[(2-methoxyethyl)(methyl)amino]-2,2'-bipyrazin-6-yl}-4-piperidinyl)-2-(2-chlorophenyl)-1,5-dimethyl-3-oxo-2,3-dihydro-1H-pyrazole-4-carboxamide TLC Rf=0.65 (ethyl acetate:methanol=5:1);
$^1$H NMR (300 MHz, CDCl$_3$) δ 1.65-1.81, 2.00-2.22, 2.75, 2.98-3.12, 3.19, 3.26, 3.58, 4.55-4.64, 4.78-4.84, 7.38-7.56, 7.58-7.62, 7.96, 8.57, 8.59-8.64.

Example 21(46)

N-(1-{(3-amino-6-[2-(dimethylamino)-1,3-thiazol-5-yl]-2-pyrazinyl}-4-piperidinyl)-2-(2-chlorophenyl)-1,5-dimethyl-3-oxo-2,3-dihydro-1H-pyrazole-4-carboxamide TLC Rf=0.45 (ethyl acetate:methanol=5:1);
$^1$H NMR (300 MHz, CDCl$_3$) δ 1.65-1.82, 2.01-2.27, 2.76, 2.95-3.08, 3.13, 3.27, 3.49-3.67, 4.05-4.23, 4.48, 7.37-7.53, 7.56-7.64, 7.89, 8.62.

Example 21(47)

N-[1-(3-amino-6-{3-[2-(4-morpholinyl)ethoxy]phenyl}-2-pyrazinyl)-4-piperidinyl]-2-(2-chlorophenyl)-1,5-dimethyl-3-oxo-2,3-dihydro-1H-pyrazole-4-carboxamide TLC Rf=0.75 (ethyl acetate:methanol=5:1);
$^1$H NMR (300 MHz, CDCl$_3$) δ 1.60-1.80, 2.10-2.20, 2.56-2.64, 2.75, 2.78-2.85, 2.98-3.10, 3.25, 3.57-3.62, 3.70-3.79, 4.10-4.20, 4.63, 6.80-6.85, 7.20-7.62, 8.10, 8.61.

Example 21(48)

N-{1-[3-amino-6-(2-cyano-4-pyridinyl)-2-pyrazinyl]-4-piperidinyl}-2-(2-chlorophenyl)-1,5-dimethyl-3-oxo-2,3-dihydro-1H-pyrazole-4-carboxamide TLC Rf=0.24 (ethyl acetate:methanol=5:1);
$^1$H NMR (300 MHz, CDCl$_3$) δ 1.70-1.83, 2.10-2.22, 2.75, 3.00-3.15, 3.27, 3.56-3.64, 4.17-4.30, 4.85, 7.36-7.50, 7.58-7.62, 7.98-8.00, 8.19-8.20, 8.24, 8.64.

Example 21(49)

N-{1-[3-amino-6-(5-amino-2-pyridinyl)-2-pyrazinyl]-4-piperidinyl}-2-(2-chlorophenyl)-1,5-dimethyl-3-oxo-2,3-dihydro-1H-pyrazole-4-carboxamide TLC Rf=0.20 (ethyl acetate:methanol=5:1);
$^1$H NMR (300 MHz, CDCl$_3$) δ 1.60-1.81, 2.08-2.20, 2.75, 2.96-3.09, 3.25, 3.50-3.62, 3.70-3.80, 4.10-4.22, 4.62, 7.00-7.08, 7.24-7.50, 7.56-7.61, 7.96, 8.05-8.10, 8.58, 8.63.

Example 21(50)

N-(1-{3-amino-6-[2-(4-morpholinyl)-4-pyrimidinyl]-2-pyrazinyl}-4-piperidinyl)-2-(2-chlorophenyl)-1,5-dimethyl-3-oxo-2,3-dihydro-1H-pyrazole-4-carboxamide TLC Rf=0.27 (ethyl acetate:methanol=9:1);
$^1$H NMR (300 MHz, CDCl$_3$) δ 8.73, 8.65, 8.37, 7.60, 7.36-7.50, 4.84, 4.18, 3.77-3.90, 3.56, 3.24, 3.05, 2.76, 2.16, 1.76.

Example 21(51)

N-{1-[3-amino-6-(1H-indazol-6-yl)-2-pyrazinyl]-4-piperidinyl}-2-(2-chlorophenyl)-1,5-dimethyl-3-oxo-2,3-dihydro-1H-pyrazole-4-carboxamide TLC Rf=0.56 (ethyl acetate:methanol=5:1);
$^1$H NMR (300 MHz, CDCl$_3$) δ 1.74-1.92, 2.08-2.27, 2.77, 3.03-3.18, 3.28, 3.51-3.72, 4.09-4.34, 4.69, 7.39-7.55, 7.58-7.64, 7.70, 7.78, 8.06, 8.11, 8.23, 8.69, 10.35.

Example 21(52)

N-{1-[3-amino-6-(3H-imidazo[4,5-b]pyridin-6-yl)-2-pyrazinyl]-4-piperidinyl}-2-(2-chlorophenyl)-1,5-dimethyl-3-oxo-2,3-dihydro-1H-pyrazole-4-carboxamide TLC Rf=0.26 (chloroform:methanol=9:1);
$^1$H NMR (300 MHz, CDCl$_3$) δ 12.6-13.04, 8.95, 8.26-8.57, 7.72, 7.56-7.63, 6.13, 3.98, 3.51, 3.21, 2.98, 2.62, 2.00, 1.68.

Example 21(53)

N-(1-{3-amino-6-[2-(3-methoxy-1-azetidinyl)-4-pyridinyl]-2-pyrazinyl}-4-piperidinyl)-2-(3-chlorophenyl)-1,5-dimethyl-3-oxo-2,3-dihydro-1H-pyrazole-4-carboxamide TLC Rf=0.38 (chloroform:methanol=9:1);
$^1$H NMR (300 MHz, CDCl$_3$) δ 8.60, 8.16, 7.34-7.46, 7.25, 7.09, 6.82, 4.76, 4.38, 4.29, 4.17, 3.94, 3.58, 3.36, 3.30, 3.04, 2.76, 2.13, 1.70.

Example 21(54)

N-{1-[3-amino-6-(3-aminophenyl)-2-pyrazinyl]-4-piperidinyl}-2-(2-chlorophenyl)-1,5-dimethyl-3-oxo-2,3-dihydro-1H-pyrazole-4-carboxamide TLC Rf=0.15 (ethyl acetate:methanol=10:1);
$^1$H NMR (300 MHz, CDCl$_3$) δ 1.65-1.81, 2.09-2.20, 2.75, 2.98-3.08, 3.26, 3.55-3.63, 4.10-4.20, 4.60, 6.60-6.68, 7.15-7.30, 7.39-7.57, 7.59-7.64, 8.09, 8.62.

Example 21(55)

N-{1-[3-amino-6-(2-fluoro-3-methoxyphenyl)-2-pyrazinyl]-4-piperidinyl}-2-(2-chlorophenyl)-1,5-dimethyl-3-oxo-2,3-dihydro-1H-pyrazole-4-carboxamide TLC Rf=0.60 (ethyl acetate:methanol=5:1);
$^1$H NMR (300 MHz, CDCl$_3$) δ 1.60-1.80, 2.10-2.20, 2.74, 2.95-3.05, 3.25, 3.50-3.62, 3.91, 4.08-4.20, 4.65, 6.85-6.90, 7.08-7.18, 7.37-7.60, 8.22, 8.60.

Example 21(56)

N-(1-{3-amino-6-[6-(4-methoxy-1-piperidinyl)-2-pyridinyl]-2-pyrazinyl}-4-piperidinyl)-2-(2-chlorophenyl)-1,5-dimethyl-3-oxo-2,3-dihydro-1H-pyrazole-4-carboxamide TLC Rf=0.31 (ethyl acetate:methanol=10:1);
$^1$H NMR (300 MHz, CDCl$_3$) δ 1.60-1.80, 1.95-2.07, 2.10-2.22, 2.75, 2.98-3.10, 3.18-3.28, 3.38-3.49, 3.50-3.60, 4.02-4.20, 4.70, 6.60, 7.38-7.62, 8.60, 8.70.

Example 21(57)

N-[1-(3-amino-6-{2-fluoro-3-[2-hydroxy-3-(1-pyrrolidinyl)propoxy]phenyl}-2-pyrazinyl)-4-piperidinyl]-2-(2-chlorophenyl)-1,5-dimethyl-3-oxo-2,3-dihydro-1H-pyrazole-4-carboxamide TLC Rf=0.25 (ethyl acetate:methanol=10:1, NH-Silica);
$^1$H NMR (300 MHz, CDCl$_3$) δ 1.62-1.82, 2.12-2.20, 2.50-2.60, 2.64-2.74, 2.75, 2.80-2.90, 2.98-3.10, 3.26, 3.58-3.64, 4.02-4.20, 4.61-4.65, 6.90-7.00, 7.02-7.18, 7.38-7.60, 8.24, 8.62.

Example 21(58)

N-(1-{3-amino-6-[6-(3-hydroxy-1-pyrrolidinyl)-2-pyridinyl]-2-pyrazinyl}-4-piperidinyl)-2-(2-chlorophenyl)-1,5-dimethyl-3-oxo-2,3-dihydro-1H-pyrazole-4-carboxamide TLC Rf=0.60 (ethyl acetate:methanol=10:1);
$^1$H NMR (300 MHz, CDCl$_3$) δ 1.60-1.82, 2.00-2.22, 2.75, 2.98-3.08, 3.25, 3.50-3.78, 4.08-4.22, 4.58-4.70, 6.30, 7.37-7.62, 8.61, 8.71.

Example 21(59)

N-(1-{3-amino-6-[6-(3-methoxy-1-pyrrolidinyl)-2-pyridinyl]-2-pyrazinyl}-4-piperidinyl)-2-(2-chlorophenyl)-1,5-dimethyl-3-oxo-2,3-dihydro-1H-pyrazole-4-carboxamide TLC Rf=0.23 (ethyl acetate:methanol=10:1);
$^1$H NMR (300 MHz, CDCl$_3$) δ 1.62-1.82, 2.07-2.22, 2.75, 2.98-3.08, 3.26, 3.39, 3.50-3.70, 4.06-4.21, 4.66, 6.30, 7.38-7.57, 7.58-7.62, 8.60, 8.73.

Example 21(60)

N-(1-{3-amino-6-[3-(tetrahydro-2H-pyran-4-yloxy)phenyl]-2-pyrazinyl}-4-piperidinyl)-2-(2-chlorophenyl)-1,5-dimethyl-3-oxo-2,3-dihydro-1H-pyrazole-4-carboxamide TLC Rf=0.31 (ethyl acetate:methanol=10:1);
$^1$H NMR (300 MHz, CDCl$_3$) δ 1.62-1.90, 1.98-2.22, 2.75, 2.98-3.10, 3.26, 3.50-3.62, 3.92-4.06, 4.08-4.22, 4.50-4.62, 6.80-6.90, 7.20-7.57, 7.58-7.63, 8.10, 8.61.

Example 21(61)

N-(1-{3-amino-6-[2-fluoro-3-(tetrahydro-2H-pyran-4-yloxy)phenyl]-2-pyrazinyl}-4-piperidinyl)-2-(2-chlorophenyl)-1,5-dimethyl-3-oxo-2,3-dihydro-1H-pyrazole-4-carboxamide TLC Rf=0.58 (ethyl acetate:methanol=10:1);
$^1$H NMR (300 MHz, CDCl$_3$) δ 1.62-1.94, 1.97-2.20, 2.74, 2.98-3.08, 3.25, 3.45-3.62, 3.98-4.09, 4.10-4.20, 4.40-4.50, 4.60-4.70, 6.90-6.99, 7.00-7.10, 7.27-7.60, 8.20, 8.60.

Example 21(62)

N-{1-[5-amino-5'-(3-hydroxy-1-pyrrolidinyl)-2,2'-bipyrazin-6-yl]-4-piperidinyl}-2-(2-chlorophenyl)-1,5-dimethyl-3-oxo-2,3-dihydro-1H-pyrazole-4-carboxamide TLC Rf=0.33 (ethyl acetate:methanol=5:1);
$^1$H NMR (300 MHz, CDCl$_3$) δ 1.60-1.87, 2.10-2.24, 2.75, 2.98-3.10, 3.26, 3.57-3.75, 4.10-4.22, 4.55-4.70, 7.37-7.60, 7.82, 8.40, 8.80, 8.90.

Example 21(63)

N-{1-[5-amino-6'-(3-methoxy-1-pyrrolidinyl)-2,2'-bipyrazin-6-yl]-4-piperidinyl}-2-(2-chlorophenyl)-1,5-dimethyl-3-oxo-2,3-dihydro-1H-pyrazole-4-carboxamide TLC Rf=0.45 (ethyl acetate:methanol=10:1);
$^1$H NMR (300 MHz, CDCl$_3$) δ 1.60-1.81, 2.04-2.26, 2.75, 2.98-3.07, 3.26, 3.39, 3.57-3.70, 4.10-4.24, 4.77, 7.36-7.63, 7.80, 8.63.

Example 21(64)

N-{1-[5-amino-6'-(3-hydroxy-1-pyrrolidinyl)-2,2'-bipyrazin-6-yl]-4-piperidinyl}-2-(2-chlorophenyl)-1,5-dimethyl-3-oxo-2,3-dihydro-1H-pyrazole-4-carboxamide TLC Rf=0.35 (ethyl acetate:methanol=5:1);
$^1$H NMR (300 MHz, CDCl$_3$) δ 1.65-1.83, 2.02-2.24, 2.75, 2.98-3.09, 3.26, 3.55-3.78, 4.10-4.22, 4.60-4.63, 4.78, 7.38-7.57, 7.59-7.62, 7.80, 8.57-8.65.

Example 21(65)

N-{1-[5-amino-5'-(4-hydroxy-1-piperidinyl)-2,2'-bipyrazin-6-yl]-4-piperidinyl}-2-(2-chlorophenyl)-1,5-dimethyl-3-oxo-2,3-dihydro-1H-pyrazole-4-carboxamide TLC Rf=0.20 (ethyl acetate:methanol=10:1);
$^1$H NMR (300 MHz, CDCl$_3$) δ 1.60-1.80, 1.90-2.08, 2.10-2.20, 2.75, 2.96-3.07, 3.18-3.36, 3.56-3.64, 3.85-4.22, 4.60, 7.36-7.58, 7.60, 8.06, 8.42, 8.60, 8.83.

Example 21(66)

N-{1-[5-amino-6'-(1-pyrrolidinyl)-2,2'-bipyrazin-6-yl]-4-piperidinyl}-2-(2-chlorophenyl)-1,5-dimethyl-3-oxo-2,3-dihydro-1H-pyrazole-4-carboxamide TLC Rf=0.32 (ethyl acetate:methanol=10:1);
$^1$H NMR (300 MHz, CDCl$_3$) δ 1.61-1.80, 1.97-2.09, 2.10-2.20, 2.75, 2.97-3.10, 3.25, 3.45-3.64, 4.10-4.23, 4.72, 7.37-7.53, 7.55-7.62, 7.79, 8.55-8.65.

Example 21(67)

N-{1-[5-amino-6'-(3-fluoro-1-pyrrolidinyl)-2,2'-bipyrazin-6-yl]-4-piperidinyl}-2-(2-chlorophenyl)-1,5-dimethyl-3-oxo-2,3-dihydro-1H-pyrazole-4-carboxamide TLC Rf=0.41 (ethyl acetate:methanol=10:1);
$^1$H NMR (300 MHz, CDCl$_3$) δ 1.60-1.83, 2.06-2.50, 2.75, 2.98-3.10, 3.26, 3.50-4.02, 4.78, 5.36-5.50, 7.37-7.56, 7.58-7.61, 7.83, 8.61-8.68.

Example 21(68)

N-{1-[5-amino-6'-(4,4-difluoro-1-piperidinyl)-2,2'-bipyrazin-6-yl]-4-piperidinyl}-2-(2-chlorophenyl)-1,5-dimethyl-3-oxo-2,3-dihydro-1H-pyrazole-4-carboxamide TKC Rf=0.42 (ethyl acetate:methanol=9:1);
$^1$H NMR (300 MHz, CDCl$_3$) δ 8.71, 8.65, 8.59, 8.13, 7.60, 7.39-7.50, 4.78, 4.18, 3.82, 3.60, 3.24, 3.05, 2.76, 2.10, 1.72.

Example 21(69)

N-(1-{3-amino-6-[3-(dimethylamino)phenyl]-2-pyrazinyl}-4-piperidinyl)-2-(2-chlorophenyl)-1,5-dimethyl-3-oxo-2,3-dihydro-1H-pyrazole-4-carboxamide TLC: Rf=0.42 (ethyl acetate:methanol=20:1, NH Silica);
$^1$H NMR (300 MHz, CDCl$_3$) δ 1.62-1.80, 2.12-2.21, 2.75, 3.00, 3.01-3.09, 3.26, 3.56-3.65, 4.08-4.22, 4.57, 6.70-6.75, 7.20-7.53, 7.59, 8.12, 8.62.

Example 22(1)

N-(4-{3-amino-6-[3-(2,3-dihydroxypropoxy)phenyl]-2-pyrazinyl}phenyl)-1,5-dimethyl-3-oxo-2-phenyl-2,3-dihydro-1H-pyrazole-4-carboxamide

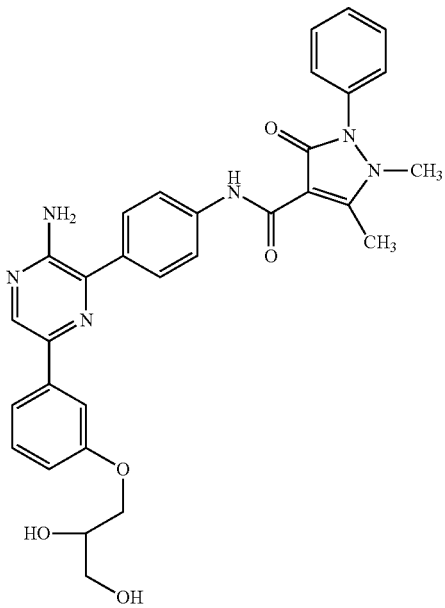 [SMILES: Cc1c(C(=O)Nc2ccc(-c3nc(-c4cccc(OCC(O)CO)c4)cnc3N)cc2)c(=O)n(-c2ccccc2)n1C]

N-(4-{3-amino-6-[3-(3-{[dimethyl(2-methyl-2-propanyl)silyl]oxy}-2-hydroxypropoxy)phenyl]-2-pyrazinyl}phenyl)-1,5-dimethyl-3-oxo-2-phenyl-2,3-dihydro-1H-pyrazole-4-carboxamide was obtained by using the compound prepared in Example 6 and using 1-(3-bromophenoxy)-3-(tert-butyldimethylsilyloxy)propan-2-ol instead of 1-(3-bromo-2-fluorophenoxy)-3-(pyrrolidin-1-yl)propan-2-ol in the process of Example 7. To a vial containing the above compound (0.040 g) in 2 mL of THF anhydrous (totally dissolved) under $N_2$ atmosphere, was added by syringe the tetra-n-butylammonium fluoride (TBAF) solution 1M in THF. The reaction was left stirring at room temperature for 90 min then it was concentrated on the rotavapor. Purification was performed on the Biotage Isolera $SiO_2$-25 g 0-10% MeOH in DCM to give the title compound (0.025 g) having the following physical data.

MS (M+H): 567.1;
$^1$H NMR (400 MHz, $CDCl_3$) δ 10.85 (s, 1H), 8.38 (s, 1H), 7.82 (d, J=8.7 Hz, 2H), 7.77 (d, J=8.7 Hz, 2H), 7.58-7.51 (4H), 7.46 (t, J=7.4 Hz, 1H), 7.38-7.31 (3H), 6.89 (d, J=8.0, 2.1 Hz, 1H), 4.81 (s, 2H), 4.16-4.08 (m, 3H), 3.89-3.72 (m, 2H), 3.36 (s, 3H), 2.80 (s, 3H), 2.56 (s, 1H), 1.94 (d, J=5.7 Hz, 1H).

Example 22(2)-22(8)

The compound having the following physical data was prepared by using the compound prepared in Example 6, 1-(3-bromophenoxy)-3-(tert-butyldimethylsilyloxy)propan-2-ol or the corresponding bromide compound instead thereof, and using the compound prepared in Example 1 or the corresponding carboxylic acid instead thereof in the process of Example 7→Example 22(1).

Example 22(2)

N-(4-{3-amino-6-[3-(2-pyrrolidinylmethoxy)phenyl]-2-pyrazinyl}phenyl)-2-(3-chlorophenyl)-1,5-dimethyl-3-oxo-2,3-dihydro-1H-pyrazole-4-carboxamide MS (M+H): 610.1;
$^1$H NMR (400 MHz, $CDCl_3$) δ 10.70 (s, 1H), 8.38 (s, 1H), 7.84-7.74 (4H), 7.54-7.27 (7H), 6.88 (d, J=7.9 Hz, 1H), 4.80 (s, 2H), 4.03-3.91 (m, 2H), 3.63-3.52 (m, 1H), 3.36 (s, 3H), 3.30-3.06 (m, 1H), 3.10-2.95 (m, 2H), 2.80 (s, 3H), 2.03-1.76 (3H), 1.68-1.57 (m, 1H).

Example 22(3)

N-(4-{3-amino-6-[3-(2,3-dihydroxypropoxy)phenyl]-2-pyrazinyl}phenyl)-2-(3-chlorophenyl)-1,5-dimethyl-3-oxo-2,3-dihydro-1H-pyrazole-4-carboxamide MS (M+H): 601.1;
$^1$H NMR (400 MHz, $CDCl_3$) δ 10.70 (s, 1H), 8.38 (s, 1H), 7.85-7.74 (4H), 7.58-7.26 (7H), 6.89 (d, J=8.0 Hz, 1H), 4.82 (s, 2H), 4.11 (s, 3H), 3.80 (d, J=20.9 Hz, 2H), 3.36 (s, 3H), 2.80 (s, 3H), 2.59 (s, 1H), 1.99 (s, 1H).

Example 22(4)

N-(4-{3-amino-6-[3-(3-pyrrolidinyl)phenyl]-2-pyrazinyl}phenyl)-2-(3-chlorophenyl)-1,5-dimethyl-3-oxo-2,3-dihydro-1H-pyrazole-4-carboxamide MS (M+H): 580.1;
$^1$H NMR (400 MHz, $CDCl_3$) δ 10.70 (s, 1H), 8.38 (s, 1H), 7.85-7.72 (6H), 7.50-7.39 (m, 2H), 7.39-7.33 (m, 2H), 7.27 (ddd, J=7.8, 2.0, 1.2 Hz, 1H), 7.22 (d, J=7.8 Hz, 1H), 4.81 (s, 2H), 3.45-3.24 (5H), 3.19 (ddd, J=10.7, 8.4, 4.7 Hz, 1H), 3.10 (dt, J=10.9, 7.6 Hz, 1H), 2.90 (dd, J=10.5, 8.3 Hz, 1H), 2.79 (s, 3H), 2.33-2.20 (m, 2H), 1.91 (dq, J=12.6, 8.3 Hz, 1H).

Example 22(5)

N-(4-{3-amino-6-[3-(3-piperidinyl)phenyl]-2-pyrazinyl}phenyl)-2-(3-chlorophenyl)-1,5-dimethyl-3-oxo-2,3-dihydro-1H-pyrazole-4-carboxamide MS (M+H): 594.3;
$^1$H NMR (400 MHz, $CDCl_3$) δ 10.70 (s, 1H), 8.38 (s, 1H), 7.83-7.74 (6H), 7.48 (t, J=7.9 Hz, 1H), 7.42 (ddd, J=8.1, 2.0, 1.2 Hz, 1H), 7.39-7.37 (m, 1H), 7.35 (d, J=7.7 Hz, 1H), 7.28 (ddd, J=7.8, 2.0, 1.2 Hz, 1H), 7.22-7.17 (m, 1H), 4.79 (s, 2H), 3.36 (s, 3H), 3.24-3.16 (m, 1H), 3.13-3.05 (m, 1H), 2.80 (s, 3H), 2.76-2.59 (3H), 2.07-1.99 (m, 1H), 1.82-1.74 (m, 1H), 1.73-1.46 (m, 3H).

Example 22(6)

1-(4-{5-amino-6-[4-({[2-(3-chlorophenyl)-1,5-dimethyl-3-oxo-2,3-dihydro-1H-pyrazol-4-yl]carbonyl}amino)phenyl]-2-pyrazinyl}-2-pyridinyl)-3-azetidinecarboxylic acid MS (M+H): 611.3;
$^1$H NMR (400 MHz, DMSO-$d_6$) δ 10.76 (s, 1H), 8.58 (s, 1H), 8.07 (d, J=5.2 Hz, 1H), 7.77-7.68 (m, 4H), 7.62-7.52 (3H), 7.40 (d, J=7.6 Hz, 1H), 7.23 (d, J=5.3 Hz, 1H), 6.91 (s, 1H), 6.50 (s, 2H), 4.17-4.09 (m, 2H), 4.02-3.93 (m, 2H), 3.54-3.48 (m, 1H), 3.37 (s, 4H), 2.69 (s, 3H).

Example 22(7)

N-(4-{3-amino-6-[3-(3-amino-2-hydroxypropoxy) phenyl]-2-pyrazinyl}phenyl)-2-(3-chlorophenyl)-1,5-dimethyl-3-oxo-2,3-dihydro-1H-pyrazole-4-carboxamide MS (M+H): 600.1;
$^1$H NMR (400 MHz, CDCl$_3$) δ 10.70 (s, 1H), 8.39 (s, 1H), 7.84-7.75 (4H), 7.55 (s, 1H), 7.55-7.50 (m, 1H), 7.47 (d, J=7.9 Hz, 1H), 7.42 (d, J=8.1 Hz, 1H), 7.38 (s, 1H), 7.33 (t, J=7.9 Hz, 1H), 7.28 (d, J=8.1 Hz, 1H), 6.90 (d, J=6.2 Hz, 1H), 4.81 (s, 2H), 4.08-4.01 (m, 2H), 3.99-3.92 (m, 1H), 3.36 (s, 3H), 2.98 (dd, J=12.9, 4.0 Hz, 1H), 2.87 (dd, J=12.8, 6.8 Hz, 1H), 2.81 (s, 3H).

Example 22(8)

N-(4-{3-amino-6-[2-(4-amino-1-piperidinyl)-4-pyridinyl]-2-pyrazinyl}phenyl)-2-(3-chlorophenyl)-1,5-dimethyl-3-oxo-2,3-dihydro-1H-pyrazole-4-carboxamide MS (M+H): 610.2;
$^1$H NMR (400 MHz, CDCl$_3$) δ 10.71 (s, 1H), 8.40 (s, 1H), 8.21 (d, J=5.2 Hz, 1H), 7.78 (dd, J=20.2, 8.7 Hz, 4H), 7.53-7.34 (m, 3H), 7.27 (dd, J=13.3, 5.5 Hz, 2H), 7.09 (d, J=5.2 Hz, 1H), 4.94 (s, 2H), 4.31 (d, J=13.1 Hz, 2H), 3.35 (s, 3H), 3.02-2.83 (m, 3H), 2.79 (s, 3H), 1.90 (d, J=10.9 Hz, 2H), 1.60-1.13 (m, 4H).

Example 23

N-[4-(3-amino-6-{3-[(4-oxo-1-piperidinyl)methyl] phenyl}-2-pyrazinyl)phenyl]-1,5-dimethyl-3-oxo-2-phenyl-2,3-dihydro-1H-pyrazole-4-carboxamide

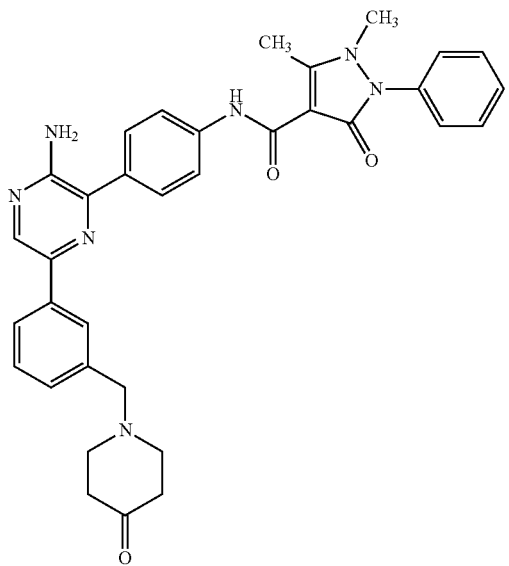 [SMILES: Cc1c(C(=O)Nc2ccc(-c3nc(-c4cccc(CN5CCC(=O)CC5)c4)cnc3N)cc2)c(=O)n(-c2ccccc2)n1C]

N-(4-{3-amino-6-[3-(1,4-dioxa-8-azaspiro[4.5]dec-8-ylmethyl)phenyl]-2-pyrazinyl}phenyl)-1,5-dimethyl-3-oxo-2-phenyl-2,3-dihydro-1H-pyrazole-4-carboxamide was obtained by using the compound prepared in Example 3, and using 3-(1,4-dioxa-8-azaspiro[4.5]dec-8-ylmethyl)phenylboronic acid instead of 4-(3-(4,4,5,5-tetramethyl-1,3,2-dioxaborolan-2-yl)benzyl)morpholine in the process of Example 5. A solution of the above compound (82 mg) in 2 N HCl (5 mL) was heated at 60° C. overnight. The solution was concentrated to give a crude product which was extracted with DCM/saturated sodium bicarbonate solution. The organic layer was dried, concentrated, and the residue was purified by prep TLC using 12% MeOH in EtOAc to give the title compound (53.3 mg) having the following physical data as a solid.
MS (M+H): 588.1;
$^1$H NMR (400 MHz, CDCl$_3$) δ 10.84 (s, 1H), 8.39 (s, 1H), 7.92 (s, 1H), 7.85-7.76 (5H), 7.55-7.51 (2H), 7.47-7.43 (1H), 7.41-7.33 (4H), 4.84 (s, 2H), 3.67 (s, 2H), 3.34 (s, 3H), 2.78 (s, 3H), 2.76 (t, J=6.0 Hz, 2H), 2.44 (t, J=6.0 Hz, 2H).

Example 24

2-methyl-2-propanyl (6-bromo-3-pyridinyl)carbamate

To a solution of 6-bromopyridin-3-amine (CAS No. 13534-97-9) (2 g) in tert-butanol (50 mL) was added di-tert-butyl dicarbonate (3.73 g) and dimethylaminopyridine (DMAP) (140 mg). The resulting mixture was stirred at room temperature overnight. The reaction was concentrated under reduced pressure and purified by silica gel chromatography using 0-10% EtOAc in heptanes to give the title compound (2.8 g) having the following physical data as a white solid.
TLC Rf=0.56 (ethyl acetate:hexane=2:1).

Example 25

2-methyl-2-propanyl[6-(tributylstannyl)-3-pyridinyl] carbamate

To a solution of the compound prepared in Example 24 (2.8 g) in anhydrous THF (40 mL) was slowly added a solution of 2.5 M n-butyllithium in hexane (8.2 mL) at −78° C. The mixture was stirred at −78° C. for another 1 hour, followed by the addition of tributyltin chloride (3.65 g). The mixture was stirred for another 3 hours and allowed to warm to room temperature slowly. The reaction was quenched with an aqueous saturated ammonium chloride solution, extracted with EtOAc (3×50 mL). The combined organic layers were washed with brine, dried with Na$_2$SO$_4$, concentrated, and purified by silica gel chromatography using 5-20% EtOAc in heptanes to give the title compound (2.8 g) having the following physical data as yellow oil.
TLC Rf=0.36 (ethyl acetate:hexane=4:1).

Example 26

2-methyl-2-propanyl[6-(3-amino-6-bromo-2-pyrazinyl)-3-pyridinyl]carbamate

The compound prepared in Example 25 (2.8 g) was dissolved in anhydrous toluene (30 mL) followed by the addition of 3,5-dibromopyrazin-2-amine (1.7 g) and tetrakis(triphenylphosphine)palladium(0) (330 mg). The mixture was heated at 110° C. overnight. The solvent was removed under reduced pressure, and the residue was purified by silica gel chromatography using 10-30% EtOAc in heptanes to give the title compound (1.2 g) having the following physical data as a yellow solid.
TLC Rf=0.36 (ethyl acetate:hexane=2:1).

Example 27

3-(5-amino-2-pyridinyl)-5-bromo-2-pyrazinamine

To a stirred solution of the compound prepared in Example 26 (1.2 g) in anhydrous dioxane (30 mL) was added a solution of 4N HCl in dioxane (15 mL). The mixture was stirred at room temperature for 4 hours. The solvent was removed under reduced pressure. The resulting residue was dissolved in THF and basified with an aqueous saturated sodium bicarbonate solution. The mixture was extracted with EtOAc (3×50 mL). The combined organic layers were dried over $Na_2SO_4$, concentrated under reduced pressure and purified by silica gel chromatography using 20-50% EtOAc in heptanes to give the title compound (0.52 g) having the following physical data as yellow solid.

TLC Rf=0.43 (ethyl acetate:hexane=1:1).

Example 28

3-(5-amino-2-pyridinyl)-5-[2-(4-morpholinyl)-4-pyridinyl]-2-pyrazinamine

A mixture of the compound prepared in Example 27 (150 mg), potassium phosphate (2M solution, 1.69 mmol), 4-(4-(4,4,5,5-tetramethyl-1,3,2-dioxaborolan-2-yl)pyridin-2-yl)morpholine (164.1 mg) in dioxane (2 mL) and water (0.1 mL) was degassed for 5 minutes. After $Pd(PPh_3)_4$ (65.1 mg) was added, the reaction was degassed for another 5 minutes. The reaction was then heated to 90° C. overnight. After the solvent was removed, the residue was redissolved in DCM, and the organic layer was washed with water, brine, dried over $Na_2SO_4$, and concentrated under reduced pressure. The crude was obtained by precipitation from a mixture of $CH_2Cl_2$, EtOAc and hexanes to give the title compound (147.2 mg) having the following physical data.

MS (M+H): 350.1.

Example 29(1)

N-(6-{(3-amino-6-[2-(4-morpholinyl)-4-pyridinyl]-2-pyrazinyl}-3-pyridinyl)-1,5-dimethyl-2-(3-methylphenyl)-3-oxo-2,3-dihydro-1H-pyrazole-4-carboxamide

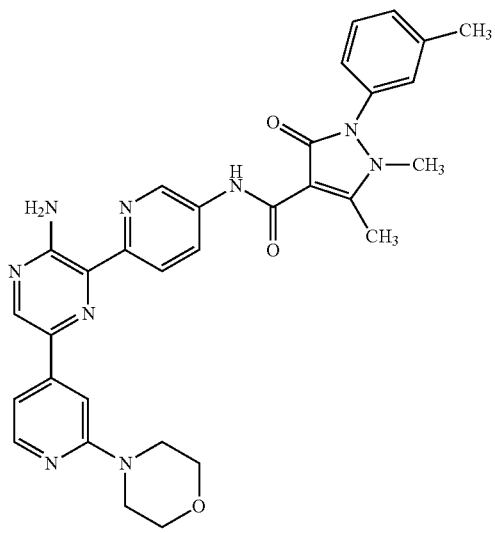 [SMILES: Cc1cccc(-n2c(=O)c(C(=O)Nc3ccc(-c4nc(-c5ccnc(N6CCOCC6)c5)cnc4N)nc3)c(C)n2C)c1]

A mixture of the compound prepared in Example 28 (27.1 mg), HATU (45.7 mg), and DIEA (0.035 ml) in DCM (6 ml) at room temperature under $N_2$ was stirred for about 20 minutes. After 3-(5-aminopyridin-2-yl)-5-(2-morpholinopyridin-4-yl)pyrazin-2-amine (35 mg) was added, the reaction mixture was stirred overnight. After the solvent was removed, the residue was purified to obtain the title compound (9.7 mg) having the following physical data.

MS (M+H): 578.2;
$^1$H NMR (400 MHz, CDCl$_3$) δ 10.99 (s, 1H), 8.84 (d, J=2.4 Hz, 1H), 8.62 (d, J=8.9 Hz, 1H), 8.47 (s, 1H), 8.32 (dd, J=8.9, 2.5 Hz, 1H), 8.27 (d, J=5.2 Hz, 1H), 7.43 (t, J=7.8 Hz, 1H), 7.31 (s, 1H), 7.29 (d, J=8.0 Hz, 1H), 7.24 (s, 1H), 7.18 (s, 1H), 7.13 (d, J=7.9 Hz, 1H), 3.92-3.83 (m, 4H), 3.65-3.56 (m, 4H), 3.36 (s, 3H), 2.79 (s, 3H), 2.44 (s, 3H).

Example 29(2)-29(59)

The compound having the following physical data was prepared by using the compound prepared in Example 27, 4-(4-(4,4,5,5-tetramethyl-1,3,2-dioxaborolan-2-yl)pyridin-2-yl)morpholine, and using the compound prepared in Example 1 or the corresponding carboxylic acid instead thereof in the process of Example 28→Example 29(1).

Example 29(2)

N-(6-{3-amino-6-[2-(4-morpholinyl)-4-pyridinyl]-2-pyrazinyl}-3-pyridinyl)-2-(3-chlorophenyl)-1,5-dimethyl-3-oxo-2,3-dihydro-1H-pyrazole-4-carboxamide MS (M+H): 598.2;
$^1$H NMR (400 MHz, CDCl$_3$) δ 10.82 (s, 1H), 8.84 (d, J=2.3 Hz, 1H), 8.63 (d, J=8.9 Hz, 1H), 8.48 (s, 1H), 8.31 (dd, J=8.9, 2.5 Hz, 1H), 8.27 (d, J=5.2 Hz, 1H), 7.50 (t, J=7.9 Hz, 1H), 7.45 (d, J=8.2 Hz, 1H), 7.38 (s, 1H), 7.31 (s, 1H), 7.28 (d, J=8.0 Hz, 2H), 7.24 (s, 1H), 3.89-3.85 (m, 4H), 3.62-3.58 (m, 4H), 3.38 (s, 3H), 2.81 (s, 3H).

Example 29(3)

N-(6-{3-amino-6-[2-(4-morpholinyl)-4-pyridinyl]-2-pyrazinyl}-3-pyridinyl)-1,5-dimethyl-3-oxo-2-phenyl-2,3-dihydro-1H-pyrazole-4-carboxamide MS (M+H): 564.2;
$^1$H NMR (400 MHz, CDCl$_3$) δ 10.97 (s, 1H), 8.84 (d, J=2.0 Hz, 1H), 8.63 (d, J=9.0 Hz, 1H), 8.48 (s, 1H), 8.32 (dd, J=8.9, 2.6 Hz, 1H), 8.27 (d, J=4.7 Hz, 1H), 7.56 (t, J=7.5 Hz, 2H), 7.49 (d, J=7.5 Hz, 1H), 7.38-7.34 (m, 2H), 7.31 (s, 1H), 7.24 (s, 1H), 3.91-3.84 (m, 4H), 3.64-3.57 (m, 4H), 3.37 (s, 3H), 2.80 (s, 3H).

Example 29(4)

N-(6-{3-amino-6-[2-(4-morpholinyl)-1,3-thiazol-4-yl]-2-pyrazinyl}-3-pyridinyl)-2-(3-chlorophenyl)-1,5-dimethyl-3-oxo-2,3-dihydro-1H-pyrazole-4-carboxamide TLC Rf=0.48 (ethyl acetate);
$^1$H NMR (300 MHz, CDCl$_3$) δ 10.80, 8.87, 8.66, 8.62, 8.24, 7.47-7.54, 7.42-7.47, 7.39, 7.29, 7.25, 5.25-5.33, 3.80-3.91, 3.50-3.61, 3.39, 2.82.

Example 29(5)

N-{6-[3-amino-6-(1-methyl-1H-pyrazol-3-yl)-2-pyrazinyl]-3-pyridinyl}-2-(3-chlorophenyl)-1,5-dimethyl-3-oxo-2,3-dihydro-1H-pyrazole-4-carboxamide TLC Rf=0.58 (ethyl acetate:methanol=9:1);
$^1$H NMR (300 MHz, CDCl$_3$) δ 10.78, 8.86, 8.59-8.67, 8.22, 7.34-7.54, 7.26-7.30, 6.83, 3.98, 3.39, 2.81.

Example 29(6)

N-(6-{3-amino-6-[6-(4-morpholinyl)-2-pyridinyl]-2-pyrazinyl}-3-pyridinyl)-2-(3-chlorophenyl)-1,5-dimethyl-3-oxo-2,3-dihydro-1H-pyrazole-4-carboxamide TLC Rf=0.49 (ethyl acetate);
$^1$H NMR (300 MHz, CDCl$_3$) δ 10.80, 9.03, 8.90, 8.68, 8.24, 7.71-7.79, 7.58-7.68, 7.43-7.55, 7.39, 7.29, 6.61, 3.81-3.94, 3.54-3.65, 3.39, 2.82.

Example 29(7)

N-[6-(3-amino-6-{3-[2-(dimethylamino)ethoxy]phenyl}-2-pyrazinyl)-3-pyridinyl]-2-(3-chlorophenyl)-1,5-dimethyl-3-oxo-2,3-dihydro-1H-pyrazole-4-carboxamide TLC Rf=0.38 (dichloromethane:methanol=9:1);
$^1$H NMR (300 MHz, CDCl$_3$) δ 10.88, 8.96, 8.63, 8.60, 8.25, 7.55-7.70, 7.30-7.46, 6.93, 4.16, 3.40, 2.72, 2.63, 2.22.

Example 29(8)

N-(6-{3-amino-6-[2-(4-morpholinyl)-4-pyridinyl]-2-pyrazinyl}-3-pyridinyl)-2-(2-chlorophenyl)-1,5-dimethyl-3-oxo-2,3-dihydro-1H-pyrazole-4-carboxamide TLC Rf=0.35 (ethyl acetate, NH Silica);
$^1$H NMR (300 MHz, CDCl$_3$) δ 2.83, 3.35, 3.56-3.70, 3.82-3.96, 7.21-7.30, 7.34, 7.45-7.61, 7.63-7.70, 8.29, 8.35, 8.50, 8.65, 8.86, 10.91.

Example 29(9)

N-(6-{3-amino-6-[6-(4-methoxy-1-piperidinyl)-2-pyridinyl]-2-pyrazinyl}-3-pyridinyl)-2-(3-chlorophenyl)-1,5-dimethyl-3-oxo-2,3-dihydro-1H-pyrazole-4-carboxamide TLC Rf=0.42 (ethyl acetate);
$^1$H NMR (300 MHz, CDCl$_3$) δ 1.62-1.77, 1.94-2.12, 2.83, 3.18-3.57, 4.01-4.23, 6.68, 7.19-7.75, 8.24, 8.69, 8.90, 9.06, 10.81.

Example 29(10)

N-(6-{3-amino-6-[1-(4-piperidinyl)-1H-pyrazol-4-yl]-2-pyrazinyl}-3-pyridinyl)-1,5-dimethyl-2-(3-methylphenyl)-3-oxo-2,3-dihydro-1H-pyrazole-4-carboxamide TLC Rf=0.56 (ethyl acetate:methanol=10:1);
$^1$H NMR (300 MHz, CDCl$_3$) δ 1.89-2.02, 2.17-2.24, 2.45, 2.70-2.85, 3.23-3.30, 3.37, 3.74, 4.20-4.40, 7.11-7.49, 7.95, 8.25, 8.58, 8.89, 10.9.

Example 29(11)

N-(6-{3-amino-6-[6-(4-morpholinyl)-2-pyridinyl]-2-pyrazinyl}-3-pyridinyl)-1,5-dimethyl-2-(3-methylphenyl)-3-oxo-2,3-dihydro-1H-pyrazole-4-carboxamide TLC Rf=0.57 (chloroform:methanol=10:1);
$^1$H NMR (300 MHz, CDCl$_3$) δ 2.45, 2.80, 3.37, 3.58-3.65, 3.84-3.90, 6.60, 7.10-7.77, 8.25, 8.67, 8.89, 9.00, 10.9.

Example 29(12)

N-(6-{3-amino-6-[6-(3-methoxy-1-azetidinyl)-2-pyridinyl]-2-pyrazinyl}-3-pyridinyl)-1,5-dimethyl-2-(3-methylphenyl)-3-oxo-2,3-dihydro-1H-pyrazole-4-carboxamide TLC Rf=0.24 (chloroform:methanol=10:1);
$^1$H NMR (300 MHz, CDCl$_3$) δ 2.45, 2.81, 3.37, 3.90-4.00, 4.22-4.32, 4.36-4.40, 6.30, 7.09-7.72, 8.24, 8.66, 8.89, 9.05, 10.9.

Example 29(13)

N-(6-{3-amino-6-[2-(3-methoxy-1-azetidinyl)-4-pyridinyl]-2-pyrazinyl}-3-pyridinyl)-1,5-dimethyl-2-(3-methylphenyl)-3-oxo-2,3-dihydro-1H-pyrazole-4-carboxamide TLC Rf=0.11 (chloroform:methanol=10:1);
$^1$H NMR (300 MHz, CDCl$_3$) δ 2.45, 2.81, 3.37, 3.38, 3.95-4.01, 4.31, 4.35-4.42, 6.92, 7.10-7.25, 7.44, 8.26, 8.30, 8.47, 8.63, 8.87, 11.0.

Example 29(14)

N-(6-{3-amino-6-[2-(4-morpholinyl)-1,3-thiazol-4-yl]-2-pyrazinyl}-3-pyridinyl)-2-(2-chlorophenyl)-1,5-dimethyl-3-oxo-2,3-dihydro-1H-pyrazole-4-carboxamide TLC Rf=0.39 (ethyl acetate);
$^1$H NMR (300 MHz, CDCl$_3$) δ 2.82, 3.35, 3.51-3.62, 3.81-3.92, 7.26, 7.43-7.59, 7.60-7.69, 8.26, 8.62, 8.67, 8.88, 10.88.

Example 29(15)

N-(6-{3-amino-6-[5-cyclopropyl-1-(tetrahydro-2H-pyran-2-yl)-1H-pyrazol-3-yl]-2-pyrazinyl}-3-pyridinyl)-2-(3-chlorophenyl)-1,5-dimethyl-3-oxo-2,3-dihydro-1H-pyrazole-4-carboxamide TLC Rf=0.55 (chloroform:methanol=10:1);
$^1$H NMR (300 MHz, CDCl$_3$) δ 0.92-1.00, 1.50-1.80, 2.00-2.33, 2.82, 3.39, 3.67-3.80, 4.09-4.15, 5.29-5.37, 7.22-7.52, 7.96, 8.25, 8.39, 8.58, 8.81, 10.8.

Example 29(16)

N-(6-{3-amino-6-[2-(3-methoxy-1-azetidinyl)-4-pyridinyl]-2-pyrazinyl}-3-pyridinyl)-2-benzyl-1,5-dimethyl-3-oxo-2,3-dihydro-1H-pyrazole-4-carboxamide TLC Rf=0.65 (dichloromethane:methanol=10:1);
$^1$H NMR (300 MHz, CDCl$_3$) δ 2.68, 3.38, 3.41, 4.00, 4.32, 4.37-4.42, 5.19, 6.93, 7.17-7.26, 7.30-7.40, 8.24, 8.33, 8.48, 8.65, 8.94, 11.0.

Example 29(17)

N-(6-{3-amino-6-[2-(3-methoxy-1-azetidinyl)-4-pyridinyl]-2-pyrazinyl}-3-pyridinyl)-2-isobutyl-1,5-dimethyl-3-oxo-2,3-dihydro-1H-pyrazole-4-carboxamide TLC Rf=0.57 (dichloromethane:methanol=10:1);
$^1$H NMR (300 MHz, CDCl$_3$) δ 0.97, 1.95-2.10, 2.72, 3.38, 3.52, 3.78, 4.00, 4.32, 4.36-4.44, 6.92, 7.23, 8.23, 8.31, 8.47, 8.63, 8.91, 11.1.

Example 29(18)

N-(6-{3-amino-6-[2-(3-methoxy-1-azetidinyl)-4-pyridinyl]-2-pyrazinyl}-3-pyridinyl)-2-(2-chlorophenyl)-1,5-dimethyl-3-oxo-2,3-dihydro-1H-pyrazole-4-carboxamide TLC Rf=0.47 (dichloromethane:methanol=10:1);
$^1$H NMR (300 MHz, CDCl$_3$) δ 2.82, 3.34, 3.38, 4.00, 4.32, 4.36-4.42, 6.92, 7.24, 7.45-7.58, 7.63, 8.23, 8.30, 8.48, 8.63, 8.88, 10.9.

Example 29(19)

N-(6-{3-amino-6-[2-(3-methoxy-1-azetidinyl)-4-pyridinyl]-2-pyrazinyl}-3-pyridinyl)-2-(2-fluoro-5-methylphenyl)-1,5-dimethyl-3-oxo-2,3-dihydro-1H-pyrazole-4-carboxamide TLC Rf=0.44 (dichloromethane:methanol=10:1);
$^1$H NMR (300 MHz, CDCl$_3$) δ 2.42, 2.81, 3.38, 3.39, 4.00, 4.31, 4.37-4.42, 6.92, 7.17-7.39, 8.23, 8.29, 8.48, 8.64, 8.87, 10.9.

Example 29(20)

N-(6-{3-amino-6-[2-(3-methoxy-1-azetidinyl)-4-pyridinyl]-2-pyrazinyl}-3-pyridinyl)-1,5-dimethyl-2-(6-methyl-2-pyridinyl)-3-oxo-2,3-dihydro-1H-pyrazole-4-carboxamide TLC Rf=0.44 (dichloromethane:methanol=10:1);
$^1$H NMR (300 MHz, CDCl$_3$) δ 2.59, 2.83, 3.38, 3.66, 4.00, 4.31, 4.37-4.42, 6.92, 7.18, 7.24, 7.60, 7.82, 8.24, 8.29, 8.48, 8.64, 8.89, 10.8.

Example 29(21)

N-(6-{3-amino-6-[2-(3-methoxy-1-azetidinyl)-4-pyridinyl]-2-pyrazinyl}-3-pyridinyl)-1,5-dimethyl-2-(4-methyl-2-pyridinyl)-3-oxo-2,3-dihydro-1H-pyrazole-4-carboxamide TLC Rf=0.47 (dichloromethane:methanol=10:1);
$^1$H NMR (300 MHz, CDCl$_3$) δ 2.51, 2.82, 3.37, 3.63, 3.99, 4.31, 4.37-4.42, 6.91, 7.14, 7.22, 7.62, 8.23, 8.28, 8.39, 8.47, 8.63, 8.88, 10.8.

Example 29(22)

N-(6-{3-amino-6-[5-cyclopropyl-1-(tetrahydro-2H-pyran-2-yl)-1H-pyrazol-3-yl]-2-pyrazinyl}-3-pyridinyl)-2-(2-chlorophenyl)-1,5-dimethyl-3-oxo-2,3-dihydro-1H-pyrazole-4-carboxamide TLC Rf=0.53 (ethyl acetate:methanol=10:1);
$^1$H NMR (300 MHz, CDCl$_3$) δ 0.91-1.01, 1.60-1.80, 1.98-2.19, 2.20-2.30, 2.81, 3.33, 3.59-3.82, 4.05-4.14, 5.29-5.37, 7.24-7.67, 7.97, 8.20-8.30, 8.39, 8.57, 8.84, 10.9.

Example 29(23)

N-(6-{3-amino-6-[2-(4-methyl-1-piperazinyl)-1,3-thiazol-4-yl]-2-pyrazinyl}-3-pyridinyl)-2-(2-chlorophenyl)-1,5-dimethyl-3-oxo-2,3-dihydro-1H-pyrazole-4-carboxamide TLC Rf=0.10 (ethyl acetate:methanol=5:1);
$^1$H NMR (300 MHz, CDCl$_3$) d 2.38, 2.53-2.63, 2.82, 3.34, 3.56-3.65, 7.23, 7.44-7.60, 7.61-7.67, 8.26, 8.62, 8.67, 8.88, 10.88.

Example 29(24)

N-(6-{3-amino-6-[2-(3-methoxy-1-azetidinyl)-4-pyridinyl]-2-pyrazinyl}-3-pyridinyl)-1,5-dimethyl-2-(2-methylphenyl)-3-oxo-2,3-dihydro-1H-pyrazole-4-carboxamide TLC Rf=0.50 (dichloromethane:methanol=10:1);
$^1$H NMR (300 MHz, CDCl$_3$) δ 2.26, 2.81, 3.30, 3.38, 3.99, 4.32, 4.37-4.42, 6.92, 7.23, 7.34-7.49, 8.23, 8.30, 8.47, 8.63, 8.88, 11.0.

Example 29(25)

N-(6-{3-amino-6-[2-(3-methoxy-1-azetidinyl)-4-pyridinyl]-2-pyrazinyl}-3-pyridinyl)-2-(3-chlorophenyl)-1-(2-hydroxy-2-methylpropyl)-5-methyl-3-oxo-2,3-dihydro-1H-pyrazole-4-carboxamide TLC Rf=0.38 (dichloromethane:methanol=20:1);
$^1$H NMR (300 MHz, CDCl$_3$) δ 1.18, 2.91, 3.38, 3.88, 3.99, 4.31, 4.35-4.42, 6.92, 7.21-7.32, 7.40-7.53, 8.23, 8.28, 8.48, 8.63, 8.86, 10.8.

Example 29(26)

N-(6-{3-amino-6-[2-(3-methoxy-1-azetidinyl)-4-pyridinyl]-2-pyrazinyl}-3-pyridinyl)-2-(cyclohexylmethyl)-1,5-dimethyl-3-oxo-2,3-dihydro-1H-pyrazole-4-carboxamide TLC Rf=0.61 (dichloromethane:methanol=10:1);
$^1$H NMR (300 MHz, CDCl$_3$) δ 0.99-1.35, 1.58-1.82, 2.71, 3.37, 3.52, 3.79, 3.99, 4.32, 4.36-4.42, 6.91, 7.23, 8.23, 8.29, 8.46, 8.62, 8.90, 11.0.

Example 29(27)

N-(6-{3-amino-6-[2-(3-methoxy-1-azetidinyl)-4-pyridinyl]-2-pyrazinyl}-3-pyridinyl)-2-(cyclopentylmethyl)-1,5-dimethyl-3-oxo-2,3-dihydro-1H-pyrazole-4-carboxamide TLC Rf=0.60 (dichloromethane:methanol=10:1);
$^1$H NMR (300 MHz, CDCl$_3$) δ 1.19-1.79, 2.18-2.23, 2.71, 3.37, 3.53, 3.90, 3.99, 4.31, 4.36-4.43, 6.91, 7.23, 8.23, 8.29, 8.47, 8.62, 8.90, 11.1.

Example 29(28)

N-(6-{(3-amino-6-[2-(3-methoxy-1-azetidinyl)-4-pyridinyl]-2-pyrazinyl}-3-pyridinyl)-2-(2-chlorophenyl)-1-ethyl-5-methyl-3-oxo-2,3-dihydro-1H-pyrazole-4-carboxamide TLC Rf=0.51 (dichloromethane:methanol=10:1);
$^1$H NMR (300 MHz, CDCl$_3$) δ 1.18, 2.82, 3.38, 3.60-3.86, 3.99, 4.31, 4.36-4.44, 6.92, 7.23, 7.41-7.57, 7.63, 8.23, 8.29, 8.47, 8.63, 8.88, 10.9.

Example 29(29)

N-(6-{3-amino-6-[2-(3-methoxy-1-azetidinyl)-4-pyridinyl]-2-pyrazinyl}-3-pyridinyl)-2-(2,3-dimethylphenyl)-1,5-dimethyl-3-oxo-2,3-dihydro-1H-pyrazole-4-carboxamide TLC Rf=0.49 (dichloromethane:methanol=10:1);
$^1$H NMR (300 MHz, CDCl$_3$) δ 2.12, 2.38, 2.81, 3.30, 3.38, 3.99, 4.31, 4.37-4.43, 6.92, 7.09, 7.21-7.37, 8.23, 8.30, 8.47, 8.63, 8.88, 11.1.

Example 29(30)

N-(6-{3-amino-6-[2-(3-methoxy-1-azetidinyl)-4-pyridinyl]-2-pyrazinyl}-3-pyridinyl)-2-(2,6-dichlorophenyl)-1,5-dimethyl-3-oxo-2,3-dihydro-1H-pyrazole-4-carboxamide TLC Rf=0.47 (dichloromethane:methanol=10:1);
$^1$H NMR (300 MHz, CDCl$_3$) δ 2.83, 3.35, 3.38, 3.99, 4.32, 4.36-4.43, 6.92, 7.23, 7.45-7.60, 8.23, 8.30, 8.47, 8.64, 8.88, 10.8.

Example 29(31)

N-(6-{3-amino-6-[2-(3-methoxy-1-azetidinyl)-4-pyridinyl]-2-pyrazinyl}-3-pyridinyl)-1,5-dimethyl-3-oxo-2-[2-(trifluoromethyl)phenyl]-2,3-dihydro-1H-pyrazole-4-carboxamide TLC Rf=0.48 (dichloromethane:methanol=10:1);
$^1$H NMR (300 MHz, CDCl$_3$) δ 2.80, 3.29, 3.37, 3.99, 4.31, 4.35-4.44, 6.92, 7.23, 7.42, 7.69-7.83, 7.93, 8.23, 8.28, 8.47, 8.63, 8.87, 10.8.

Example 29(32)

N-(6-{3-amino-6-[2-(3-methoxy-1-azetidinyl)-4-pyridinyl]-2-pyrazinyl}-3-pyridinyl)-2-(2,5-dichlorophenyl)-1,5-dimethyl-3-oxo-2,3-dihydro-1H-pyrazole-4-carboxamide TLC Rf=0.49 (dichloromethane:methanol=10:1);
$^1$H NMR (300 MHz, CDCl$_3$) δ 2.81, 3.35, 3.37, 3.99, 4.31, 4.36-4.43, 6.91, 7.22, 7.44-7.60, 8.23, 8.28, 8.47, 8.63, 8.86, 10.8.

Example 29(33)

N-(6-{3-amino-6-[2-(3-methoxy-1-azetidinyl)-4-pyridinyl]-2-pyrazinyl}-3-pyridinyl)-2-(3-methoxyphenyl)-1,5-dimethyl-3-oxo-2,3-dihydro-1H-pyrazole-4-carboxamide TLC Rf=0.47 (dichloromethane:methanol=10:1);
$^1$H NMR (300 MHz, CDCl$_3$) δ 2.81, 3.37, 3.39, 3.87, 3.99, 4.31, 4.36-4.43, 6.87-6.95, 7.02, 7.22, 7.45, 8.22, 8.28, 8.47, 8.63, 8.87, 11.0.

Example 29(34)

N-(6-{3-amino-6-[2-(4-methyl-1-piperazinyl)-1,3-thiazol-5-yl]-2-pyrazinyl}-3-pyridinyl)-2-(2-chlorophenyl)-1,5-dimethyl-3-oxo-2,3-dihydro-1H-pyrazole-4-carboxamide TLC Rf=0.15 (ethyl acetate:methanol=2:1);
$^1$H NMR (300 MHz, CDCl$_3$) δ 2.38, 2.50-2.61, 2.83, 3.35, 3.53-3.68, 7.26, 7.43-7.69, 8.16-8.24, 8.29, 8.51, 8.91, 10.86.

Example 29(35)

N-(6-{3-amino-6-[1-(3-oxetanyl)-1H-1,2,4-triazol-3-yl]-2-pyrazinyl}-3-pyridinyl)-2-(2-chlorophenyl)-1,5-dimethyl-3-oxo-2,3-dihydro-1H-pyrazole-4-carboxamide TLC Rf=0.26 (dichloromethane:methanol=20:1);
$^1$H NMR (300 MHz, CDCl$_3$) δ 2.81, 3.33, 5.07-5.21, 5.57-5.66, 7.45-7.57, 7.61-7.65, 8.22, 8.31, 8.73, 8.83, 8.93, 10.9.

Example 29(36)

N-(6-{3-amino-6-[2-(3-methoxy-1-azetidinyl)-1,3-thiazol-4-yl]-2-pyrazinyl}-3-pyridinyl)-2-(2-chlorophenyl)-1,5-dimethyl-3-oxo-2,3-dihydro-1H-pyrazole-4-carboxamide TLC Rf=0.35 (ethyl acetate);
$^1$H NMR (300 MHz, CDCl$_3$) δ 2.82, 3.35, 3.36, 4.06, 4.27-4.48, 7.23, 7.43-7.70, 8.26, 8.62, 8.65-8.68, 8.89, 10.88.

Example 29(37)

N-(6-{3-amino-6-[2-(4-methoxy-1-piperidinyl)-1,3-thiazol-4-yl]-2-pyrazinyl}-3-pyridinyl)-2-(2-chlorophenyl)-1,5-dimethyl-3-oxo-2,3-dihydro-1H-pyrazole-4-carboxamide TLC Rf=0.25 (ethyl acetate);
$^1$H NMR (300 MHz, CDCl$_3$) δ 1.68-1.85, 1.95-2.14, 2.83, 3.27-3.59, 3.77-3.98, 7.21, 7.45-7.70, 8.21-8.30, 8.62, 8.68, 8.88, 10.87.

Example 29(38)

N-(6-{3-amino-6-[6-(4-methyl-1,4-diazepan-1-yl)-2-pyridinyl]-2-pyrazinyl}-3-pyridinyl)-2-(3-chlorophenyl)-1,5-dimethyl-3-oxo-2,3-dihydro-1H-pyrazole-4-carboxamide TLC Rf=0.41 (ethyl acetate:methanol=20:1, NH Silica);
$^1$H NMR (300 MHz, CDCl$_3$) δ 2.02-2.12, 2.40, 2.57-2.62, 2.74-2.79, 2.82, 3.39, 3.72, 3.91-3.97, 6.46, 7.26-7.31, 7.38-7.40, 7.42-7.63, 8.23, 8.68, 8.89, 9.04, 10.8.

Example 29(39)

N-(6-{3-amino-6-[1-(1-methyl-4-piperidinyl)-1H-pyrazol-4-yl]-2-pyrazinyl}-3-pyridinyl)-1,5-dimethyl-2-(3-methylphenyl)-3-oxo-2,3-dihydro-1H-pyrazole-4-carboxamide TLC Rf=0.28 (ethyl acetate:methanol=20:1, NH Silica);
$^1$H NMR (300 MHz, CDCl$_3$) δ 2.09-2.26, 2.35, 2.45, 2.80, 2.95-3.04, 3.37, 4.11-4.23, 7.12-7.20, 7.27-7.32, 7.44, 7.94, 8.21, 8.24, 8.57, 8.89, 11.0.

Example 29(40)

N-(6-{3-amino-6-[6-(3-methoxy-1-azetidinyl)-2-pyridinyl]-2-pyrazinyl}-3-pyridinyl)-2-(2-chlorophenyl)-1,5-dimethyl-3-oxo-2,3-dihydro-1H-pyrazole-4-carboxamide TLC Rf=0.31 (ethyl acetate, NH Silica);
$^1$H NMR (300 MHz, CDCl$_3$) δ 2.82, 3.34, 3.37, 3.96, 4.28, 4.34-4.42, 6.29, 7.45-7.72, 8.27, 8.67, 8.89, 9.05, 10.9.

Example 29(41)

N-(6-{3-amino-6-[6-(3-methoxy-1-azetidinyl)-2-pyridinyl]-2-pyrazinyl}-3-pyridinyl)-2-(3-chlorophenyl)-1,5-dimethyl-3-oxo-2,3-dihydro-1H-pyrazole-4-carboxamide TLC Rf=0.38 (ethyl acetate, NH Silica);
$^1$H NMR (300 MHz, CDCl$_3$) δ 2.82, 3.37, 3.39, 3.96, 4.28, 4.36-4.42, 6.30, 7.27-7.31, 7.38-7.61, 7.69, 8.23, 8.67, 8.89, 9.06, 10.8.

Example 29(42)

N-{6-[5-amino-6'-(4-morpholinyl)-2,2'-bipyrazin-6-yl]-3-pyridinyl}-2-(3-methoxyphenyl)-1,5-dimethyl-3-oxo-2,3-dihydro-1H-pyrazole-4-carboxamide TLC Rf=0.40 (ethyl acetate);
$^1$H NMR (300 MHz, CDCl$_3$) δ 2.82, 3.41, 3.67, 3.85-3.94, 6.88-6.97, 7.04, 7.47, 8.10, 8.31, 8.69, 8.91, 8.89, 8.93, 10.98.

Example 29(43)

N-(5-{3-amino-6-[2-(4-morpholinyl)-4-pyridinyl]-2-pyrazinyl}-2-pyridinyl)-2-(2-chlorophenyl)-1,5-dimethyl-3-oxo-2,3-dihydro-1H-pyrazole-4-carboxamide TLC Rf=0.51 (ethyl acetate:methanol=9:1);
$^1$H NMR (300 MHz, CDCl$_3$) δ 11.08, 8.68, 8.36, 8.20, 8.16, 7.77, 7.57-7.65, 7.36, 7.28, 6.67, 3.70, 3.51, 3.30, 2.74.

Example 29(44)

N-{6-[5-amino-6'-(4-morpholinyl)-2,2'-bipyrazin-6-yl]-3-pyridinyl}-2-(2,5-dichlorophenyl)-1,5-dimethyl-3-oxo-2,3-dihydro-1H-pyrazole-4-carboxamide TLC Rf=0.45 (ethyl acetate:chloroform:methanol=6:3:1);
$^1$H NMR (300 MHz, CDCl$_3$) δ 2.83, 3.37, 3.67, 3.90, 7.49, 7.54, 7.57, 8.10, 8.31, 8.69, 8.89, 8.93, 10.78.

Example 29(45)

N-(6-{5-amino-6'-[4-(2-hydroxyethyl)-1-piperazinyl]-2,2'-bipyrazin-6-yl}-3-pyridinyl)-2-(2,5-dichlorophenyl)-1,5-dimethyl-3-oxo-2,3-dihydro-1H-pyrazole-4-carboxamide TLC Rf=0.27 (chloroform:methanol=9:1);
$^1$H NMR (300 MHz, CDCl$_3$) δ 2.46-2.78, 2.83, 3.36, 3.67-3.80, 7.49, 7.54, 7.59, 8.11, 8.30, 8.69, 8.87-8.91, 8.92, 10.78.

Example 29(46)

N-[6-[3-amino-6-[(2R,6S)-2,6-dimethylmorpholin-4-yl]pyrazin-2-yl]pyrazin-2-yl]-3-pyridyl]-1-(3-methoxyphenyl)-2,3-dimethyl-5-oxo-pyrazole-4-carboxamide TLC Rf=0.51 (chloroform:methanol=9:1);
$^1$H NMR (300 MHz, CDCl$_3$) δ 1.33, 2.67, 2.83, 3.41, 3.73-3.86, 3.89, 4.22, 6.90-6.98, 7.47, 8.08, 8.31, 8.68, 8.87-8.91, 8.95, 10.98.

Example 29(47)

N-(6-{5-amino-6'-[4-(2-hydroxyethyl)-1-piperazinyl]-2,2'-bipyrazin-6-yl}-3-pyridinyl)-2-(3-methoxyphenyl)-1,5-dimethyl-3-oxo-2,3-dihydro-1H-pyrazole-4-carboxamide TLC Rf=0.27 (chloroform:methanol=9:1);
$^1$H NMR (300 MHz, CDCl$_3$) δ 2.66, 2.71, 2.82, 3.41, 3.68-3.77, 3.88, 6.89-6.98, 7.03, 7.47, 8.11, 8.30, 8.68, 8.88, 8.90, 8.92, 10.98.

Example 29(48)

N-(6-{3-amino-6-[1-(2-hydroxyethyl)-1H-pyrazol-4-yl]-2-pyrazinyl}-3-pyridinyl)-2-(3-methoxyphenyl)-1,5-dimethyl-3-oxo-2,3-dihydro-1H-pyrazole-4-carboxamide TLC Rf=0.56 (ethyl acetate:methanol=3:1);
$^1$H NMR (300 MHz, CDCl$_3$) δ 2.81, 3.39, 3.87, 4.00-4.10, 4.30-4.38, 6.85-7.05, 7.38-7.50, 7.92-8.00, 8.18-8.25, 8.59, 8.80-8.85, 10.9.

Example 29(49)

(4-{5-amino-6-[5-({[2-(3-methoxyphenyl)-1,5-dimethyl-3-oxo-2,3-dihydro-1H-pyrazol-4-yl]carbonyl}amino)-2-pyridinyl]-2-pyrazinyl}-1H-pyrazol-1-yl)acetic acid TLC Rf=0.66 (chloroform:methanol:acetic acid=5:1:1);
$^1$H NMR (300 MHz, DMSO-d$_6$) δ 2.72, 3.40, 3.82, 5.00, 6.96-7.04, 7.07-7.13, 7.50, 7.87, 8.04, 8.22, 8.29, 8.40, 8.58, 8.94, 11.01, 13.11.

Example 29(50)

[(6-{5-amino-6-[5-({[2-(3-methoxyphenyl)-1,5-dimethyl-3-oxo-2,3-dihydro-1H-pyrazol-4-yl]carbonyl}amino)-2-pyridinyl]-2-pyrazinyl}-2-pyridinyl)(methyl)amino]acetic acid TLC Rf=0.67 (chloroform:methanol:acetic acid=10:1:1);
$^1$H NMR (300 MHz, DMSO-d$_6$) δ 2.72, 3.14, 3.42, 3.82, 4.30, 6.67, 6.96-7.05, 7.05-7.15, 7.41-7.54, 7.53-7.61, 7.63-7.71, 8.26, 8.63, 8.88, 8.95, 11.02.

Example 29(51)

[{5'-amino-6'-[5-({[2-(3-methoxyphenyl)-1,5-dimethyl-3-oxo-2,3-dihydro-1H-pyrazol-4-yl]carbonyl}amino)-2-pyridinyl]-2,2'-bipyrazin-6-yl}(methyl)amino]acetic acid TLC Rf=0.78 (chloroform:methanol:acetic acid=10:1:1);

¹H NMR (300 MHz, DMSO-d₆) δ 2.72, 3.20, 3.39, 3.82, 4.32, 6.94-7.05, 7.07-7.15, 7.41-7.55, 8.15, 8.27, 8.66, 8.75, 8.82, 8.94, 11.02.

Example 29(52)

N-(6-{3-amino-6-[2-(4-morpholinyl)-1,3-thiazol-4-yl]-2-pyrazinyl}-3-pyridinyl)-2-(3-methoxyphenyl)-1,5-dimethyl-3-oxo-2,3-dihydro-1H-pyrazole-4-carboxamide TLC Rf=0.40 (ethyl acetate);
¹H NMR (300 MHz, CDCl₃) δ 2.82, 3.40, 3.57, 3.87, 3.88, 6.89-6.97, 7.03, 7.47, 7.96, 8.26, 8.63, 8.67, 8.88, 10.96.

Example 29(53)

N-(6-{3-amino-6-[2-(4-morpholinyl)-1,3-thiazol-4-yl]-2-pyrazinyl}-3-pyridinyl)-2-(2,5-dichlorophenyl)-1,5-dimethyl-3-oxo-2,3-dihydro-1H-pyrazole-4-carboxamide TLC Rf=0.45 (ethyl acetate):
¹H NMR (300 MHz, CDCl₃) δ 2.82, 3.40, 3.57, 3.88, 6.88-6.98, 7.03, 7.47, 7.96, 8.26, 8.63, 8.67, 8.88, 10.96.

Example 29(54)

N-(6-{3-amino-6-[6-(3-methoxy-1-azetidinyl)-3-pyridinyl]-2-pyrazinyl}-3-pyridinyl)-2-(2,5-dichlorophenyl)-1,5-dimethyl-3-oxo-2,3-dihydro-1H-pyrazole-4-carboxamide TLC Rf=0.45 (ethyl acetate);
¹H NMR (300 MHz, CDCl₃) δ 2.83, 3.36, 3.38, 3.97, 4.29, 4.35-4.44, 6.31, 7.45-7.63, 7.70, 7.96, 8.25, 8.68, 8.90, 9.07, 10.75.

Example 29(55)

N-(6-{3-amino-6-[2-(2-oxo-1-pyrrolidinyl)-1,3-thiazol-4-yl]-2-pyrazinyl}-3-pyridinyl)-2-(2,5-dichlorophenyl)-1,5-dimethyl-3-oxo-2,3-dihydro-1H-pyrazole-4-carboxamide TLC Rf=0.45 (ethyl acetate);
¹H NMR (300 MHz, CDCl₃) δ 2.23-2.36, 2.74, 2.83, 3.27, 3.36, 4.30, 4.45-4.63, 7.49, 7.54, 7.57, 7.65, 8.26, 8.66, 8.74, 8.89, 10.77.

Example 29(56)

N-{6-[5-amino-6'-(4-morpholinyl)-2,2'-bipyrazin-6-yl]-3-pyridinyl}-2-(2,5-dichlorophenyl)-1,5-dimethyl-3-oxo-2,3-dihydro-1H-pyrazole-4-carboxamide TLC Rf=0.45 (ethyl acetate);
¹H NMR (300 MHz, CDCl₃) δ 2.84, 3.37, 3.67, 3.90, 7.49, 7.54, 7.57, 8.10, 8.31, 8.69, 8.89, 8.92, 8.94, 10.78.

Example 29(57)

N-(6-{3-amino-6-[6-(3-methoxy-1-azetidinyl)-3-pyridinyl]-2-pyrazinyl}-3-pyridinyl)-2-(3-methoxyphenyl)-1,5-dimethyl-3-oxo-2,3-dihydro-1H-pyrazole-4-carboxamide TLC Rf=0.40 (ethyl acetate);
¹H NMR (300 MHz, CDCl₃) δ 2.81, 3.38, 3.39, 3.88, 3.97, 4.29, 4.35-4.44, 6.31, 6.85-6.97, 7.02, 7.46, 7.58, 7.68, 7.95, 8.25, 8.68, 8.90, 9.05, 10.94.

Example 29(58)

N-(6-{3-amino-6-[2-(2-oxo-1-pyrrolidinyl)-1,3-thiazol-4-yl]-2-pyrazinyl}-3-pyridinyl)-2-(3-methoxyphenyl)-1,5-dimethyl-3-oxo-2,3-dihydro-1H-pyrazole-4-carboxamide TLC Rf=0.40 (ethyl acetate);
¹H NMR (300 MHz, CDCl₃) δ 2.23-2.38, 2.74, 2.82, 3.41, 3.86, 4.30, 6.89-6.97, 7.03, 7.47, 7.65, 8.27, 8.65, 8.73, 8.90, 10.97.

Example 29(59)

N-[6-[3-amino-6-[6-[(2R,6S)-2,6-dimethylmorpholin-4-yl]pyrazin-2-yl]pyrazin-2-yl]-3-pyridyl]-1-(2,5-dichlorophenyl)-2,3-dimethyl-5-oxo-pyrazole-4-carboxamide TLC Rf=0.55 (chloroform:methanol=9:1);
¹H NMR (300 MHz, CDCl₃) δ 1.33, 2.67, 2.83, 3.36, 3.70-3.85, 4.21, 7.42-7.73, 8.08, 8.30, 8.68, 8.85-8.90, 8.96, 10.78.

Example 30 tert-Butyl 3-(5-amino-6-(4-(1,5-dimethyl-3-oxo-2-phenyl-2,3-dihydro-1H-pyrazole-4-carboxamido)phenyl)pyrazin-2-yl)-5,6-dihydropyridine-1(2H)-carboxylate A suspension of the compound prepared in Example 3 (0.7374 g), tert-butyl 3-(4,4,5,5-tetramethyl-1,3,2-dioxaborolan-2-yl)-5,6-dihydropyridine-1(2H)-carboxylate (0.571 g), Pd(PPh₃)₄ (0.178 g), and 2.0 M aqueous Na₂CO₃ solution (2.308 mL) in dioxane (8.0 mL) in a pressure tube was degassed by bubbling N₂ through for several minutes. The tube was sealed and then heated to 100° C. for 2 hours. The reaction was cooled to room temperature and partitioned between DCM and saturated NaHCO₃ solution and separated. The aqueous layer was reextracted with DCM. The organic layers were combined and washed with water, and brine, then dried with Na₂SO₄ and concentrated. Flash chromatography on silica yielded the title compound (0.44 g) having the following physical data.
MS (M+H): 582.5.

Example 31 tert-Butyl 3-(5-amino-6-(4-(1,5-dimethyl-3-oxo-2-phenyl-2,3-dihydro-1H-pyrazole-4-carboxamido)phenyl)pyrazin-2-yl)piperidine-1-carboxylate A solution of the compound prepared in Example 30 (0.190 g) in 2:1 THF-EtOH (12 mL) in a Parr bottle was degassed by bubbling N₂ through the mixture. Platinum oxide (PtO₂) (0.048 g) was added, and the reaction was placed on the Parr apparatus under H₂ at ~65 psi overnight. LC-MS still showed some starting material—the reaction was purged with N₂ and an additional 48 mg of PtO₂ was added before being placed on the Parr apparatus overnight. The reaction was partitioned between DCM and saturated NaHCO₃ solution and separated. The aqueous layer was reextracted with DCM. The organic layers were combined and washed with water, and brine, then dried with Na₂SO₄ and concentrated. Flash chromatography on silica yielded the title compound (0.0368 g) having the following physical data.
MS (M+H): 584.4.

Example 32

N-(4-(3-amino-6-(piperidin-3-yl)pyrazin-2-yl)phenyl)-1,5-dimethyl-3-oxo-2-phenyl-2,3-dihydro-1H-pyrazole-4-carboxamide To a solution of the compound prepared in Example 31 (0.037 g) in DCM (2.0 mL) at 0° C. under $N_2$ was added TFA (0.5 mL) dropwise. The mixture stirred at 0° C. for 3 hours. The reaction was partitioned between DCM and saturated $NaHCO_3$ solution and separated. The aqueous layer was reextracted with DCM. The organic layers were combined and washed with water, and brine, then dried with $Na_2SO_4$ and concentrated to yield the title compound as a yellowish foam (0.0244 g), which was used without further purification.

Example 33

N-(4-(3-amino-6-(1-(3-(phenylsulfonyl)propanoyl)piperidin-3-yl)pyrazin-2-yl)phenyl)-1,5-dimethyl-3-oxo-2-phenyl-2,3-dihydro-1H-pyrazole-4-carboxamide A solution of the compound prepared in Example 32 (0.0244 g), 3-(phenylsulfonyl)propanoic acid (0.013 g), DIPEA (0.026 mL), HOBt (0.011 g) and EDC (0.013 g) in DMF (1.5 mL) under $N_2$ was stirred at room temperature overnight. The reaction was partitioned between DCM and saturated $NaHCO_3$ solution and separated. The aqueous layer was reextracted with DCM. The organic layers were combined and washed with water, and brine, then dried with $Na_2SO_4$ and concentrated. Purification by preparative HPLC, followed by workup with DCM-saturated aqueous $NaHCO_3$ solution and concentration yielded the title compound (0.01213 g) having the following physical data.
MS (M+H): 680.6.

Example 34

N-{4-[6-(1-acryloyl-3-piperidinyl)-3-amino-2-pyrazinyl]phenyl}-1,5-dimethyl-3-oxo-2-phenyl-2,3-dihydro-1H-pyrazole-4-carboxamide

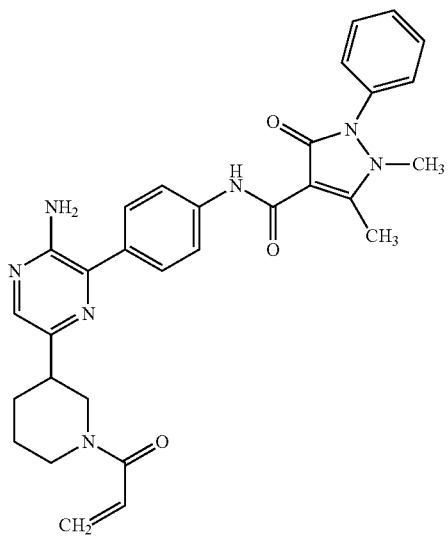 [SMILES: C=CC(=O)N1CCCC(c2cnc(N)c(-c3ccc(NC(=O)c4c(C)n(C)n(-c5ccccc5)c4=O)cc3)n2)C1]

To a solution of the compound prepared in Example 33 (0.0121 g) in anhydrous THF (1.0 mL) at room temperature under $N_2$ was added tBuOK (0.0030 g). The reaction immediately turned yellow, then a darker brown. After 2 hours, the reaction was partitioned between DCM and saturated $NaHCO_3$ solution and separated. The aqueous layer was reextracted with DCM. The organic layers were combined and washed with water, and brine, then dried with $Na_2SO_4$ and concentrated. Purification by preparative TLC yielded the title compound (0.0074 g) having the following physical data.
MS (M+H): 538.5;
$^1$H NMR (400 MHz, CDCl$_3$) δ 10.77 (d, J=6.2 Hz, 1H), 7.81-7.66 (m, 3H), 7.66-7.57 (m, 2H), 7.52-7.45 (m, 2H), 7.43-7.37 (m, 1H), 7.34-7.23 (m, 2H), 6.55 (dd, J=16.8, 10.6 Hz, 1H), 6.19 (d, J=16.9 Hz, 1H), 5.59 (t, J=11.6 Hz, 1H), 4.74-4.42 (m, 2H), 4.05 (d, J=13.5 Hz, 1H), 3.93 (d, J=13.4 Hz, 1H), 3.70-3.55 (m, 1H), 3.30 (s, 3H), 3.05 (t, J=12.6 Hz, 1H), 2.89 (t, J=12.4 Hz, 1H), 2.76-2.62 (m, 4H), 2.00 (t, J=12.7 Hz, 1H), 1.93-1.73 (m, 1H), 1.56 (dd, J=26.5, 15.5 Hz, 1H).

Example 35

N-[4-(3-amino-6-{4-[(cyclopentylcarbamoyl)amino]phenyl}-2-pyrazinyl)phenyl]-1,5-dimethyl-3-oxo-2-phenyl-2,3-dihydro-1H-pyrazole-4-carboxamide

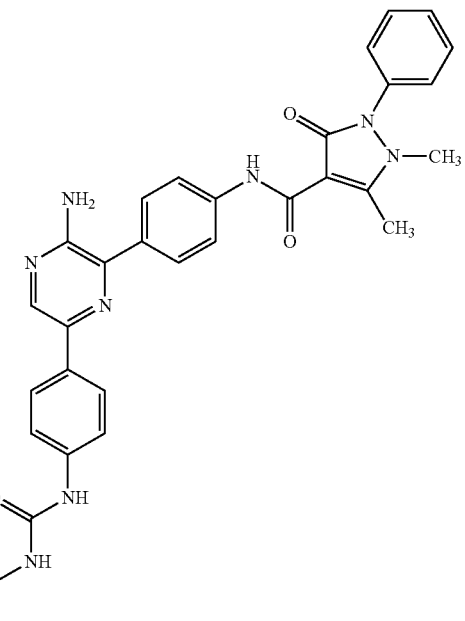

N-{4-[3-amino-6-(4-aminophenyl)-2-pyrazinyl]phenyl}-1,5-dimethyl-3-oxo-2-phenyl-2,3-dihydro-1H-pyrazole-4-carboxamide was obtained by using the compound prepared in Example 3 and using (4-aminophenyl)boronic acid instead of 3-fluorophenylboronic acid in the process of Example 5. The above described amide compound (69 mg), 1-cyclopentyl-3-(4-(4,4,5,5-tetramethyl-1,3,2-dioxaborolan-2-yl)phenyl)urea and the isocyanatocyclopentane (0.024 mL) were dissolved and stirred at room temperature for 1 hour. The title compound having the following physical data was purified by prep TLC.

$^1$H NMR (250 MHz, DMSO-d$_6$/CDCl$_3$) δ 10.90 (s, 1H), 8.34 (s, 1H), 8.17 (s, 1H), 7.82 (d, J=8.8 Hz, 2H), 7.79 (s, 4H), 7.63-7.44 (m, 5H), 7.40 (d, J=7.0 Hz, 2H), 5.93 (d, J=7.5 Hz, 1H), 5.35 (s, 2H), 4.16-3.99 (m, 1H), 3.42 (s, 3H), 2.81 (s, 3H), 2.05-1.86 (m, 2H), 1.79-1.53 (m, 4H), 1.50-1.33 (m, 2H).

Example 36

N-[4-(6-bromo-3-{[(E)-(dimethylamino)methylene]amino}-2-pyrazinyl)phenyl]-1,5-dimethyl-3-oxo-2-phenyl-2,3-dihydro-1H-pyrazole-4-carboxamide The bromide (248 mg) was mixed with DMF(OMe)$_2$ (0.460 mL) and DMF (1 mL) and heated to 60° C. for 10 minutes. Diethylether (5 mL) was added to the reaction mixture and the solid was triturated and the liquid was removed by filtration. The solid was washed with diethylether to give the title compound (200 mg) which was carried to the next step without further purification.

Example 37

N-{4-[3-amino-6-(1-piperidinyl)-2-pyrazinyl]phenyl}-1,5-dimethyl-3-oxo-2-phenyl-2,3-dihydro-1H-pyrazole-4-carboxamide

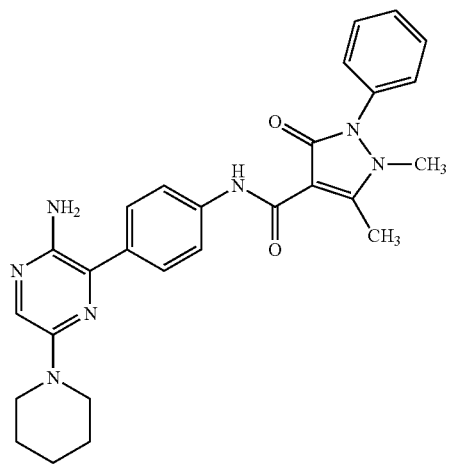 [SMILES: Cc1c(C(=O)Nc2ccc(-c3nc(N4CCCCC4)cnc3N)cc2)c(=O)n(-c2ccccc2)n1C]

The compound prepared in Example 36 (80 mg) and piperidine (0.300 mg) were mixed in DMSO (0.400 mL) and heated to 120° C. for 18 hours. The reaction mixture was then diluted with MeCN (10 mL) and aqueous 1M K$_2$CO$_3$ (7 mL) and heated to 155° C. for 17 minutes in the microwave. The organic products were extracted with EtOAc/CH$_2$Cl$_2$ (9:1) and washed with brine. The material was purified by HPLC (H$_2$O/MeCN with 0.1% TFA). The solvent was removed and the residue was dissolved in CH$_2$Cl$_2$ and the residual TFA was removed by PL-HCO$_3$ MP SPE ion exchange column to give the title compound (10 mg) having the following physical data.

$^1$H NMR (250 MHz, CDCl$_3$) δ 10.81 (s, 1H), 7.77 (s, 4H), 7.61 (s, 1H), 7.59-7.43 (m, 3H), 7.37 (d, J=7.1 Hz, 2H), 4.24 (s, 2H), 3.44-3.37 (m, 4H), 3.36 (s, 3H), 2.81 (s, 3H), 1.74-1.58 (m, 6H).

Example 38(1)

N-((1R,4R)-4-{3-amino-6-[2-(4-morpholinyl)-4-pyridinyl]-2-pyrazinyl}cyclohexyl)-1,5-dimethyl-3-oxo-2-phenyl-2,3-dihydro-1H-pyrazole-4-carboxamide Example 38(2)

N-((1S,4S)-4-{3-amino-6-[2-(4-morpholinyl)-4-pyridinyl]-2-pyrazinyl}cyclohexyl)-1,5-dimethyl-3-oxo-2-phenyl-2,3-dihydro-1H-pyrazole-4-carboxamide The compound prepared in Example 5(91) (50 mg) was dissolved in 1:1 EtOH:THF (6 mL). The reaction vessel was purged with nitrogen and platinum oxide (6 mg) was added. The reaction was shaken under H$_2$ atmosphere (PARR, 60 psi). At 24 and 48 hours, additional catalyst (12 mg) was added. After 72 hours, the reaction was removed from the Parr and filtered through a pad od Celite. The filtrate was concentrated in vacuo. Purification by preparative TLC (4% MeOH in dichloromethane) followed by reverse phase chromatography (95-5 to 5-95 H$_2$O/ACN with 0.1% TFA, C18 Sunfire column) afforded the title compounds having the following physical data.

Example 38(1)

(3.0 mg);
MS (M+H): 569.2;
$^1$H NMR (400 MHz, CDCl$_3$) δ 8.57 (d, J=7.9 Hz, 1H), 8.34 (s, 1H), 8.23 (d, J=5.4 Hz, 1H), 7.51 (t, J=7.7 Hz, 2H), 7.41 (t, J=7.4 Hz, 1H), 7.32 (m, 3H), 7.13 (br s, 1H), 4.69 (br s, 2H), 4.14-3.97 (m, 1H), 3.89 (s, 4H), 3.63-3.52 (m, 4H), 3.29 (s, 3H), 2.74 (s, 3H), 2.55 (t, J=11.6 Hz, 1H), 2.23 (d, J=10.2 Hz, 2H), 2.04-1.97 (m, 2H), 1.90 (dd, J=24.7, 12.4 Hz, 2H), 1.40 (dd, J=13.9, 10.8 Hz, 2H).

Example 38(2)

(3.2 mg);
MS (M+H): 569.3;
$^1$H NMR (400 MHz, CDCl$_3$) δ 8.96 (d, J=7.4 Hz, 1H), 8.32 (s, 1H), 8.16 (d, J=5.3 Hz, 1H), 7.50 (t, J=7.7 Hz, 2H), 7.40 (t, J=7.4 Hz, 1H), 7.33-7.27 (m, 3H), 7.17 (d, J=5.2 Hz, 1H), 4.73 (s, 2H), 4.34-4.26 (m, 1H), 3.77-3.72 (m, 4H), 3.54-3.49 (m, 4H), 3.26 (s, 3H), 2.72 (d, J=12.2 Hz, 4H), 2.10-2.02 (m, 4H), 1.88-1.74 (m, 4H).

Example 39

3-Bromo-5-iodopyridin-2-amine

To the 2-amino-4-iodopyridine (CAS No. 552331-00-7) (1.0 g) in 10 mL of acetonitrile was added the NBS (0.809 g) and stirred at room temperature in dark for 2 hours. The reaction mixture was extracted with DCM, washed with water, brine and dried over any Na$_2$SO$_4$, filtered and concentrated. The crude was chromatographed on silica gel using 1:1 hexane:EtOAc to give the title compound (0.65 g) having the following physical data.
MS (M+H): 298.7.

Example 40

3-Bromo-5-(3-fluorophenyl)pyridin-2-amine

To the compound prepared in Example 39 (0.65 g), 3-fluorophenylboronic acid (0.265 g), Na$_2$CO$_3$ (0.277 g) in 10 mL mixture of toluene:EtOH:H₂O 5:5:1 after degassing with argon was added the Pd(PPh₃)₄ (0.126 g) and heated at 80° C. for 16 hours. The reaction mixture was filtered through celite and concentrated. The crude was chromatographed on silica gel using 10:1 DCM:MeOH to give the title compound (0.4 g) having the following physical data.

MS (M+H): 268.8.

Example 41

3-(4-Aminophenyl)-5-(3-fluorophenyl)pyridin-2-amine

To the compound prepared in Example 40 (0.4 g), 4-(4,4,5,5-tetramethyl-1,3,2-dioxaborolan-2-yl)aniline (0.394 g), Na₂CO₃ (0.190 g) in 5 mL mixture of toluene:EtOH:H₂O 5:5:1 after degassing with argon was added the Pd(PPh₃)₄ (0.087 g) and heated at 100° C. for 16 hours. The reaction mixture was filtered through celite and concentrated. The crude was chromatographed on silica gel using 10:1 DCM:MeOH to give the title compound (0.19 g) having the following physical data.

MS (M+H): 280.0;
¹H NMR (400 MHz, CDCl₃) δ 8.24 (d, J=2.3 Hz, 1H), 7.70-7.61 (m, 1H), 7.53 (d, J=2.3 Hz, 1H), 7.45 (td, J=7.4, 2.8 Hz, 1H), 7.40-7.17 (m, 3H), 6.97 (td, J=8.3, 1.5 Hz, 1H), 6.77 (d, J=8.4 Hz, 2H), 4.69 (s, 2H), 3.76 (bs, 2H).

Example 42(1)

N-{4-[2-amino-5-(3-fluorophenyl)-3-pyridinyl]phenyl}-1,5-dimethyl-3-oxo-2-phenyl-2,3-dihydro-1H-pyrazole-4-carboxamide

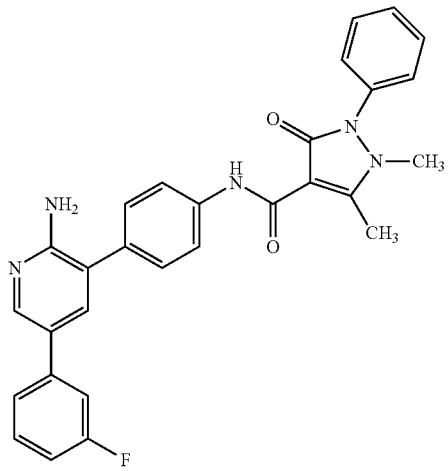 [SMILES: Cc1c(C(=O)Nc2ccc(-c3cc(-c4cccc(F)c4)cnc3N)cc2)c(=O)n(-c2ccccc2)n1C]

To the antipyric acid (0.05 g) in 1 mL of DCM, 0.1 mL of DMF and TEA (0.065 g) was added the HATU (0.09 g) and stirred for 30 minutes. To the activated ester was added the compound prepared in Example 41 (0.060 g) and stirred for 1 hour. The reaction mixture was diluted with water, extracted with additional DCM, and the organic layer was washed with water, brine and dried over anhydrous sodium sulfate. The DCM layer was filtered and concentrated, and the crude was chromatographed on silica gel using 10:1 DCM:MeOH to give the title compound (0.055 g) having the following physical data.

MS (M+H): 494.0;
¹H NMR (400 MHz, CD₃OD) δ 10.75 (s, 1H), 8.15 (d, J=2.2 Hz, 1H), 7.74-7.66 (m, 3H), 7.63-7.49 (m, 4H), 7.45 (d, J=8.5 Hz, 2H), 7.42-7.29 (m, 3H), 7.24 (d, J=10.2 Hz, 1H), 6.97 (s, 1H), 3.40 (s, 3H), 2.75 (d, J=4.3 Hz, 3H).

Example 42(2)-42(22)

The compound having the following physical data was prepared by using the compound prepared in Example 41 or the corresponding aniline instead thereof, and antipyric acid or the corresponding carboxylic acid instead thereof in the process of Example 41→Example 42(1).

Example 42(2)

N-{4-[2-amino-5-(5-pyrimidinyl)-3-pyridinyl]phenyl}-1,5-dimethyl-3-oxo-2-phenyl-2,3-dihydro-1H-pyrazole-4-carboxamide MS (M+H): 478.1;
¹H NMR (400 MHz, DMSO-d₆) δ 10.83 (s, 1H), 9.10 (s, 2H), 9.05 (s, 1H), 8.37 (d, J=2.3 Hz, 1H), 7.76 (d, J=2.3 Hz, 1H), 7.68 (d, J=8.5 Hz, 2H), 7.57 (t, J=7.6 Hz, 2H), 7.50-7.46 (m, 3H), 7.41 (d, J=7.4 Hz, 2H), 5.94 (s, 2H), 3.33 (s, 3H), 2.69 (s, 3H).

Example 42(3)

N-[4-(2-amino-5-cyclopentyl-3-pyridinyl)phenyl]-1,5-dimethyl-3-oxo-2-phenyl-2,3-dihydro-1H-pyrazole-4-carboxamide MS (M+H): 468.2;
¹H NMR (400 MHz, Acetone-d₆) δ 11.03 (s, 1H), 7.97 (d, J=11.1 Hz, 2H), 7.83 (d, J=8.6 Hz, 2H), 7.60 (t, J=7.6 Hz, 2H), 7.49 (dt, J=12.2, 7.7 Hz, 4H), 7.27 (s, 1H), 3.48 (s, 3H), 3.15-3.03 (m, 1H), 2.79 (s, 4H), 2.17-2.06 (m, 2H), 1.87-1.76 (m, 2H), 1.75-1.58 (m, 4H).

Example 42(4)

N-{4-[2-amino-5-(4-methoxyphenyl)-3-pyridinyl]phenyl}-1,5-dimethyl-3-oxo-2-phenyl-2,3-dihydro-1H-pyrazole-4-carboxamide MS (M+H): 506.1;
¹H NMR (400 MHz, Acetone-d₆) δ 10.84 (s, 1H), 8.18 (d, J=2.2 Hz, 1H), 7.73 (d, J=8.5 Hz, 2H), 7.68 (s, 1H), 7.55-7.48 (m, 2H), 7.46-7.35 (m, 7H), 6.91 (d, J=8.7 Hz, 2H), 4.96 (s, 2H), 3.77 (s, 3H), 3.42 (s, 3H), 2.76 (s, 4H).

Example 42(5)

N-{4-[2-amino-5-(4-methoxyphenyl)-3-pyridinyl]phenyl}-1-(2-hydroxy-2-methylpropyl)-5-methyl-3-oxo-2-phenyl-2,3-dihydro-1H-pyrazole-4-carboxamide MS (M+H): 564.2;
¹H NMR (400 MHz, CDCl₃) δ 10.77 (s, 1H), 8.20 (s, 1H), 7.74 (d, J=8.5 Hz, 2H), 7.56-7.47 (m, 3H), 7.42 (dt, J=16.9, 8.5 Hz, 5H), 7.30-7.23 (m, 2H), 6.94 (d, J=8.7 Hz, 2H), 4.67 (s, 2H), 3.81 (s, 3H), 2.87 (s, 3H), 1.12 (s, 6H).

Example 42(6)

N-{4-[2-amino-5-(3,5-difluorophenyl)-3-pyridinyl]phenyl}-1,5-dimethyl-3-oxo-2-phenyl-2,3-dihydro-1H-pyrazole-4-carboxamide MS (M+H): 512.1;
$^1$H NMR (400 MHz, DMSO-$d_6$) δ 10.83 (s, 1H), 8.34 (d, J=2.4 Hz, 1H), 7.69-7.66 (m, 3H), 7.57 (t, J=7.6 Hz, 2H), 7.51-7.46 (m, 3H), 7.44-7.40 (m, 4H), 7.06 (t, J=9.3 Hz, 1H), 5.89 (s, 2H), 3.33 (s, 3H), 2.69 (s, 3H).

Example 42(7)

N-{4-[2-amino-5-(4-cyanophenyl)-3-pyridinyl]phenyl}-1,5-dimethyl-3-oxo-2-phenyl-2,3-dihydro-1H-pyrazole-4-carboxamide MS (M+H): 501.1;
$^1$H NMR (400 MHz, DMSO-$d_6$) δ 10.83 (s, 1H), 8.36 (d, J=2.3 Hz, 1H), 7.86 (d, J=8.5 Hz, 2H), 7.80 (d, J=8.4 Hz, 2H), 7.69-7.67 (m, 3H), 7.57 (t, J=7.6 Hz, 2H), 7.51-7.45 (m, 3H), 7.41 (d, J=7.6 Hz, 2H), 5.96 (s, 2H), 3.33 (s, 3H), 2.69 (s, 3H).

Example 42(8)

N-{4-[2-amino-5-(3-methoxyphenyl)-3-pyridinyl]phenyl}-1,5-dimethyl-3-oxo-2-phenyl-2,3-dihydro-1H-pyrazole-4-carboxamide MS (M+H): 506.2;
$^1$H NMR (400 MHz, Acetone-$d_6$) δ 10.80 (s, 1H), 8.17 (s, 1H), 7.68 (d, J=8.1 Hz, 2H), 7.48 (dd, J=14.9, 7.2 Hz, 3H), 7.35 (dd, J=13.3, 8.1 Hz, 5H), 7.21 (t, J=7.9 Hz, 1H), 7.07-6.98 (m, 2H), 6.74 (d, J=7.1 Hz, 1H), 5.03 (s, 1H), 3.74 (s, 2H), 3.37 (s, 3H), 2.70 (s, 3H).

Example 42(9)

N-{4-[2-amino-5-(4-nitrophenyl)-3-pyridinyl]phenyl}-1,5-dimethyl-3-oxo-2-phenyl-2,3-dihydro-1H-pyrazole-4-carboxamide MS (M+H): 521.1;
$^1$H NMR (400 MHz, DMSO-$d_6$) δ 10.84 (s, 1H), 8.42 (d, J=2.4 Hz, 1H), 8.20 (d, J=8.9 Hz, 2H), 7.95 (d, J=8.9 Hz, 2H), 7.74 (d, J=2.4 Hz, 1H), 7.69 (d, J=8.6 Hz, 2H), 7.57 (t, J=7.6 Hz, 2H), 7.51-7.45 (m, 3H), 7.41 (d, J=7.3 Hz, 2H), 6.05 (s, 2H), 3.34 (s, 3H), 2.69 (s, 3H).

Example 42(10)

N-(4-{2-amino-5-[3-(4-morpholinylmethyl)phenyl]-3-pyridinyl}phenyl)-1,5-dimethyl-3-oxo-2-phenyl-2,3-dihydro-1H-pyrazole-4-carboxamide MS (M+H): 575.2;
$^1$H NMR (400 MHz, CDCl$_3$) δ 10.79 (s, 1H), 8.26 (d, J=2.2 Hz, 1H), 7.77 (d, J=8.5 Hz, 2H), 7.60 (d, J=2.3 Hz, 1H), 7.54 (t, J=7.6 Hz, 2H), 7.48-7.41 (5H), 7.35 (dd, J=10.4, 4.3 Hz, 3H), 7.27 (s, 1H), 4.82 (s, 2H), 3.71-3.67 (m, 4H), 3.53 (s, 2H), 3.35 (s, 3H), 2.79 (s, 3H), 2.46 (s, 4H).

Example 42(11)

N-(4-{2-amino-5-[4-(4-morpholinylcarbonyl)phenyl]-3-pyridinyl}phenyl)-1,5-dimethyl-3-oxo-2-phenyl-2,3-dihydro-1H-pyrazole-4-carboxamide MS (M+H): 559.2;
$^1$H NMR (400 MHz, CDCl$_3$) δ 10.80 (s, 1H), 8.29 (d, J=2.3 Hz, 1H), 7.77 (d, J=8.5 Hz, 2H), 7.59-7.52 (5H), 7.45 (dt, J=10.1, 6.6 Hz, 5H), 7.35 (d, J=7.4 Hz, 2H), 4.70 (s, 2H), 3.82-3.51 (br m, 8H), 3.35 (s, 3H), 2.79 (s, 3H).

Example 42(12)

N-[4-(2-amino-5-{3-[(4-methyl-1-piperazinyl)methyl]phenyl}-3-pyridinyl)phenyl]-1,5-dimethyl-3-oxo-2-phenyl-2,3-dihydro-1H-pyrazole-4-carboxamide $^1$H NMR (400 MHz, CDCl$_3$) δ 10.79 (s, 1H), 8.29 (d, J=2.3 Hz, 1H), 7.76 (d, J=8.5 Hz, 2H), 7.59 (d, J=2.3 Hz, 1H), 7.54 (t, J=6.7 Hz, 2H), 7.48-7.40 (m, 5H), 7.35 (dd, J=7.6, 2.4 Hz, 3H), 7.26 (s, 1H), 4.62 (s, 2H), 3.54 (s, 2H), 3.35 (s, 3H), 2.80 (s, 3H), 2.44 (br m, 8H), 2.26 (s, 3H).

Example 42(13)

N-(4-{5-[3-(acryloylamino)phenyl]-2-amino-3-pyridinyl}phenyl)-1,5-dimethyl-3-oxo-2-phenyl-2,3-dihydro-1H-pyrazole-4-carboxamide MS (M+H): 545.3;
$^1$H NMR (400 MHz, CDCl$_3$) δ 10.76 (s, 1H), 8.23 (d, J=2.0 Hz, 1H), 8.08 (s, 1H), 7.71 (t, J=7.9 Hz, 2H), 7.68-7.60 (m, 2H), 7.56-7.48 (m, 3H), 7.42 (dd, J=13.5, 6.0 Hz, 1H), 7.39-7.30 (m, 5H), 7.25 (d, J=6.1 Hz, 1H), 6.40 (d, J=16.7 Hz, 1H), 6.25 (dd, J=16.8, 10.1 Hz, 1H), 5.73-5.64 (m, 1H), 4.71 (s, 2H), 3.32 (s, 3H), 2.76 (s, 3H).

Example 42(14)

N-{4-[2-amino-5-(3-methoxyphenyl)-4-methyl-3-pyridinyl]phenyl}-1,5-dimethyl-3-oxo-2-phenyl-2,3-dihydro-1H-pyrazole-4-carboxamide MS (M+H): 520.2;
$^1$H NMR (400 MHz, CDCl$_3$) δ 10.76 (s, 1H), 7.92 (s, 1H), 7.77 (d, J=8.6 Hz, 2H), 7.54 (dd, J=10.4, 4.8 Hz, 2H), 7.49-7.40 (m, 1H), 7.36 (dd, J=5.3, 3.2 Hz, 2H), 7.30 (t, J=7.8 Hz, 1H), 7.24-7.20 (m, 2H), 6.92-6.81 (m, 3H), 4.24 (s, 2H), 3.82 (s, 3H), 3.34 (d, J=5.0 Hz, 3H), 2.79 (s, 3H), 1.91 (s, 3H).

Example 42(15)

N-{4-[2-amino-5-(2-fluoro-3-methoxyphenyl)-4-methyl-3-pyridinyl]phenyl}-1,5-dimethyl-3-oxo-2-phenyl-2,3-dihydro-1H-pyrazole-4-carboxamide MS (M+H): 538.2;
$^1$H NMR (400 MHz, CDCl$_3$) δ 10.70 (s, 1H), 7.83 (s, 1H), 7.71 (d, J=8.8 Hz, 2H), 7.49 (t, J=7.6 Hz, 2H), 7.39 (t, J=7.5 Hz, 1H), 7.34-7.27 (m, 2H), 7.18 (d, J=9.1 Hz, 5H), 7.03 (dd, J=12.5, 4.7 Hz, 1H), 6.90 (dd, J=7.9, 6.5 Hz, 1H), 6.81-6.72 (m, 1H), 4.23 (s, 2H), 3.85 (s, 3H), 3.29 (s, 3H), 2.74 (s, 3H), 1.79 (d, J=1.4 Hz, 2H).

Example 42(16)

N-{4-[6-amino-4-methyl-2'-(4-morpholinyl)-3,4'-bipyridin-5-yl]phenyl}-1,5-dimethyl-3-oxo-2-phenyl-2,3-dihydro-1H-pyrazole-4-carboxamide MS (M+H): 576.3;
$^1$H NMR (400 MHz, CDCl$_3$) δ 10.77 (s, 1H), 8.18 (d, J=5.1 Hz, 1H), 7.87 (s, 1H), 7.80-7.72 (m, 2H), 7.58-7.39 (m, 4H), 7.34 (dt, J=3.5, 1.9 Hz, 2H), 7.23-7.15 (m, 2H), 6.65-6.47 (m, 3H), 4.34 (s, 2H), 3.84-3.78 (m, 4H), 3.55-3.48 (m, 4H), 3.34 (s, 3H), 2.78 (s, 3H), 1.91 (s, 3H).

Example 42(17)

N-[4-(2-amino-4-methyl-5-{3-[2-(4-morpholinyl)ethoxy]phenyl}-3-pyridinyl)phenyl]-1,5-dimethyl-3-oxo-2-phenyl-2,3-dihydro-1H-pyrazole-4-carboxamide MS (M+H): 619.4;
$^1$H NMR (400 MHz, CDCl$_3$) δ 10.76 (s, 1H), 7.90 (s, 1H), 7.80-7.72 (m, 2H), 7.57-7.50 (m, 2H), 7.47-7.42 (m, 1H), 7.35 (dd, J=8.4, 1.2 Hz, 2H), 7.28 (t, J=7.8 Hz, 1H), 7.23-7.18 (m, 2H), 6.90-6.83 (m, 3H), 4.22 (d, J=18.0 Hz, 2H), 4.16-4.07 (m, 2H), 3.75-3.68 (m, 5H), 3.34 (s, 3H), 2.83-2.76 (m, 6H), 2.62-2.52 (m, 5H), 1.91 (d, J=2.1 Hz, 3H).

Example 42(18)

N-{4-[2-amino-5-(3,5-dimethoxyphenyl)-4-methyl-3-pyridinyl]phenyl}-1,5-dimethyl-3-oxo-2-phenyl-2,3-dihydro-1H-pyrazole-4-carboxamide MS (M+H): 550.3;
$^1$H NMR (400 MHz, CDCl$_3$) δ 10.76 (s, 1H), 7.92 (s, 1H), 7.77 (d, J=8.6 Hz, 2H), 7.54 (t, J=7.6 Hz, 2H), 7.45 (t, J=7.4 Hz, 1H), 7.38-7.34 (m, 2H), 7.22 (d, J=8.6 Hz, 2H), 6.44 (q, J=1.7 Hz, 3H), 4.24 (s, 2H), 3.80 (s, 6H), 3.35 (s, 3H), 2.79 (s, 3H), 1.92 (s, 3H).

Example 42(19)

N-(4-{2-amino-5-[3-(1H-pyrazol-3-yl)phenyl]-3-pyridinyl}phenyl)-2-(3-chlorophenyl)-1,5-dimethyl-3-oxo-2,3-dihydro-1H-pyrazole-4-carboxamide MS (M+H): 576.0;
$^1$H NMR (400 MHz, DSMO-d$_6$) δ 10.71 (s, 1H), 8.32 (d, J=2.0 Hz, 1H), 8.00 (s, 1H), 7.73-7.63 (m, 4H), 7.63-7.52 (5H), 7.49 (d, J=8.5 Hz, 2H), 7.45-7.36 (3H), 6.79 (d, J=1.7 Hz, 1H), 5.74 (s, 2H), 3.36 (s, 3H), 2.68 (s, 3H).

Example 42(20)

N-(4-{2-amino-5-[3-(1H-pyrazol-3-yl)phenyl]-3-pyridinyl}phenyl)-1,5-dimethyl-3-oxo-2-phenyl-2,3-dihydro-1H-pyrazole-4-carboxamide MS (M+H): 542.1;
$^1$H NMR (400 MHz, DMSO-d$_6$) δ 10.81 (s, 1H), 8.30 (s, 1H), 7.99 (s, 1H), 7.78-7.61 (5H), 7.61-7.53 (m, 3H), 7.52-7.46 (m, 4H), 7.46-7.36 (m, 3H), 6.78 (s, 1H), 5.69 (s, 2H), 3.32 (s, 3H), 2.68 (s, 3H).

Example 42(21)

N-{4-[6-amino-2'-(4-morpholinyl)-3,4'-bipyridin-5-yl]phenyl}-1,5-dimethyl-3-oxo-2-phenyl-2,3-dihydro-1H-pyrazole-4-carboxamide MS (M+H): 562.1;
$^1$H NMR (400 MHz, DMSO-d$_6$) δ 10.82 (s, 1H), 8.36 (d, J=2.3 Hz, 1H), 8.07 (d, J=5.3 Hz, 1H), 7.73-7.62 (m, 3H), 7.61-7.53 (m, 2H), 7.49 (d, J=7.3 Hz, 1H), 7.47-7.38 (m, 4H), 7.01 (s, 1H), 6.97 (d, J=5.3 Hz, 1H), 5.88 (s, 2H), 3.69-3.62 (m, 4H), 3.51-3.44 (m, 4H), 3.33 (s, 3H), 2.69 (s, 3H).

Example 42(22)

N-{4-[6-amino-2'-(4-morpholinyl)-3,4'-bipyridin-5-yl]phenyl}-2-(3-chlorophenyl)-1,5-dimethyl-3-oxo-2,3-dihydro-1H-pyrazole-4-carboxamide MS (M+H): 596.0;
$^1$H NMR (400 MHz, DMSO-d$_6$) δ 10.70 (s, 1H), 8.37 (d, J=2.3 Hz, 1H), 8.07 (d, J=5.3 Hz, 1H), 7.73-7.65 (3H), 7.64-7.52 (3H), 7.45 (d, J=8.5 Hz, 2H), 7.39 (d, J=7.5 Hz, 1H), 7.01 (s, 1H), 6.97 (d, J=5.3 Hz, 1H), 5.88 (s, 2H), 3.70-3.62 (m, 4H), 3.51-3.43 (m, 4H), 3.36 (s, 3H), 2.69 (s, 3H).

Example 43

3-(4-Aminophenyl)-5-bromopyridin-2-amine

To the 5-bromo-3-iodopyridin-2-amine (CAS No. 381233-96-1) (1.144 g), 4-(4,4,5,5-tetramethyl-1,3,2-dioxaborolan-2-yl)aniline (0.922 g), Na$_2$CO$_3$ (0.487 g) in 10 mL mixture of toluene:EtOH:H$_2$O 5:5:1 after degassing with argon was added the Pd(PPh$_3$)$_4$ (0.221 g) and heated at 80° C. for 16 hours. The reaction mixture was filtered through celite and concentrated. The crude was chromatographed on silica gel using 10:1 DCM:MeOH to give the title compound (0.84 g) having the following physical data.

MS (M+H): 265.9.

Example 44

N-(4-(2-amino-5-bromopyridin-3-yl)phenyl)-1,5-dimethyl-3-oxo-2-phenyl-2,3-dihydro-1H-pyrazole-4-carboxamide To the antipyric acid (0.163 g) in 5 mL of DCM, 0.5 mL of DMF and TEA (1.4 mmol) was added the HATU (0.266 g) and stirred for 30 minutes. To the activated ester was added the compound prepared in Example 43 (0.185 g) and stirred for 1 hour. The reaction mixture was diluted with water, extracted with additional DCM, and the organic layer was washed with water, brine and dried over anhydrous sodium sulfate. The DCM layer was filtered and concentrated, and the crude was chromatographed on silica gel using 10:1 DCM:MeOH to give the title compound (0.3 g) having the following physical data.

MS (M+H): 480.0.

Example 45

N-[4-(2-amino-5-cyclohexyl-3-pyridinyl)phenyl]-1,5-dimethyl-3-oxo-2-phenyl-2,3-dihydro-1H-pyrazole-4-carboxamide

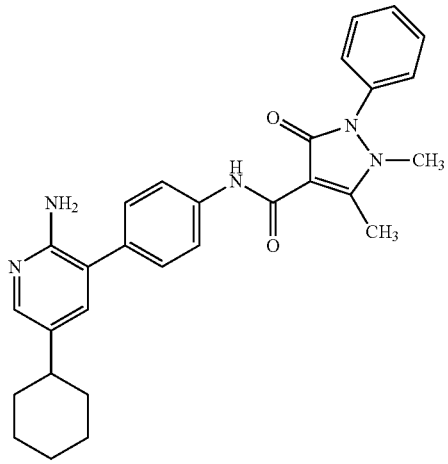 [SMILES: Cc1c(C(=O)Nc2ccc(-c3cc(C4CCCCC4)cnc3N)cc2)c(=O)n(-c2ccccc2)n1C]

To the compound prepared in Example 44 (0.05 g), 2-cyclohexenyl-4,4,5,5-tetramethyl-1,3,2-dioxaborolane (0.058 g), Na$_2$CO$_3$ (0.022 g) in 3 mL mixture of toluene:EtOH:H$_2$O 5:5:1 after degassing with argon was added the Pd(PPh$_3$)$_4$ (0.007 g) and heated at 100° C. for 16 hours. The reaction mixture was filtered through celite and concentrated. The crude was chromatographed on silica gel using 10:1 DCM:MeOH to give the cyclohexenyl coupled product which was subjected to hydrogenation using Pd/C to give the title compound (0.012 mg) having the following physical data.

MS (M+H): 582.3;
$^1$H NMR (400 MHz, CDCl$_3$) δ 10.76 (s, 1H), 7.86 (d, J=2.0 Hz, 1H), 7.73 (d, J=8.5 Hz, 2H), 7.54 (t, J=7.6 Hz, 2H), 7.45 (t, J=7.4 Hz, 1H), 7.36 (dd, J=10.4, 8.0 Hz, 4H), 7.21 (d, J=2.1 Hz, 1H), 4.50 (s, 2H), 3.34 (s, 3H), 2.79 (s, 3H), 2.45-2.36 (m, 1H), 2.04 (d, J=6.3 Hz, 1H), 1.89-1.75 (m, 4H), 1.71 (d, J=12.4 Hz, 1H), 1.43-1.28 (m, 4H).

Example 46

N-(1-{3-amino-6-[6-(3-methoxy-1-azetidinyl)-2-pyridinyl]-2-pyrazinyl}-4-piperidinyl)-2-(3-chlorophenyl)-1,5-dimethyl-3-oxo-2,3-dihydro-1H-pyrazole-4-carboxamide

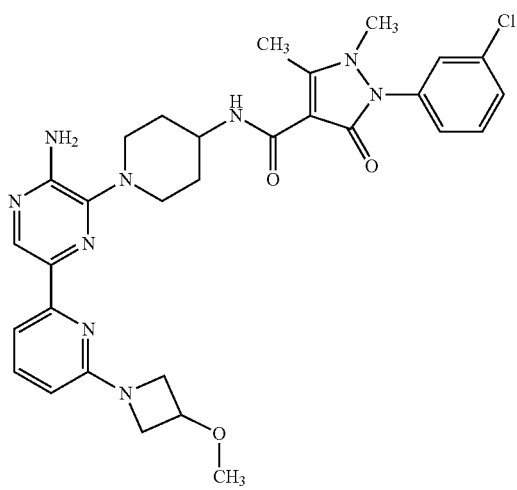 [SMILES: COC1CN(c2cccc(-c3cnc(N)c(N4CCC(NC(=O)c5c(C)n(C)n(-c6cccc(Cl)c6)c5=O)CC4)n3)n2)C1]

The compound having the following physical data was prepared by using the compound prepared in Example 19, the compound prepared in Example 11 and 2-(3-methoxy-1-azetidinyl)-6-(4,4,5,5-tetramethyl-1,3,2-dioxaborolan-2-yl)pyridine in the process of Example 22→Example 17→Example 13.

MS (M+H): 604.2;
$^1$H NMR (400 MHz, CDCl$_3$) δ 8.58 (d, J=7.6 Hz, 1H), 8.40 (s, 1H), 7.50-7.44 (m, 1H), 7.41-7.30 (m, 3H), 7.28 (s, 1H), 7.16 (s, 1H), 6.25 (d, J=8.2 Hz, 1H), 4.35-4.27 (m, 1H), 4.23-4.11 (m, 3H), 3.90-3.82 (m, 2H), 3.60-3.50 (m, 2H), 3.30 (s, 3H), 3.24 (s, 3H), 3.09 (t, J=12.0 Hz, 2H), 2.68 (s, 3H), 2.15-2.03 (m, 2H), 1.77-1.65 (m, 2H).

Example 47

N-(4-{6-[3-(acryloylamino)phenyl]-3-amino-2-pyrazinyl}phenyl)-1,5-dimethyl-3-oxo-2-phenyl-2,3-dihydro-1H-pyrazole-4-carboxamide The title compound having the following physical data was prepared by using the compound prepared in Example 3, bis(pinacolato)diboron, 3-bromoaniline and acryloyl chloride in the process of Example 6→Example 7→Example 2.

TLC Rf=0.60 (dichloromethane:methanol=9:1);
$^1$H NMR (300 MHz, CDCl$_3$) δ 10.84, 8.40, 7.32-8.00, 6.42, 6.24, 5.75, 4.87, 3.37, 2.80.

Example 47(1)-47(2)

The compound having the following physical data was prepared by using the corresponding bromide compound instead of the compound prepared in Example 3, bis(pinacolato)diboron, 3-bromoaniline and acryloyl chloride in the process of Example 47.

Example 47(1)

N-(1-{6-[3-(acryloylamino)phenyl]-3-amino-2-pyrazinyl}-4-piperidinyl)-2-(2-chlorophenyl)-1,5-dimethyl-3-oxo-2,3-dihydro-1H-pyrazole-4-carboxamide TLC Rf=0.60 (chloroform:methanol=10:1);
$^1$H NMR (300 MHz, CDCl$_3$) δ 1.70-1.82, 2.08-2.20, 2.75, 3.00-3.12, 3.26, 3.50-3.60, 4.10-4.23, 4.62, 5.70-5.80, 6.20-6.50, 7.37-7.50, 7.58-7.70, 7.80-7.90, 8.13, 8.64.

Example 47(2)

N-[1-(3-amino-6-{3-[(chloroacetyl)amino]phenyl}-2-pyrazinyl)-4-piperidinyl]-2-(2-chlorophenyl)-1,5-dimethyl-3-oxo-2,3-dihydro-1H-pyrazole-4-carboxamide TLC Rf=0.56 (ethyl acetate:methanol=10:1);
$^1$H NMR (300 MHz, CDCl$_3$) δ 1.63-1.82, 2.04, 2.06-2.20, 2.75, 2.99-3.10, 3.26, 3.55-3.65, 4.00-4.20, 4.60, 7.36-7.70, 7.90, 8.14, 8.36, 8.60.

Example 48

N-{6-[3-amino-6-(5-cyclopropyl-1H-pyrazol-3-yl)-2-pyrazinyl]-3-pyridinyl}-2-(3-chlorophenyl)-1,5-dimethyl-3-oxo-2,3-dihydro-1H-pyrazole-4-carboxamide The compound prepared in Example 29(15) was subjected to deprotection reaction in the process of Example 22 to obtain the title compound having the following physical data.

TLC Rf=0.50 (ethyl acetate:methanol=10:1);
$^1$H NMR (300 MHz, CDCl$_3$) δ 0.85-0.92, 1.02-1.26, 2.30-2.38, 2.62, 2.82, 3.39, 7.23-7.32, 7.36-7.52, 7.96, 8.28, 8.38, 8.58, 8.83, 10.8.

Example 48(1)-48(2)

The compound having the following physical data was prepared by using the corresponding compound protected by tetrahydropyran instead of the compound prepared in Example 29(15), in the same process of Example 48.

Example 48(1)

N-{6-[3-amino-6-(5-cyclopropyl-1H-pyrazol-3-yl)-2-pyrazinyl]-3-pyridinyl}-1,5-dimethyl-2-(3-methylphenyl)-3-oxo-2,3-dihydro-1H-pyrazole-4-carboxamide TLC Rf=0.51 (ethyl acetate:methanol=10:1);
$^1$H NMR (300 MHz, CDCl$_3$) δ 0.86-0.90, 1.00-1.08, 2.29-2.38, 2.44, 2.80, 3.37, 7.10-7.20, 7.24-7.32, 7.44, 7.95, 8.29-8.33, 8.38, 8.57, 8.82, 10.9.

Example 48(2)

N-{6-[3-amino-6-(5-cyclopropyl-1H-pyrazol-3-yl)-2-pyrazinyl]-3-pyridinyl}-2-(2-chlorophenyl)-1,5-dimethyl-3-oxo-2,3-dihydro-1H-pyrazole-4-carboxamide TLC Rf=0.35 (ethyl acetate:methanol=10:1);
$^1$H NMR (300 MHz, CDCl$_3$) δ 0.84-0.91, 1.00-1.10, 2.24-2.35, 2.81, 3.33, 7.49-7.66, 7.95, 8.30, 8.37, 8.57, 8.82, 10.9.

Example 49

5-amino-N-(3,3-dimethyl-2-butanyl)-6-(4-{[(1,5-dimethyl-3-oxo-2-phenyl-2,3-dihydro-1H-pyrazol-4-yl)carbonyl]amino}phenyl)-2-pyrazinecarboxamide To a solution of the compound prepared in Example 3 (150 mg) in DMF (2.00 ml) was added 2-amino-3,3-dimethylbutane (300 mg), PdCl$_2$(dppf)-CH$_2$Cl$_2$ (51 mg), DIPEA (109 ul). The reaction mixture was degassed and then stirred overnight at 80° C. under CO atmosphere. The reaction mixture was poured into H$_2$O, extracted with CHCl$_3$ twice, and washed with brine. The organic phase was dried over Na$_2$SO$_4$, filtered and concentrated. The residue was purified by column chromatography on silica gel (5% MeOH in CHCl$_3$) to yield the title compound (61 mg) having the following physical data.
TLC Rf=0.45 (ethyl acetate:methanol=10:1);
$^1$H NMR (300 MHz, CDCl$_3$) δ 0.949, 1.14, 2.81, 3.37, 3.98-4.08, 5.10, 7.31-7.68, 7.82, 8.78, 10.8.

Example 49(1)

5-amino-6-[4-({[2-(2-chlorophenyl)-1,5-dimethyl-3-oxo-2,3-dihydro-1H-pyrazol-4-yl]carbonyl}amino)-1-piperidinyl]-N-(3,3-dimethyl-2-butanyl)-2-pyrazinecarboxamide The compound having the following physical data was prepared by using the corresponding compound instead of the compound prepared in Example 3, in the same process of Example 49.

TLC Rf=0.42 (ethyl acetate:methanol=10:1);
$^1$H NMR (300 MHz, CDCl$_3$) δ 0.96, 1.17, 1.60-1.80, 2.10-2.22, 2.75, 2.90-3.05, 3.27, 3.40-3.60, 3.98-4.08, 4.10-4.22, 4.90, 7.31-7.62, 8.50, 8.62.

BIOLOGICAL EXAMPLES

It was proved by the following experiments that the compounds of the present invention have selective Itk inhibitory activity. The methods for experiments are shown below, but they are not limited thereto.

Biological Example 1

Itk In Vitro Inhibitory Activity in TR-FRET Assay

Itk activity was determined by time-resolved fluorescence resonance energy transfer (TR-FRET) assay using LanthaScreen system (Invitrogen). The dilution series of the compounds of the present invention were dissolved in dimethyl sulfoxide (DMSO). Then they were diluted by addition of buffer (50 mM HEPES (pH7.5), 0.01% Brij35, 10 mM MgCl$_2$ solution, 1 mM EGTA). The diluted compound solution (5 μl) was added to a 96-well assay plate. Additionally, the kinase solution (10 μl), composed of 4 nM Itk (Carna Biosciences) and assay buffer, was added to the assay plate and the reaction solution was pre-incubated for 30 minutes at 25° C. Then, the enzyme reaction was started by addition of the ATP/substrate solution (10 μl), composed of 0.6 μM adenosine triphosphate (ATP), 200 nM Fluorescein-Poly GT (Invitrogen) and assay buffer, to each well. The assay was performed for 1 hour at 25° C. with shaking in the dark. The assay was terminated by addition of the development solution (25 μl), composed of 20 mM EDTA, 4 nM Tb—PY-20 antibody and TR-FRET dilution buffer and incubated for more than 30 minutes at 25° C. with shaking in the dark. The fluorescence of each well was excited with wavelength of 340 nm and the emission was measured on Analyst GT (Molecular Devices) at wavelengths of 495 nm and 520 nm. The FRET ratio was calculated by dividing the emission at 520 nm by the emission at 495 nm.

Inhibition rate (%) of the compound was calculated with the following formula:

$$\text{Inhibition rate}(\%) = \{1 - (A_X - A_{100})/(A_0 - A_{100})\} \times 100$$

$A_X$: FRET ratio for the compound
$A_{100}$: FRET ratio for 100% inhibition control (i.e., no enzyme, no compound)
$A_0$: FRET ratio for 0% inhibition control (i.e., no compound)

The value of 50% inhibition rate (IC$_{50}$) for the compound was determined from inhibition curve based on inhibition rate at each concentration of the compound.

As a result, IC$_{50}$ over Itk of the compounds of the present invention showed below 1 μM.

Study of inhibitory activity to Lck was performed in similar procedure above described.

Biological Example 2

Itk In Vitro Inhibitory Activity in Radioassay

The Itk protein kinase activity (Invitrogen) was determined by measuring the incorporation of $^{33}$P from γ-[$^{33}$P] ATP into the Phospholipase C-γ-1 substrate (Calbiochem). The dilution series of the compound of the present invention were dissolved in DMSO. The diluted solution (1 μl) of the compounds of the present invention in DMSO was added to a 96-well assay plate. Additionally, Itk kinase solution (39 μL) composed of 3.2 nM Itk (Invitrogen) in reaction buffer (12.5 mM Tris (pH 7.5), 0.01% Triton X-100, 5% glycerol, 10 mM $MgCl_2$, 1 mM EGTA, 5 mM glycerol 2-phosphate, 2 mM DTT and 0.5 mM sodium orthovanadate) was added to the assay plates. The solution was pre-incubated for 20 minutes at 30° C. with shaking. Then ATP/substrate solution (10 μl) composed of 1.13 M Phospholipase C-γ-1 (Calbiochem), 1.5% v/v γ-$^{33}$P-ATP (PerkinElmer), 20 μM ATP and reaction buffer was added. After incubating at 30° C. with shaking for 70 minutes, the reaction was stopped by adding 10 μl of 0.6 M phosphoric acid to each well. The each reaction from the assay plate was transferred and captured on a phosphocellulose 96-well plate (Millipore MAPHNOB). The reaction mixture was analyzed on the PerkinElmer TopCount NXT HTS 96-well Liquid Scintillation counter.

Inhibition rate (%) of the compound was calculated with the following formula:

$$\text{Inhibition rate}(\%) = \{1-(B_x-B_{100})/(B_0-B_{100})\} \times 100$$

$B_X$: average counts for the compound $B_{100}$: average counts for 100% inhibition control (i.e., no enzyme, no compound)

$B_0$: average counts for 0% inhibition control (i.e., no compound)

The value of 50% inhibition rate ($IC_{50}$) for the compound was defined as the concentration of the test compound that caused a 50% decrease in the maximum inhibition. $IC_{50}$ values were calculated from replicate curves by non-linear regression using the sigmoidal dose-response equation in GraphPad Prism software.

As a result, the compounds of the present invention possess potent Itk inhibitory activity. For example, $IC_{50}$ over Itk of the compound prepared in Example 7(6), 14(12), 17(11), 29(2), 29(33) and 40(19) showed 0.002 μM, 0.002 μM, 0.001 μM, 0.001 μM, 0.004 μM and 0.003 μM respectively.

Study of inhibitory activity to other various kinases (e.g. Lck, InsR, Btk) was performed in similar procedure above described.

As a result of Biological Example 1 and 2, the compounds of the present invention possess the potent selectivity of Itk inhibitory activity over the other various kinases, especially Lck, InsR and Btk shown below table 1.

TABLE 1

| Example No. | Lck[IC50]/Itk[IC50] | InsR[IC50]/Itk[IC50] | Btk[IC50]/Itk[IC50] |
|---|---|---|---|
| 7 (6) | 85 | 100 | >200 |
| 14 (12) | 185 | 1400 | >500 |
| 17 (11) | >300 | >300 | >1000 |
| 29 (2) | >360 | >1000 | >1000 |

In addition, the compounds of the present invention also possess the potent selectivity of Itk inhibitory activity over c-Met kinase. For example, the compound prepared in Example 7(6) has an $IC_{50}$ for Itk inhibition that is about 230 times lower than the $IC_{50}$ of c-Met kinase inhibition.

Alternatively, the compound described in example 8 of prior art (WO 2008/086014) showed that its $IC_{50}$ over Itk and Lck is 1.6 μM and >10 μM, respectively. Therefore, it was found that the compounds of present invention possess more superior selectivity of Itk inhibitory activity over Lck than the prior art.

Biological Example 3

Mouse Whole Blood IL-2 Assay

The dilution series of the compound of the present invention in DMSO were further diluted by addition of RPMI1640 medium (Invitrogen). The diluted compound solution (6.5 μl) was added to a 96-well plate. BALB/c mouse heparinized peripheral blood was diluted 1:2 in RPMI1640, and added 123.5 μl of the diluted blood to the compound plate. The blood samples were pre-incubated at 37° C. for 30 minutes. Anti-CD3 and anti-CD28 antibody mixture (6 μl; 20 μg/mL each) was spotted into a 96 well assay plates. Pre-treated blood samples (114 μl) were added to each well and the plate was incubated for 18 hours at 37° C. in 5% $CO_2$. After the incubation, supernatants were collected by centrifugation at 300×g for 10 min. IL-2 concentration was determined by ELISA method. The inhibition rate (%) of the compound was calculated with the following formula:

$$\text{Inhibition rate}(\%) = \{1-(C_x-C_{100})/(C_0-C_{100})\} \times 100$$

$C_X$: IL-2 concentration for the compound $C_{100}$: IL-2 concentration for 100% inhibition control (i.e., no stimulation, no compound)

$C_0$: IL-2 concentration for 0% inhibition control (i.e., no compound)

The value of 50% inhibition rate ($IC_{50}$) for the compound was determined from inhibition curve based on inhibition rate at each concentration of the compound of the present invention.

As a result, the compounds of the present invention showed potent inhibitory activity for mouse whole blood IL-2 production. For example, $IC_{50}$ of the compound prepared in Example 29(2) showed 0.35 μM.

Formulation Example 1

The following components are admixed in conventional method and punched out to obtain 10,000 tablets each containing 10 mg of active ingredient.

| | |
|---|---|
| N-(6-{3-amino-6-[2-(4-morpholinyl)-4-pyridinyl]-2-pyrazinyl}-3-pyridinyl)-2-(3-chlorophenyl)-1,5-dimethyl-3-oxo-2,3-dihydro-1H-pyrazole-4-carboxamide | 100 g |
| carboxymethylcellulose calcium (disintegrating agent) | 20 g |
| magnesium stearate (lubricating agent) | 10 g |
| microcrystalline cellulose | 870 g |

Formulation Example 2

The following components are admixed in conventional method. The solution is sterilized in conventional manner, filtered through dust removal equipment, placed 5 ml portions into ampoules and sterilized by autoclave to obtain 10,000 ampoules each containing 20 mg of the active ingredient.

| | |
|---|---|
| N-(6-{3-amino-6-[2-(4-morpholinyl)-4-pyridinyl]-2-pyrazinyl}-3-pyridinyl)-2-(3-chlorophenyl)-1,5-dimethyl-3-oxo-2,3-dihydro-1H-pyrazole-4-carboxamide | 200 g |
| mannitol | 20 g |
| distilled water | 50 L |

INDUSTRIAL APPLICABILITY

Since the compound represented by the formula (I), a salt thereof, a solvate thereof, an N-oxide thereof or a prodrug thereof, has an Itk inhibitory activity, it is useful as a method for preventing and/or treating Itk related disease.

The invention claimed is:
1. A compound represented by formula (I)

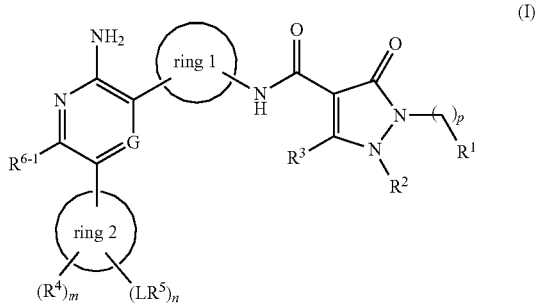

wherein G represents N, CH or $CR^{6-2}$;
ring1 represents benzene, pyridine, piperidine, cyclohexene, or cyclohexane, any of which is optionally substituted with 1-4 substituent(s) selected from among (1) C1-4 alkyl, (2) C1-4 alkoxy, (3) halogen, and (4) oxo;
ring2 represents 5-10 membered aromatic monocyclic or bicyclic aromatic heterocyclic ring containing 1-4 heteroatom(s) selected from a nitrogen atom, an oxygen atom and/or a sulfur atom optionally oxidized;
$R^1$ represents cyclopropane, cyclobutane, cyclopentane, cyclohexane, cyclobutene, cyclopentene, cyclohexene, cyclobutadiene, cyclopentadiene, cyclohexadiene, benzene or pyridine, any ring of which is optionally substituted with 1-5 substituent(s) selected from among (1) C1-4 alkyl, (2) C1-4 alkoxy, (3) halogen, (4) $CF_3$, and (5) CN;
$R^2$ and $R^3$ each independently represent (1) $CF_3$, or (2) C1-4 alkyl optionally substituted with 1-3 substituent(s) selected from among (1) $OR^{2-1}$, (2) $NR^{2-2}R^{2-3}$ and (3) halogen;
$R^4$ represents (1) halogen, (2) C1-4 alkyl, (3) C1-4 alkoxy, (4) $CF_3$, (5) OH, (6) CN, (7) ring3, (8) $NR^{4-1}R^{4-2}$, or (9) $NO_2$;
$R^5$ represents (1) ring3, (2) C1-4 alkyl optionally substituted with halogen, OH, C1-4 alkoxy, CN, $COOR^{5-8}$, or $NR^{5-1}R^{5-2}$, (3) C2-4 alkenyl, (4) C1-4 alkoxy, (5) $NR^{5-3}R^{5-4}$, (6) OH, (7) $SO_2R^{5-5}$, (8) $SO_2NR^{5-6}R^{5-7}$, (9) $COOR^{5-8}$, (10) $COR^{5-9}$, (11) $CONR^{5-10}R^{5-11}$, (12) halogen, or (13) hydrogen;
$R^{6-1}$ and $R^{6-2}$ each independently represent (1) hydrogen, (2) C1-4 alkyl, or (3) $NH_2$;
L represents (1) —O—, (2) —C1-6 alkylene-, (3) —C(O)—, (4) —O—C1-6 alkylene-, (5) —C1-6 alkylene-O—, (6) —$NR^{7-1}$—, (7) —S—, (8) —SO—, (9) —$SO_2$—, (10) —CNH— (11) —$NR^{7-2}$C(O)—, (12) —$NR^{7-3}$C(O)$NR^{7-4}$—, (13) —C(O)$NR^{7-5}$—, (14) —$SO_2NR^{7-6}$—, (15) —$NR^{7-7}SO_2$—, (16) C2-4 alkenylene, or (17) C2-4 alkynylene, wherein C1-6 alkylene is optionally substituted with OH;
ring3 represents (1) C3-7 carbocyclic ring selected from among cyclopropane, cyclobutane, cyclopentane, cyclohexane, cycloheptane, cyclobutene, cyclopentene, cyclohexene, cycloheptene, cyclobutadiene, cyclopentadiene, cyclohexadiene, cycloheptadiene, and benzene, or (2) 3-7 membered monocyclic unsaturated or saturated heterocyclic ring containing 1-4 heteroatom(s) selected from a nitrogen atom, an oxygen atom and/or a sulfur atom optionally oxidized, any of which is optionally substituted with 1-5 substituent(s) selected from among (1) halogen, (2) C1-4 alkyl optionally substituted with OH, C1-4 alkoxy, or $NR^{8-1}R^{8-2}$, (3) oxo, (4) OH, (5) C1-4 alkoxy, (6) C(O)$CH_3$, (7) $NR^{8-3}R^{8-4}$, (8) $SO_2CH_3$, (9) $COOR^{8-5}$, and (10) C(O)$NR^{8-6}R^{8-7}$;
$R^{2-1}$, $R^{2-2}$ and $R^{2-3}$ each independently represent hydrogen, or C1-4 alkyl;
$R^{4-1}$ and $R^{4-2}$ each independently represent hydrogen or C1-4 alkyl;
$R^{5-1}$, $R^{5-2}$, $R^{5-3}$, $R^{5-4}$, $R^{5-5}$, $R^{5-6}$, $R^{5-7}$, $R^{5-8}$, $R^{5-9}$, $R^{5-10}$ and $R^{5-11}$ each independently represent hydrogen or C1-6 alkyl;
$R^{7-1}$, $R^{7-2}$, $R^{7-3}$, $R^{7-4}$ $R^{7-5}$, $R^{7-6}$ and $R^{7-7}$ each independently represent hydrogen or C1-4 alkyl;
$R^{8-1}$, $R^{8-2}$, $R^{8-3}$, $R^{84}$, $R^{8-5}$, $R^{8-6}$ and $R^{8-7}$ each independently represent hydrogen or C1-4 alkyl;
m represents 0 or an integer of 1-3, wherein when m is more than 1, each $R^4$ may be same or different;
n represents 0 or an integer of 1-2, wherein n is 2, each $LR^5$ may be same or different;
p represents 0 or 1;
or a pharmaceutically acceptable salt thereof.

2. The compound according to claim 1, wherein G represents N.

3. The compound according to claim 1, wherein G represents CH.

4. The compound according to claim 3, wherein $R^4$ represents (1) C1-4 alkyl, (2) $CF_3$, (3) ring3, or (4) halogen.

5. The compound according to claim 1, wherein L represents (1) —$C_1$-6 alkylene-, (2) —O—C1-6 alkylene-, (3) —C1-6 alkylene-O—, (4) C2-4 alkenylene, or (5) C2-4 alkynylene, wherein C1-6 alkylene is optionally substituted with OH.

6. The compound according to claim 1, wherein L represents (1) —C1-6 alkylene-, (2) —O—C1-6 alkylene-, (3) —C1-6 alkylene-O—, (4) C2-4 alkenylene, or (5) C2-4 alkynylene, wherein C1-6 alkylene is optionally substituted with OH and at least one of $R^4$ and $R^5$ is ring3.

7. The compound according to claim 1, which is the compound represented by formula (I-1)

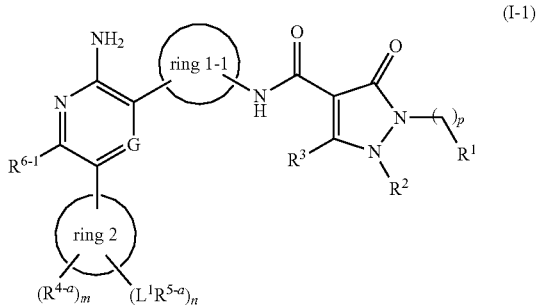

wherein ring1-1 has the same meaning as ring 1 described in claim 1;
$R^{4-a}$ represents (1) C1-4 alkyl, (2) $CF_3$, (3) ring3-1, or (4) halogen;
$R^{5-a}$ represents (1) ring3, (2) C1-4 alkyl optionally substituted with halogen, OH, C1-4 alkoxy, CN, $COOR^{5-8}$, or $NR^{5-1}R^{5-2}$, (3) C2-4 alkenyl, (4) C1-4 alkoxy, (5) $NR^{5-3}$ $R^{5-4}$, (6) OH, (7) $SO_2R^{5-5}$, (8) $SO_2NR^{5-6}R^{5-7}$, (9) $COOR^{5-8}$, (10) $COR^{5-9}$, (11) $CONR^{5-10}R^{5-11}$, (12) halogen, or (13) hydrogen;

$L^1$ represents (1) —C1-6 alkylene-, (2) —O—C1-6 alkylene-, (3) C2-4 alkenylene, or (4) C2-4 alkynylene, wherein C1-6 alkylene is optionally substituted with OH;

the other symbols have the same meanings as described above and at least one of $R^{4-a}$ and $R^{5-a}$ is ring3.

8. The compound according to claim 1, which is the compound represented by formula (I-2)

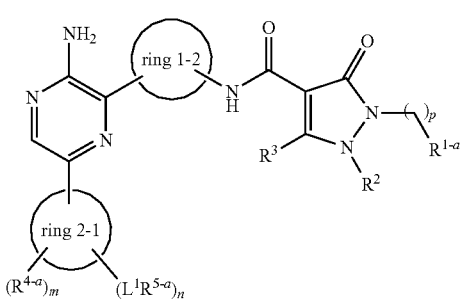

(I-2)

wherein ring1-2 represents benzene, pyridine, or piperidine;

ring2-1 represents benzene, pyridine, thiazole, thiophene, pyrazole, pyrazole, pyrazine, triazole, pyrimidine, indole, indazole, benzomidazole, 2,3-dihydro-[1,4]dioxino[2,3-b]pyridine, imidazo[1,5-a]pyridine, 2,3-dihydro-1H-pyrrolo[2,3-b]pyridine, or 3H-imidazo[4,5-b]pyridine;

$R^{1-a}$ represents benzene which is optionally substituted with 1-5 substituent(s) selected from among (1) C1-4 alkyl, (2) C1-4 alkoxy, (3) halogen, (4) $CF_3$, and (5) CN;

the other symbols have the same meanings as the above and at least one of $R^{4-a}$ and $R^{5-a}$ is ring 3.

9. The compound according to claim 1, which is
(1) N-(4-{3-amino-6-[5-(4-morpholinyl)-3-pyridinyl]-2-pyrazinyl}phenyl)-1,5-dimethyl-3-oxo-2-phenyl-2,3-dihydro-1H-pyrazole-4-carboxamide,
(2) N-(4-{3-amino-6-[2-(3-methoxy-1-azetidinyl)-4-pyridinyl]-2-pyrazinyl}phenyl)-2-(3-chlorophenyl)-1,5-dimethyl-3-oxo-2,3-dihydro-1H-pyrazole-4-carboxamide,
(3) N-(4-{3-amino-6-[6-(3-methoxy-1-azetidinyl)-2-pyridinyl]-2-pyrazinyl}phenyl)-2-(3-chlorophenyl)-1,5-dimethyl-3-oxo-2,3-dihydro-1H-pyrazole-4-carboxamide,
(4) N-[4-(3-amino-6-{6-[(2-methoxyethyl)(methyl)amino]-2-pyridinyl}-2-pyrazinyl)phenyl]-2-(3-chlorophenyl)-1,5-dimethyl-3-oxo-2,3-dihydro-1H-pyrazole-4-carboxamide,
(5) N-(6-{3-amino-6-[2-(4-morpholinyl)-4-pyridinyl]-2-pyrazinyl}-3-pyridinyl)-1,5-dimethyl-2-(3-methylphenyl)-3-oxo-2,3-dihydro-1H-pyrazole-4-carboxamide,
(6) N-(6-{3-amino-6-[2-(4-morpholinyl)-4-pyridinyl]-2-pyrazinyl}-3-pyridinyl)-2-(3-chlorophenyl)-1,5-dimethyl-3-oxo-2,3-dihydro-1H-pyrazole-4-carboxamide, or
(7) N-(4-{3-amino-6-[6-(4-methoxy-1-piperidinyl)-2-pyridinyl]-2-pyrazinyl}phenyl)-1,5-dimethyl-2-(3-methylphenyl)-3-oxo-2,3-dihydro-1H-pyrazole-4-carboxamide.

10. The compound according to claim 1, which is
(1) N-(6-{3-amino-6-[2-(3-methoxy-1-azetidinyl)-4-pyridinyl]-2-pyrazinyl}-3-pyridinyl)-2-(3-methoxyphenyl)-1,5-dimethyl-3-oxo-2,3-dihydro-1H-pyrazole-4-carboxamide,
(2) N-{1-[5-amino-6'-(4-methoxy-1-piperidinyl)-2,2'-bipyrazin-6-yl]-4-piperidinyl}-2-(2-chlorophenyl)-1,5-dimethyl-3-oxo-2,3-dihydro-1H-pyrazole-4-carboxamide,
(3) N-{1-[5-amino-6'-(3-methoxy-1-pyrrolidinyl)-2,2'-bipyrazin-6-yl]-4-piperidinyl}-2-(2-chlorophenyl)-1,5-dimethyl-3-oxo-2,3-dihydro-1H-pyrazole-4-carboxamide, or
(4) N-{4-[5-amino-6'-(3-methoxy-1-pyrrolidinyl)-2,2'-bipyrazin-6-yl]phenyl}-1,5-dimethyl-3-oxo-2-phenyl-2,3-dihydro-1H-pyrazole-4-carboxamide.

11. (1) N-{4-[6-(1-acryloyl-3-piperidinyl)-3-amino-2-pyrazinyl]phenyl}-1,5-dimethyl-3-oxo-2-phenyl-2,3-dihydro-1H-pyrazole-4-carboxamide,
(2) N-{4-[3-amino-6-(1-piperidinyl)-2-pyrazinyl]phenyl}-1,5-dimethyl-3-oxo-2-phenyl-2,3-dihydro-1H-pyrazole-4-carboxamide,
(3) N-[4-(2-amino-5-cyclohexyl-3-pyridinyl)phenyl]-1,5-dimethyl-3-oxo-2-phenyl-2,3-dihydro-1H-pyrazole-4-carboxamide, or a pharmaceutically acceptable salt thereof.

12. A pharmaceutical composition comprising the compound represented by formula (I) of claim 1 or a pharmaceutically acceptable salt thereof and a pharmaceutically acceptable carrier.

13. A method for treating an Itk related disease in a mammal, which comprises administering to a mammal affected with Itk-related disease, which is selected from asthma, allergic rhinitis, atopic dermatitis, inflammatory bowel disease, T-cell and natural killer (NK)-cell neoplasm, and HIV infection, an effective amount of the compound of formula (I) of claim 1 or a pharmaceutically acceptable salt thereof.

* * * * *